(12) United States Patent
Moon et al.

(10) Patent No.: US 11,479,612 B2
(45) Date of Patent: Oct. 25, 2022

(54) ANTI-C-MET ANTIBODY AND USE THEREOF

(71) Applicant: CHONG KUN DANG PHARMACEUTICAL CORP., Seoul (KR)

(72) Inventors: Seung Kee Moon, Gyeonggi-do (KR); Kyung Woo Lee, Gyeonggi-do (KR); Eun Ju Jeon, Gyeonggi-do (KR); Ki Young An, Gyeonggi-do (KR); Eun Su Choi, Gyeonggi-do (KR)

(73) Assignee: Chong Kun Dang Pharmaceutical Corp.

( * ) Notice: Subject to any disclaimer, the term of this patent is extended or adjusted under 35 U.S.C. 154(b) by 0 days.

(21) Appl. No.: 16/616,345

(22) PCT Filed: May 30, 2018

(86) PCT No.: PCT/KR2018/006182
§ 371 (c)(1),
(2) Date: Nov. 22, 2019

(87) PCT Pub. No.: WO2018/221969
PCT Pub. Date: Dec. 6, 2018

(65) Prior Publication Data
US 2020/0231681 A1   Jul. 23, 2020

(30) Foreign Application Priority Data

May 30, 2017 (KR) .................. 10-2017-0067106
May 30, 2018 (KR) .................. 10-2018-0061888

(51) Int. Cl.
| | | |
|---|---|---|
| C07K 16/28 | (2006.01) | |
| A61K 39/395 | (2006.01) | |
| G01N 33/574 | (2006.01) | |
| A61K 38/00 | (2006.01) | |
| A61K 39/00 | (2006.01) | |

(52) U.S. Cl.
CPC ...... *C07K 16/2863* (2013.01); *A61K 39/3955* (2013.01); *G01N 33/5748* (2013.01); *A61K 38/00* (2013.01); *A61K 2039/505* (2013.01); *C07K 2317/24* (2013.01); *C07K 2317/31* (2013.01); *C07K 2317/34* (2013.01); *C07K 2317/53* (2013.01); *C07K 2317/565* (2013.01); *C07K 2317/622* (2013.01); *C07K 2317/73* (2013.01); *C07K 2317/77* (2013.01); *C07K 2317/92* (2013.01); *G01N 2333/71* (2013.01); *G01N 2333/912* (2013.01)

(58) Field of Classification Search
None
See application file for complete search history.

(56) References Cited

U.S. PATENT DOCUMENTS

| 8,637,027 B2 * | 1/2014 | Hultberg ............... C07K 16/32 |
| | | 424/138.1 |
| 9,631,027 B2 | 4/2017 | Hultberg et al. |
| 2010/0254988 A1 | 10/2010 | Bossenmaier et al. |
| 2014/0141000 A1 | 5/2014 | Chiu et al. |
| 2014/0154251 A1 | 6/2014 | Lee et al. |
| 2014/0294814 A1 | 10/2014 | Lee et al. |
| 2014/0370022 A1 | 12/2014 | Kim et al. |
| 2015/0118238 A1 | 4/2015 | Beuerlein et al. |
| 2015/0299305 A1 | 10/2015 | Andrien, Jr. et al. |
| 2016/0144028 A1 | 5/2016 | Lee et al. |

FOREIGN PATENT DOCUMENTS

| EA | 020398 | 10/2012 |
| EP | 2832748 | 2/2015 |
| JP | 2013545455 | 12/2013 |
| JP | 2015519335 | 7/2015 |
| JP | 2016505537 | 2/2016 |
| KR | 10-1420274 | 7/2014 |
| KR | 10-1515535 | 5/2015 |
| KR | 10-2016-0061199 A | 5/2016 |
| RU | 2585488 | 5/2016 |
| WO | WO 8801649 | 3/1988 |
| WO | WO 8806630 | 9/1988 |
| WO | WO 1988007085 | 9/1988 |
| WO | WO 1988007086 | 9/1988 |
| WO | WO 1988009344 | 12/1988 |
| WO | 2006015371 A2 | 2/2006 |
| WO | 2010059654 A1 | 5/2010 |
| WO | WO 2017076492 | 5/2017 |

OTHER PUBLICATIONS

Martinelli et al., Clinical and Experimental Immunology, 158: 1-9, 2006.*
AU Examination Report in Australian Appln. No. 2018278730, dated Sep. 18, 2020, 10 pages.
Bravo et al., "Analysis of crylAa expression in sigE and sigK mutants of Bacillus thuringiensis," Mol. Gen. Genet., 1996, 250(6):734-741.
CA Examination Report in Canadian Appln. No. 3061704, dated Oct. 6, 2020, 9 pages.
Chong et al., "The quest to overcome resistance to EGFR-targeted therapies in cancer," Nature Medicine, Nov. 2013, 19(11):1389-1400.
Corso et al.. "Cell-autonomous and non-cell-autonomous mechanisms of HGF/MET-driven resistance to targeted therapies: from basic research to a clinical perspective," Cancer Discovery, Jul. 30, 2013, 3:978-992.

(Continued)

*Primary Examiner* — Marianne P Allen
(74) *Attorney, Agent, or Firm* — Fish & Richardson P.C.

(57) ABSTRACT

The present invention relates to a novel antibody or an antigen binding fragment thereof that specifically binds to a human hepatocyte growth factor receptor (c-Met), and a composition for preventing or treating cancer, wherein the antibody shows an excellent cancer cell proliferation inhibitory activity and a remarkably excellent anticancer activity even by a little amount thereof, thus effectively preventing or treating cancer.

11 Claims, 20 Drawing Sheets

Specification includes a Sequence Listing.

(56) References Cited

OTHER PUBLICATIONS

Cross et al., "AZD9291, an Irreversible EGFR TKI, Overcomes T790M-Mediated Resistance to EGFR Inhibitors in Lung Cancer," Cancer Discovery, Sep. 2014, 4(9):1046-1061.
Engelman et al.. "MET Amplification Leads to Gefitinib Resistance in Lung Cancer by Activating ERBB3 Signaling," Science, May 18, 2007, 316:1039-1343.
Herskowitz, "The lysis-lysogeny decision of phage λ: explicit programming and responsiveness," Annual Review Genetics. 1980. 14:399-445.
Park et al., "Optimization of Cry3A Yields in Bacillus thuringiensis by Use of Sporulation-Dependent Promoters in Combination with the STAB-SD mRNA Sequence." Appl. Environ. Microbiology, Oct. 1988, 64(10)3932-3938.
Reiter et al., "Stabilization of the Fv fragments in recombinant immunotoxins by disulfide bonds engineered into conserved framework regions," Biochemistry, May 10, 1994, 33(18):5451-5459.
Rouet et al., "Expression of high-affinity human antibody fragments in bacteria," Nature Protocols, Feb. 2, 2012, 7(2):364-373.
RU Office Action in Russion Appln No. 2019143101, dated Jul. 30, 2020, 15 pages.
Uhlman et al., "Antisense oligonucleotides: a new therapeutic principle." Chemical Reviews, Jun. 1990, 90(4):543-584.
Wheeler et al., "Understanding resistance to EgFR inhibitors—impact on future treatment strategies." Nature Reviews Clinical Oncology, Jun. 15, 2010, 7(9):493-507.
Yanofsky et al., "Repression is relieved before attenuation in the trp operon of *Escherichia coli* as tryptophan starvation becomes increasingly severe," Journal of Bacteriology, Jun. 1984, 158(3):1018-1024.
Yewale et al., "Epidermal growth factor receptor targeting in cancer: A review of trends and strategies," Biomaterials, Aug. 13, 2013, 34:8690-707.
International Search Report for PCT/KR2018/006182, dated Nov. 15, 2018. 6 pages.
Office Action for KR10-2018-0061888, dated Jul. 11, 2019. 4 pages.
Office Action for TW107118588, dated Aug. 7, 2019. 12 pages.
Laird, et al. "Small molecule tyrosine kinase inhibitors: clinical development of anticancer agents", Expert Opinion, Investig. Drugs, 2003, 12, pp. 51-64.
Bottaro, et al., "identification of the Hepatocyte Growth Factor Receptor as the c-met Proto-Oncogene Product":, Science, vol. 251, Feb. 15, 1991, pp. 802-804.

Day, et al., "Differential signaling by alternative HGF isoforms through c-Met: activation of both MAP kinase and PI 3-kinase pathways is insufficient for mitogenesis", Oncogene, 1999, 18, pp. 3399-3406.
Lefebvre, et al., "Met degradation: more than one stone to shoot a receptor down", The FASEB Journal, vol. 26, Apr. 2012, pp. 1387-1399.
Liu et al., "Developing c-MET pathway inhibitors for cancer therapy: progress and challenges", Trends in Molecular Medicine vol. 16, No. 1, 2010, pp. 37-45.
Smolen, et al., "Amplification of MET may identify a subset of cancers with extreme sensitivity to the selective tyrosine kinase inhibitor PHA-665752", PNAS, Feb. 14, 2006, vol. 103, No. 7, pp. 2316-2321.
Foveau, et al., "Down-Regulation of the Met Receptor Tyrosine Kinase by Presenilin-dependent Regulated Intramembrane Proteolysis", Molecular Biology of the Cell, vol. 20, May 1, 2009, pp. 2495-2507.
Wang, et al., "Anti-c-Met monoclonal antibody ABT-700 breaks oncogene addiction in tumors with MET amplification", BMC Cancer, 2016, pp. 105-118.
Merchant et al., "Monovalent antibody design and mechanism of action of onartuzumab, a MET antagonist with antitumor activity as a therapeutic agent", PNAS PLUS, 110 (32), Jul. 23, 2013, E2987-E2996.
Moores, et al., "A Novel Bispecific Antibody Targeting EGFR and cMet Is Effective against EGFR Inhibitor-Resistant Lung Tumors", Cancer Research, Jul. 1, 2016, vol. 76, No. 13, pp. 3942-3953.
International Search Report and Written Opinion for PCT/KR2018/006182, dated Nov. 15, 2018. 7 pages.
EP Extended European Search Report in International Appln. No. 18809820.6, dated Feb. 2, 2021, 10 pages.
JP Office Action in Japanese Appln. No. 2019-566586, dated Dec. 1, 2020, 13 pages (with English Translation).
Lee, "Biochemical Engineering," eBook Version 2.32, Washington State University, Prentice-Hall Inc., 1992, Updated Aug. 10, 2001 Chapter 5, 44 pages.
Pakula et al., "Genetic Analysis of Protein Stability and Function," Annu. Rev. Genet., 1989, 23:289-310.
Rudikoff et al., "Single Amino Acid Substitution Altering Antigen-Binding Specificity," Proc. Natl. Acad. Sci. USA, Mar. 1982, 79:1979-1983.
Trouet et al., "Targeting of Antitumour and Antiprotozoal Drugs by Covalent Linkage to Protein Carriers," Targeting of Drugs, NATO Advanced Study Institutes Series, Springer, Plenum Press, New York and London, 1982, vol. 47, pp. 19-30.

\* cited by examiner

ANTI-C-MET ANTIBODY AND USE THEREOF

CROSS-REFERENCE TO PRIOR APPLICATION

This is the U.S. National Phase Application under 35 U.S.C. § 371 of International Patent Application No. PCT/KR2018/006182, filed May 30, 2018, which claims the benefit of Korean Patent Application Nos. 10-2017-0067106 filed May 30, 2017 and 10-2018-0061888, filed May 30, 2018, all of which are incorporated by reference herein. The International Application was published in Korean on Dec. 6, 2018 as WO2018/221969 A1 under PCI Article 21(3).

SEQUENCE LISTING

The instant application contains a Sequence Listing which has been submitted electronically in ASCII format and is hereby incorporated by reference in its entirety. Said ASCII copy, created on Mar. 20, 2020, is named 45695_0009US1_ST25.txt and is 195 KB (199,840 bytes) in size.

TECHNICAL FIELD

The present invention relates to an antibody or an antigen binding fragment thereof, specifically binding to a human hepatocyte growth factor receptor (c-Met), and a composition for preventing or treating cancer comprising the same.

BACKGROUND ART

Receptor tyrosine kinases (RTK) act as a vital modulator in cell growth, differentiation, neovascularization, tissue recovery, etc. Besides such general physiological processes, an abnormal expression of a certain RTK is associated with the development and progression of many kinds of cancer. Thus, such RTK has been considered as a promising drug target for cancer treatment.

A hepatocyte growth factor receptor (HGFR; c-Met), which is a kind of the RTK, is a receptor on the surface of cells with regard to hepatocyte growth factor known as a scatter factor (HGF/SF) (Laird A D et al., Expert. Opin. Investig. Drugs 12: 51-64 (2003)). An abnormal c-Met activation by HGF, which is one of the representative oncogenic mechanisms, is known to be associated with tumor proliferation, apoptosis inhibition, neovascularization, invasion, metastasis and the like (Bottaro D P et al., Science 251: 802-804 (1991), Day R M et al., Oncogene 18: 3399-3406 (1999)). And also, it is reported that the abnormal c-Met activation by c-Met mutation and amplification is associated with various cancers such as lung cancer, colon cancer, head and neck cancer, stomach cancer, breast cancer, etc., and is also involved in an increase in tumor aggressiveness and its unfavorable prognosis (Lefebvre J et al., FASEB J 26: 1387-1399 (2012), Liu X et al., Trends Mol Med 16: 37-45 (2010), Smolen G A et al., Proc Natl Acad Sci USA 103: 2316-2321 (2006), Foveau B et al., Mol Biol Cell 20: 2495-2507 (2009)).

Thus, c-Met has drawn much attention as a target antigen for treating such various cancers and various approaches have been made to inhibit the expression and activity of c-Met. As a c-Met-specific small molecule tyrosine kinase inhibitor, which has been known so far, there are Tivantinib (ArQule), INC280 (Novatis), AMG337 (Amgen), etc. And, Rilotumumab (Amgen), Ficlatuzumab (AVEP Pharmaceuticals), HuL2G7 (Galaxy Biotech), etc., have been developed as an HGF-specific monoclonal antibody, which is a ligand of c-Met. Also, as an antagonist monoclonal antibody, which targets c-Met, there are Onartuzumab (WO 2006/015371) in clinical phase III of development by Genentech, Emibetuzumab (WO 2010/059654) in clinical phase II by Lilly, SAIT301 (US 2014154251) in clinical phase I of development, ABT-700 (Wang J et al., BMC Cancer. 16: 105-118 (2016)), etc. Onartuzumab is a monovalent antagonistic antibody derived from a bivalent monoclonal antibody (5D5), which acts on c-Met as an agent (Mark Merchant, et al., Proc Natl Acad Sci USA. 110(32): E2987-E299 (2013)). As such, various drugs have been developed with regard to c-Met, but c-Met is associated with the occurrence and progression of various cancers as described above, thus it is constantly driving a continuous demand for developing a new therapeutic agent capable of treating cancer by targeting c-Met.

DISCLOSURE OF INVENTION

Technical Problem

The present inventors have developed a novel anti-c-Met antibody binding to c-Met with a high affinity and have also identified that such anti-c-Met antibody, a chimera thereof and humanized and affinity-optimized antibodies remarkably inhibit a proliferation of tumor cells and have an excellent anticancer effect, thus having completed the present invention.

Solution to Problem

One objective of the present invention is to provide an antibody or an antigen binding fragment thereof that specifically binds to a hepatocyte growth factor receptor (c-Met).

Another objective of the present invention is to provide a nucleic acid molecule encoding the antibody or the antigen binding fragment thereof, an expression vector comprising the nucleic acid molecule, a host cell having the expression vector introduced therein, a method for producing an antibody or an antigen binding fragment thereof using the host cell.

Yet another objective of the present invention is to provide a composition for detecting c-Met comprising the antibody or the antigen binding fragment thereof, a kit for detection comprising the same, and a method for detecting a c-Met antigen using the same.

Still yet another objective of the present invention is to provide a composition for preventing or treating cancer comprising the antibody or the antigen binding fragment thereof.

Advantageous Effects of Invention

The antibody or the antigen binding fragment thereof of the present invention that specifically binds to a hepatocyte growth factor receptor (c-Met), has a novel sequence, and shows an excellent cancer cell proliferation inhibitory activity and a remarkably excellent anticancer activity even by a little amount thereof, thus effectively preventing or treating the disease such as cancer.

BEST MODE FOR CARRYING OUT THE INVENTION

Figure 1:
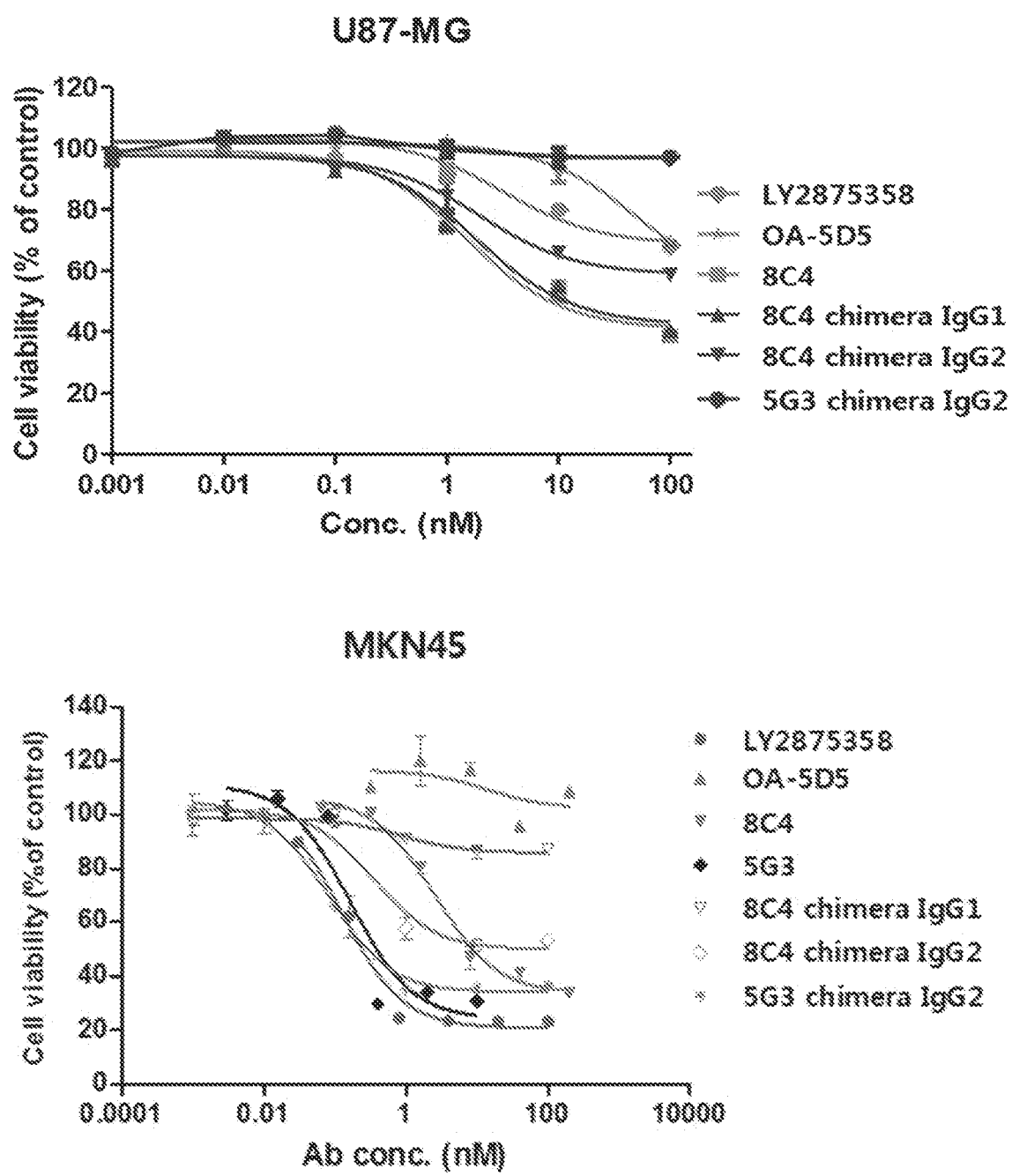
FIG. 1 shows results of an in vitro test on tumor cell proliferation inhibitory activity of hybridoma c-Met antibody of the present invention.

Hereinafter, the present invention will be described in more detail as follows. Meanwhile, each description and embodiment disclosed in the present invention may be applied to other descriptions and embodiments respectively as well. In other words, all the combinations of various elements disclosed in the present invention are within the scope of the present invention. Also, the scope of the present invention may not be restricted by the detailed descriptions below.

To achieve the objectives above, one aspect of the present invention provides an antibody or an antigen binding fragment thereof that specifically binds to a hepatocyte growth factor receptor (c-Met).

The antibody or the antigen binding fragment thereof of the present invention, specifically binding to c-Met, binds to c-Met with a high affinity to inhibit an expression or activity thereof, thus showing an excellent tumor cell proliferation inhibitory activity, such that the antibody alone or with conventional pharmaceutically acceptable carriers, other anticancer drugs, anticancer adjuvants, etc. may be valuably used as an anticancer composition for preventing or treating cancer.

In the present invention, the term "antibody" means a protein molecule serving as a receptor for specifically recognizing an antigen, comprising an immunoglobulin molecule immunologically having reactivity with a certain antigen, wherein examples thereof may comprise a monoclonal antibody, a polyclonal antibody, a full-length antibody and antibody fragments all. Also, the term may comprise a bivalent or bispecific molecule (e.g., a bispecific antibody), a diabody, a triabody or a tetrabody.

In the present invention, the term "monoclonal antibody" refers to an antibody molecule of a single molecule composition obtained from substantially the same antibody population, wherein such monoclonal antibody shows a single binding specificity and affinity for a certain epitope. In the present invention, the term "full-length antibody" has a structure with two full-length light chains and two full-length heavy chains, wherein each of light chains is linked to a heavy chain by a disulfide bond. A constant region of the heavy chain has gamma (γ), mu (μ), alpha (α), delta (δ) and epsilon (ε) types, and also has gamma1 (γ1), gamma2 (γ2), gamma3 (γ3), gamma4 (γ4), alpha1 (α1) and alpha2 (α2) as a subclass. A constant region of the light chain has kappa (κ) and lambda (λ) types. IgG comprises IgG1, IgG2, IgG3 and IgG4 as a subtype.

In the present invention, the terms "fragment," "antibody fragment" and "antigen binding fragment" refer to any fragments of the antibody of the present invention having an antigen binding function of the antibody, wherein such terms are used interchangeably with each other. Exemplary antigen binding fragments comprise Fab, Fab', F(ab')$_2$, Fv and the like, but not limited thereto.

The Fab has a structure with a variable region of light and heavy chains, a constant region of light chain and a first constant region of heavy chain (CH1 domain), and also has one antigen binding site. An antigen binding fragment of an antibody molecule or an antibody fragment means a fragment having an antigen binding function, and Fab' is different from Fab in that the former has a hinge region having one or more cysteine residue in C terminus of a heavy chain CH1 domain. F(ab')$_2$ antibody is created in such a way that a cysteine residue of a hinge region of Fab' forms a disulfide bond. Fv is a minimal antibody fragment having only a heavy chain variable region and a light chain variable region, wherein a recombinant technology for creating Fv fragments is disclosed in PCT International Patent Publication Applications WO 88/01649, WO 88/06630, WO 88/07085, WO 88/07086, WO 88/09344 and the like. Two-chain Fv is formed in such a way that a heavy chain variable region and a light chain variable region are linked to each other by a non-covalent bond, while single-chain Fv is formed in such a way that a heavy chain variable region and a single chain variable region are generally linked with each other either by a covalent bond through a peptide linker or directly linked in C-terminus, thus forming a structure like a dimer as shown in the two-chain Fv. Such antibody fragment may be obtained by using a protein hydrolase (for example, Fab may be obtained by performing a restriction digestion of a whole antibody by papain and F(ab')$_2$ fragment may be obtained by performing a digestion of the same by pepsin) or may be produced by a gene recombination technology, but not limited thereto.

Particularly in the present invention, it may be provided that the antibody specifically binding to c-Met is:

(a) an antibody comprising a light chain variable region comprising a light chain CDR1 represented by SEQ ID NO: 1; a light chain CDR2 represented by SEQ ID NO: 2; a light chain CDR3 represented by SEQ ID NO: 3, and a heavy chain variable region comprising a heavy chain CDR1 represented by SEQ ID NO: 7; a heavy chain CDR2 represented by SEQ ID NO: 8; and a heavy chain CDR3 represented by SEQ ID NO: 9;

(b) an antibody comprising a light chain variable region comprising a light chain CDR1 represented by SEQ ID NO: 4; a light chain CDR2 represented by SEQ ID NO: 5; a light chain CDR3 represented by SEQ ID NO: 6, and a heavy chain variable region comprising a heavy chain CDR1 represented by SEQ ID NO: 10; a heavy chain CDR2 represented by SEQ ID NO: 11; and a heavy chain CDR3 represented by SEQ ID NO: 12; or (c) affinity-optimized antibodies thereof.

In the present invention, the term "heavy chain" may comprise both a full-length heavy chain and a fragment thereof comprising a variable region domain VH with an amino acid sequence having a variable region sequence enough to give specificity to an antigen, as well as three constant region domains CH1, CH2 and CH3. Also, in the present invention, the term "light chain" may comprise both a full-length light chain and a fragment thereof comprising a variable region domain VL with an amino acid sequence having a variable region sequence enough to give specificity to an antigen, as well as a constant region domain CL.

In the present invention, the antibody may comprise both a mouse antibody produced from a mouse, and a mutant thereof, wherein a part of an amino acid sequence of a parent antibody is substituted, added and/or deleted to improve the affinity, immunity, etc., of the antibody. The mutant may comprise a chimeric antibody, a humanized antibody, an affinity-optimized antibody, etc., as an example, but not limited thereto. In the present invention, the mutant comprehensively refers to an antibody, wherein a part of a CDR amino acid sequence of a parent antibody is mutated (substituted, added or deleted) on condition of having the same CDR as that of the parent antibody or targeting the same epitope as that of the parent antibody. Such mutant may be appropriately adjusted by those skilled in the art to improve the affinity, immunity and the like of an antibody within the scope of maintaining a binding capacity for the same epitope.

In other words, the antibody or the antigen binding fragment thereof of the present invention may comprise a sequence of anti-c-Met antibody described herein as well as biological equivalents thereof, within the scope of specifically recognizing c-Met. For example, an additional change may be made in an amino acid sequence of the antibody, in order to further improve the binding affinity and/or other biological characteristics of the antibody. Such change comprises, for example, the deletion, insertion and/or substitution of an amino acid sequence residue of the antibody. Such amino acid mutation is made based on relative similarity of amino acid side chain substituent, e.g., hydrophobicity, hydrophilicity, charge, size, etc. By analyzing the size, shape and type of amino acid side chain substituent, it can be seen that arginine, lysine and histidine are all positive charge residues; alanine, glycine and serine have a similar size; and phenylalanine, tryptophan and tyrosine have a similar shape. Thus, based on such considerations, it can be seen that arginine, lysine and histidine; alanine, glycine and serine; and phenylalanine, tryptophan and tyrosine are biologically functional equivalents.

In the present invention, the term "chimeric antibody" is an antibody formed in such a way that a variable region of a mouse antibody is recombined with a constant region of a human antibody, which results in a greatly improved immune reaction in comparison with a mouse antibody.

In the present invention, the term "humanized antibody" means an antibody formed in such a way that a protein sequence of an antibody derived from other species than human is modified to be similar to that of an antibody mutant naturally produced from human. For example, the humanized antibody may be prepared by preparing a humanized variable region through a recombination of CDR derived from a mouse with FR derived from a human antibody and then by recombining the same with a constant region of a preferred human antibody. However, a simple CDR grafting only results in a low affinity of the humanized antibody, so several key FR amino acid residues, which are considered to possibly influence a three-dimensional structure of CDR, may develop an affinity with those of mouse antibody, thus reaching the same level as the affinity of an original mouse antibody.

In the present invention, the term "affinity-optimized antibody," which is a mutant formed in such a way that a part of CDR sequence of a certain antibody is substituted, added or deleted, means an antibody with a better binding affinity to an antigen while binding to the same antigen epitope as that of the certain antibody. Particularly, the affinity-optimized antibody of the present invention refers to a mutant antibody binds to the same epitope as that of: (a) an antibody comprising a light chain variable region comprising a light chain CDR1 represented by SEQ ID NO: 1; a light chain CDR2 represented by SEQ ID NO: 2; a light chain CDR3 represented by SEQ ID NO: 3, and a heavy chain variable region comprising a heavy chain CDR1 represented by SEQ ID NO: 7; a heavy chain CDR2 represented by SEQ ID NO: 8; a heavy chain CDR3 represented by SEQ ID NO: 9; or (b) an antibody comprising a light chain variable region comprising a light chain CDR1 represented by SEQ ID NO: 4; a light chain CDR2 represented by SEQ ID NO: 5; a light chain CDR3 represented by SEQ ID NO: 6, and a heavy chain variable region comprising a heavy chain CDR1 represented by SEQ ID NO: 10; a heavy chain CDR2 represented by SEQ ID NO: 11; a heavy chain CDR3 represented by SEQ ID NO: 12. A person of ordinary skill in the art may prepare the affinity-optimized antibody by using a known technology based on certain light chain and heavy chain CDR sequences. For example, the affinity-optimized antibody of the present invention may be prepared through a phage display. In the present invention, the term "phage display" refers to a technology, which displays a mutant polypeptide as a fusion protein with at least a part of coat protein on a phage, for example, on the surface of fibrous phage particles. The usefulness of the phage display lies in the fact that it targets a large library of randomized protein mutants, thus promptly and efficiently classifying sequences binding to a target antigen with a high affinity. Displaying a library of peptides and proteins on the phage has been used for screening millions of polypeptides in order to see a polypeptide with a specific binding characteristic.

In one exemplary embodiment of the present invention, it may be provided that the antibody is an antibody comprising: (a) a light chain variable region represented by SEQ ID NO: 13 and a heavy chain variable region represented by SEQ ID NO: 15; or (b) a light chain variable region represented by SEQ ID NO: 14 and a heavy chain variable region represented by SEQ ID NO: 16. As an example, it may be provided that the antibody is an antibody comprising: (a) a light chain variable region coded by a nucleotide represented by SEQ ID NO: 17 and a heavy chain variable region coded by a nucleotide represented by SEQ ID NO: 19; or (b) a light chain variable region coded by a nucleotide represented by SEQ ID NO: 18 and a heavy chain variable region coded by a nucleotide represented by SEQ ID NO: 20, but not limited thereto.

According to one specific embodiment of the present invention, a hybridoma cell group was obtained from a mouse, wherein a human c-Met Sema domain/Fc fusion protein is an antigen, from which anti-c-Met antibody specifically binding to c-Met was selected by screening with an ELISA analysis method using c-Met/His fusion protein as an antigen. The selected antibody and the chimeric antibody thereof have a tumor cell proliferation inhibitory activity, which is equal to or more excellent than even commercially available known LY2875358 and OA-5D5 (Table 3 and FIG. 1), thus being very valuably used in prevention or treatment of cancer.

In another exemplary embodiment of the present invention, it may be provided that the antibody comprises:
(a) a light chain variable region represented by SEQ ID NO: 21 and a heavy chain variable region represented by SEQ ID NO: 23; (b) a light chain variable region represented by SEQ ID NO: 22 and a heavy chain variable region represented by SEQ ID NO: 24; (c) a light chain variable region represented by SEQ ID NO: 29 and a heavy chain variable region represented by SEQ ID NO: 31; or (d) a light chain variable region represented by SEQ ID NO: 30 and a heavy chain variable region represented by SEQ ID NO: 32. As an example, it may be provided that the antibody is an antibody comprising: (a) a light chain variable region coded by a nucleotide represented by SEQ ID NO: 25 and a heavy chain variable region coded by a nucleotide represented by SEQ ID NO: 27; (b) a light chain variable region coded by a nucleotide represented by SEQ ID NO: 26 and a heavy chain variable region coded by a nucleotide represented by SEQ ID NO: 28; (c) a light chain variable region coded by a nucleotide represented by SEQ ID NO: 33 and a heavy chain variable region coded by a nucleotide represented by SEQ ID NO: 35; or (d) a light chain variable region coded by a nucleotide represented by SEQ ID NO: 34 and a heavy chain variable region coded by a nucleotide represented by SEQ ID NO: 36, but not limited thereto. Also, it may be provided that the antibody comprises a hinge region represented by one of SEQ ID NO: 37 to SEQ ID NO: 44.

In one specific embodiment of the present invention, a humanized antibody comprising CDR of the antibody obtained through a phage display selection was prepared, and it was identified that such antibody showed an anticancer activity, which was similar to that of the chimera antibody of the present invention (Examples 2 and 3). Also, in another specific embodiment of the present invention, a tumor cell proliferation inhibitory activity of the antibody was evaluated according to a hinge region sequence, and it was identified that a proliferation of most tumor cells was effectively inhibited, even with a somewhat difference in the activity depending on the difference of hinge sequence (Table 7).

In yet another exemplary embodiment of the present invention, but not limited thereto, it may be provided that an affinity-optimized antibody for the humanized antibody is an antibody, wherein one or more amino acid sequence is substituted from an antibody comprising: a light chain variable region comprising a light chain CDR1 represented by SEQ ID NO: 1; a light chain CDR2 represented by SEQ ID NO: 2; a light chain CDR3 represented by SEQ ID NO: 3, and a heavy chain variable region comprising a heavy chain CDR1 represented by SEQ ID NO: 7; a heavy chain CDR2 represented by SEQ ID NO: 8; a heavy chain CDR3 represented by SEQ ID NO: 9, and wherein, (i) G in a 1st position of the light chain CDR1 is substituted with A, E, K, L, N, R, S, V or W; A in a 2nd position thereof is substituted with C, G, I, P, S, T or V; S in a 3rd position thereof is substituted with G, M, N, P, Q, R, S or T; E in a 4th position thereof is substituted with A, D, F, G, H, K, M, Q, R, S, T or V; N in a 5th position thereof is substituted with A, D, E, G, K, L, P, Q, R, S, T or V; I in a 6th position thereof is substituted with A, F, L, M, Q, R, S, T or V; Y in a 7th position thereof is substituted with F, H, R or V; or G in a 8th position thereof is substituted with D, F, H, M, N, R, S, T or V; (ii) G in a 1st position of the light chain CDR2 is substituted with D, F, H, K, P, Q, S, V or Y; T in a 3rd position thereof is substituted with Q; or N in a 4th position thereof is substituted with G; (iii) Q in a 1st position of the light chain CDR3 is substituted with E, G, I, M or N; N in a 2nd position thereof is substituted with A, D, E, H, L, Q, S or T; V in a 3rd position thereof is substituted with I, L, M, N, Q, S or T; L in a 4th position thereof is substituted with F, H, I, M, R, S, V, W or Y; S in a 5th position thereof is substituted with C, D, E, F, G, H, K, L, N, Q, R, T, V or Y; S in a 6th position thereof is substituted with D, E, F, G, H, I, L, M, N, P, Q, R, T, V or Y; P in a 7th position thereof is substituted with A, D, E, G, N, Q, S or V; Y in an 8th position thereof is substituted with E, F, L, M or Q; or T in a 9th position thereof is substituted with D, F, G, I, L, N, S, V, W or Y; (iv) D in a 1st position of the heavy chain CDR1 is substituted with G or Q; Y in a 2nd position thereof is substituted with Q; or I in a 4th position thereof is substituted with A or Q; (v) F in a 3rd position of the heavy chain CDR2 is substituted with D, E, W or Y; G in a 5th position thereof is substituted with D, H or Y; S in a 6th position thereof is substituted with F, P, W or Y; G in a 7th position thereof is substituted with A, F, L, N or T; N in an 8th position thereof is substituted with F, P, S, T or Y; T in a 9th position thereof is substituted with A, D, E, F, G, H, L, P, S or V; H in a 10th position thereof is substituted with A, D, F, M, R, S, T, V, W or Y; F in an 11th position thereof is substituted with G, H, I, L, M, N, P, Q, V or Y; S in a 12th position thereof is substituted with A, D, G, H, I, L, P, T or V; A in a 13th position thereof is substituted with D, E, F, G, H, I, K, L, M, P, R, S, T, V or Y; R in a 14th position thereof is substituted with A, E, G, H, L, N, P, Q, S, W or Y; F in a 15th position thereof is substituted with D, E, G, L, M, P, R, S, V or W; K in a 16th position thereof is substituted with A, E, F, G, H, L, R, S, T, V or Y; or G in a 17th position thereof is substituted with E, F, H, L, M, N, P, Q, R, S, T, V or W; or (vi) G in a 1st position of the heavy chain CDR3 is substituted with E, F, H, N, Q, V or W; D in a 2nd position thereof is substituted with E; Y in a 3rd position thereof is substituted with L, Q, T or V; G in a 4th position thereof is substituted with W; F in a 5th position thereof is substituted with L or Y; L in a 6th position thereof is substituted with Q, S or Y; or Y in a 7th position thereof is substituted with C, L, M, N or Q. Herein, it may be provided that the light chain CDR1 comprises 0 to 5 substitutions, the light chain CDR2 comprises 0 to 1 substitution, the light chain CDR3 comprises 0 to 7 substitutions, the heavy chain CDR1 comprises 0 to 1 substitution, the heavy chain CDR2 comprises 0 to 11 substitutions, and the heavy chain CDR3 comprises 0 to 6 substitutions.

Particularly, in still yet another exemplary embodiment of the present invention, it may be provided that the affinity-optimized antibody comprises a light chain variable region comprising a light chain CDR1 represented by any one of SEQ ID NO: 1 and SEQ ID NO: 229 to SEQ ID NO: 268; a light chain CDR2 represented by any one of SEQ ID NO: 2, SEQ ID NO: 182 to SEQ ID NO: 190, SEQ ID NO: 227 and SEQ ID NO: 228; a light chain CDR3 represented by any one of SEQ ID NO: 3, SEQ ID NO: 142 to SEQ ID NO: 181, SEQ ID NO: 191 to SEQ ID NO: 226 and SEQ ID NO: 269 to SEQ ID NO: 301; and a heavy chain variable region comprising a heavy chain CDR1 represented by any one of SEQ ID NO: 7 and SEQ ID NO: 108 to SEQ ID NO: 112; a heavy chain CDR2 represented by any one of SEQ ID NO: 8, SEQ ID NO: 54 to SEQ ID NO: 63, SEQ ID NO: 72 to SEQ ID NO: 107 and SEQ ID NO: 118 to SEQ ID NO: 141; a heavy chain CDR3 represented by any one of SEQ ID NO: 9, SEQ ID NO: 64 to SEQ ID NO: 71 and SEQ ID NO: 113 to SEQ ID NO: 117, more particularly, comprising a light chain variable region represented by any one of SEQ ID NO: 21 and SEQ ID NO: 306 to SEQ ID NO: 311, and a heavy chain variable region represented by any one of SEQ ID NO: 23 and SEQ ID NO: 302 to SEQ ID NO: 305, and much more particularly comprising: (a) a light chain variable region represented by SEQ ID NO: 21 and a heavy chain variable region represented by SEQ ID NO: 302; (b) a light chain variable region represented by SEQ ID NO: 21 and a heavy chain variable region represented by SEQ ID NO: 305; (c) a light chain variable region represented by SEQ ID NO: 310 and a heavy chain variable region represented by SEQ ID NO: 23; (d) a light chain variable region represented by SEQ ID NO: 308 and a heavy chain variable region represented by SEQ ID NO: 305; (e) a light chain variable region represented by SEQ ID NO: 306 and a heavy chain variable region represented by SEQ ID NO: 303; (f) a light chain variable region represented by SEQ ID NO: 307 and a heavy chain variable region represented by SEQ ID NO: 304; (g) a light chain variable region represented by SEQ ID NO: 308 and a heavy chain variable region represented by SEQ ID NO: 304; (h) a light chain variable region represented by SEQ ID NO: 309 and a heavy chain variable region represented by SEQ ID NO: 304; (i) a light chain variable region represented by SEQ ID NO: 311 and a heavy chain variable region represented by SEQ ID NO: 304; or (j) a light chain variable region represented by SEQ ID NO: 306 and a heavy chain variable region represented by SEQ ID NO: 302, but not limited thereto.

In one specific embodiment of the present invention, a competitive selection method was used to select an antibody with a more improved affinity than the humanized antibody, thus obtaining a number of affinity-optimized antibodies (Tables 8 to 10 and 12). The affinity-optimized antibody has a tumor cell proliferation inhibitory effect that is 4.3 to 28.5 times more excellent than the humanized body (Table 11, 13 and FIG. 3).

In the present invention, it may be provided that the antibody is an antibody or an antigen binding fragment thereof specifically further binding to an epidermal growth factor receptor (EGFR) in addition to specifically binding to c-Met.

It is known that the EGFR, one of ErbB tyrosine kinases, is abnormally activated in many epidermal cell tumors comprising non-small-cell lung carcinoma, causes cell proliferation, invasion, metastasis and angiogenesis, and increases cell survival. Gefitinib (Iressa), elotinib (Tarceva) and osimertinib (Tagrisso), which are EGFR tyrosine kinase inhibitors, are used as a representative lung cancer therapeutic agent; and cetuximab (Erbitux) and panitumumab (Vectibix), which are EGFR target antibodies, are used as a colon cancer therapeutic agent (Yewale C et al., Biomaterials. 2013 34(34):8690-707 (2013), Deric L. Wheeler et al., Nature Reviews Clinical Oncology 7, 493-507 (2010)).

Such EGFR target therapeutic agents cause resistance one year before and after treatment, wherein c-Met amplification, mutation and HGF-induced activation are known as a key mechanism of resistance (Simona Corso Cancer Discovery 3:978-992 (2013), Curtis R Chong et al., Nature Medicine 19, 1389-1400 (2013)). Also, it is reported that EGFR and c-Met are simultaneously expressed in various tumor cells, wherein, upon inhibiting EGFR, c-Met becomes activated, thus promptly developing the resistance of EGFR TKI (Engelman, J. A., et al., Science, 316:1039-43 (2007)).

Based on such mechanism, a single treatment with a c-Met target drug alone and a combined treatment with an EGFR target drug have been now in a clinical trial, but their efficacy has not been verified yet as a therapeutic agent and there is a need for developing a therapeutic agent for c-Met-related cancerous tumors, known as a key cause of resistance. Accordingly, the present inventors have prepared c-Met/EGFR bispecific antibody based on the antibody described above. The bispecific antibody not only effectively inhibits a proliferation of tumor cells, which are resistant to existing EGFR therapeutic agents, but also shows an excellent proliferation inhibitory activity against tumor cells, thus being valuably used in treatment of diseases such as c-Met-mediated cancers through various mechanisms.

It may be provided that the bispecific antibody is formed in such a way that an antibody or an antigen binding fragment thereof specifically binding to EGFR is linked to one light chain or heavy chain terminus of c-Met specific antibody, for example, being linked to a heavy chain C-terminus, but not limited thereto.

It may be provided that the binding fragment specifically binding to EGFR is Fab, Fab', F(ab')$_2$ or Fv.

In one exemplary embodiment of the present invention, it may be provided that the Fv is a scFv fragment, wherein the scFv fragment is linked by a connector capable of linking the scFv fragment to one light chain or heavy chain terminus of c-Met antibody. In one exemplary embodiment of the present invention, an antibody specifically binding to EGFR is further prepared by linking with a connector represented by SEQ ID NO: 312.

It may be provided that the EGFR scFv fragment is an EGFR scFv capable of specifically binding to EGFR, known in the art, wherein, for example, there are Erbitux, Vectibix, Portrazza, TheraCIM or the like, but not limited thereto.

In one exemplary embodiment of the present invention, it may be provided that the EGFR scFv is an Erbitux or Vectibix scFv fragment, particularly the EGFR scFv comprises an amino acid sequence represented by SEQ ID NO: 313 or SEQ ID NO: 314, wherein the Vectibix scFv comprises an amino acid sequence represented by SEQ ID NO: 315, but not limited thereto.

According to one specific embodiment of the present invention, as a result of identifying a tumor cell proliferation inhibitory activity of the bispecific antibody, it was identified that the antibody had a more excellent tumor activity inhibitory efficacy than a hu8C4 optimized antibody (Tables 16 and 17, and FIGS. 4, 5, 16 and 17). In particular, it was identified that the antibody of the present invention had an excellent cell proliferation inhibitory effect on even NCI-H292 and NCI-H1648 cell lines, in which c-Met and EGFR are normally expressed (Tables 17 and 19 and FIG. 6). Based on such results, it can be seen that an anticancer effect of the antibody of the present invention is not particularly limited by an abnormality of c-Met expression or a presence or absence of c-Met mutation, etc.

Figure 6:
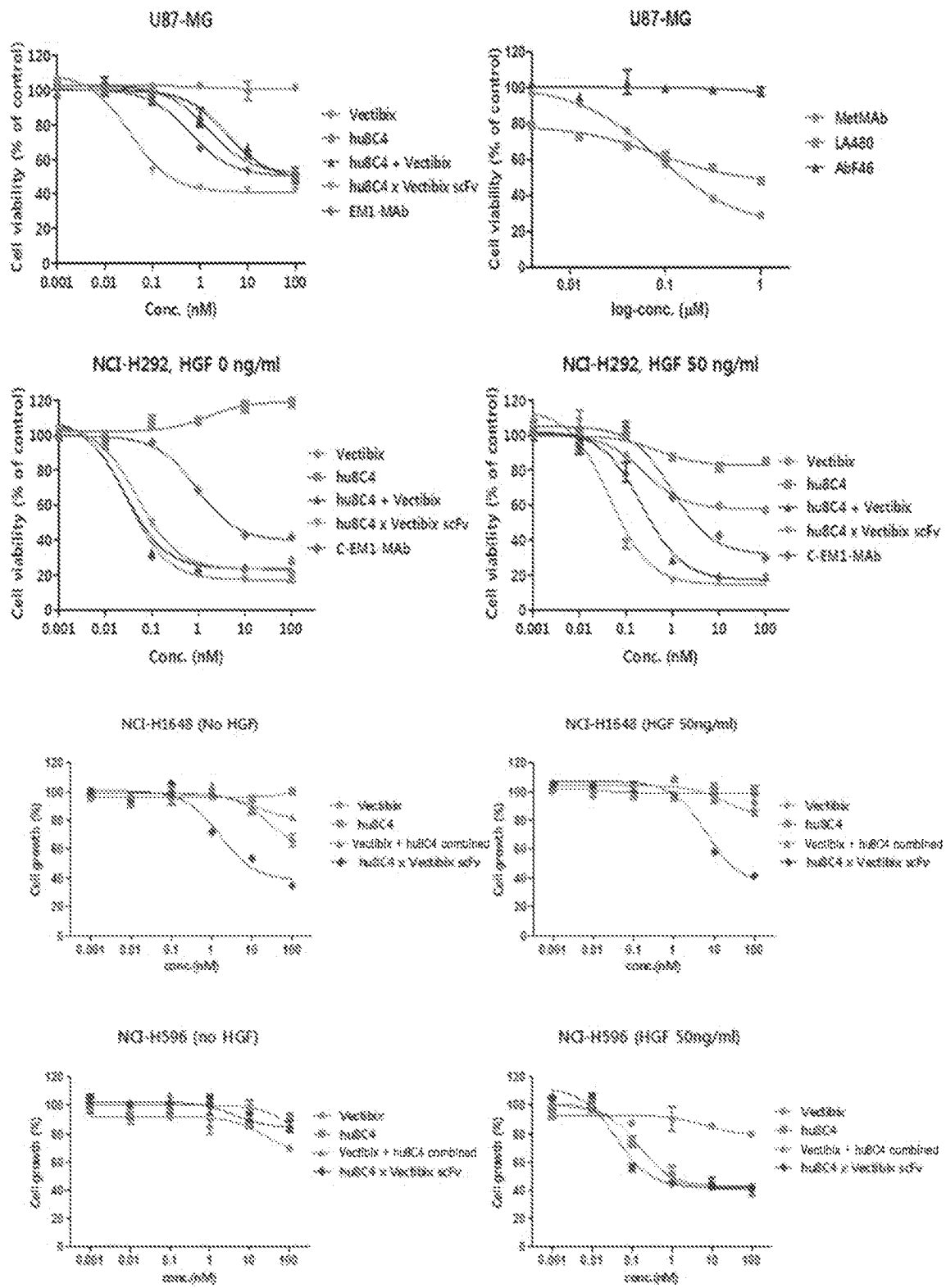
FIG. 6 shows results of comparing a tumor cell proliferation inhibitory activity between the bispecific antibody of the present invention and a combined therapy in U-87 MG (glioblatoma), NCI-H292 (NSCLC), NCI-H1648 (NSCLC) and NCI-H596 (NSCLC) cell lines.
Figure 7:
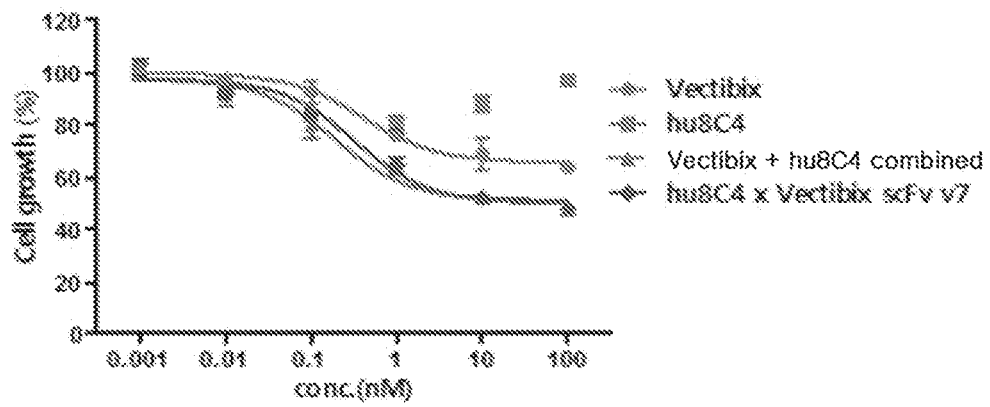
FIG. 7 shows results of comparing a tumor cell proliferation inhibitory activity between the bispecific antibody of the present invention and a combined therapy in LS174T (colon), BT20 (TNBC) and KP4 (pancreatic) cell lines.
Figure 7:
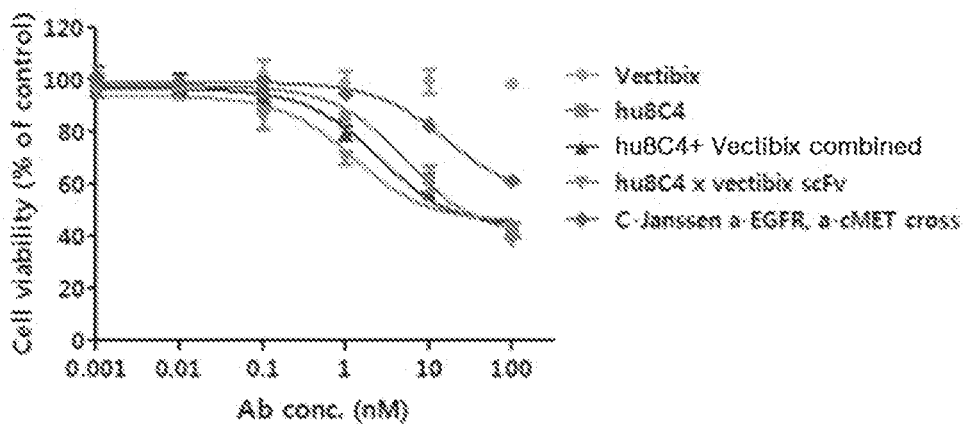
Figure 7:
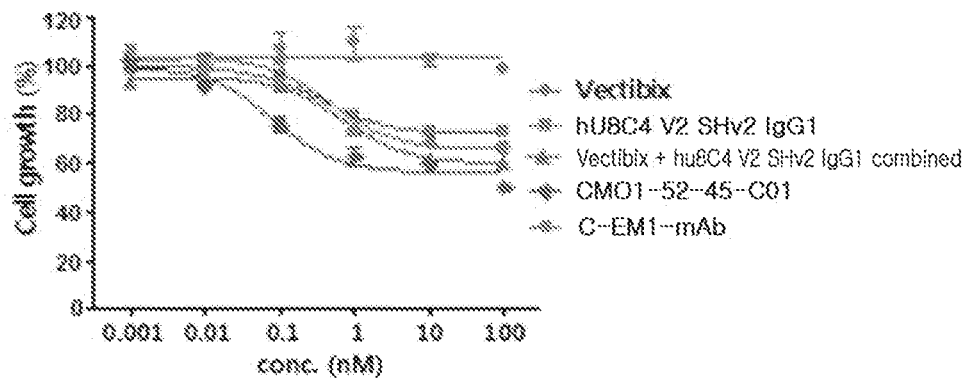
Figure 8:
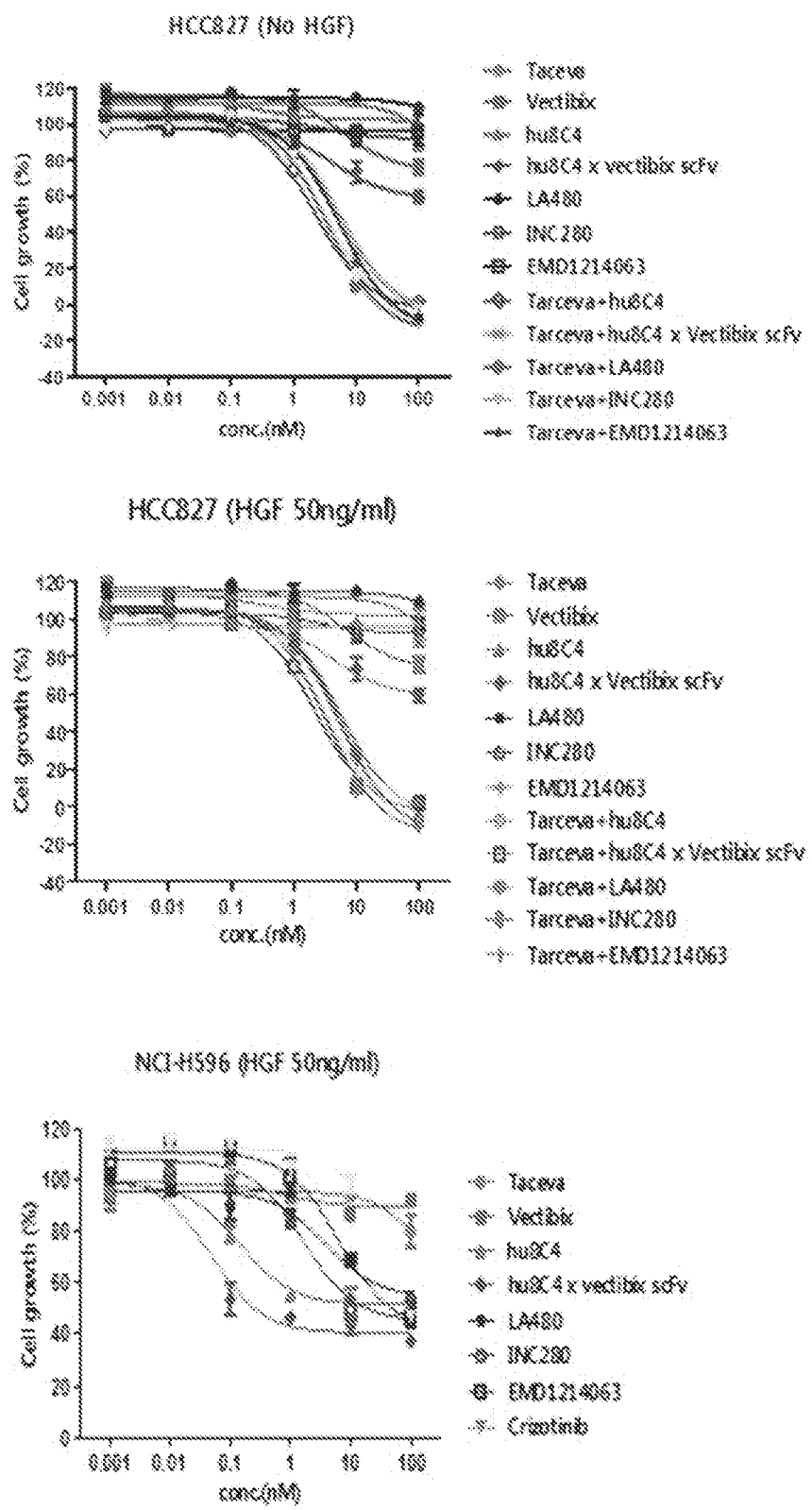
FIG. 8 shows results of comparing a tumor cell proliferation inhibitory activity between the bispecific antibody of the present invention and a combined therapy in HCC827 (NSCLC) and NCI-H596 (NSCLC) cell lines.
Figure 11:
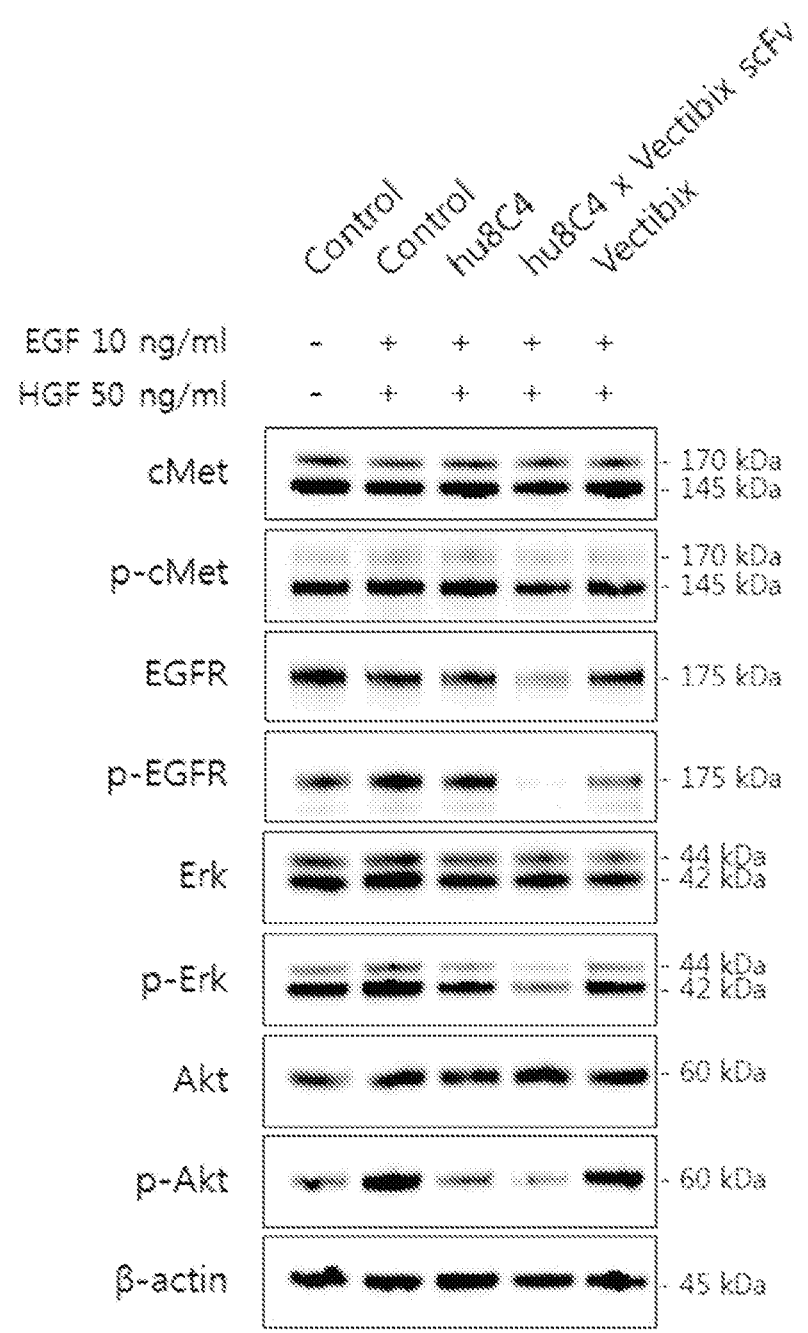
FIG. 11 shows results of measuring an inhibition of c-Met and EGFR phosphorylation by the anti-c-Met antibody and the bispecific antibody of the present invention in an NCI-H820 (NSCLC) cell line.

Furthermore, it was identified that the bispecific antibody of the present invention had a more excellent tumor cell proliferation inhibitory capacity than a combined therapy of two antibodies (Tables 18 to 21 and FIGS. 6 to 8). Also, as a result of identifying an effect of the bispecific antibody of the present invention on the activity of antigens and signal transduction materials, it was identified that the bispecific antibody of the present invention had a more excellent signal transduction inhibitory efficacy than an antibody alone (FIG. 11).

It may be provided that the antibody or the antigen binding fragment thereof of the present invention binds to an epitope region represented by an amino acid sequence selected from the group represented by SEQ ID NO: 331, SEQ ID NO: 332, SEQ ID NO: 333 and/or SEQ ID NO: 334. An affinity-optimized antibody prepared based on a certain antibody (reference antibody) is characterized by having a high homology with the light chain and heavy chain CDR sequences of a variable region with regard to the reference antibody, thus binding to the same epitope region as the reference antibody, such that such affinity-optimized antibody can share all the biological characteristics such as a pharmaceutical mechanism and a pharmaceutical efficacy caused by a binding site, specificity and antibody and exhibit a more excellent effect on binding affinity than the reference antibody.

The epitope region respectively means, for example, YVSKPGAQL (SEQ ID NO: 331) in 321th to 329th positions, IGASLNDDI (SEQ ID NO: 332) in 333th to 341th positions, PIKYVND (SEQ ID NO: 333) in 366th to 372th positions, and QVVVSRSGPST (SEQ ID NO: 334) in 464th to 474th positions from N-terminus of a reference c-Met antigen (SEQ ID NO: 335), wherein c-Met antigen sequence with the antibody or the antigen binding fragment thereof of the present invention binding thereto comprises a partial mutation (substitution, addition or deletion) or a binding antigen exists in a form of a c-Met fragment, precursor or subtype, thus its binding sites or sequences may somewhat vary accordingly. Nevertheless, a person of ordinary skill in the art may clearly specify a position and a sequence, to which the antigen or the antigen binding fragment thereof of the present invention binds based on an epitope sequence information of a reference c-Met antigen.

In one specific embodiment of the present invention, it was identified that the bispecific antibody hu8C4×Vectibix scFv of the present invention binds to 4 epitope regions of Y321-L329 (SEQ ID NO: 331), I333-I341 (SEQ ID NO: 332), P366-D372 (SEQ ID NO: 333), and Q464-S474 (SEQ ID NO: 334) of a human c-Met sema domain β chain (Table 28).

The "antibody or antigen binding fragment thereof specifically binding to c-Met" of the present invention means the one binding to a human c-Met by $K_D$ $1\times10^{-7}$ M or less. It may be provided that the antibody or the antigen binding fragment thereof binds to human c-Met, for example, by $K_D$ $5\times10^{-8}$ M or less, $K_D$ $1\times10^{-8}$ M or less, $K_D$ $5\times10^{-9}$ M or less, or $K_D$ $1\times10^{-9}$ M or less, but not limited thereto.

Figure 9:
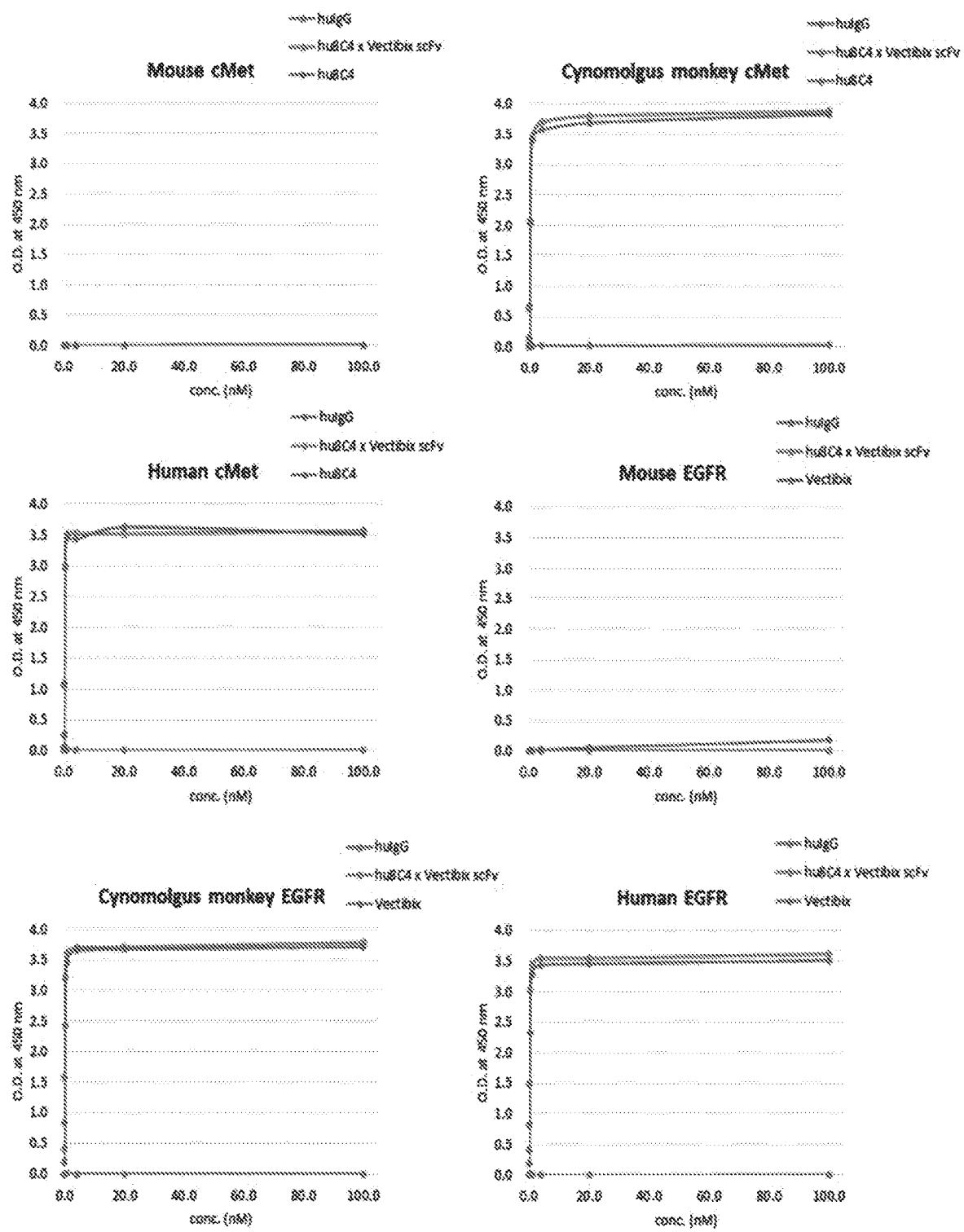
FIG. 9 shows results of measuring a binding capacity of the anti-c-Met antibody and the bispecific antibody of the present invention with regard to various kinds of c-Met and EGFR antigens by an ELISA method.

In one specific embodiment of the present invention, it was directly identified that the antibody or the antigen binding fragments thereof of the present invention had a high binding affinity to c-Met antigen by identifying a binding affinity of hu8C4, hu8C4 AH71 and hu8C4× Vectibix scFv to c-Met ECD, thus identifying $K_D$ values of $3.173\times10^{-10}$, $9.993\times10^{-11}$ and $2.78\times10^{-10}$, respectively (Table 22). It was identified that the antibody or the antigen binding fragment thereof of the present invention had a cross-reactivity to a c-Met antigen of a cynomolgus monkey, which is an ape (Table 22), but did not bind to other animal-derived antigens (e.g., rodents) (FIG. 9). Also, it was identified that the antibody or the antigen binding fragment thereof of the present invention did not bind to other receptors on the surface of cells than c-Met (Table 24). Thus, it can be seen from the results above that the antibody or the antigen binding fragment thereof of the present invention showed a binding specificity to c-Met antigen of humans and monkeys.

As used herein, the term "binding constant ($K_{on}$)" means a binding ratio of a certain antibody-antigen interaction, and the term "dissociation constant ($K_{off}$)" means a dissociation ratio of a certain antibody-antigen interaction. Also, in the present invention, the term "affinity to antigen ($K_D$)" is the one that a ratio of $K_{off}$:$K_{on}$ (i.e., $K_{off}/K_{on}$) is indicated as a molar concentration (M). It may be provided that a $K_D$ value for an antibody is measured by using a method widely established in the art. For example, as a method for measuring a $K_D$ value of an antibody, it may be provided by a surface plasmon resonance analysis using a Biocore™ system, but not limited thereto.

Another aspect of the present invention provides a method for producing a nucleic acid molecule for coding the antibody or the antigen binding fragment thereof, an expression vector comprising the nucleic acid molecule, a host cell having the expression vector introduced therein, an antibody using the host cell or an antigen binding fragment thereof.

The antibody and the antigen binding fragment thereof are such as that described above.

As used herein, the term "nucleic acid molecule" has a meaning that comprehensively comprises DNA and RNA molecules, wherein a nucleotide, a basic constituent unit in the nucleic acid molecule, comprises not only a natural nucleotide, but also an analogue, in which a sugar or base portion is modified (Scheit, Nucleotide Analogs, John Wiley, New York (1980); Uhlman and Peyman, Chemical Reviews, (1990) 90:543-584). A sequence of a nucleic acid molecule for coding the heavy chain and light chain variable regions of the present invention may be modified, wherein the modification comprises an addition, deletion, or non-conservative or conservative substitution of nucleotide.

It is understood that the nucleic acid molecule of the present invention also comprises a nucleotide sequence representing a substantial identity with the aforementioned nucleotide sequence. In the present invention, in case of aligning the aforementioned nucleotide sequence of the present invention with any other sequences in the most corresponding way and analyzing the aligned sequences by an algorithm conventionally used in the art, the substantial identity means a nucleotide sequence that represents a minimal 80% homology, particularly a minimal 90% homology, more particularly a minimal 95% homology.

As used herein, the term "vector," which is a means for expressing a target gene in a host cell, comprises a plasmid vector; a cosmid vector; and virus vector such as a bacteriophage vector, an adenovirus vector, a retrovirus vector and an adeno-related virus, particularly a plasmid vector, but not limited thereto.

In the vector of the present invention, it may be provided that a nucleic acid molecule for coding a light chain variable region and a nucleic acid molecule for coding a heavy chain variable region are operatively linked with a promoter.

In the present invention, the term "operatively linked" means a functional binding between a nucleic acid expression regulatory sequence (e.g., a promoter, a signal sequence, or an array in a transcriptional regulatory factor binding site) and other nucleic acid sequence, thus the regulatory sequence controls a transcription and/or decoding of the other nucleic acid sequence.

The recombinant vector system of the present invention may be built through various methods known in the art. For example, such detailed methods are disclosed in Sambrook et al., Molecular Cloning, A Laboratory Manual, Cold Spring Harbor Laboratory Press (2001), the documents of which are hereby incorporated by reference.

The vector of the present invention may be typically built as a vector for cloning or a vector for expression. Also, the vector of the present invention may be built in such a way that a prokaryotic cell or an eukaryotic cell is a host.

For example, if the vector of the present invention is an expression vector and the prokaryotic cell is a host, it is general to comprise powerful promotors capable of carrying out transcription (e.g., tac promotor, lac promotor, lacUV5 promotor, lpp promotor, pLλ promotor, pRλ promotor, rac5 promotor, amp promotor, recA promotor, SP6 promotor, trp promotor, T7 promotor and the like), a ribosome binding site for starting decoding and transcription/decoding termination sequence. If *E. coli* (e.g., HB101, BL21, DH5α, etc.) is used as a host cell, promotor and operator portions of *E. coli* tryptophan biosynthetic pathway (Yanofsky, C., J. Bacteriol., (1984) 158:1018-1024), and a leftward promotor of phage λ (pLλ promotor, Herskowitz, I. and Hagen, D., Ann. Rev. Genet., (1980) 14:399-445) may be used as a regulatory portion. If *Bacillus* sp. is used as a host cell, a promotor of toxin protein gene of *Bacillus thuringiensis* (Appl. Environ. Microbiol. (1998) 64:3932-3938; Mol. Gen. Genet. (1996) 250:734-741) or any promotors expressible in *Bacillus* sp. may be used as a regulatory portion.

Meanwhile, the recombinant vector of the present invention may be prepared by manipulating plasmid (e.g., pCL, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19 and the like), phage (e.g., λgt4·λB, λ-Charon, λΔz1, M13 and the like) or virus (e.g., SV40, etc.) often used in the art.

Meanwhile, if the vector of the present invention is an expression vector and an eukaryotic cell is a host, promotors derived from a genome of mammal cells (e.g., metallothionein promotor, β-actin promotor, human hemoglobin promotor and human muscle creatin promotor) or promotors derived from mammal virus (e.g., adenoviral late promotor, vaccinia virus 7.5K promotor, SV40 promotor, cytomegalovirus (CMV) promotor, tk promotor of HSV, mouse breast tumor virus (MMTV) promotor, LTR promotor of HIV, promotor of Moloney virus, promotor of Epstein-barr virus (EBV) and promotor of Rous sarcoma virus (RSV)) may be used, wherein they generally have a polyadenylation sequence as a transcription termination sequence. Particularly, the recombinant vector of the present invention comprises a CMV promotor.

The recombinant vector of the present invention may be fused with other sequences in order to facilitate refining of an antibody expressed therefrom. As examples of fused sequences, there are glutathione S-transferase (Pharmacia, USA), maltose binding protein (NEB, USA), FLAG (IBI, USA), 6×His (hexahistidine; Quiagen, USA) and the like. Also, a protein expressed by the vector of the present invention is an antibody, thus the expressed antibody may be easily purified through a protein A column, etc., without an additional sequence for refining.

Meanwhile, the recombinant vector of the present invention comprises an antibiotic resistance gene conventionally used in the art as a selected marker, wherein it may comprise, for example, resistance genes to ampicillin, gentamicin, carbenicillin, chloramphenicol, streptomycin, kanamycin, geneticin, neomycin and tetracycline.

As a vector for expressing the antibody of the present invention, there may be both a vector system, in which a light chain and a heavy chain are simultaneously expressed in one vector, and a system, in which a light chain and a heavy chain are respectively expressed in a separate vector. In the latter case, two vectors may be introduced into a host cell, for example, through co-transformation or targeted transformation. The co-transformation is a method for selecting cells that express both light and heavy chains after simultaneously introducing each vector DNA for coding light and heavy chains into a host cell. The targeted transformation is a method for selecting a cell transformed with a vector comprising a light (or heavy) chain and transforming a selected cell again with a vector comprising a heavy (or light) chain to finally select a cell that expresses both light and heavy chains.

As long as they are capable of stably and continuously cloning and expressing the vector of the present invention, any host cells known in the art may be used, wherein such host cells may comprise *Bacillus* sp. strains such as *Escherichia coli*, *Bacillus subtilis* and *Bacillus thuringiensis* and prokaryotic host cells such as *Streptomyces*, *Pseudomonas* (e.g., *Pseudomonas putida*), *Proteus mirabilis* or *Staphylococcus* (e.g., *Staphylococcus carnosus*), but not limited thereto.

As suitable eukaryotic host cells of the vector, there may be mycetes such as Aspergillus species, yeasts such as *Pichia pastoris, Saccharomyces cerevisiae, Schizosaccharomyces* and *Neurospora crassa*, other lower eukaryotic cells, cells of higher eukaryotes such as insect-derived cells, and cells derived from plants or mammals.

Particularly, host cells may be COST cells (monkey kidney cells), NSO cells, SP2/0, Chinese hamster ovary (CHO) cells, W138, baby hamster kidney (BHK) cells, MDCK, myeloma cell lines, HuT 78 cells or 293 cells, more particularly CHO cells, but not limited thereto.

In the present invention, "transformation" and/or "transfection" into host cells may be performed by selecting a suitable standard technology according to host cells as known in the art, comprising any methods for introducing nucleic acid into organisms, cells, tissues or organs. The methods comprise electroporation, plasmogamy, calcium phosphate ($CaPO_4$) precipitation, calcium chloride ($CaCl_2$)) precipitation, agitation using silicon carbide fiber, agrobacteria-mediated transformation, PEG, dextran sulfate, lipofectamine, drying/suppression-mediated transformation and the like, but not limited thereto.

In the present invention, the method for producing an antibody or an antigen binding fragment thereof using a host cell may particularly comprise steps of: (a) culturing a host cell transformed with a recombinant vector of the present invention; and (b) expressing an anti-c-Met antibody or an antigen binding fragment thereof in the host cell.

In preparing the antibody above, culturing of a transformed host cell may be performed in an appropriate medium and under culturing conditions known in the art. Such culturing process may be easily adjusted according to a selected strain by those skilled in the art. Such culturing method is disclosed in various documents (e.g., James M. Lee, Biochemical Engineering, Prentice-Hall International Editions, 138-176). Cell culture is divided into suspension culture and attachment culture according to a cell growth type, and batch culture, fed-batch culture and continuous culture according to a culture method. A medium used in culture has to appropriately satisfy requirements of a certain strain.

In culturing of animal cells, the medium comprises various carbon sources, nitrogen sources and microelement ingredients. Examples of usable carbon sources may comprise carbohydrates such as glucose, sucrose, lactose, fructose, maltose, starch and cellulose; fats such as soybean oil, sunflower oil, castor oil and coconut oil; fat acids such as palmitic acid, stearic acid and linoleic acid; alcohols such as glycerol and ethanol; and organic acids such as acetic acid, wherein such carbon sources may be used alone or in combination.

Nitrogen sources, which may be used in the present invention, may comprise, for example, organic nitrogen sources such as peptone, yeast extract, meat juice, malt extract, corn steep liquor (CSL) and soybean-wheat, and inorganic nitrogen sources such as urea, ammonium sulfate, ammonium chloride, ammonium phosphate, ammonium carbonate and ammonium nitrate, wherein such nitrogen sources may be used alone or in combination. As a phosphorus source, the medium may comprise potassium dihydrogen phosphate, dipotassium hydrogen phosphate and sodium-containing salt corresponding thereto. Also, the medium may comprise metallic salts such as magnesium sulphate or iron sulfate. Besides, the medium may comprise amino acids, vitamins, appropriate precursors and the like.

During culture, compounds such as ammonium hydroxide, potassium hydroxide, ammonia, phosphoric acid and sulfuric acid are added to a culture product in an appropriate way to adjust a pH of the culture product. Also, during culture, bubble formation may be suppressed by using a defoaming agent such as fatty acid polyglycol ester. Also, oxygen or oxygen-containing gas (e.g., air) is injected into a culture product in order to maintain an aerobic state of the culture product. A temperature of the culture product is normally 20° C. to 45° C., preferably 25° C. to 40° C.

The production method may further comprise a step of: (c) collecting an anti-c-Met antibody or an antigen binding fragment thereof expressed in the host cell. An antibody obtained by culturing the transformed host cell may be used in a non-purified state, or further used in a purified state with high purity by using various conventional methods, for example, dialysis, salt precipitation, chromatography and the like. Out of those methods, a method for using chromatography is most often used, wherein a type and order of column may be selected from ion-exchange chromatography, size exclusion chromatography, affinity chromatography, etc., according to antibody characteristics, culture method, etc.

Another aspect of the present invention provides a composition for detecting c-Met, comprising the antibody or the antigen binding fragment thereof, a kit for detection comprising the same, and a method for detecting c-Met antibody using the same.

The composition for detecting c-Met and the kit comprising the same form an antigen-antibody complex in such a way that an antibody specifically binding to c-Met or an antigen binding fragment thereof comes into contact with a specimen sample, thus effectively detecting c-Met.

As used herein, the term "antigen-antibody complex" means a conjugate between c-Met and an antibody for recognizing the same, in order to identify a tumor or a cancer cell of expressing c-Met in a sample.

A method for quantifying c-Met antigen using a composition for detecting c-Met and using a kit comprising the same may be performed by identifying a formation of an antigen-antibody complex, wherein identifying of the formation of an antigen-antibody complex may be performed by enzyme immunoassay (ELISA), western blotting, immunofluorescence, immunohistochemistry staining, flow cytometry, immunocytochemistry, radioimmunoassay (RIA), immunoprecipitation assay, immunodiffusion assay, complement fixation assay, a protein chip, etc., but not limited thereto. The ELISA comprises various ELISA methods such as a direct ELISA using a labeled antibody for recognizing an antigen attached to a solid support; an indirect ELISA using a labeled secondary antibody for recognizing a capture antibody in a complex of an antibody for recognizing an antigen attached to a solid support; a direct sandwich ELISA using another labeled antibody for recognizing an antigen in a complex of an antibody and an antigen attached to a solid support; an indirect sandwich ELISA using a labeled secondary antibody for reacting with another antibody for recognizing an antigen in a complex of an antibody and an antigen attached to a solid support and then recognizing such antibody, etc.

As a label for qualitatively or quantitatively making a formation of an antigen-antibody complex measurable, there are an enzyme, a fluorescent material, a ligand, a luminous material, a microparticle, a redox molecule, radio isotope and the like, but not necessarily limited thereto. As the enzymes, there are β-glucuronidase, β-D-glucosidase, β-D-galactosidase, urease, peroxidase, alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphoenolpyruvate decarboxylase, β-lactamase, etc., but not limited thereto.

Another aspect of the present invention provides a composition for preventing or treating cancer comprising the antibody or the antigen binding fragment thereof of the present invention.

Yet another aspect of the present invention provides a method for preventing or treating cancer, comprising a step of administering a composition comprising the antibody or the antigen binding fragment thereof of the present invention to an individual being in danger of developing cancer or having the same.

Still yet another aspect of the present invention provides a use of cancer treatment and a use of preparing an anticancer drug, with regard to a composition comprising the antibody or the antigen binding fragment thereof of the present invention.

The antibody and the antigen binding fragment thereof are such as that described above.

The antibody or the antigen binding fragment thereof of the present invention is capable of binding to c-Met alone or a combination of c-Met and EGFR with high affinity to inhibit a growth of cancer cells, such that the antibody alone or in combination with conventional pharmaceutically acceptable carriers can be used in treatment, prevention and diagnosis of hyperproliferative diseases such as cancer.

In the present invention, the term "prevention" means all the acts, which prevent or delay diseases such as cancer, etc., from occurrence or recurrence by an administration of the composition of the present invention, and the term "treatment" means an inhibition of development of diseases such as cancer, reduction of cancer, or removal of cancer.

It may be provided that cancer, a disease applied to the composition of the present invention, is particularly lung cancer, stomach cancer, colon cancer, rectal cancer, triple negative breast cancer (TNBC), glioblastoma, pancreatic cancer, head and neck cancer, breast cancer, ovarian cancer, renal cancer, bladder cancer, prostate cancer, solenoma, salivary gland tumor or thyroid cancer, more particularly lung cancer, stomach cancer, colon cancer, rectal cancer, triple negative breast cancer (TNBC), glioblastoma, pancreatic cancer, head and neck cancer, breast cancer, and much more particularly lung cancer, stomach cancer, colon cancer, rectal cancer, triple negative breast cancer (TNBC), glioblastoma, pancreatic cancer, head and neck cancer, but not limited thereto. In the present invention, it may be provided that cancer is the one caused by, in particular, c-Met overexpression, amplification, mutation or activation, but not limited thereto. In other words, a composition comprising the antibody or the binding fragment thereof of the present invention has an inhibitory effect on proliferation of all the cancerous tumors irrespective of abnormal expression or mutation of c-Met, such that a pharmaceutical use of the present invention is not limited by an expression aspect or presence or absence of mutation of c-Met.

The composition may be a form of a pharmaceutical composition, a quasi-drug composition and a composition for health food.

The composition of the present invention for preventing or treating cancer may further comprise a pharmaceutically acceptable carrier. The pharmaceutically acceptable carrier is the one conventionally used in preparing a formulation, comprising lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, mineral oil and the like, but not limited thereto. Besides the ingredients, the composition of the present invention for preventing or treating cancer may further comprise lubricant, humectant, sweetening agent, flavoring agent, emulsifier, suspending agent, preservative, etc. Suitable pharmaceutically acceptable carriers and preparations are described in detail in Remington's Pharmaceutical Sciences (19th ed., 1995).

The composition of the present invention may be administered orally or parenterally wherein a parenteral administration may be performed by intravenous infusion, subcutaneous infusion, intramuscular injection, intraperitoneal injection, endothelial administration, local administration, intranasal administration, intrapulmonary administration, rectal administration and the like. During an oral administration, protein or peptide is digested, so an oral composition may be formulated in such a way that its active drug is coated or protected from decomposition in stomach. A composition of the present invention may be administered by a predetermined device through which an active substance may be moved into a target cell.

A suitable dosage of the composition of the present invention for preventing or treating cancer varies depending on such factors as a formulation method, an administration type, a patient' age, weight, gender, morbid condition, food, administration time, administration path, excretion speed and response sensitivity, wherein an ordinary skilled doctor may easily determine and prescribe an effective dose for a desired treatment or prevention. According to one exemplary embodiment of the present invention, a daily dose of the pharmaceutical composition of the present invention may amount to 0.001-100 mg/kg or more. In the present specifications, the term "pharmaceutical effective dose" means an amount enough to treat, prevent and diagnose diseases such as cancer.

The composition of the present invention for preventing or treating cancer may be formulated into a preparation by using pharmaceutically acceptable carriers and/or expedients according to a method, which may be easily performed by those skilled in the art, to which the present invention pertains, such that such composition can be prepared in a mono-dose form or prepared by being inserted into a multi-dose container. At this time, a dosage form may be in a form of solution in oil or aqueous medium, suspension or emulsion, or in a form of extract, powder, suppository, powdered drug, granule, tablet or capsule, and may further comprise a dispersing agent or a stabilizer.

The composition of the present invention may be administered as an individual therapeutic agent or administered in combination with other therapeutic agents, and may be administered sequentially or simultaneously with conventional therapeutic agents.

The antibody or the antigen binding fragment thereof of the present invention may be used in treatment of cancer in such a way that it is injected in vivo in a form of an antibody-therapeutic agent (functional molecule) and a bispecific antibody-therapeutic agent (functional molecule) conjugate, which are such as that described above. Appropriate and desirable various conditions for targeting a drug to a specific target site are reported in documents, for example, Trouet et al., Plenum Press, New York and London, (1982) 19-30.

Figure 12:
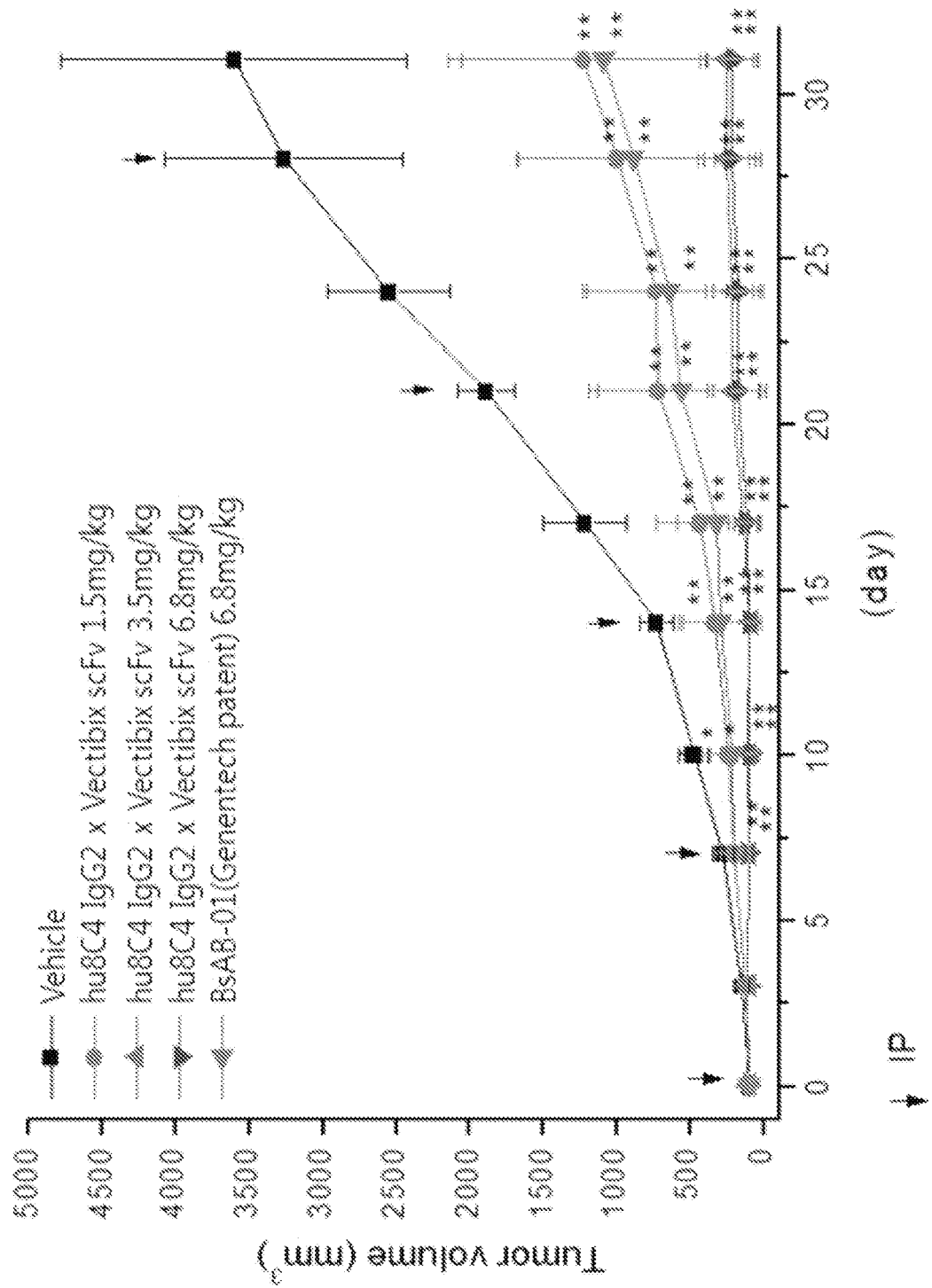
FIG. 12 shows results of measuring an anticancer effect of the bispecific antibody of the present invention in a U-87 MG (glioblastoma) cell xenograft model.
Figure 13:
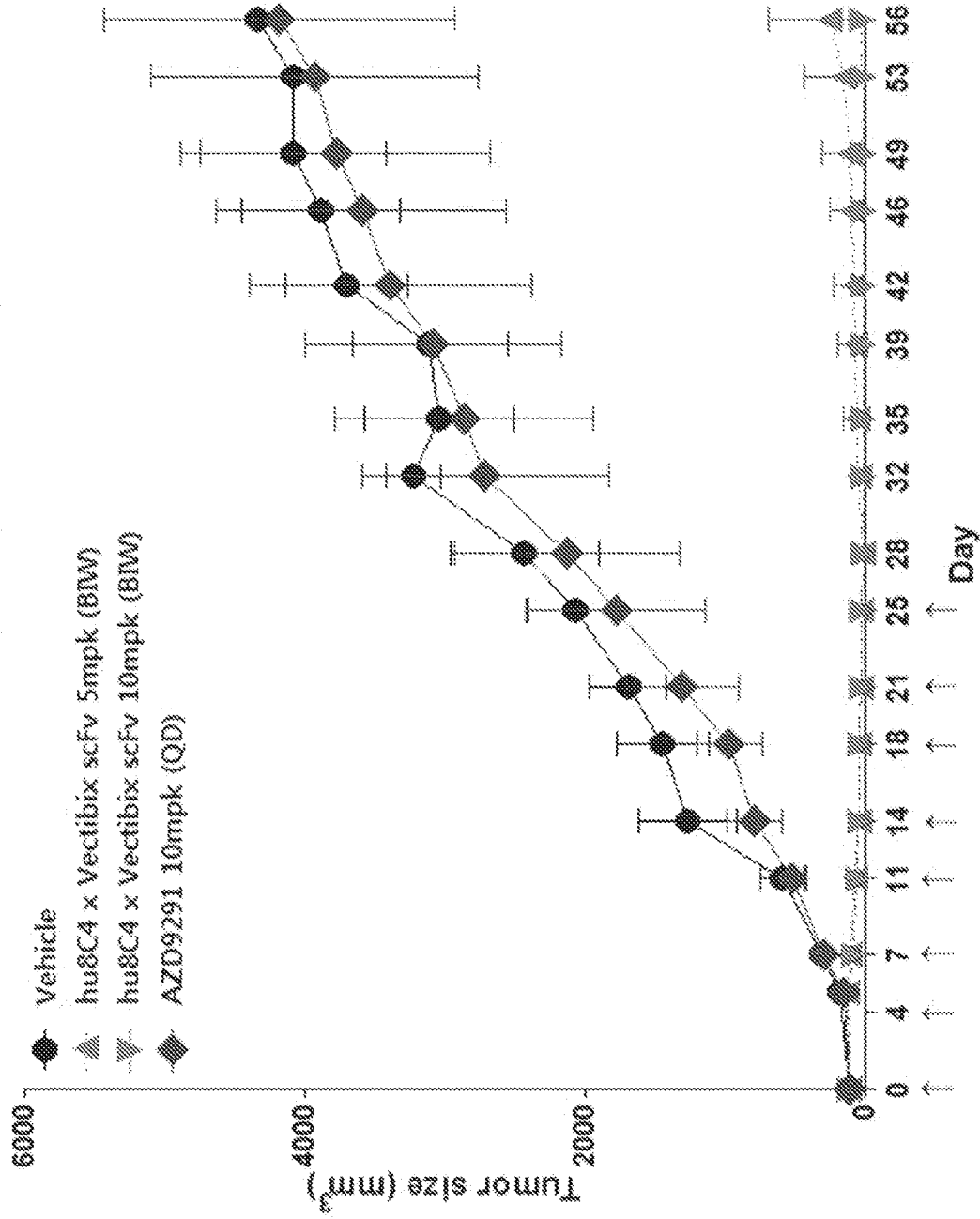
FIG. 13 shows results of measuring an anticancer effect of the bispecific antibody of the present invention in an NCI-H820 (NSCLC) cell xenograft model.

According to one specific embodiment of the present invention, as a result of identifying an antitumor activity of the composition of the present invention for preventing or treating cancer in a xenograft mouse model, it was identified that its tumor activity inhibitory efficacy was remarkably excellent compared to the control group (FIGS. 12 and 13).

c-Met, targeted by an antibody or an antigen binding fragment thereof included in the composition of the present invention is a molecule expressed on the surface of cancer cells, thus it may be used in the prevention, treatment and diagnosis of c-Met related cancer in such a way that a functional molecule further is bound to the antibody of the present invention or is administered in combination therewith. The functional molecule may comprise a chemical substance, radioactive nuclide, immunotherapeutic agent, cytokine, chemokine, toxin, biotic agent, enzyme inhibitor and the like.

The functional molecule capable of coupling with the antibody or the fragment thereof of the present invention results in antibody drug-conjugates (ADC) may be a chemical substance, cytokine or chemokine, but not limited thereto. The chemical substance may be, for example, an anticancer drug, particularly, acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacytidine, azathioprine, *bacillus* calmette-guerin (BCG), Baker's antifol, beta-2-dioxythioguanosine, bisantrene HCl, bleomycin sulfate, bulsufan, buthionine sulfoximine, BWA773U82, BW502U83/HCl, BW 7U85 mesylate, ceracemide, carbetimer, carboplatin, carmustine, chlorambucil, chloroquinoxalin-sulfonamide, chlorozotocin, chromomycin A3, cisplatin, cladribine, corticosteroid, *Corynebacterium parvum*, CPT-11, crisnatol, cyclocytidine, cyclophosphamide, cytarabine, cytembena, dabis maleate, decarbazine, dactinomycin, daunorubicin HCl, deazauridine, dexrazoxane, dianhydro galactitol, diaziquone, dibromodulcitol, didemnin B, diethyldithio carbamate, diglycoaldehyde, dihydro-5-azacytidine, doxorubicin, echinomycin, dedatrexate, edelfosine, eflornithine, Elliot's solution, elsamitrucin, epirubicin, esorubicin, estramustine phosphate, estrogen, etanidazole, ethiophos, etoposide, fadrazole, fazarabine, fenretinide, filgrastim, finasteride, flavone acetic acid, floxuridine, fludarabine phosphate, 5'-fluorouracil, Fluosol™, flutamide, gallium nitrate, gemcitabine, goserelin acetate, hepsulfam, hexamethylene bisacetamide, homoharringtonine, hydrazine sulfate, 4-hydroxyandrostenedione, hydroxyurea, idarubicin HCl, ifosfamide, 4-ipomeanole, iproplatin, isotretinoin, leucovorin calcium, leuprolide acetate, levamisol, liposomal daunorubicin, liposome trapping doxorubicin, lomustine, lonidamine, maytansine, mechlorethamine hydrochloride, melphalan, menogaril, merbarone, 6-mercaptopurine, mesna, methanol extract of *bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxorere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor (TNF), uracil mustard, vinblastin sulfate, vincristine sulfate, vindesine, vinorelbine, vinzolidine, Yoshi 864, zorubicin, cytosine arabinoside, etoposide, melphalan, taxotere, taxol and mixtures thereof, but not limited thereto.

MODE FOR THE INVENTION

Hereinafter, the present invention will be described in more detail through Examples. The following Examples are provided only for the purpose of illustrating the present invention in more detail. Thus, according to the purpose of the present invention, it is apparent to those skilled in the art that the Examples are not construed to limit the scope of the present invention.

Example 1. Preparation of Hybridoma Cell for Producing c-Met Specific Antibody and Identification of Tumor Cell Proliferation Inhibitory Activity Thereof (1) Preparation and Selection of Hybridoma Cell Line for Producing Monoclonal Antibody to c-Met Protein A human c-Met Sema domain/Fc fusion protein (self-produced) was intraperitoneally injected as an antigen into a mouse, in order to obtain an immunized mouse needed for developing a hybridoma cell line through animal immunization. Screening was performed through an ELISA analysis method using a human c-Met/His fusion protein as an antigen, in order to select a hybridoma cell specifically responding to c-Met protein only out of a hybridoma cell group.

(2) c-Met Antibody

Light chain and heavy chain CDR amino acid sequences of a mouse antibody obtained from a selected hybridoma cell line are shown in Tables 1 and 2 respectively.

TABLE 1

Hybridoina light chain CDR

| Antibody | CDR 1 | SEQ ID NOs | CDR 2 | SEQ ID NOs | CDR 3 | SEQ ID NOs |
| --- | --- | --- | --- | --- | --- | --- |
| 8C4 | GASENIYGALN | 1 | GATNLAD | 2 | QNVLSSPYT | 3 |
| 5G3 | SATSSVRYMY | 4 | DTSNLAS | 5 | QQWSSYPRT | 6 |

TABLE 2

Hybridoma heavy chain CDR

| Antibody | CDR 1 | SEQ ID NOs | CDR 2 | SEQ ID NOs | CDR 3 | SEQ ID NOs |
| --- | --- | --- | --- | --- | --- | --- |
| 8C4 | DYYIN | 7 | EIFPGSGNTHFSARFKG | 8 | GDYGFLY | 9 |
| 5G3 | DYTLH | 10 | YINPYSGYTNYNQKFKD | 11 | GHMDY | 12 |

(3) In Vitro Tumor Cell Proliferation Inhibitory Activity of Hybridoma C-Met Antibody With regard to a c-Met specific mouse antibody obtained from a hybridoma cell line as well as a chimera antibody prepared by fusing the antibody with human heavy chain and light chain constant regions, a tumor cell proliferation inhibitory activity was tested in a human glioblastoma cell line U-87 MG and a human stomach cancer cell line MKN45.

Particularly, the U-87 MG cells (ATCC, # HTB14) were diluted in a culture medium EMEM (ATCC, #30-2003) containing 10% (v/v) FBS, 100 U/500 ml penicillin and 100 μg/500 ml streptomycin (Invitrogen, #15140-122), after which resulting cells were added by 100 μl into each well of a 96-well plate at a concentration of $2.5 \times 10^3$ cells, such that the plate was cultured under 37° C., 95% RH and 5% (v/v) $CO_2$ conditions for 18-24 hours. The cell culture medium was removed from each well, after which an EMEM medium containing 2% (v/v) FBS was added by 100 μl into each well, and an antibody prepared at 2× of a final concentration (100 nM) was continuously diluted at a ratio of 1/10, such that resulting cells were added by 100 μl into each well at six concentrations (i.e., 200 nM, 20 nM, 2 nM, 200 pM, 20 pM and 2 pM) for each antibody. Then, the plate was cultured for 5 days under 37° C., 95% RH and 5% (v/v) $CO_2$ conditions, after which resulting cells were fixed with 10% TCA (Trichloroacetic acid; Sigma, # T0699) solution on a final day. The resulting fixed cells were dyed for 25 minutes in such a way that 80 μl of 0.4% SRB (sulforhodamine B) solution was added into each well, after which resulting cells were washed 5 times with 1% acetic acid solution. Then, 150 μl of 10 mM Tris solution was inserted into each well of a dried plate to dissolve SRB dye, after which its optical density was measured at a wavelength of 540 nm by using a microplate reader.

Also, MKN45 (# JCRB0254) cell lines were diluted in an RPMI-1640 medium (Gibco, # A10491) containing 10% (v/v) FBS, after which the resulting cell lines were divided by $2.5 \times 10^3$ into each well of a 96-well plate, such that the resulting plate was cultured overnight under 37° C., 5% $CO_2$ conditions. Then, the medium of each well of the plate was replaced with 100 μl of an RPMI-1640 medium containing 1% (v/v) FBS, after which a test antibody was sequentially diluted at a ratio of 1/10 (i.e., 100 nM, 10 nM, 1 nM, 100 pM, 10 pM and 1 pM) to reach 1 pM at a final concentration of 100 nM, such that the resulting antibody was added by 100 μl into each well. Then, the plate was cultured for 5 days under 37° C., 5% $CO_2$ conditions, after which the medium was removed therefrom, such that a TCA solution was inserted by 200 μl into each well to fix cells. As shown in the test on the U87 MG cell, the cells of the plate were dyed according to a conventional SRB colorimetric assay method, after which an optical density of each well was measured at a wavelength of 540 nm by using a microplate reader. Results of the U87 MG and MKN45 cell lines are shown in Table 3 and FIG. 1.

TABLE 3

Results of in vitro test on tumor cell proliferation inhibitory activity of hybridoma c-Met antibody

|  | U-87 MG (GBM, HGF autocrine) $IC_{50}$ (nM) | MKN45 (Gastric cancer, c-Met amplified) $IC_{50}$ (nM) |
|---|---|---|
| LY2875358 (Eli Lilly) | >100 | 0.34 |
| OA-5D5 (Genentech) | >100 | >100 |
| hybridoma 8C4 | 17.5 | 9.78 |
| hybridoma 5G3 | >100 | 0.32 |
| 8C4 chimera IgG1 | 32.4 | >100 |
| 8C4 chimera IgG2 | >100 | 12.92 |
| 5G3 chimera IgG2 | >100 | 0.41 |

As seen in Table 3 and FIG. 1 above, the anti-c-Met 8C4, 5G3 antibodies and chimera antibodies thereof of the present invention all have a tumor cell proliferation inhibitory activity, which is equal to or more excellent than the known c-Met antibodies LY2875358 and OA-5D5 (control group). Thus, the 8C4, 5G3 antibodies and mutants thereof such as chimera antibodies, humanized antibodies and affinity-optimized antibodies to antigen of the present invention may be very valuably used in preventing or treating c-Met related cancer.

Specific consensus sequences for light chain and heavy chain variable regions of the 8C4, 5G3 antibodies of the present invention are shown in the following Table 4.

TABLE 4

Consensus SEQ ID NOs for light chain and heavy chain variable regions of 8C4, 5G3 antibodies

|  | Consensus amino acids sequence | | Consensus nucleotides sequence | |
|---|---|---|---|---|
|  | light chain | heavy chain | light chain | heavy chain |
| 8C4 | DILMTQSPASLSASVGE TVTITCGASENIYGALN WYQRKQGKSPQLLIYGA TNLADGMSSRFSGSGSG RQFSLKITSLHPDDVAT YYCQNVLSSPYTFGGGT KEIK (SEQ ID NO: 13) | EVQLQQSGAELARPGAS VKLSCKASGYTFSDYYI NWVKQGTGQGLEWIGEI FPGSGNTHFSARFKGKA TLTADKSSSTAYMQLSS LTSTDSAVYFCAGGDYG FLYWGRGTLVTVSA (SEQ ID NO: 15) | gatattctgatgaccca gtctccagcttcactgt ctgcatctgtgggagaa actgtcaccatcacatg tggagcaagtgagaata tttacggtgctttaaat tggtatcagcgaaaaca gggaaaatctcctcagc tcctgatctatggtgca accaacttggcagatgg catgtcatcgaggttca gtggcagtgggtctggt agacagttttctctcaa gatcactagcctgcatc ctgacgatgttgcaacg tattactgtcaaaatgt gctaagtagtccgtaca cgttcggaggggggacc aagctggaaatcaaa (SEQ ID NO: 17) | gaggttcagctgcagca gtctggagctgagctgg cgaggcccggggcttca gtgaagctgtcctgcaa ggcttctggctacacct tcagtgactactatata aactgggtgaagcaggg gactggacagggccttg agtggattggagagatt tttcctggaagtggaaa tactcacttcagtgcga ggttcaagggcaaggcc acactgactgcagacaa atcctccagcacagcct acatgcagctcagcagc ctgacatctacggactc tgcagtctatttctgtg ccggggggtgactacggg tttctttactggggccg agggactctggtcactg tctctgca (SEQ ID NO: 19) |

TABLE 4-continued

Consensus SEQ ID NOs for light chain and heavy chain variable regions of 8C4, 5G3 antibodies

| | Consensus amino acids sequence | | Consensus nucleotides sequence | |
|---|---|---|---|---|
| | light chain | heavy chain | light chain | heavy chain |
| 5G3 | QIVLTQSPAIMSASPGE KVTMTCSATSSVRYMYW YQQKPGSSPRLLIYDTS NLASGVPGRFSGSGSGT SNSLTISRLEAEDAATY YCQQWSSYPRTFGGGTK LEIK (SEQ ID NO: 14) | QGQLQQSGAELARPGAS VKMSCKASGYTFTDYTL HWVKQRPGQGLEWIGYI NPYSGYTNYNQKFKDKA TLTADKSSSTAYMQLSG LTSEDSAVFYCARGHMD YWGQGTSVTVSS (SEQ ID NO: 16) | caaattgttctcaccca gtctccagcaatcatgt ctgcatctccagggag aaggtcaccatgacctg cagtgccacctcaagtg tacgttacatgtactgg taccagcagaagccagg atcctcccccagactcc tgatttatgacacatcc aacctggcttctggagt ccctggtcgcttcagcg gcagtgggtctgggacc tctaactctctcacaat cagccgattggaggctg aagatgctgccacttat tactgccagcagtggag tagttacccacggacgt tcggtggaggcaccaag ctggaaatcaaa (SEQ ID NO: 18) | cagggccagctgcagca gtctggggctgaactgg caagacctggggcctca gtgaagatgtcctgcaa ggcttctggctacacct ttactgactacacgctg cactgggtaaaacagag gcctggacagggtctgg aatggattggatacatt aatccttacagtggtta tactaattacaatcaga aattcaaggacaaggcc acattgactgcagacaa atcctccagcacagcct acatgcaactgagcggc ctgacatctgaagactc tgcagtcttttattgtg caagaggacatatggac tactggggtcaaggaac ctcagtcaccgtctcct ca (SEQ ID NO: 20) |

Example 2. Preparation of Humanized Antibody of 8C4 Antibody and Identification of In Vitro Tumor Cell Proliferation Inhibitory Activity Thereof As one example, the mouse antibody 8C4 was humanized and an in vitro tumor cell proliferation inhibitory activity thereof was identified, in order to further identify an effect of an antibody prepared in the present invention.

For a humanized design of 8C4 antibody heavy chains, a human germline gene having a high homology with a gene in a heavy chain variable region of a mouse antibody 8C4 was analyzed first through Ig Blast (http://www.ncbi.nlm.nih.gov/igblast/). In result, it was identified that IGHV3-23 had 48% homology with the 8C4 antibody in an amino acid level, and also identified that IGHV3-11 had 46% homology with the 8C4 antibody in an amino acid level.

The CDR-H1, CDR-H2 and CDR-H3 of the mouse antibody 8C4 was defined by Kabat numbering, and hu8C4-1 was prepared in such a way that the CDR portion of the mouse antibody 8C4 was represented by be introduced into a framework of IGHV3-23. At this time, no. 48 (V→I), no. 49 (S→G), no. 71 (R→A), no. 73 (N→K), no. 78 (L→A) and no. 94 (K→G) amino acids were back-mutated into an original amino acid sequence of the mouse antibody 8C4 to finally build a heavy chain of hu8C4-1. In case of hu8C4-2, the CDR portion of the mouse antibody 8C4 was represented by be introduced into a framework of IGHV3-11, and no. 48 (V→I), no. 49 (S→G), no. 71 (R→A), no. 73 (N→K), no. 78 (L→A) and no. 94 (R→G) amino acids were back-mutated into an original amino acid sequence of the mouse antibody 8C4 to finally build a heavy chain of hu8C4-2.

Even in case of a light chain of 8C4 antibody, for a humanized design, a human germline gene having a high homology with a gene in a light chain variable region of the mouse antibody 8C4 was analyzed through Ig Blast (http://www.ncbi.nlm.nih.gov/igblast/). In result, it was identified that IGKV1-27 had 65.3% homology with the 8C4 antibody in an amino acid level, and that IGKV1-33 had 64.2% homology with the 8C4 antibody in an amino acid level.

The CDR-L1, CDR-L2 and CDR-L3 of the mouse antibody 8C4 were defined by Kabat numbering, and the CRD portion of the mouse antibody 8C4 was represented by be introduced into a framework of IGKV1-33 and a framework of IGKV1-27, thus preparing hu8C4-1 and hu8C4-2 respectively. At this time, amino acid no. 69 (T→R) of both and hu8C4-2 were back-mutated into an original amino acid sequence of the mouse antibody 8C4.

The 8C4 humanized antibody was expressed in a 293T cell by using a pCLS05 vector (Korea Patent Registration No. 10-1420274). With regard to such obtained humanized antibodies in a form of IgG1, it was identified whether or not they had a tumor cell proliferation inhibitory activity in U-87 MG, a human glioblastoma cell line, by the same method as shown in Example 1 above.

In result, it was identified that the $IC_{50}$ values of hu8C4-1 and hu8C4-2 amounted to 30 nM and 24.6 nM respectively, thus indicating a similar level of anticancer activity to that of a chimera 8C4 antibody ($IC_{50}$=32.4 nM).

Specific consensus sequences for light chain and heavy chain variable regions of the hu8C4-1 and hu8C4-2 humanized antibodies are shown in Table 5.

TABLE 5

Consensus SEQ ID NOs for light chain and heavy chain variable regions of hu8C4-1 and hu8C4-2 humanized antibodies

| | Consensus amino acids sequence | | Consensus nucleotides sequence | |
|---|---|---|---|---|
| | light chain | heavy chain | light chain | heavy chain |
| hu8C4-1 | DIQMTQSPSSLSASV GDRVTITCGASENIY | EVQLVESGGGLVQPG GSLRLSCAASGYTFS | gatatccagatgacc cagtctcccagcagt | gaggttcagttagtg gaatccggaggagga |

TABLE 5-continued

Consensus SEQ ID NOs for light chain and heavy chain variable regions of hu8C4-1 and hu8C4-2 humanized antibodies

| | Consensus amino acids sequence | | Consensus nucleotides sequence | |
|---|---|---|---|---|
| | light chain | heavy chain | light chain | heavy chain |
| | GALNWYQQKPGKAPK LLIYGATNLADGVPS RFSGSGSGRDFTFTI SSLQPEDIATYYCQN VLSSPYTFGQGTKVE IK (SEQ ID NO: 21) | DYYINWVRQAPGKGL WEIGEIFPGSGNTHF SARFKGRATLSADKS KNTAYLQMNSLRAED TAVYYCAGGDYGFLY WGQGTLVTVV (SEQ ID NO: 23) | ctttccgcttctgtg ggtgatagggtgacg ataacttgcggagca agtgagaatatttac ggtgctttaaattgg taccagcagaagcct gggaaagctccaaag ctgctgatctatggt gcaaccaacttggca gatggcgtccctagc aggttcagcggcagt ggaagcggcagagac ttcactttcacaatc tcctccctgcaaccc gaggacattgcaacc tactattgtcaaaat gtgctaagtagtccg tacacgtttggccag ggaaccaaggttgaa attaaa (SEQ ID NO: 25) | ctggtgcagcctggt ggaagtttgaggctg tcatgcgcagccagt ggctacaccttcagt gactactatataaac tggggtaagacaggct cccgaaaagggctg gagtggattggagag attttcctggaagt ggaaatactcacttc agtgcgaggttcaag ggccgagccaccctc tcagcagacaaaagc aagaataccgcctat ctgcagatgaatagc cttcgcgcagaagat actgccgtgtattac tgtgccggggtgac tacgggtttctttac tggggacagggcacc ttggtgacagtctct tct (SEQ ID NO: 27) |
| hu8C4-2 | DIQMTQSPSSLSASV GDRVTITCGASENIY GALNWYQQKPGKVPK LLIYGATNLADGVPS RFSGSGSGRDFTLTI SSLQPEDVATYYCQN VLSSPYTFGQGTKVE IK (SEQ ID NO: 22) | QVQLVESGGGLVKPG GSLRLSCAASGYTFS DYYINWIRQAPGKGL EWIGEIFPGSGNTHF SARFKGRATISADKA KNSAYLQMNSLRAED TAVYYCAGGDYGFLY WGQGTLVTVSS (SEQ ID NO: 24) | gacatccagatgacc cagtctccatcctcc ctgtctgcatctgta ggagacagagtcacc atcacttgcggagca agtgagaatatttac ggtgctttaaattgg tatcagcagaaacca gggaaagttcctaag ctcctgatctatggt gcaaccaacttggca gatgggtcccatct cggttcagtggcagt ggatctgggcgagat ttcactctcaccatc agcagcctgcagcct gaagatgttgcaact tattactgtcaaaat gtgctaagtagtccg tacacgtttggccag ggaaccaaggttgaa attaaa (SEQ ID NO: 26) | caggttcagttagtg gaatccggaggagga ctggtgaagcctggt ggaagtttgaggctg tcatgcgcagccagt ggctacaccttcagt gactactatataaac tggattagacaggct cccgaaaagggctg gagtggattggagag attttcctggaagt ggaaatactcacttc agtgcgaggttcaag ggccgagccaccatc tcagcagacaaagcg aagaatagcgcctat ctgcagatgaatagc cttcgcgcagaagat actgccgtgtattac tgtgccggggtgac tacgggtttctttac tggggacagggcacc ttggtgacagtctct tct (SEQ ID NO: 28) |

Example 3. Preparation of Humanized Antibody of 5G3 Antibody and Identification of In Vitro Tumor Cell Proliferation Inhibitory Activity Thereof Then, the mouse antibody 5G3 of the present invention was humanized to identify an in vitro tumor cell proliferation inhibitory activity thereof.

Particularly, for a heavy chain design of hu5G3-1, a human germline gene having a highest homology with a gene in a heavy chain variable region of the mouse antibody 5G3 was analyzed first through Ig Blast (http://www.ncbi.nlm.nih.gov/igblast/). In result, it was identified that IGHV1-46 had 67.3% homology with the 5G3 antibody in an amino acid level. The CDR-H1, CDR-H2 and CDR-H3 of the mouse antibody 5G3 were defined by Kabat numbering, and the CRD portion of the mouse antibody 5G3 was represented by be introduced into a framework of IGHV1-46. At this time, amino acid no. 48 (M→I), no. 69 (M→L), no. 71 (R→A), no. 73 (T→K) and no. 78 (V→A) were back-mutated into an original amino acid sequence of the mouse antibody 5G3. By doing so, a heavy chain of hu5G3-1 was built.

For a light chain of hu5G3-1, CDR-grafting was performed in IGKV3-20 gene having 63.5% homology with the 5G3 antibody, and amino acid no. 43 (A→S), no. 60 (D→A) and no. 71 (F→N) were back-mutated to build a light chain of hu5G3-1.

Also, to design a heavy chain of hu5G3-2, the CDR-H1, CDR-H2 and CDR-H3 of the mouse antibody 5G3 defined by Kabat numbering were introduced by using VH3 subtype, which was conventionally known to be most stable. At this time, amino acid no. 67 (F→A), no. 69 (I→L), no. 73 (T→K), no. 90 (Y→F) and no. 94 (T→R) were back-mutated into an original amino acid sequence of the mouse antibody 5G3. By doing so, a heavy chain of hu5G3-2 was built.

For a light chain of hu5G3-2, CDR-grafting was performed in IGVK III gene, which was known to stably form a structure with VH3 subtype, and back-mutation was not performed.

The 5G3 humanized antibody was expressed in a 293T cell by using a pCLS05 vector (Korea Patent Registration No. 10-1420274). With regard to such obtained humanized antibodies in a form of IgG2, it was identified whether or not they had a tumor cell proliferation inhibitory activity in MKN45, a human stomach cancer cell line, by the same method as shown in Example 1 above.

In result, it was identified that the $IC_{50}$ values of hu5G3-1 and hu5G3-2 amounted to 0.52 nM and 0.5 nM respectively, thus indicating a similar level of anticancer activity to that of a chimera 5G3 antibody ($IC_{50}$=0.41 nM).

Consensus sequences for light chain and heavy chain variable regions of the hu5G3-1 and hu5G3-2 humanized antibodies are shown in Table 6.

Example 4. Preparation of Hinge Mutant and Testing of Tumor Cell Proliferation Inhibitory Activity Thereof Then, a test on tumor cell proliferation inhibitory activity was performed according to a hinge sequence of human IgG1 heavy chain constant region.

First of all, a hinge of the human IgG1 heavy chain constant region had an amino acid sequence of "EPKSCDKTHTCPPCP (SEQ ID NO: 37)," which was substituted to obtain a hinge region mutant having an amino acid sequence of SEQ ID NO: 38 to SEQ ID NO: 44.

The resulting mutants were respectively cloned into a vector comprising the heavy chain variable region of hu8C4-1, hu8C4-2 humanized antibodies prepared in Example 2 above. An in vitro tumor cell proliferation inhibitory activity according to a hinge sequence was identified in U-87 MG by the same method as shown in Example 1 above.

TABLE 6

Consensus SEQ ID NOs for light chain and heavy chain variable regions of hu5G3-1 and hu5G3-2 humanized antibodies

| | Consensus amino acids sequence | | Consensus nucleotides sequence | |
|---|---|---|---|---|
| | light chain | heavy chain | light chain | heavy chain |
| hu5G3-1 | EIVLIQSPATLSLSP GERATLSCSATSSVR YMYWYQQKPGQSPRL LIYDTSNLASGIPAR FSGSGSGTDNTLTIS RLEPEDFAVYYCQQW SSYPRTFGGGTKVEI K (SEQ ID NO: 29) | QVQLVQSGAEVKKPG ASVKVSCKASGYTFT DYTLHWVRQAPGQGL EWIGYINPYSGYTNY NQKFKDRVTLTADKS TSTAYMELSSLRSED TAVYYCARGHMDYWG QGTLVTVSS (SEQ ID NO: 31) | gaaattgtgttgaca cagtctccagccacc ctgtctttgtctcca ggggaaagagccacc ctctcctgcagtgcc acctcaagtgtacgt tacatgtactggtac cagcagaaacctggc cagtctcccaggctc ctcatctatgacaca tccaacctggcttct ggcatcccagcaagg ttcagtggcagtggg tctgggacagacaac actctcaccatcagc agactggagcctgaa gattttgcagtttat tactgtcagcagtgg agtagttacccacgg acgttcggcggaggg accaaggtggagatc aaa (SEQ ID NO: 33) | caggtgcagctggtg cagtctggggctgag gtgaagaagcctggg gcctcagtgaaggtt tcctgcaaggcatct ggatacaccttcacc gactacacgctgcac tgggtgcgacaggcc cctggacaagggctt gagtggataggatac attaatccttacagt ggttatactaattac aatcagaaattcaag gacagagtcaccttg accgcagacaaatcc acgagcacagcctac atggagctgagcagc ctgagatctgaggac acggccgtgtattac tgtgctagaggacat atggactactgggc caaggaaccctggtc accgtctcctca (SEQ ID NO: 35) |
| hu5G3-2 | DIQMTQSPSSLSASV GDRVTITCSATSSVR YMYWYQQKPGKAPKL LIYDTSNLASGVPSR FSGSGSGTDFTLTIS SLQPEDFATYYCQQW SSYPRTFGQGTKVEI K (SEQ ID NO: 30) | EVQLVESGGGLVQPG GSLRLSCAASGYTFT DYTLHWVRQAPGKGL EWVGYINPYSGYTNY NQKFKDRATLSADKS KNTAYLQMNSLRAED TAVFYCARGHMDYWG QGTLVTVSS (SEQ ID NO: 32) | gacatccagatgact cagtccctcttct ctgtctgcctcagtg ggagatcgggtcaca atcacatgttcagca acaagctcagtgcga tacatgtattggtac cagcagaagccaggc aaagcccccaaagctg ctgatctatgacaca tctaatctggccagc ggcgtcccatctcgc ttctcaggtccgga agcggtactgatttt accctgactatttct tccttgcagcctgag gacttcgcaacctat tattgccagcagtgg tctagctaccctcgc acattcggccaggga accaaggtcgaaatt aaa (SEQ ID NO: 34) | gaagtccaacttgtg gagtcaggaggcggg ctcgtgcagccaggc ggatcattgcgactt tcttgtgctgcctca gggtacaccttcact gattataccttgcat tgggttcgccaagca cccggtaagggtctc gaatgggtaggatac attaatccatacagc ggctacaccaactac aaccagaaattcaaa gacagggctaccctt agtgccgacaagtct aagaacaccgcctac cttcagatgaactcc cttagagccgaggat actgctgtgttttat tgcgctagggtcat atggactactggga caggggaccttggtg actgtgtcttcc (SEQ ID NO: 36) |

Also, an effect of the 8C4 humanized antibody was analyzed as follows with regard to non-small cell lung cancer cell line NCI-H1993 (ATCC, # CRL-5909). The NCI-H1993 cell lines were diluted in an RPMI-1640 medium (Gibco, # A10491) containing 10% (v/v) FBS, after which resulting cell lines were divided by $3.0 \times 10^3$ into each well of a 96-well plate, such that the resulting plate was cultured overnight under 37° C., 5% $CO_2$ conditions. After that, the medium of each well of the plate was replaced with 100 µl of an RPMI-1640 medium containing 2% (v/v) FBS, after which a test antibody was sequentially diluted at a ratio of 1/10 (i.e., 100 nM, 10 nM, 1 nM, 100 pM, 10 pM and 1 pM) to reach 0.001 nM at a final concentration of 100 nM, such that the resulting antibody was added by 100 µl into each well. Then, the plate was cultured for 5 days under 37° C., 5% $CO_2$ conditions, after which the medium was removed therefrom, such that a TCA solution (Sigma, # T0699) was inserted by 200 µl into each well to fix the cells. Also, the cells of the plate were dyed according to a conventional SRB colorimetric assay method, after which an optical density of each well was measured at a wavelength of 540 nm by using a microplate reader.

Results of hu8C4-1 in U-87 MG and NCI-H1993 (ATCC, # CRL-5909) are shown in Table 7.

TABLE 7

Hinge region mutant sequences and results of in vitro test on tumor cell proliferation inhibitory activity

| SEQ ID NOs amino acids | | SEQ ID NOs Nucleotides | | U-87 MG (GBM, HGF amplified) ($IC_{50}$ nM) | NCI-H1993 (NSCLC, c-Met autocrine) ($IC_{50}$ nM) |
|---|---|---|---|---|---|
| 37 | EPKSCD KTHTCP PCP | 45 | gagcccaaatcttgtgacaaaac tcacacatgcccaccgtgccca | 12.6 | >100 |
| 38 | ERKCCV ECPPCP | 46 | gagcgaaaatgttgtgtcgagtg cccaccgtgccca | 31.0 | 0.30 |
| 39 | ECCVEC PPCP | 47 | gagtgttgtgtcgagtgcccacc gtgccca | 57.3 | >100 |
| 40 | ERKCCC PPCP | 48 | gagcgaaaatgttgttgcccacc gtgccca | 37.6 | 0.23 |
| 41 | ECCCPP CP | 49 | gagtgttgttgcccaccgtgccc a | 25.3 | >100 |
| 42 | EKCCVE CPPCP | 50 | gagaaatgttgtgtcgagtgccc accgtgccca | 31.4 | 0.48 |
| 43 | ERKCCV CPPCP | 51 | gagcgaaaatgttgtgtctgccc accgtgccca | 30.8 | 0.47 |
| 44 | EKCCVC PPCP | 52 | gagaaatgttgtgtctgcccacc gtgccca | 75.9 | 0.38 |

As seen in Table 7, there is some difference in the tumor cell proliferation inhibitory activity of the hu8C4 antibody according to a difference of hinge sequence, but it was identified that such antibody effectively inhibited a proliferation of most tumor cells. Accordingly, hereinafter an IgG1 humanized antibody representatively having a hinge region of SEQ ID NO: 38 in hu8C4-1 was named as hu8C4, and an affinity-optimized antibody thereto was prepared to identify an effect thereof.

Figure 2:
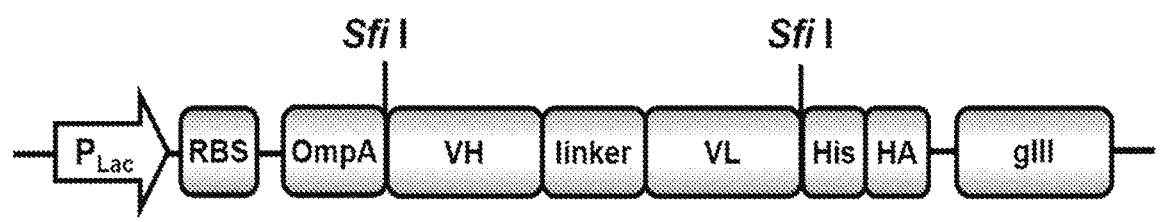
FIG. 2 shows a schematic diagram of a vector for expressing a separate transcriptome for scFv display.

Example 5. Preparation of Affinity-Optimized Antibody of hu8C4 and Identification of In Vitro Tumor Cell Proliferation Inhibitory Activity Thereof To prepare an affinity-optimized antibody of hu8C4, a phage-displayed scFv library was first prepared by using a phagemid vector displayed in a combined form of scFv and pIII, wherein a schematic structure of the vector is illustrated in FIG. 2. The phagemid vector comprises a scFv fragment of an antibody under a control of an IPTG-inductive lac promotor, wherein a linker sequence used was GGGGS GGGGS GGGGS (SEQ. No. 53).

Then, a mutation-inducing oligonucleotide having an NNK codon was used to introduce variety into the heavy chain and light chain CDR domain of hu8C4. Accordingly, a hu8C4 scFv library with a fusion of His, HA and pIII was prepared, after which a human c-Met specific antibody was selected from the prepared antibody library.

Particularly, a competitive selection method was used to select an antibody with an improved affinity. A human c-Met antigen was bound according to the manufacturer guidelines in Dynabeads® M-280 (Thermo Fisher Scientific, 11205D). A bead with an antigen binding thereto was blocked for 2 hours by a superblock Tris buffered saline (TBS, Pierce). Also recombinant phage grew overnight at 37° C., and then recombinant phage was centrifuged and a phage of its supernatant was blocked with superblock TBS, 0.05% Tween 20 for 2 hours. Then, the bead was washed with PBS containing 0.05% Twin 20. A blocked phage solution was added into the washed bead, after which the resulting bead was incubated in a rotator for 2 hours for phage binding, such that the resulting bead was washed with PBS containing 0.05% Twin 20. Then, a human c-Met antigen was added into PBS 1 ml containing 0.05% Twin 20, after which the resulting antigen was incubated in a rotator for 24 hours (Rouet R et al. (2012) *Nat Protoc.* 7:364-373). After that, the phage binding to the bead was eluted with 100 mM triethanolamine for 5 minutes, after which an eluent was neutralized with 0.5 M Tris/Cl (pH 7.2). An eluted phage neutralization liquid was infected with *E. coli* TG1.

An individual clone selected through the experiment grew in a 96-well format of 2×YT broth 200 µl with added carbenicillin and ampicillin, after which a culture supernatant thereof was directly used for ELISA to select a phage-displayed scFv binding to a plate coated with target protein. Amino acid sequences of light chain and heavy chain CDR regions of a detected antibody are shown in Tables 8 and 9, and the representative amino acid sequences of light chain and heavy chain variable regions of an affinity-optimized antibody are shown in Table 10.

TABLE 8

List of heavy chain CDR sequences

| | CDR1 | SEQ ID NOs | CDR2 | SEQ ID NOs | CDR3 | SEQ ID NOs |
|---|---|---|---|---|---|---|
| AH01 | DYYIN | 7 | EIDPGSGNTHFSARFKG | 54 | GDYGFLY | 9 |
| AH02 | DYYIN | 7 | EIEPGSGNTHFSARFKG | 55 | GDYGFLY | 9 |
| AH03 | DYY1N | 7 | EIWPGSGNTHFSARFKG | 56 | GDYGFLY | 9 |
| AH04 | DYYIN | 7 | EIYPGSGNTHFSARFKG | 57 | GDYGFLY | 9 |
| AH05 | DYYIN | 7 | EIFPGWGNTHFSARFKG | 58 | GDYGFLY | 9 |
| AH06 | DYYIN | 7 | EIFPGYGNTHFSARFKG | 59 | GDYGFLY | 9 |
| AH07 | DYYIN | 7 | EIFPGSGYTHFSARFKG | 60 | GDYGFLY | 9 |
| AH08 | DYYIN | 7 | EIFPGSGNTWFSARFKG | 61 | GDYGFLY | 9 |
| AH09 | DYYIN | 7 | EIFPGSGNTYFSARFKG | 62 | GDYGFLY | 9 |
| AH12 | DYYIN | 7 | EIFPGWGNTYFSARFKG | 63 | GDYGFLY | 9 |
| AH13 | DYYIN | 7 | EIFPGSGNTHFSARFKG | 8 | QDYGFLY | 64 |
| AH14 | DYYIN | 7 | EIFPGSGNTHFSARFKG | 8 | EDYGFLY | 65 |
| AH15 | DYYIN | 7 | EIFPGSGNTHFSARFKG | 8 | HDYGFLY | 66 |
| AH16 | DYYIN | 7 | EIFPGSGNTHFSARFKG | 8 | NDYGFLY | 67 |
| AH17 | DYYIN | 7 | EIFPGSGNTHFSARFKG | 8 | VELGFLY | 68 |
| AH18 | DYYIN | 7 | EIFPGSGNTHFSARFKG | 8 | FETGYYL | 69 |
| AH19 | DYYIN | 7 | EIFPGSGNTHFSARFKG | 8 | GEYGYQN | 70 |
| AH20 | DYYIN | 7 | EIFPGSGNTHFSARFKG | 8 | WEYGLSM | 71 |
| AH21 | DYYIN | 7 | EIFPHFTSDHFSARFKG | 72 | GDYGFLY | 9 |
| AH22 | DYYIN | 7 | EIFPGSGNTHFSAWMGT | 73 | GDYGFLY | 9 |
| AH23 | DYYIN | 7 | EIFPGSGNESVSFRFKG | 74 | GDYGFLY | 9 |
| AH24 | DYYIN | 7 | EIFPGSGNSAVISRFKG | 75 | GDYGFLY | 9 |
| AH25 | DYYIN | 7 | EIFPGSGNHTVVRRFKG | 76 | GDYGFLY | 9 |
| AH26 | DYYIN | 7 | EIFPGSGNLSMHCRFKG | 77 | GDYGFLY | 9 |
| AH27 | DYYIN | 7 | EIFPGSGNHTPVRFKG | 78 | GDYGFLY | 9 |
| AH28 | DYYIN | 7 | EIFPGSGNPFLTIRFKG | 79 | GDYGFLY | 9 |
| AH29 | DYYIN | 7 | EIFPGSGNSHVVSRFKG | 80 | GDYGFLY | 9 |
| AH30 | DYYIN | 7 | EIFPGSGNLSGIRSFKG | 81 | GDYGFLY | 9 |
| AH31 | DYYIN | 7 | EIFPGSGNFFHGKRFKG | 82 | GDYGFLY | 9 |
| AH32 | DYYIN | 7 | EIFPGSGNPRLGARFKG | 83 | GDYGFLY | 9 |
| AH33 | DYYIN | 7 | EIFPGSGNVSQVERFKG | 84 | GDYGFLY | 9 |
| AH34 | DYYIN | 7 | EIFPGSGNFHGASRFKG | 85 | GDYGFLY | 9 |
| AH35 | DYYIN | 7 | EIFPGSGNVVGGYRFKG | 86 | GDYGFLY | 9 |
| AH36 | DYYIN | 7 | EIFPGSGNPMYDERFKG | 87 | GDYGFLY | 9 |
| AH37 | DYYIN | 7 | EIFPGSGNADLTIRFKG | 88 | GDYGFLY | 9 |
| AH38 | DYYIN | 7 | EIFPGSGNSTNLYRFKG | 89 | GDYGFLY | 9 |
| AH39 | DYYIN | 7 | EIFPGSGNLDIPPRFKG | 90 | GDYGFLY | 9 |

TABLE 8-continued

List of heavy chain CDR sequences

| | CDR1 | SEQ ID NOs | CDR2 | SEQ ID NOs | CDR3 | SEQ ID NOs |
|---|---|---|---|---|---|---|
| AH40 | DYYIN | 7 | EIFPGSGNTHFSSAPLP | 91 | GDYGFLY | 9 |
| AH41 | DYYIN | 7 | EIFPGSGNTHFSSEFVS | 92 | GDYGFLY | 9 |
| AH42 | DYYIN | 7 | EIFPGSGNTHFSMSESF | 93 | GDYGFLY | 9 |
| AH43 | DYYIN | 7 | EIFPGSGNTHFSDGSRN | 94 | GDYGFLY | 9 |
| AH44 | DYYIN | 7 | EIFPGSGNTHFSSSVSR | 95 | GDYGFLY | 9 |
| AH45 | DYYIN | 7 | EIFPGSGNTHFSRSVSG | 96 | GDYGFLY | 9 |
| AH46 | DYYIN | 7 | EIFPGSGNTHFSGLSEV | 97 | GDYGFLY | 9 |
| AH47 | DYYIN | 7 | EIFPGSGNTHFSHYWAS | 98 | GDYGFLY | 9 |
| AH48 | DYYIN | 7 | EIFPGSGNTHFSTGLTQ | 99 | GDYGFLY | 9 |
| AH49 | DYYIN | 7 | EIFPGSGNTHFSRHRLH | 100 | GDYGFLY | 9 |
| AH50 | DYYIN | 7 | EIFPGSGNTHFSVPRSM | 101 | GDYGFLY | 9 |
| AH51 | DYYIN | 7 | EIFPGSGNTHFSLQDYL | 102 | GDYGFLY | 9 |
| AH52 | DYYIN | 7 | EIFPGSGNTHFSDGVSS | 103 | GDYGFLY | 9 |
| AH53 | DYYIN | 7 | EIFPGSGNTHFSMQGSE | 104 | GDYGFLY | 9 |
| AH54 | DYYIN | 7 | EIFPGSGNTHFSGNVHW | 105 | GDYGFLY | 9 |
| AH55 | DYYIN | 7 | EIFPGSGNTHFSRSPTP | 106 | GDYGFLY | 9 |
| AH56 | DYYIN | 7 | EIFPGSGNTHFSLRMFP | 107 | GDYGFLY | 9 |
| AH57 | DYYAN | 108 | EIFPGSGNTHFSARFKG | 8 | GDYGFLY | 9 |
| AH58 | GYYIN | 109 | EIFPGSGNTHFSARFKG | 8 | GDYGFLY | 9 |
| AH59 | QYYIN | 110 | EIFPGSGNTHFSARFKG | 8 | GDYGFLY | 9 |
| AH60 | DQYIN | 111 | EIFPGSGNTHFSARFKG | 8 | GDYGFLY | 9 |
| AH61 | DYYQN | 112 | EIFPGSGNTHFSARFKG | 8 | GDYGFLY | 9 |
| AH62 | DYYIN | 7 | EIFPGSGNTHFSARFKG | 8 | GDVGFLY | 113 |
| AH63 | DYYIN | 7 | EIFPGSGNTHFSARFKG | 8 | GDYGFQY | 114 |
| AH64 | DYYIN | 7 | EIFPGSGNTHFSARFKG | 8 | GDYGFLQ | 115 |
| AH65 | DYYIN | 7 | EIFPGSGNTHFSARFKG | 8 | GDQWLLC | 116 |
| AH66 | DYYIN | 7 | EIFPGSGNTHFSARFKG | 8 | WDYGFLY | 117 |
| AH67 | DYYIN | 7 | EIFPDSAPSHFSARFKG | 118 | GDYGFLY | 9 |
| AH68 | DYYIN | 7 | EIFPYFLPPHFSARFKG | 119 | GDYGFLY | 9 |
| AH69 | DYYIN | 7 | EIFPGPFTPHFSARFKG | 120 | GDYGFLY | 9 |
| AH70 | DYYIN | 7 | EIFPGSNFGHFSARFKG | 121 | GDYGFLY | 9 |
| AH71 | DYYIN | 7 | EIFPGWGNTHFSARFKG | 58 | QDYGFLY | 64 |
| AH72 | DYYIN | 7 | EIFPGWGNTHFSRSPTP | 122 | GDYGFLY | 9 |
| AH73 | DYYIN | 7 | EIFPGWGNSHVVSRFRG | 123 | GDYGFLY | 9 |
| AH74 | DYYIN | 7 | EIFPGYGNTHFSARFKG | 59 | QDYGFLY | 64 |
| AH75 | DYYIN | 7 | EIFPGYGNTYFSARFKG | 124 | GDYGFLY | 9 |
| AH76 | DYYIN | 7 | EIFPGYGNTHFSRSPTP | 125 | GDYGFLY | 9 |

TABLE 8-continued

List of heavy chain CDR sequences

| | CDR1 | SEQ ID NOs | CDR2 | SEQ ID NOs | CDR3 | SEQ ID NOs |
|---|---|---|---|---|---|---|
| AH77 | DYYIN | 7 | EIFPGYGNSHVVSRFKG | 126 | GDYGFLY | 9 |
| AH78 | DYYIN | 7 | EIFPGSGNTYFSARFKG | 62 | QDYGFLY | 64 |
| AH79 | DYYIN | 7 | EIFPGSGNTYFSREPTP | 127 | GDYGFLY | 9 |
| AH80 | DYYIN | 7 | EIFPGSGNSHVVSRFKG | 80 | QDYGFLY | 64 |
| AH81 | DYYIN | 7 | EIFPGSGNSHVVRSPTP | 128 | GDYGFLY | 9 |
| AH82 | DYYIN | 7 | EIFPGSGNSHVVRSPTP | 128 | GDYGFLY | 9 |
| AH83 | DYYIN | 7 | EIFPGWGNTYFSARFKG | 63 | QDYGFLY | 64 |
| AH84 | DYYIN | 7 | EIFPGWGNTHFSRSPTP | 199 | QDYGFLY | 64 |
| AH85 | DYYIN | 7 | EIFPGWGNSHVVSRFKG | 123 | QDYGFLY | 64 |
| AH86 | DYYIN | 7 | EIFPGYGNTYFSARFKG | 124 | QDYGFLY | 64 |
| AH87 | DYYIN | 7 | EIFPGYGNSHVVSRFKG | 126 | QDYGFLY | 64 |
| AH88 | DYYIN | 7 | EIFPGSGNTHFSRSPTP | 106 | QDYGFLY | 64 |
| AH89 | DYYIN | 7 | EIFPGYGNTHFSRSPTP | 125 | QDYGFLY | 64 |
| AH90 | DYYIN | 7 | EIFPGSGNTYFSRSPTP | 127 | QDYGFLY | 64 |
| AH91 | DYYIN | 7 | EIFPGSGNSHVVRSPTP | 128 | QDYGFLY | 64 |
| AH92 | DYYIN | 7 | EIFPGSGNSHVVSSPTP | 129 | QDYGFLY | 64 |
| AH93 | DYYIN | 7 | EIFPDSAPSYFSARFKG | 130 | GDYGFLY | 9 |
| AH94 | DYYIN | 7 | EIFPGPFTPYFSARFKG | 131 | GDYGFLY | 9 |
| AH95 | DYYIN | 7 | EIFPGSNFGYFSRSPTP | 132 | GDYGFLY | 9 |
| AH96 | DYYIN | 7 | EIFPDSAPSHVVSRFKG | 133 | GDYGFLY | 9 |
| AH97 | DYYIN | 7 | EIFPGPFTSHVVSRFKG | 134 | GDYGFLY | 9 |
| AH98 | DYYIN | 7 | EIFPGSNFSHVVSRFKG | 135 | GDYGFLY | 9 |
| AH99 | DYYIN | 7 | EIFPDSAPSHFSRSPTP | 136 | GDYGFLY | 9 |
| AH100 | DYYIN | 7 | EIFPGPFTPHFSRSPTP | 137 | GDYGFLY | 9 |
| AH101 | DYYIN | 7 | EIFPGSNFGHFSRSPTP | 138 | GDYGFLY | 9 |
| AH102 | DYYIN | 7 | EIFPDSAPSHVVSSPTP | 139 | GDYGFLY | 9 |
| AH103 | DYYIN | 7 | EIFPGPFTSHVVSSPTP | 140 | GDYGFLY | 9 |
| AH104 | DYYIN | 7 | EIFPGSNFSHVVSSPTP | 141 | GDYGFLY | 9 |
| AH105 | QYYIN | 110 | EIFPDSAPSHFSARFKG | 118 | GDYGFLY | 9 |
| AH106 | QYYIN | 110 | EIFPGPFTPHFSARFKG | 120 | GDYGFLY | 9 |
| AH107 | QYYIN | 110 | EIFPGSNFGHFSARFKG | 121 | GDYGFLY | 9 |
| AH108 | DYYIN | 7 | EIFPDSAPSHFSARFKG | 118 | QDYGFLY | 64 |
| AH109 | DYYIN | 7 | EIFPGPFTPHFSARFKG | 120 | QDYGFLY | 64 |
| AH110 | DYYIN | 7 | EIFPGSNFGHFSARFKG | 121 | QDYGFLY | 64 |
| AH111 | DYYIN | 7 | EIFPDSAPSHFSARFKG | 118 | GDYGFQY | 114 |
| AH112 | DYYIN | 7 | EIFPGPFTPHFSARFKG | 120 | GDYGFQY | 114 |
| AH113 | DYYIN | 7 | EIFPGSNFGHFSARFKG | 121 | GDYGFQY | 114 |

TABLE 8-continued

List of heavy chain CDR sequences

| | CDR1 | SEQ ID NOs | CDR2 | SEQ ID NOs | CDR3 | SEQ ID NOs |
|---|---|---|---|---|---|---|
| AH114 | DYYIN | 7 | EIFPDSAPSHFSARFKG | 118 | GDYGFLQ | 115 |
| AH115 | DYYIN | 7 | EIFPGPFTPHFSARFKG | 120 | GDYGFLQ | 115 |
| AH116 | DYYIN | 7 | EIFPGSNFGHFSARFKG | 121 | GDYGFLQ | 115 |
| AH117 | DYYIN | 7 | EIFPGSGNTHFSMSESF | 93 | HDYGFLY | 66 |
| AH118 | DYYIN | 7 | EIFPGSGNTHFSLQDYL | 102 | HDYGFLY | 66 |
| AH119 | DYYIN | 7 | EIFPGSGNTHFSMQGSE | 104 | HDYGFLY | 66 |

TABLE 9

List of light chain CDR sequences

| | CDR1 | SEQ ID NOs | CDR2 | SEQ ID NOs | CDR3 | SEQ ID NOs |
|---|---|---|---|---|---|---|
| AL01 | GASENIYGALN | 1 | GATNLAD | 2 | QNVWSSPYT | 142 |
| AL02 | GASENIYGALN | 1 | GATNLAD | 2 | QNVLNSPYT | 143 |
| AL03 | GASENIYGALN | 1 | GATNLAD | 2 | QNVLESPYT | 144 |
| AL04 | GASENIYGALN | 1 | GATNLAD | 2 | QNVLKSPYT | 145 |
| AL05 | GASENIYGALN | 1 | GATNLAD | 2 | QNVLYSPYT | 146 |
| AL06 | GASENIYGALN | 1 | GATNLAD | 2 | QNVLSRPYT | 147 |
| AL07 | GASENIYGALN | 1 | GATNLAD | 2 | QNVLSSPET | 148 |
| AL08 | GASENIYGALN | 1 | GATNLAD | 2 | QNVLSEPYT | 149 |
| AL11 | GASENIYGALN | 1 | GATNLAD | 2 | QNVLESPET | 150 |
| AL12 | GASENIYGALN | 1 | GATNLAD | 2 | QNVLSVPET | 151 |
| AL13 | GASENIYGALN | 1 | GATNLAD | 2 | QNVLSLPET | 152 |
| AL14 | GASENIYGALN | 1 | GATNLAD | 2 | QNVLSIPET | 153 |
| AL15 | GASENIYGALN | 1 | GATNLAD | 2 | QNVLSMPET | 154 |
| AL16 | GASENIYGALN | 1 | GATNLAD | 2 | QNILSSPET | 155 |
| AL17 | GASENIYGALN | 1 | GATNLAD | 2 | QNLISSPET | 156 |
| AL18 | GASENIYGALN | 1 | GATNLAD | 2 | QNMISSPET | 157 |
| AL19 | GASENIYGALN | 1 | GATNLAD | 2 | QNIISLPET | 158 |
| AL20 | GASENIYGALN | 1 | GATNLAD | 2 | QNIISIPET | 159 |
| AL21 | GASENIYGALN | 1 | GATNLAD | 2 | QNSLSSPET | 160 |
| AL22 | GASENIYGALN | 1 | GATNLAD | 2 | QNTLSSPET | 161 |
| AL23 | GASENIYGALN | 1 | GATNLAD | 2 | QNVSSSPET | 162 |
| AL24 | GASENIYGALN | 1 | GATNLAD | 2 | QNVISSPET | 163 |
| AL25 | GASENIYGALN | 1 | GATNLAD | 2 | QNVFSSPET | 164 |
| AL26 | GASENIYGALN | 1 | GATNLAD | 2 | QNVYSSPET | 165 |
| AL27 | GASENIYGALN | 1 | GATNLAD | 2 | QNVRSSPET | 166 |
| AL28 | GASENIYGALN | 1 | GATNLAD | 2 | QNLVSSPET | 167 |
| AL29 | GASENIYGALN | 1 | GATNLAD | 2 | QNLISSPET | 156 |
| AL30 | GASENIYGALN | 1 | GATNLAD | 2 | QNLMSSPET | 168 |
| AL31 | GASENIYGALN | 1 | GATNLAD | 2 | QNIMSSPET | 169 |
| AL32 | GASENIYGALN | 1 | GATNLAD | 2 | QNVHSSPET | 170 |
| AL33 | GASENIYGALN | 1 | GATNLAD | 2 | QNVMSSPET | 171 |
| AL34 | GASENIYGALN | 1 | GATNLAD | 2 | QNLLSSPET | 172 |
| AL35 | GASENIYGALN | 1 | GATNLAD | 2 | QSVLFSPFS | 173 |
| AL36 | GASENIYGALN | 1 | GATNLAD | 2 | QQVLFFPET | 174 |
| AL37 | GASENIYGALN | 1 | GATNLAD | 2 | QNLLSPSFY | 175 |
| AL38 | GASENIYGALN | 1 | GATNLAD | 2 | QSVLFSPFT | 176 |
| AL39 | GASENIYGALN | 1 | GATNLAD | 2 | QNILSSPLF | 177 |
| AL40 | GASENIYGALN | 1 | GATNLAD | 2 | QNTLHYSLV | 178 |
| AL41 | GASENIYGALN | 1 | GATNLAD | 2 | QQVLFFPLL | 179 |
| AL42 | GASENIYGALN | 1 | GATNLAD | 2 | QQVLDFVFY | 180 |
| AL43 | GASENIYGALN | 1 | GATNLAD | 2 | QNVVSSPET | 181 |
| AL44 | GASENIYGALN | 1 | DATNLAD | 182 | QNVLSSPYT | 3 |
| AL45 | GASENIYGALN | 1 | FATNLAD | 183 | QNVLSSPYT | 3 |
| AL46 | GASENIYGALN | 1 | HATNLAD | 184 | QNVLSSPYT | 3 |
| AL47 | GASENIYGALN | 1 | KATNLAD | 185 | QNVLSSPYT | 3 |
| AL48 | GASENIYGALN | 1 | PATNLAD | 186 | QNVLSSPYT | 3 |
| AL49 | GASENIYGALN | 1 | QATNLAD | 187 | QNVLSSPYT | 3 |
| AL50 | GASENIYGALN | 1 | SATNLAD | 188 | QNVLSSPYT | 3 |
| AL51 | GASENIYGALN | 1 | VATNLAD | 189 | QNVLSSPYT | 3 |
| AL52 | GASENIYGALN | 1 | YATNLAD | 190 | QNVLSSPYT | 3 |
| AL53 | GASENIYGALN | 1 | GATNLAD | 2 | ITVLSPPYT | 191 |

TABLE 9-continued

List of light chain CDR sequences

| | CDR1 | SEQ ID NOs | CDR2 | SEQ ID NOs | CDR3 | SEQ ID NOs |
|---|---|---|---|---|---|---|
| AL54 | GASENIYGALN | 1 | GATNLAD | 2 | QNNLVPPFN | 192 |
| AL55 | GASENIYGALN | 1 | GATNLAD | 2 | QHVLFLPYV | 193 |
| AL56 | GASENIYGALN | 1 | GATNLAD | 2 | QAVLTNAYT | 194 |
| AL57 | GASENIYGALN | 1 | GATNLAD | 2 | QNVLRVGYL | 195 |
| AL58 | GASENIYGALN | 1 | GATNLAD | 2 | QSVLRVGYL | 196 |
| AL59 | GASENIYGALN | 1 | GATNLAD | 2 | QNIISSPYT | 197 |
| AL60 | GASENIYGALN | 1 | GATNLAD | 2 | QQVLCESFL | 198 |
| AL61 | GASENIYGALN | 1 | GATNLAD | 2 | QNVLSQSLL | 199 |
| AL62 | GASENIYGALN | 1 | GATNLAD | 2 | QNVLQPSYL | 200 |
| AL63 | GASENIYGALN | 1 | GATNLAD | 2 | QNLLFQPLS | 201 |
| AL64 | GASENIYGALN | 1 | GATNLAD | 2 | QNVLFQPLV | 202 |
| AL65 | GASENIYGALN | 1 | GATNLAD | 2 | QNQLDPSLF | 203 |
| AL66 | GASENIYGALN | 1 | GATNLAD | 2 | MDVLESPYT | 204 |
| AL67 | GASENIYGALN | 1 | GATNLAD | 2 | QALLLSPYT | 205 |
| AL68 | GASENIYGALN | 1 | GATNLAD | 2 | QQLLESPYT | 206 |
| AL69 | GASENIYGALN | 1 | GATNLAD | 2 | NLTLVSPYT | 207 |
| AL70 | GASENIYGALN | 1 | GATNLAD | 2 | GNILDSPYT | 208 |
| AL71 | GASENIYGALN | 1 | GATNLAD | 2 | EQVLLSPYT | 209 |
| AL72 | GASENIYGALN | 1 | GATNLAD | 2 | NNLLDSPYT | 210 |
| AL73 | GASENIYGALN | 1 | GATNLAD | 2 | EEVLSSPYT | 211 |
| AL74 | GASENIYGALN | 1 | GATNLAD | 2 | QNILFVDYT | 212 |
| AL75 | GASENIYGALN | 1 | GATNLAD | 2 | QNVLHLNYT | 213 |
| AL76 | GASENIYGALN | 1 | GATNLAD | 2 | QNVLQTPYT | 214 |
| AL77 | GASENIYGALN | 1 | GATNLAD | 2 | QNILHPGYT | 215 |
| AL78 | GASENIYGALN | 1 | GATNLAD | 2 | QNVLTRGYT | 216 |
| AL79 | GASENIYGALN | 1 | GATNLAD | 2 | ENILYSPYT | 217 |
| AL80 | GASENIYGALN | 1 | GATNLAD | 2 | QNVLGGGQG | 218 |
| AL81 | GASENIYGALN | 1 | GATNLAD | 2 | QNVLEHPLI | 219 |
| AL82 | GASENIYGALN | 1 | GATNLAD | 2 | QNVLDDPFD | 220 |
| AL83 | GASENIYGALN | 1 | GATNLAD | 2 | QNVLDFPLL | 221 |
| AL84 | GASENIYGALN | 1 | GATNLAD | 2 | QNVLYPSLV | 222 |
| AL85 | GASENIYGALN | 1 | GATNLAD | 2 | QNVLFDQQS | 223 |
| AL86 | GASENIYGALN | 1 | GATNLAD | 2 | QNYLSNEET | 224 |
| AL87 | GASENIYGALN | 1 | GATNLAD | 2 | QNVLKHPYT | 225 |
| AL88 | GASENIYGALN | 1 | GATNLAD | 2 | QNVLSPGMW | 226 |
| AL89 | GASENIYGALN | 1 | GATGLAD | 227 | QNVLSSPYT | 3 |
| AL90 | GASENIYGALN | 1 | GAQNLAD | 228 | QNVLSSPYT | 3 |
| AL91 | GSSRSIYGALN | 229 | GATNLAD | 2 | QNVLSSPYT | 3 |
| AL92 | RAGRSIYGALN | 230 | GATNLAD | 2 | QNVLSSPYT | 3 |
| AL93 | LGRRGIYGALN | 231 | GATNLAD | 2 | QNVLSSPYT | 3 |
| AL94 | EVQVGIYGALN | 232 | GATNLAD | 2 | QNVLSSPYT | 3 |
| AL95 | RPSEKIYGALN | 233 | GATNLAD | 2 | QNVLSSPYT | 3 |
| AL96 | RASAVIYGALN | 234 | GATNLAD | 2 | QNVLSSPYT | 3 |
| AL97 | KTGDLIYGALN | 235 | GATNLAD | 2 | QNVLSSPYT | 3 |
| AL98 | SCRVPIYGALN | 236 | GATNLAD | 2 | QNVLSSPYT | 3 |
| AL99 | VASRGIYGALN | 237 | GATNLAD | 2 | QNVLSSPYT | 3 |
| AL100 | RGRQNIYGALN | 238 | GATNLAD | 2 | QNVLSSPYT | 3 |
| AL101 | AAPRGIYGALN | 239 | GATNLAD | 2 | QNVLSSPYT | 3 |
| AL102 | SAPFKIYGALN | 240 | GATNLAD | 2 | QNVLSSPYT | 3 |
| AL103 | LGMDDIYGALN | 241 | GATNLAD | 2 | QNVLSSPYT | 3 |
| AL104 | NVRRGTYGALN | 242 | GATNLAD | 2 | QNVTSSPYT | 3 |
| AL105 | NTSGRIYGALN | 243 | GATNLAD | 2 | QNVLSSPYT | 3 |
| AL106 | LVSRPIYGALN | 244 | GATNLAD | 2 | QNVLSSPYT | 3 |
| AL107 | WTNRPIYGALN | 245 | GATNLAD | 2 | QNVLSSPYT | 3 |
| AL108 | RIPSAIYGALN | 246 | GATNLAD | 2 | QNVLSSPYT | 3 |
| AL109 | GATRGIYGALN | 247 | GATNLAD | 2 | QNVLSSPYT | 3 |
| AL110 | EGGSPIYGALN | 248 | GATNLAD | 2 | QNVLSSPYT | 3 |
| AL111 | GASRGMFRALN | 249 | GATNLAD | 2 | QNVLSSPYT | 3 |
| AL112 | GASGLVFSALN | 250 | GATNLAD | 2 | QNVLSSPYT | 3 |
| AL113 | GASRGTHMALN | 251 | GATNLAD | 2 | QNVLSSPYT | 3 |
| AL114 | GASSRFHNALN | 252 | GATNLAD | 2 | QNVLSSPYT | 3 |
| AL115 | GASRTAFTALN | 253 | GATNLAD | 2 | QNVLSSPYT | 3 |
| AL116 | GASRSTFSALN | 254 | GATNLAD | 2 | QNVLSSPYT | 3 |
| AL117 | GASGPMFDALN | 255 | GATNLAD | 2 | QNVLSSPYT | 3 |
| AL118 | GASHDLYGALN | 256 | GATNLAD | 2 | QNVLSSPYT | 3 |
| AL119 | GASGTLFGALN | 257 | GATNLAD | 2 | QNVLSSPYT | 3 |
| AL120 | GASKAAFGALN | 258 | GATNLAD | 2 | QNVLSSPYT | 3 |
| AL121 | GASEGIVGALN | 259 | GATNLAD | 2 | QNVLSSPYT | 3 |
| AL122 | GASHEIHVALN | 260 | GATNLAD | 2 | QNVLSSPYT | 3 |
| AL123 | GASRGVFGALN | 261 | GATNLAD | 2 | QNVTSSPYT | 3 |
| AL124 | GASGRVRGALN | 262 | GATNLAD | 2 | QNVLSSPYT | 3 |
| AL125 | GASTGSFSALN | 263 | GATNLAD | 2 | QNVLSSPYT | 3 |
| AL126 | GASGNSFDALN | 264 | GATNLAD | 2 | QNVLSSPYT | 3 |
| AL127 | GASEQSYFALN | 265 | GATNLAD | 2 | QNVLSSPYT | 3 |

TABLE 9-continued

List of light chain CDR sequences

| | CDR1 | SEQ ID NOs | CDR2 | SEQ ID NOs | CDR3 | SEQ ID NOs |
|---|---|---|---|---|---|---|
| AL128 | GASFRQFSALN | 266 | GATNLAD | 2 | QNVLSSPYT | 3 |
| AL129 | GASAPRHSALN | 267 | GATNLAD | 2 | QNVLSSPYT | 3 |
| AL130 | GASMRLFHALN | 268 | GATNLAD | 2 | QNVLSSPYT | 3 |
| AL131 | GASENIYGALN | 1 | GATNLAD | 2 | QNILSSPYT | 269 |
| AL132 | GASENIYGALN | 1 | GATNLAD | 2 | QNVLSMPYT | 270 |
| AL133 | GASENIYGALN | 1 | GATNLAD | 2 | QNVLSEPET | 271 |
| AL134 | GASENIYGALN | 1 | GATNLAD | 2 | QNVLYSPET | 272 |
| AL135 | GASENIYGALN | 1 | GATNLAD | 2 | QNVLEEPYT | 273 |
| AL136 | GASENIYGALN | 1 | GATNLAD | 2 | QNVLELPET | 274 |
| AL137 | GASENIYGALN | 1 | GATNLAD | 2 | QNVLEMPET | 275 |
| AL138 | GASENIYGALN | 1 | GATNLAD | 2 | QNILESPET | 276 |
| AL139 | GASENIYGALN | 1 | GATNLAD | 2 | QNVIESPET | 277 |
| AL140 | GASENIYGALN | 1 | GATNLAD | 2 | QNVMESPET | 278 |
| AL141 | GASENIYGALN | 1 | GATNLAD | 2 | QNLLESPET | 279 |
| AL142 | GASENIYGALN | 1 | GATNLAD | 2 | QNVLYEPYT | 280 |
| AL143 | GASENIYGALN | 1 | GATNLAD | 2 | QNILSEPET | 281 |
| AL144 | GASENIYCALN | 1 | GATNLAD | 2 | QNVISEPET | 282 |
| AL145 | GASENIYGALN | 1 | GATNLAD | 2 | QNVMSEPET | 283 |
| AL146 | GASENIYGALN | 1 | GATNLAD | 2 | QNLLSEPFT | 284 |
| AL147 | GASENIYGALN | 1 | GATNLAD | 2 | QSVLFEPFS | 285 |
| AL148 | GASENIYGALN | 1 | GATNLAD | 2 | QSVLFEPFT | 286 |
| AL149 | GASENIYGALN | 1 | GATNLAD | 2 | QNILYSPET | 287 |
| AL150 | GASENIYGALN | 1 | GATNLAD | 2 | QNILSLPET | 288 |
| AL151 | GASENIYGALN | 1 | GATNLAD | 2 | QNILSMPET | 289 |
| AL152 | GASENIYGALN | 1 | GATNLAD | 2 | QNVLYMPET | 290 |
| AL153 | GASENIYGALN | 1 | GATNLAD | 2 | QNVISMPET | 291 |
| AL154 | GASENIYGALN | 1 | GATNLAD | 2 | QNVMSMPET | 292 |
| AL155 | GASENIYGALN | 1 | GATNLAD | 2 | QNLLSMPET | 293 |
| AL156 | GASENIYGALN | 1 | GATNLAD | 2 | QNIISSPET | 294 |
| AL157 | GASENIYGALN | 1 | GATNLAD | 2 | QNVLYLPET | 295 |
| AL158 | GASENIYGALN | 1 | GATNLAD | 2 | QNVIYSPET | 296 |
| AL159 | GASENIYGALN | 1 | GATNLAD | 2 | QNVMYSPET | 297 |
| AL160 | GASENIYGALN | 1 | GATNLAD | 2 | QNLLYSPET | 298 |
| AL161 | GASENIYGALN | 1 | GATNLAD | 2 | QNVISLPET | 299 |
| AL162 | GASENIYGALN | 1 | GATNLAD | 2 | QNVMSLPET | 300 |
| AL163 | GASENIYGALN | 1 | GATNLAD | 2 | QNLLSLPET | 301 |
| AL164 | RASAVIYGALN | 234 | GATGLAD | 227 | QNVLSSPYT | 3 |
| AL165 | GASENIYGALN | 1 | GATGLAD | 227 | QNVLESPYT | 144 |
| AL166 | GASENIYGALN | 1 | GATGLAD | 227 | QNVLSEPYT | 149 |
| AL167 | GASENIYGALN | 1 | GATGLAD | 227 | QNVLSSPET | 148 |
| AL168 | GASENIYGALN | 1 | GATGLAD | 227 | QNVLYSPYT | 146 |
| AL169 | GASENIYGALN | 1 | GATGLAD | 227 | QNILSSPET | 155 |
| AL170 | GASENIYGALN | 1 | GATGLAD | 227 | QNLLSSPET | 172 |
| AL171 | GASENIYGALN | 1 | GATGLAD | 227 | QNVISSPET | 163 |
| AL172 | GASENIYGALN | 1 | GATGLAD | 227 | QNVMSSPET | 171 |
| AL173 | GASENIYGALN | 1 | GATGLAD | 227 | QNVLSLPET | 152 |
| AL174 | GASENIYGALN | 1 | GATGLAD | 227 | QNVLSMPET | 154 |
| AL175 | GASENIYGALN | 1 | GATGLAD | 227 | QSVLFSPFS | 173 |
| AL176 | GASENIYGALN | 1 | GATGLAD | 227 | QNLLFQPLS | 201 |
| AL177 | GASENIYGALN | 1 | GATGLAD | 227 | QQVLFFPLL | 179 |
| AL178 | GASENIYGALN | 1 | GATGLAD | 227 | QSVLFSPFT | 176 |
| AL179 | RASAVIYGALN | 234 | GATNLAD | 2 | QNVLESPYT | 144 |
| AL180 | RASAVIYGALN | 234 | GATNLAD | 2 | QNVLSEPYT | 149 |
| AL181 | RASAVIYGALN | 234 | GATNLAD | 2 | QNVLSSPET | 148 |
| AL182 | RASAVIYGALN | 234 | GATNLAD | 2 | QNVLYSPYT | 146 |
| AL183 | RASAVIYGALN | 234 | GATNLAD | 2 | QNILSSPET | 155 |
| AL184 | RASAVIYGALN | 234 | GATNLAD | 2 | QNLLSSPET | 172 |
| AL185 | RASAVIYGALN | 234 | GATNLAD | 2 | QNVISSPET | 163 |
| AL186 | RASAVIYGALN | 234 | GATNLAD | 2 | QNVMSSPET | 171 |
| AL187 | RASAVIYGALN | 234 | GATNLAD | 2 | QNVLSLPET | 152 |
| AL188 | RASAVIYGALN | 234 | GATNLAD | 2 | QNVLSMPET | 154 |
| AL189 | RASAVIYGALN | 234 | GATNLAD | 2 | QSVLFSPFS | 173 |
| AL190 | RASAVIYGALN | 234 | GATNLAD | 2 | QNLLFQPLS | 201 |
| AL191 | RASAVIYGALN | 234 | GATNLAD | 2 | QQVLFFPLL | 179 |
| AL192 | RASAVIYGALN | 234 | GATNLAD | 2 | QSVLFSPFT | 176 |
| AL193 | GASRSTFSALN | 254 | GATNLAD | 2 | QNVLSIPET | 153 |
| AL194 | GASMPLFHALN | 268 | GATNLAD | 2 | QNVLSIPET | 153 |
| AL195 | GASRSTFSALN | 254 | GATNLAD | 2 | QNVLEEPYT | 273 |
| AL196 | GASMPLFHALN | 268 | GATNLAD | 2 | QNVLEEPYT | 273 |

TABLE 10

List of sequences of light chain and heavy chain variable regions of affinity-optimized antibody

| Amino acids sequence | | SEQ ID NOs |
|---|---|---|
| AH71 | EVQLVESGGGLVQPGGSLRLSCAASGYTFSDYYINWVRQ APGKGLEWIGEIFPGWGNTHFSARFKGRATLSADKSKNT AYLQMNSLRAEDTAVYYCAGQDYGFLYWGQGTLVTVSS | 302 |
| AH72 | EVQLVESGGGLVQPGGSLRLSCAASGYTFSDYYINWVRQ APGKGLEWIGEIFPGWGNTHFSRSPTPRATLSADKSKNT AYLQMNSLRAEDTAVYYCAGGDYGFLYWGQGTLVTVSS | 303 |
| AH73 | EVQLVESGGGLVQPGGSLRLSCAASGYTFSDYYINWVRQ IAPGKGLEWGEIFPGWGNSHVVSRFKGRATLSADKSKNT AYLQMNSLRAEDTAVYYCAGGDYGFLYWGQGTLVTVSS | 304 |
| AH85 | EVQLVESGGGLVQPGGSLRLSCAASGYTFSDYYINWVRQ APGKGLEWIGEIFPGWGNSHVVSRFKGRATLSADKSKNT AYLQMNSLRAEDTAVYYCAGGDYGFLYWGQGTLVTVSS | 305 |
| AL130 | DIQMTQSPSSLSASVGDRVTITCGASMPLFHALNWYQQK PGKAPKLLIYGATNLADGVPSRFSGSGSGRDFTFTISSL QPEDIATYYCQNVLSSPYTFGQGTKVEIK | 306 |
| AL135 | DIQMTQSPSSLSASVGDRVTITCGASENIYGALNWYQQK PGKAPKLLIYGATNLADGVPSRFSGSGSGRDFTFTISSL QPEDIATYYCQNVLEEPYTFGQGTKVEIK | 307 |
| AL165 | DIQMTQSPSSLSASVGDRVTITCGASENIYGALNWYQQK PGKAPKLLIYGATGLADGVPSRFSGSGSGRDFTFTISSL QPEDIATYYCQNVLESPYTFGQGTKVEIK | 308 |
| AL166 | DIQMTQSPSSLSASVGDRVTITCGASENIYGALNWYQQK PGKAPKLLIYGATGLADGVPSRFSGSGSGRDFTFTISSL QPEDIATYYCQNVLSEPYTFGQGTKVEIK | 309 |
| AL194 | DIQMTQSPSSLSASVGDRVTITCGASMPLFHALNWYQQK PGKAPKLLIYGATNLADGVPSRFSGSGSGRDFTFTISSL QPEDIATYYCQNVLSIPETFGQGTKVEIK | 310 |
| AL195 | DIQMTQSPSSLSASVGDRVTITCGASRSTFSALNWYQQK PGKAPKLLIYGATNLADGVPSRFSGSGSGRDFTFTISSL QPEDIATYYCQNVLEEPYTFGQGTKVEIK | 311 |

Also, an in vitro test on proliferation inhibitory activity was performed on U-87 MG cell line by using a part of the affinity-optimized antibodies, wherein results thereof are shown in Table 11.

TABLE 11

In vitro tumor cell proliferation inhibitory activity by hu8C4 light chain and heavy chain affinity-optimized antibodies

| | U-87 MG (GBM, HGF autocrine) Cell proliferation inhibition assay, IC$_{50}$ (nM) | | |
|---|---|---|---|
| Antibodies | affinity-optimized antibodies | hu8C4 | IC$_{50}$ Fold |
| hu8C4 AH71 | 11.3 | 95.5 | 8.5 |
| hu8C4 AH72 | 10.9 | 95.5 | 8.8 |
| hu8C4 AH73 | 10.9 | 95.5 | 8.8 |
| hu8C4 AH85 | 10.1 | 95.5 | 9.5 |
| hu8C4 AL130 | 5.0 | 45.0 | 9.0 |
| hu8C4 AL135 | 7.1 | 31.9 | 4.5 |
| hu8C4 AL165 | 6.8 | 39.0 | 5.7 |
| hu8C4 AL166 | 9.1 | 39.0 | 4.3 |
| hu8C4 AL194 | 9.6 | 94.5 | 9.8 |
| hu8C4 AL195 | 18.0 | 94.5 | 5.3 |

As seen in Table 11, it was identified that IC$_{50}$ of tumor cell proliferation inhibitory activity of a hu8C4 affinity-optimized antibody in a U-87 MG cell amounted to 5.0 18 nM, wherein efficacy thereof was increased 4.3-9.8 times more than a parent antibody hu8C4. The results above represent a test performed on a part of antibodies having an amino acid sequence presented in Tables 8 to 10, wherein an affinity of the parent hu8C4 antibody was optimized and all the antibodies were selected based on an antigen affinity through a selection process. Thus, it is expected that there may be a sufficiently equal effect even with regard to the rest of affinity-optimized antibodies as well as antibodies with a combination of presented heavy chain and light chain variable region CDRs.

For an additional experiment, 10 kinds of affinity-optimized antibody were prepared by combining the light chain and heavy chain variable regions. A specific combination of light chain and heavy chain sequences are shown in Table 12.

TABLE 12

List of combined variable region sequences of affinity-optimized antibody

| | Heavy chain variable region | Light chain variable region |
|---|---|---|
| hu8C4 AH71 | AH71(SEQ ID NO: 302) | Light chain variable region of hu8C4-1 antibody (SEQ ID NO: 21) |
| hu8C4 AH85 | AH85(SEQ ID NO: 305) | Light chain variable region of hu8C4-1 antibody (SEQ ID NO: 21) |
| hu8C4 AL194 | Heavy chain variable region of hu8C4-1 antibody (SEQ ID NO: 23) | AL194(SEQ ID NO: 310) |
| hu8C4 A56 | AH85(SEQ ID NO: 305) | AL165(SEQ ID NO: 308) |
| hu8C4 A62 | AH72(SEQ ID NO: 303) | AL130(SEQ ID NO: 306) |
| hu8C4 A71 | AH73(SEQ ID NO: 304) | AL135(SEQ ID NO: 307) |
| hu8C4 A72 | AH73(SEQ ID NO: 304) | AL165(SEQ ID NO: 308) |
| hu8C4 A73 | AH73(SEQ ID NO: 304) | AL166(SEQ ID NO: 309) |
| hu8C4 A76 | AH73(SEQ ID NO: 304) | AL195(SEQ ID NO: 311) |
| hu8C4 A78 | AH71(SEQ ID NO: 302) | AL130(SEQ ID NO: 306) |

Figure 3:
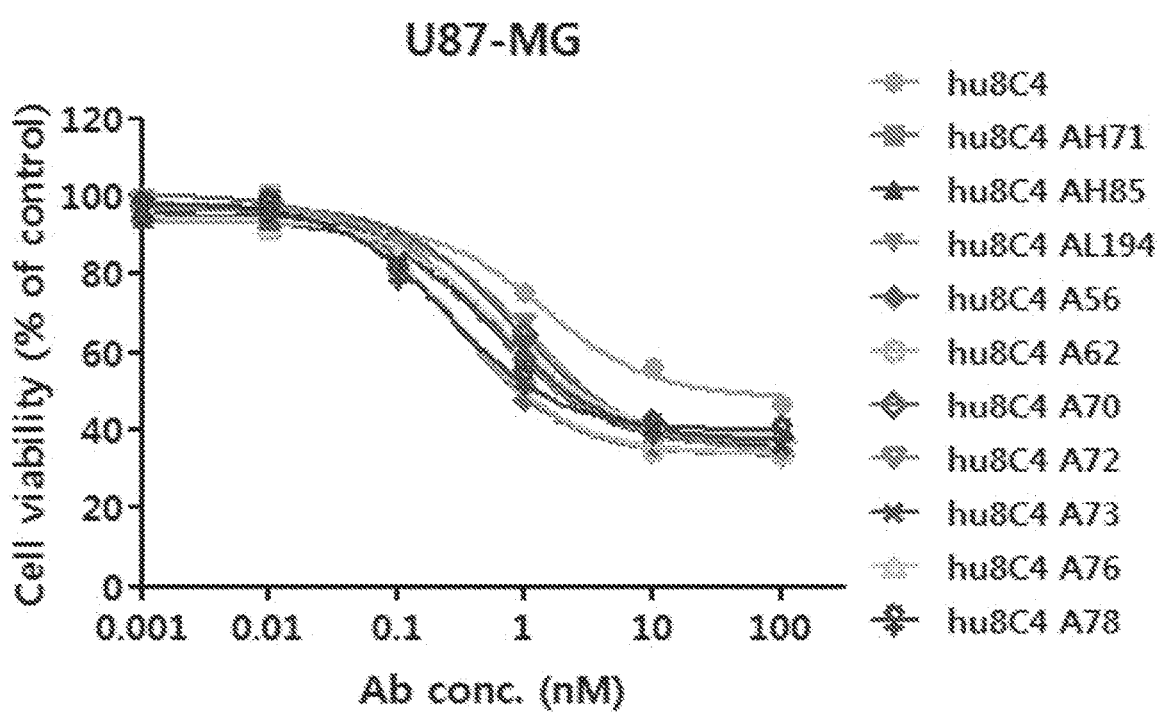
FIG. 3 shows results of analyzing a tumor cell proliferation inhibitory activity by hu8C4 affinity-optimized antibody of the present invention.

Then, a tumor cell proliferation inhibitory activity was evaluated by the same method as shown in Example 1 above, wherein results thereof are shown in Table 13 and FIG. 3.

TABLE 13

In vitro tumor cell proliferation inhibitory activity by affinity-optimized antibody

| | U-87 MG (GBM, HGF autocrine) Cell proliferation inhibition assay, IC$_{50}$ (nM) | | |
|---|---|---|---|
| Antibodies | Affinity-optimized antibody | hu8C4 | IC$_{50}$ Fold |
| hu8C4 AH71 | 3.6 | 49.0 | 13.6 |
| hu8C4 AH85 | 3.2 | 49.0 | 15.2 |
| hu8C4 AL194 | 5.3 | 49.0 | 9.2 |
| hu8C4 A56 | 1.7 | 49.0 | 28.5 |
| hu8C4 A62 | 1.8 | 49.0 | 27.6 |
| hu8C4 A71 | 5.0 | 49.0 | 9.7 |
| hu8C4 A72 | 3.6 | 49.0 | 13.8 |
| hu8C4 A73 | 4.0 | 49.0 | 12.3 |
| hu8C4 A76 | 4.3 | 49.0 | 11.3 |
| hu8C4 A78 | 2.6 | 49.0 | 18.9 |

As seen in Table 13 above, it was identified that hu8C4 as well as 10 kinds of key antibody with a combination of light chain and heavy chain variable regions of an affinity-optimized antibody thereof showed a tumor cell proliferation inhibitory activity, too. In particular, $IC_{50}$ of the 10 kinds of antibody amounted to 1.7-5.3 nM and it was identified that they had a tumor cell proliferation inhibitory effect, which was 9.2-28.5 times more excellent than the parent antibody hu8C4.

Example 6. Preparation of Bispecific Antibody and In Vitro Tumor Cell Proliferation Inhibitory Activity To prepare a bispecific antibody specifically binding to c-Met and EGFR, Erbitux and Vectibix scFv fragments, known to specifically bind to EGFR, were linked respectively to a heavy chain C-terminus of the c-Met antibody of the present invention by a GGGGSGGGGS (SEQ. No. 312) connector.

To increase the stability of the scFv, a 44th residue of a heavy chain and a 100th residue of a light chain were substituted with cystine (Reiter Y. et al., Biochemistry 33(18):5451-5459 (1994)). Erbitux and Vectibix scFv sequences, amino acid sequences of heavy chain of bispecific antibody and a combination of variable regions of bispecific antibody are shown in the following Tables 14 and 15.

TABLE 14

List of amino acid sequences of EGFR antibody for preparing bispecific antibody as well as bispecific antibody

| | Amino acids sequence | SEQ ID NOs |
|---|---|---|
| Erbitux scFv HL | QVQLKQSGPGLVQPSQSLSITCTVSGFSLTNYGVHWVRQSPGKCLEWLGVIWSGGNTDYNTPF TSRLSINKDNSKSQVFFKMNSLQSNDTAIYYCARALTYYDYEFAYWGQGTLVTVSAGGGGSGG GGSGGGGSGGGGSDILLTQSPVILSVSPGERVSFSCRASQSIGTNIHWYQQRTNGSPRLLIKY ASESISGIPSRFSGSGSGTDFTLSINSVESEDIADYYCQQNNNWPTTFGCGTKLELK | 313 |
| Erbitux scFv LH | DILLTQSPVILSVSPGERVSFSCRASQSIGTNIHWYQQRTNGSPRLLIKYASESISGIPSNFS GSGSGTDFTLSINSVESEDIADYYCQQNNNWPTTFGCGTKLELKGGGGSGGGGSGGGGSGGGG SQVQLKQSGPGLVQPSQSLSITCTVSGFSLTNYGVHWVRQSPGKCLEWLGVIWSGGNTDYNTP FTSRLSINKDNSKSQVFFKMNSLQSNDTAIYYCARALTYYDYEFAYWGQGTLVTVSA | 314 |
| Vectibix scFv | QVQLQESGPGLVKPSETLSLTCTVSGGSVSSGDYYWTWIRQSPGKCLEWIGIHYYSGNTNYNP SLKSELTISIDTSKTQFSLKLSSVTAADTAIYYCVRDRVTGAFDIWGQGTMVTVSSGGGGSGG GGSGGGGSGGGGSDIQMTQSPSSLSASVGDRVTITCQASQDISNYLNWYQQKPGKAPKLLIYD ASNLETGVPSRFSGSGSGTDFTFTISSLQPEDIATYFCQHFDHLPLAFGCGTKVEIK | 315 |
| hu8C4 x Erbitux scFv IIL heavy chain | EVQLVESGGGLVQPGGSLRLSCAASGYTFSDYYINWVRQAPGKGLEWIGEIFPGSGNTHFSAR FKGRATLSADKSKNTAYLQMNSLRAEDTAVYYCAGGDYGFLYWGQGTLVTVSSASTKGPSVFP LAPSSKSTSGGTAALGCLVKDYFPEPVTVSWNSGALTSGVHTFPAVLQSSGLYSLSSVVTVPS SSLGTQTYICNVNHKPSNTKVDKKVERKCCVECPPCPAPELLGGPSVFLPPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQKSLSLSP GKGGGGSGGGGSQVQLKQSGPGLVQPSQSLSITQTVSGFSLTNYGVHWVRQSPGKCLEWLGVI WSGGNTDYNTPFTSRLSINKDNSKSQVFFKMNSLQSNDTAIYYCARALTYYDYEFAYWGQGTL VTVSAGGGGSGGGGSGGGGSGGGGSDILLTQSPVILSVSPGERVSFSCRASQSIGTNIHWYQQ RTNGSPRLLIKYASESISGIPSRFSGSGSGTDFTLSINSVESEDIADYYCQQNNNWPTTFGCG TKLELK | 316 |
| hu8C4 AH71 x Erbitux scFv HL heavy chain | EVQLVESGGGLVQPGGSLRTSCAASGYTFSDYYINWVRQAPGKGLEWIGEIFPGWGNTHFSAR FKGRATLSADKSKNTAYLQMNSLRAEDTAVYYCAGQDYGFLYWGQGTLVTVSSASTKGPSVFP LAPSSKSTSGGTAALGCLVKDYFPEPVTVSWNSGALTSGVHTFPAVLQSSGLYSLSSVVTVPS SSLGTQTYICNVNHKPSNTKVDKKVERKCCVECPPCPAPELLGGPSVFLPPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSQSVMHEALHNHYTQKSLSLSP GKGGGGSGGGGSQVQLKQSGPGLVQPSQSLSITCTVSGFSLTNYGVHWVRQSPGKCLEWLGVI WSGGNTDYNTPFTSRLSINKDNSKSQVFFKMNSLQSNDTAIYYCARALTYYDYEFAYWGQGTL VTVSAGGGGSGGGGSGGGGSGGGGSDILLTQSPVILSVSPGERVSFSCRASQSIGTNIHWYQQ RTNGSPRLLIKYASESISGIPSRFSGSGSGTDFTLSINSVESEDIADYYCQQNNNWPTTFGCG TKLELK | 317 |
| hu8C4 AH72 x Erbitux scFv HL heavy chain | EVQTVESGGGLVQPGGSLRLSCAASGYTFSDYYINWVRQAPGKGLEWIGEIFPGWGNTHFSRS PTPRATLSADKSKNTAYLQMNSLRAEDTAVYYCAGGDYGFLYWGQGTLVTVSSASTKGPSVFP LAPSSKSTSGGTAATGCLVKDYFPEPVTVSWNSGALTSGVHTFPAVLQSSGLYSTSSVVTVPS SSLGTQTYICNVNHKPSNTKVDKKVERKCCVECPPCPAPELLGGPSVFLPPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQKSLSLSP GKGGGGSGGGGSQVQLKQSGPGLVQPSQSLSITCTVSGFSLTNYGVHWVRQSPGKCLEWLGVI WSGGNTDYNTPFTSRLSINKDNSKSQVFFKMNSLQSNDTAIYYCARALTYYDYEFAYWGQGTL VTVSAGGGGSGGGGSGGGGSGGGGSDILLTQSPVILSVSPGERVSFSCRASQSIGTNIHWYQQ RTNGSPRLLIKYASESISGIPSRFSGSGSGTDFTLSINSVESEDIADYYCQQNNNWPTTFGCG TKLELK | 318 |
| hu8C4 AH73 x Erbitux | EVQLVESGGGLVQPGGSLRLSCAASGYTFSDYYINWVRQAPGKGLEWIGEIFPGWGNSHVVSR FKGRATLSADKSKNTAYLQMNSLRAEDTAVYYCAGGDYGFLYWGQGTLVTVSSASTKGPSVFP LAPSSKSTSGGTAALGCLVKDYFPEPVTVSWNSGALTSGVHTFPAVLQSSGLYSLSSVVTVPS | 319 |

TABLE 14-continued

List of amino acid sequences of EGFR antibody for preparing
bispecific antibody as well as bispecific antibody

| | Amino acids sequence | SEQ ID NOs |
|---|---|---|
| scFv HL heavy chain | SSLGTQTYICNVNHKPSNTKVDKKVERKCCVECPPCPAPELLGGPSVFLFPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQNSLSLSP GKGGGGSGGGGSQVQLKQSGPGLVQPSQSLSITCTVSGFSLTNYGVHWVRQSPGKCLEWLGVI WSGGNTDYNTPFTSRLSINKDNSKSQVFFKMNSLQSNDTAIYYCARALTYYDYEFAYWGQGTL VTVSAGGGGSGGGGSGGGGSGGGGSDILLTQSPVILSVSPGERVSFSCRASQSIGTNIHWYQQ RTNGSPRLLIKYASESISGIPSRFSGSGSGTDFTLSINSVESEDIADYYCQQNNNWPTTFGCG TKLELK | |
| hu8C4 AH85 x Erbitux scFv HL heavy chain | EVQLVESGGGLVQPGGSLRLSCAASGYTFSDYYINWVRQAPGKGLEWIGEIFPGWGNSHVVSR FKGRATLSADKSKNTAYLQMNSLRAEDTAVYYCAGGDYGFLYWGQGTLVTVSSASTKGPSVFP LAPSSKSTSGGTAALGCLVKDYFPEPVTVSWNSGALTSGVHTFPAVLQSSGLYSLSSVVTVPS SSLGTQTYICNVNHKPSNTKVDKKVERKCCVECPPCPAPELLGGPSVFLFPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQNSLSLSP GKGGGGSGGGGSQVQLKQSGPGLVQPSQSLSITCTVSGFSLTNYGVHWVRQSPGKCLEWLGVI WSGGNTDYNTPFTSRLSINKDNSKSQVFFKMNSLQSNDTAIYYCARALTYYDYEFAYWGQGTL VTVSAGGGGSGGGGSGGGGSGGGGSDILLTQSPVILSVSPGERVSFSCRASQSIGTNIHWYQQ RTNGSPRLLIKYASESISGIPSRFSGSGSGTDFTLSINSVESEDIADYYCQQNNNWPTTFGCG TKLELK | 320 |
| hu8C4 x Erbitux scFv LH heavy chain | EVQLVESGGGLVQPGGSLRLSCAASGYTFSDYYINWVRQAPGKGLEWIGEIFPGSGNTHFSAR FKGRATLSADKSKNTAYLQMNSLRAEDTAVYYCAGGDYGFLYWGQGTLVTVSSASTKGPSVFP LAPSSKSTSGGTAALGCLVKDYFPEPVTVSWNSGALTSGVHTFPAVLQSSGLYSLSSVVTVPS SSLGTQTYICNVNHKPSNTKVDKKVERKCCVECPPCPAPELLGGPSVFLFPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQKSLSLSP GKGGGGSGGGGSDILLTQSPVILSVSPGERVSFSCRASQSIGTNIHWYQQRTNGSPRLLIKYA SESISGIPSRFSGSGSGTDFTLSINSVESEDIADYYCQQNNNWPTTFGCGTKLELKGGGGSGG GGSGGGGSGGGGSQVQLKQSGPGLVQPSQSLSITCTVSGFSLTNYGVHWVRQSPGKCLEWLGV IWSGGNTDYNTPFTSRLSINKDNSKSQVFFKMNSLQSNDTAIYYCARALTYYDYEFAYWGQGT LVTVSA | 321 |
| hu8C4 AH71 x Erbitux scFv LH heavy chain | EVQLVESGGGLVQPGGSLRLSCAASGYTFSDYYINWVRQAPGKGLEWIGEIFPGSGNTHFSAR FKGRATLSADKSKNTAYLQMNSLRAEDTAVYYCAGGDYGFLYWGQGTLVTVSSASTKGPSVFP LAPSSKSTSGGTAALGCLVKDYFPEPVTVSWNSGALTSGVHTFPAVLQSSGLYSLSSVVTVPS SSLGTQTYICNVNHKPSNTKVDKKVERKCCVECPPCPAPELLGGPSVFLFPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQKSLSLSP GKGGGGSGGGGSDILLTQSPVILSVSPGERVSFSCRASQSIGTNIHWYQQRTNGSPRLLIKYA SESISGIPSRFSGSGSGTDFTLSINSVESEDIADYYCQQNNNWPTTFGCGTKLELKGGGGSGG GGSGGGGSGGGGSQVQLKQSGPGLVQPSQSLSITCTVSGFSLTNYGVHWVRQSPGKCLEWLGV IWSGGNTDYNTPFTSRLSINKDNSKSQVFFKMNSLQSNDTAIYYCARALTYYDYEFAYWGQGT LVTVSA | 322 |
| hu8C4 AH72 x Erbitux scFv LH heavy chain | EVQLVESGGGLVQPGGSLRLSCAASGYTFSDYYINWVRQAPGKCLEWIGEIFPGWGNTHFSRS PTPRATLSADKSKNTAYLQMNSLRAEDTAVYYCAGGDYGFLYWGQGTLVTVSSASTKGPSVFP LAPSSKSTSGGTAALGCLVKDYFPEPVTVSWNSGALTSGVHTFPAVLQSSGLYSLSSVVTVPS SSLGTQTYICNVNHKPSNTKVDKKVERKCCVECPPCPAPELLGGPSVFLFPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQKSLSLSP GKGGGGSGGGGSDILLTQSPVILSVSPGERVSFSCRASQSIGTNIHWYQQRTNGSPRLLIKYA SESISGIPSRFSGSGSGTDFTLSINSVESEDIADYYCQQNNNWPTTFGCGTKLELKGGGGSGG GGSGGGGSGGGGSQVQLKQSGPGLVQPSQSLSITCTVSGFSLTNYGVHWVRQSPGKCLEWLGV IWSGGNTDYNTPFTSRLSINKDNSKSQVFFKMNSLQSNDTAIYYCARALTYYDYEFAYWGQGT LVTVSA | 323 |
| hu8C4 AH73 x Erbitux scFv LH heavy chain | EVQLVESGGGLVQPGGSLRLSCAASGYTFSDYYINWVRQAPGKGLEWIGEIFPGWGNSHVVSR FKGRATLSADKSKNTAYLQMNSLRAEDTAVYYCAGGDYGFLYWGQGTLVTVSSASTKGPSVFP LAPSSKSTSGGTAALGCLVKDYFPEPVTVSWNSGALTSGVHTFPAVLQSSGLYSLSSVVTVPS SSLGTQTYICNVNHKPSNTKVDKKVERKCCVECPPCPAPELLGGPSVFLFPPKPKDTLMISRT PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQKSLSLSP GKGGGGSGGGGSDILLTQSPVILSVSPGERVSFSCRASQSIGTNIHWYQQRTNGSPRLLIKYA SESISGIPSRFSGSGSGTDFTLSINSVESEDIADYYCQQNNNWPTTFGCGTKLELKGGGGSGG | 324 |

TABLE 14-continued

List of amino acid sequences of EGFR antibody for preparing bispecific antibody as well as bispecific antibody

| Amino acids sequence | SEQ ID NOs |
|---|---|
| GGSGGGGSGGGGSQVQLKQSGPGLVQPSQSLSITCTVSGFSLTNYGVHWVRQSPGKCLEWLGV<br>IWSGGNTDYNTPFTSRLSINKDNSKSQVFFKMNSLQSNDTAIYYCARALTYYDYEFAYWGQGT<br>LVTVSA | |
| hu8C4 AH85 x Erbitux scFv LH heavy chain — EVQLVESGGGLVQPGGSLRLSCAASGYTFSDYYINWVRQAPGKGLEWIGEIFPGWGNSHVVSR<br>FKGRATLSADKSKNTAYLQMNSLRAEDTAVYYCAGGDYGFLYWGQGTLVTVSSASTKGPSVFP<br>LAPSSKSTSGGTAALGCLVKDYFPEPVTVSWNSGALTSGVHTFPAVLQSSGLYSLSSVVTVPS<br>SSLGTQTYICNVNHKPSNTKVDKKVERKCCVECPPCPAPELLGGPSVFLFPPKPKDTLMISRT<br>PEVTCVVVDVSHEDPEVKFNWYVDGVEVHNAKTKPREEQYNSTYRVVSVLTVLHQDWLNGKEY<br>KCKVSNKALPAPIEKTISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHEALHNHYTQKSLSLSP<br>GKGGGGSGGGGSDILLTQSPVILSVSPGERVSFSCRASQSIGTNIHWTQQRTNGSPRLLIKYA<br>SESISGIPSRFSGSGSGTDFTLSINSVESEDIADYYCQQNNNWPTTFGCGTKLELKGGGGSGG<br>GGSGGGGSGGGGSQVQLKQSGPGLVQPSQSLSITCTVSGFSLTNYGVHWVRQSPGKCLEWLGV<br>IWSGGNTDYNTPFTSRLSINKDNSKSQVFFKMNSLQSNDTAIYYCARALTYYDYEFAYWGQGT<br>LVTVSA | 325 |
| hu8C4 x Vectibix scFv heavy chain | 326 |
| hu8C4 AH71 x Vectibix scFv heavy chain | 327 |
| hu8C4 AH72 x Vectibix scFv heavy chain | 328 |
| hu8C4 AH73 x Vectibix scFv heavy chain | 329 |
| hu8C4 AH85 x Vectibix scFv | 330 |

EVQLVESGGGLVQPGGSLRLSCAASGYTFSDYYINWVRQAPGKGLEWIGEIFPGSNTHFSAR
FKGRATLSADKSKNTAYLQMNSLRAEDTAVYYCAGGDYGFLYWGQGTLVTVSSASTKGPSVFP
LAPSSKSTSGGTAALGCLVKDYFPEPVTVSWNSGALTSGVHTFPAVLQSSGLYSLSSVVTVPS
SSLGTQTYICNVNHKPSNTKVDKKVERKCCVECPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSP
GKGGGGSGGGGSQVQLQESGPGLVKPSETLSLTCTVSGGSVSSGDYYWTWIRQSPGKCLEWIG
HIYYSGNTNYNPSLKSRLTISIDTSKTQFSLKLSSVTAADTAIYYCVRDRVTGAFDIWGQGTM
VTVSSGGGGSGGGGSGGGGSGGGGSDIQMTQSPSSLSASVGDRVTITCQASQDISNYLNWYQQ
KPGKAPKLLIYDASNLETGVPSRFSGSGSGTDFTFTISSLQPEDIATYFCQHFDHLPLAFGCG
TKVEIK

EVQLVESGGGLVQPGGSLRLSCAASGYTFSDYYINWVRQAPGKGLEWIGEIFPGWGNTHFSAR
FKGRATLSADKSKNTAYLQMNSLRAEDTAVYYCAGGDYGFLYWGQGTLVTVSSASTKGPSVFP
LAPSSKSTSGGTAALGCLVKDYFPEPVTVSWNSGALTSGVHTFPAVLQSSGLYSLSSVVTVPS
SSLGTQTYICNVNHKPSNTKVDKKVERKCCVECPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSP
GKGGGGSGGGGSQVQLQESGPGLVKPSETLSLTCTVSGGSVSSGDYYWTWIRQSPGKCLEWIG
HIYYSGNTNYNPSLKSRLTISIDTSKTQFSLKLSSVTAADTAIYYCVRDRVTGAFDIWGQGTM
VTVSSGGGGSGGGGSGGGGSGGGGSDIQMTQSPSSLSASVGDRVTITCQASQDISNYLNWYQQ
KPGKAPKLLIYDASNLETGVPSRFSGSGSGTDFTFTISSLQPEDIATYFCQHFDHLPLAFGCG
TKVEIK

EVQLVESGGGLVQPGGSLRLSCAASGYTFSDYYINWVRQAPGKCLEWIGEIFPGWGNTHFSRS
PTPRATLSADKSKNTAYLQMNSLRAEDTAVYYCAGGDYGFLYWGQGTLVTVSSASTKGPSVFP
LAPSSKSTSGGTAALGCLVKDYFPEPVTVSWNSGALTSGVHTFPAVLQSSGLYSLSSVVTVPS
SSLGTQTYICNVNHKPSNTKVDKKVERKCCVECPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSP
GKGGGGSGGGGSQVQLQESGPGLVKPSETLSLTCTVSGGSVSSGDYYWTWIRQSPGKCLEWIG
HIYYSGNTNYNPSLKSRLTISIDTSKTQFSLKLSSVTAADTAIYYCVRDRVTGAFDIWGQGTM
VTVSSGGGGSGGGGSGGGGSGGGGSDIQMTQSPSSLSASVGDRVTITCQASQDISNYLNWYQQ
KPGKAPKLLIYDASNLETGVPSRFSGSGSGTDFTFTISSLQPEDIATYFCQHFDHLPLAFGCG
TKVEIK

EVQLVESGGGLVQPGGSLRLSCAASGYTFSDYYINWVRQAPGKGLEWIGEIFPGWGNSHVVSR
FKGRATLSADKSKNTAYLQMNSLRAEDTAVYYCAGGDYGFLYWGQGTLVTVSSASTKGPSVFP
LAPSSKSTSGGTAALGCLVKDYFPEPVTVSWNSGALTSGVHTFPAVLQSSGLYSLSSVVTVPS
SSLGTQTYICNVNHKPSNTKVDKKVERKCCVECPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSP
GKGGGGSGGGGSQVQLQESGPGLVKPSETLSLTCTVSGGSVSSGDYYWTWIRQSPGKCLEWIG
HIYYSGNTNYNPSLKSRLTISIDTSKTQFSLKLSSVTAADTAIYYCVRDRVTGAFDIWGQGTM
VTVSSGGGGSGGGGSGGGGSGGGGSDIQMTQSPSSLSASVGDRVTITCQASQDISNYLNWYQQ
KPGKAPKLLIYDASNLETGVPSRFSGSGSGTDFTFTISSLQPEDIATYFCQHFDHLPLAFGCG
TKVEIK

EVQLVESGGGLVQPGGSLRLSCAASGYTFSDYYINWVRQAPGKGLEWIGEIFPGWGNSHVVSR
FKGRATLSADKSKNTAYLQMNSLRAEDTAVYYCAGGDYGFLYWGQGTLVTVSSASTKGPSVFP
LAPSSKSTSGGTAALGCLVKDYFPEPVTVSWNSGALTSGVHTFPAVLQSSGLYSLSSVVTVPS
SSLGTQTYICNVNHKPSNTKVDKKVERKCCVECPPCPAPELLGGPSVFLFPPKPKDTLMISRT

TABLE 14-continued

List of amino acid sequences of EGFR antibody for preparing bispecific antibody as well as bispecific antibody

| | Amino acids sequence | SEQ ID NOs |
|---|---|---|
| heavy chain | PEVTCVVVDVSHEDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQKSLSLSP GKGGGGSGGGGSQVQLQESGPGLVKPSETLSLTCTVSGGSVSSGDYYWTWIRQSPGKCLEWIG HIYYSGNTNYNPSLKSRLTISIDTSKTQFSLKLSSVTAADTAIYYCVRDRVTGAFDIWGQGTM VTVSSGGGGSGGGGSGGGGSGGGGSDIQMTQSPSSLSASVGDRVTITCQASQDISNYLNWYQQ KPGKAPKLLIYDASNLETGVPSRFSGSGSGTDFTFTISSLQPEDIATYFCQHFDHLPLAFGCG TKVEIK | |

TABLE 15

List of combined variable region sequences of bispecific antibody

| | Heavy chain variable region | Light chain variable region |
|---|---|---|
| hu8C4 × Erbitux scFv HL | hu8C4 × Erbitux scFv HL (SEQ ID NO: 316) | light chain variable region of hu8C4-1 antibody (SEQ ID NO: 21) |
| hu8C4 AH71 × Erbitux scFv HL | hu8C4 AH71 × Erbitux scFv HL (SEQ ID NO: 317) | light chain variable region of hu8C4-1 antibody (SEQ ID NO: 21) |
| hu8C4 AH85 × Erbitux scFv HL | hu8C4 AH85 × Erbitux scFv HL (SEQ ID NO: 320) | light chain variable region of hu8C4-1 antibody (SEQ ID NO: 21) |
| hu8C4 AL194 × Erbitux scFv HL | hu8C4 × Erbitux scFv HL (SEQ ID NO: 316) | AL194(SEQ ID NO: 310) |
| hu8C4 A56 × Erbitux scFv HL | hu8C4 AH85 × Erbitux scFv HL (SEQ ID NO: 320) | AL165(SEQ ID NO: 308) |
| hu8C4 A62 × Erbitux scFv HL | hu8C4 AH72 × Erbitux scFv HL (SEQ ID NO: 318) | AL130(SEQ ID NO: 306) |
| hu8C4 A71 × Erbitux scFv HL | hu8C4 AH73 × Erbitux scFv HL (SEQ ID NO: 319) | AL135(SEQ ID NO: 307) |
| hu8C4 A72 × Erbitux scFv HL | hu8C4 AH73 × Erbitux scFv HL (SEQ ID NO: 319) | AL165(SEQ ID NO: 308) |
| hu8C4 A73 × Erbitux scFv HL | hu8C4 AH73 × Erbitux scFv HL (SEQ ID NO: 319) | AL166(SEQ ID NO: 309) |
| hu8C4 A76 × Erbitux scFv HL | hu8C4 AH73 × Erbitux scFv HL (SEQ ID NO: 319) | AL195(SEQ ID NO: 311) |
| hu8C4 A78 × Erbitux scFv HL | hu8C4 AH71 × Erbitux scFv HL (SEQ ID NO: 317) | AL130(SEQ ID NO: 306) |
| hu8C4 × Erbitux scFv LH | hu8C4 × Erbitux scFv LH (SEQ ID NO: 321) | light chain variable region of hu8C4-1 antibody (SEQ ID NO: 21) |
| hu8C4 AH71 × Erbitux scFv LH | hu8C4 AH71 × Erbitux scFv LH (SEQ ID NO: 322) | light chain variable region of hu8C4-1 antibody (SEQ ID NO: 21) |
| hu8C4 AH85 × Erbitux scFv LH | hu8C4 AH85 × Erbitux scFv LH (SEQ ID NO: 325) | light chain variable region of hu8C4-1 antibody (SEQ ID NO: 21) |
| hu8C4 AL194 × Erbitux scFv LH | hu8C4 × Erbitux scFv LH (SEQ ID NO: 321) | AL194(SEQ ID NO: 310) |
| hu8C4 A56 × Erbitux scFv LH | hu8C4 AH85 × Erbitux scFv LH (SEQ ID NO: 325) | AL165(SEQ ID NO: 308) |
| hu8C4 A62 × Erbitux scFv LH | hu8C4 AH72 × Erbitux scFv LH (SEQ ID NO: 323) | AL130(SEQ ID NO: 306) |
| hu8C4 A71 × Erbitux scFv LH | hu8C4 AH73 × Erbitux scFv LH (SEQ ID NO: 324) | AL135(SEQ ID NO: 307) |
| hu8C4 A72 × Erbitux scFv LH | hu8C4 AH73 × Erbitux scFv LH (SEQ ID NO: 324) | AL165(SEQ ID NO: 308) |
| hu8C4 A73 × Erbitux scFv LH | hu8C4 AH73 × Erbitux scFv LH (SEQ ID NO: 324) | AL166(SEQ ID NO: 309) |
| hu8C4 A76 × Erbitux scFv LH | hu8C4 AH73 × Erbitux scFv LH (SEQ ID NO: 324) | AL195(SEQ ID NO: 311) |
| hu8C4 A78 × Erbitux scFv LH | hu8C4 AH71 × Erbitux scFv LH (SEQ ID NO: 322) | AL130(SEQ ID NO: 306) |
| hu8C4 × Vectibix scFv | hu8C4 × Vectibix scFv (SEQ ID NO: 326) | light chain variable region of hu8C4-1 antibody (SEQ ID NO: 21) |

TABLE 15-continued

List of combined variable region sequences of bispecific antibody

|  | Heavy chain variable region | Light chain variable region |
|---|---|---|
| hu8C4 AH71 × Vectibix scFv | hu8C4 AH71 × Vectibix scFv (SEQ ID NO: 327) | light chain variable region of hu8C4-1 antibody (SEQ ID NO: 21) |
| hu8C4 AH85 × Vectibix scFv | hu8C4 AH85 × Vectibix scFv (SEQ ID NO: 330) | light chain variable region of hu8C4-1 antibody (SEQ ID NO: 21) |
| hu8C4 AL194 × Vectibix scFv | hu8C4 × Vectibix scFv (SEQ ID NO: 326) | AL194(SEQ ID NO: 310) |
| hu8C4 A56 × Vectibix scFv | hu8C4 AH85 × Vectibix scFv (SEQ ID NO: 330) | AL165(SEQ ID NO: 308) |
| hu8C4 A62 × Vectibix scFv | hu8C4 AH72 × Vectibix scFv (SEQ ID NO: 328) | AL130(SEQ ID NO: 306) |
| hu8C4 A71 × Vectibix scFv | hu8C4 AH73 × Vectibix scFv (SEQ ID NO: 329) | AL135(SEQ ID NO: 307) |
| hu8C4 A72 × Vectibix scFv | hu8C4 AH73 × Vectibix scFv (SEQ ID NO: 329) | AL165(SEQ ID NO: 308) |
| hu8C4 A73 × Vectibix scFv | hu8C4 AH73 × Vectibix scFv (SEQ ID NO: 329) | AL166(SEQ ID NO: 309) |
| hu8C4 A76 × Vectibix scFv | hu8C4 AH73 × Vectibix scFv (SEQ ID NO: 329) | AL195(SEQ ID NO: 311) |
| hu8C4 A78 × Vectibix scFv | hu8C4 AH71 × Vectibix scFv (SEQ ID NO: 327) | AL130(SEQ ID NO: 306) |

Then, an in vitro anticancer efficacy of a bispecific antibody linking Erbitux and Vectibix scFv fragments was evaluated in a U-87 MG tumor cell line by the same method as shown in Example 1.

Also, a tumor cell proliferation inhibitory activity was evaluated by using NCI-H1993, NCI-H292 and NCI-H820 lung cancer cell lines. Particularly, with regard to an NCI-H1993 (ATCC, # CRL-5909) cell line with c-Met gene overexpressed therein, an NCI-H292 (ATCC, # CRL-1848) cell line with EGFR and c-Met normally expressed therein, and NCI-H820 (ATCC, # HTB-181) with threonine (T) mutated into methionine (M) in EGFR amino acid no. 790, a tumor cell proliferation inhibitory activity was performed by the following method. Each cell line was diluted in an RPMI-1640 medium (Gibco, # A10491) containing 10% (v/v) FBS, after which the resulting cell lines were divided by $2.0 \times 10^3$ into each well of a 96-well plate, such that the resulting plate was cultured overnight under 37° C., 5% $CO_2$ conditions. Then, each well of the plate was replaced with 100 μl of a serum-free medium, after which the resulting plate was cultured under 37° C., 5% $CO_2$ conditions for 18 hours. After that, the medium was replaced with 100 μl of the RPMI-1640 medium containing 2% (v/v) FBS or HGF 50 ng/ml, after which a test antibody was sequentially diluted at a ratio of 1/10 (i.e., 100 nM, 10 nM, 1 nM, 100 pM, 10 pM and 1 pM) to reach 0.001 nM at a final concentration of 100 nM, such that the resulting antibody was added by 100 μl into each well. Subsequently, the plate was cultured for 5 days under 37° C., 5% $CO_2$ conditions, after which the medium was removed therefrom, such that a TCA solution was inserted by 200 μl into each well to fix cells. Also, the cells of the plate were dyed according to a conventional SRB colorimetric assay method, after which an optical density of each well was measured at a wavelength of 540 nm by using a microplate reader.

Figure 4:
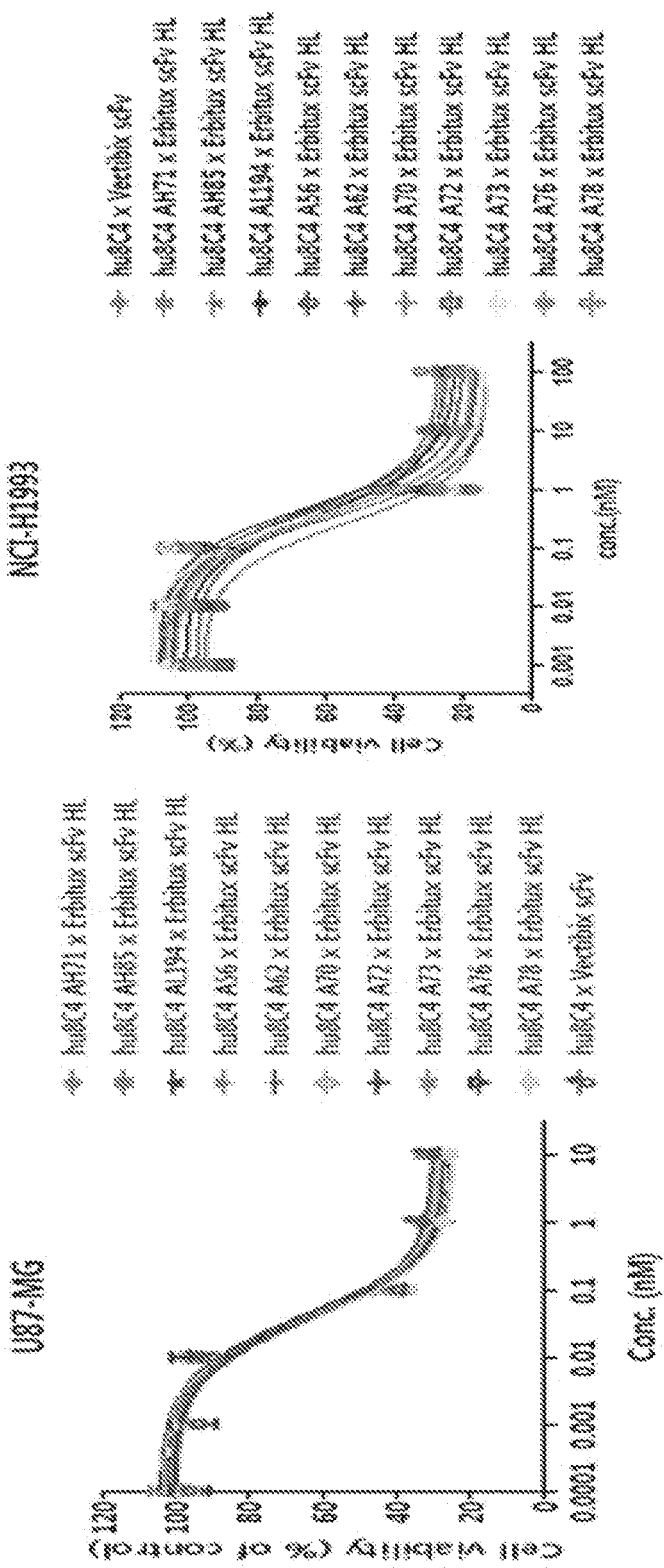
FIG. 4 shows results of analyzing a tumor cell proliferation inhibitory activity by a bispecific antibody of the present invention.
Figure 5:
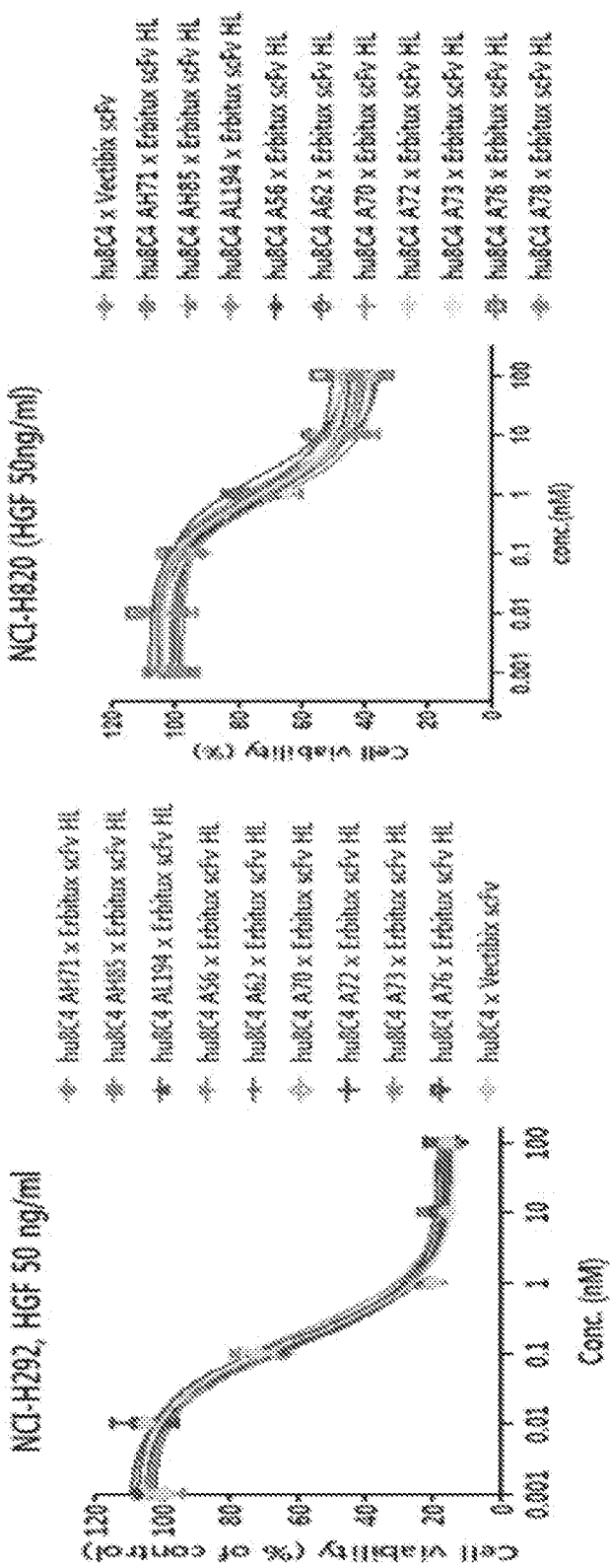
FIG. 5 shows results of analyzing a tumor cell proliferation inhibitory activity by a bispecific antibody of the present invention.

Results of proliferation inhibitory activity in each cell line above are shown in Tables 16 and 17 and FIGS. 4 and 5.

TABLE 16

In vitro tumor cell proliferation inhibitory activity by bispecific antibody

| | Cell proliferation inhibition assay, $IC_{50}$ (nM) | |
|---|---|---|
| Bispecific antibodies | U-87 MG (GBM, IIGF autocrine) | NCI-H1993 (NSCLC, c-Met amplified) |
| hu8C4 × Vectibix scFv | 0.06 | 0.32 |
| hu8C4 AH71 × Erbitux scFv HL | 0.06 | 0.41 |
| hu8C4 AH85 × Erbitux scFv HL | 0.06 | 0.48 |
| hu8C4 AL194 × Erbitux scFv HL | 0.07 | 0.64 |
| hu8C4 A56 × Erbitux scFv HL | 0.07 | 0.57 |
| hu8C4 A62 × Erbitux scFv HL | 0.08 | 0.65 |
| hu8C4 A70 × Erbitux scFv HL | 0.07 | 0.67 |
| hu8C4 A72 × Erbitux scFv HL | 0.06 | 0.49 |
| hu8C4 A73 × Erbitux scFv HL | 0.06 | 0.50 |
| hu8C4 A76 × Erbitux scFv HL | 0.06 | 0.49 |
| hu8C4 A78 × Erbitux scFv HL | 0.06 | 0.76 |

TABLE 17

In vitro lung cancer cell line proliferation inhibitory activity by bispecific antibody

| | Cell proliferation inhibition assay, $IC_{50}$ (nM) | | | |
|---|---|---|---|---|
| | NCI-H292 (NSCLC) | | NCI-H820 (NSCLC:EGFR T790M, c-Met amplified) | |
| Bispecific antibodies | no HGF | HGF 50 ng/ml | no HGF | HGF 50 ng/ml |
| hu8C4 × Vectibix scFv | 0.70 | 0.24 | >100 | 4.2 |
| hu8C4 AH71 × Erbitux scFv HL | 0.51 | 0.22 | >100 | 8.5 |
| hu8C4 AH85 × Erbitux scFv HL | 0.43 | 0.23 | >100 | 7.6 |
| hu8C4 AL194 × Erbitux scFv HL | 0.41 | 0.24 | >100 | 19.0 |

TABLE 17-continued

In vitro lung cancer cell line proliferation inhibitory activity by bispecific antibody

| | Cell proliferation inhibition assay, $IC_{50}$ (nM) | | | |
|---|---|---|---|---|
| | NCI-H292 (NSCLC) | | NCI-H820 (NSCLC:EGFR T790M, c-Met amplified) | |
| Bispecific antibodies | no HGF | HGF 50 ng/ml | no HGF | HGF 50 ng/ml |
| hu8C4 A56 × Erbitux scFv HL | 0.42 | 0.29 | >100 | 21.7 |
| hu8C4 A62 × Erbitux scFv HL | 0.74 | 0.28 | >100 | 40.2 |
| hu8C4 A70 × Erbitux scFv HL | 0.74 | 0.23 | >100 | 40.9 |
| hu8C4 A72 × Erbitux scFv HL | 0.78 | 0.23 | >100 | 19.5 |
| hu8C4 A73 × Erbitux scFv HL | 0.87 | 0.26 | >100 | 38.4 |
| hu8C4 A76 × Erbitux scFv HL | 0.73 | 0.21 | >100 | 10.3 |

In result, there was no difference in efficacy between bispecific antibodies prepared from U-87 MG tumor cell line by the method and it was identified that an activity inhibitory efficacy thereof was about 15 times more excellent than $IC_{50}$ of hu8C4 optimized antibody. Also, as a result of evaluating a tumor cell proliferation inhibitory activity using NCI-H1993, NCI-H292 and NCI-H820 lung cancer cell lines, it was identified that there was no difference in efficacy between bispecific antibodies prepared.

Such the results suggest that the antibody of the present invention has a proliferation inhibitory effect on all the cancer types regardless of an overexpression or mutation of c-Met and EGFR, thus may be effectively used in these cancer types.

Example 7. Comparative Evaluation of In Vitro Tumor Cell Proliferation Inhibitory Activity of Bispecific Antibody Compared to Combined Therapy Eight types of cancer were used to compare a tumor cell proliferation inhibitory activity between a combined therapy of each antibody targeting c-Met and EGFR respectively and the bispecific antibody of the present invention.

Particularly, a tumor cell proliferation inhibitory activity was evaluated in a lung cancer cell line NCI-H292 (ATCC, # CRL-1848), an HGF-autocrinal glioblastoma cell line U-87 MG (ATCC, # HTB-14), lung cancer cell lines NCI-H1648 (ATCC # CRL-5882) and NCI-H596 (ATCC # HTB-178), HCC827 (ATCC, # CRL2868), a colon cancer cell line LS174T (ATCC, # CL-188), a triple negative breast cancer (TNBC) cell line BT20 (ATCC, # HTB-19) and a pancreatic cancer cell line KP4 (JCRB, # RCB1005). The NCI-H1648 cell line is characterized by a normal expression of EGFR and c-Met, the NCI-H596 cell line is characterized by a deletion of some sequence of exon no. 14 of MET gene, and the HCC827 cell line is characterized by a deletion of some sequence of exon no. 19 of EGFR gene. Also, the LS174T cell line has a KRAS mutation and the KP4 is characterized by autocrining HGF.

The U-87 MG cell line was evaluated by a method of Example 1 and the NCI-H292 cell line was evaluated by a method of Example 6. Also, the NCI-H1648, NCI-H596 and HCC827 cell lines were diluted in an RPMI-1640 medium (Gibco, # A10491) containing 10% (v/v) FBS, after which the resulting cell lines were divided by $2.0 \times 10^3$ in each well of a 96-well plate. The LS174T cell line was diluted in a DMEM medium (Gibco, #11995-065) containing 10% (v/v) FBS, after which the resulting cell lines were divided by $2.0 \times 10^3$. The BT20 cell line was diluted in an EMEM medium (ATCC, #30-2003) containing 10% (v/v) FBS, after which the resulting cell lines were divided by $3.0 \times 10^3$. And, the KP4 cell line was diluted in an RPMI-1640 medium (Gibco, # A10491) containing 10% (v/v) FBS, after which the resulting cell lines were divided by $1.5 \times 10^3$, such that the resulting plate was cultured overnight under 37° C., 5% $CO_2$ conditions. Then, each well of the plate was replaced with 100 μl of a serum-free medium, after which the resulting plate was cultured under 37° C., 5% $CO_2$ conditions for 18 hours. After that, the medium was replaced with 100 μl of the RPMI-1640 medium containing 2% (v/v) FBS or HGF 50 ng/ml, after which a test antibody was sequentially diluted at a ratio of 1/10 (i.e., 100 nM, 10 nM, 1 nM, 100 pM, 10 pM and 1 pM) to reach 1 pM at a final concentration of 100 nM, such that the resulting antibody was added by 100 μl into each well. Then, the plate was incubated for 5 days under 37° C., 5% $CO_2$ conditions, after which the medium was removed therefrom, such that a TCA solution was inserted by 200 μl into each well to fix cells. Also, the cells of the plate were dyed according to a conventional SRB colorimetric assay method, after which an optical density of each well was measured at a wavelength of 540 nm by using a microplate reader.

Results of this Example are shown in Tables 18 to 21 and FIGS. 6 to 8.

TABLE 18

Comparative evaluation of in vitro tumor cell proliferation inhibitory activity between combined therapy and bispecific antibody in U-87 MG and NCI-H292 cell lines

| | Cell proliferation inhibition assay, $IC_{50}$ (nM) | | |
|---|---|---|---|
| | U-87 MG | NCI-H292 (NSCLC) | |
| Antibodies | (GBM, HGF autocrine) | No HGF | HGF 50 ng/ml |
| Vectibix | >100 | 0.09 | >100 |
| hu8C4 | 83.9 | >100 | >100 |
| hu8C4 + Vectibix combined | 79.0 | 0.10 | 0.34 |
| hu8C4 × Vectibix scFv | 0.4 | 0.15 | 0.12 |
| C-EM1-MAb | >100 | 5.29 | 5.73 |
| C-LA480 | 858.8 | — | — |
| C-OA-5D5 | 171.9 | — | — |
| C-AbF46 | >100 | — | — |

TABLE 19

Comparative evaluation of in vitro tumor cell proliferation inhibitory activity between combined therapy and bispecific antibody in NCI-H1648 and NCI-H596 cell lines

| | Cell proliferation inhibition assay, IC$_{50}$ (nM) | | | |
|---|---|---|---|---|
| | NCI-H1648 (NSCLC) | | NCI-H596 (NSCLC, c-Met mutated) | |
| Antibodies | No HGF | HGF 50 ng/ml | No HGF | HGF 50 ng/ml |
| Vectibix | >100 | >100 | >100 | >100 |
| hu8C4 | >100 | >100 | >100 | 2.3 |
| hu8C4 + Vectibix combined | >100 | >100 | >100 | 2.4 |
| hu8C4 × Vectibix scFv | 15.4 | 29.5 | >100 | 0.4 |

TABLE 20

Comparative evaluation of in vitro tumor cell proliferation inhibitory activity between combined therapy and bispecific antibody in LS174T, BT20 and KP4 cell lines

| | Cell proliferation inhibition assay, IC$_{50}$ (nM) | | |
|---|---|---|---|
| | LS174T (Colon, KRAS G12V) HGF 50 ng/ml | BT20 (TNBC) HGF 50 ng/ml | KP4 (Pancreas) HGF autocrine |
| Antibodies | | | |
| Vectibix | >100 | >100 | >100 |
| hu8C4 | >100 | >100 | 42.0 |
| hu8C4 + Vectibix combined | 34.4 | >100 | 36.4 |
| hu8C4 × Vectibix scFv | 33.4 | ~100 | 27.0 |
| C-EM1-MAb | — | >100 | >100 |

TABLE 21

Comparative evaluation of in vitro tumor cell proliferation inhibitory activity between combined therapy and bispecific antibody in HCC827 and NCI-H596 cell lines

| | Cell proliferation inhibition assay, IC$_{50}$ (nM) | | |
|---|---|---|---|
| | HCC827 (NSCLC, EGFR mutated) | | NCI-H596 (NSCLC, c-Met mutated) |
| Antibodies | No HGF | HGF 50 ng/ml | HGF 50 ng/ml |
| Tarceva | 2.96 | >100 | >100 |
| Vectibix | >100 | >100 | >100 |
| hu8C4 | >100 | >100 | 67.2 |
| hu8C4 × Vectibix scFv | >100 | >100 | 0.8 |
| LA480 | >100 | >100 | >100 |
| INC280 | >100 | >100 | 42.5 |
| EMD1214063 | >100 | >100 | 68.2 |
| Xalkori | — | — | 87.3 |
| Tarceva + hu8C4 combined | 3.24 | 3.09 | — |
| Tarceva + hu8C4 × Vectibix scFv combined | 2.35 | 2.42 | — |
| Tarceva + LA480 combined | 3.24 | 4.78 | — |
| Tarceva + INC280 combined | 3.06 | 2.88 | — |
| Tarceva + EMD1214063 combined | 2.80 | 4.10 | — |

In result, it was identified that a tumor cell proliferation inhibitory capacity of the bispecific antibody of the present invention was more excellent than that of hu8C4, Vectibix or a combined therapy of two antibodies in the 8 kinds of tumor cell line all. Also, it was identified that it had a remarkably excellent tumor cell proliferation inhibitory capacity in U-87MG, NCI-H292, BT20 and KP4 cell lines when compared to EM1-MAb (Janssen) used as a control bispecific antibody.

Moreover, it was identified that both hu8C4 and hu8C4× Vectibix scFv had an excellent tumor cell proliferation inhibitory capacity compared to a control antibody, when compared to LA480 (Lilly), OA-5D5 (Genentech) and AbF46 (Samsung), which were c-Met target antibodies in U-87MG cell lines.

Also, Tarceva, an EGFR tyrosine kinase inhibitor in HCC827 cell line, showed resistance under HGF processing conditions, but it was identified that it showed an excellent tumor cell proliferation inhibitory capacity when being processed in combination with Tarceva, hu8C4, hu8C4× Vectibix scFv or c-Met inhibitors under such conditions.

Also, as a result of comparing various EGFR inhibitors and c-Met inhibitors in NCI-H596 cell line, it was identified that a tumor cell proliferation inhibitory capacity of hu8C4× Vectibix scFv was excellent compared to EGFR or c-Met single target drug.

Example 8. Measurement of Binding Capacity to ECD (BIAcore)

Then, to measure a binding capacity of the c-Met antibody of the present invention to an extracellular domain (ECD), binding of c-Met antibody and bispecific antibody to c-Met ECD and EGFR ECD was measured between human and cynomolgus monkey by using BIAcore.

Particularly, a human c-Met ECD (ACROBiosystems, MET-H5227), a cynomolgus monkey c-Met ECD (SiNo. Biological, 90304-CO8H), a human EGFR ECD strep (ACROBiosystems, EGR-H5285) and a cynomolgus monkey EGFR ECD (SiNo. Biological, 90285-008B) were used.

First of all, to capture an anti-c-Met antibody and a bispecific antibody, an Fc-specific anti-human IgG antibody (SouthernBiotech, 2047-01) was fixed to a CM5 sensor chip in the level of 10000 RU. The antibodies were diluted in HBS-EP buffer (0.01 M HEPES pH 7.4, 0.15 M NaCl, 3 mM EDTA and 0.005% (v/v) Surfactant P20) at a concentration of 1-2 μg/ml, after which the resulting antibodies were injected into a CM5 chip with an anti-human Ig Fc fixed thereto at a flow rate of 30 μl/min for 10-120 seconds, and then captured in a range of 150-200 RU. Each antigen was used after being diluted at 10, 5, 2.5, 1.25, 0.625, 0.3125 and 0.15625 nM, after which the resulting antigens were sequentially injected from a lower concentration. Then, the resulting antigens were injected at a flow rate of 30 μl/min for 5 minutes to carry out binding, after which a running buffer was injected thereinto for 10-15 minutes to carry out a dissociation. 15 μl of 10 mM Glycine-HCl (pH 1.5) was used to revive the chip. A binding and dissociation speed for each cycle was evaluated by using a "1:1 Langmuir binding" model in BIAevaluation software version 4.1, and biacore data are summarized in Tables 22 and 23.

TABLE 22

Measurement of affinity to c-Met ECD

| | Binding constant ($k_{on}$, 1/Ms) | Dissociation constant ($k_{off}$, 1/s) | Affinity to antigen ($K_D$, M) |
|---|---|---|---|
| hu8C4 | | | |
| Human c-Met | $6.77 \times 10^5$ | $2.148 \times 10^{-4}$ | $3.173 \times 10^{-10}$ |
| Cynomolgus monkey c-Met | $7.467 \times 10^5$ | $3.447 \times 10^{-4}$ | $4.616 \times 10^{-10}$ |
| hu8C4 AH71 | | | |
| Human c-Met | $8.306 \times 10^5$ | $8.301 \times 10^{-5}$ | $9.993 \times 10^{-11}$ |
| Cynomolgus monkey c-Met | — | — | — |
| hu8C4 × Vectibix scFv | | | |
| Human c-Met | $7.339 \times 10^5$ | $2.041 \times 10^{-4}$ | $2.78 \times 10^{-10}$ |
| Cynomolgus monkey c-Met | $7.77 \times 10^5$ | $3.37 \times 10^{-4}$ | $4.338 \times 10^{-10}$ |

TABLE 23

Measurement of affinity to EGFR ECD

| | Binding constant ($k_{on}$, 1/Ms) | Dissociation constant ($k_{off}$, 1/s) | Affinity to antigen ($K_D$, M) |
|---|---|---|---|
| Vectibix | | | |
| Human EGFR | $5.278 \times 10^5$ | $1.5 \times 10^{-4}$ | $2.841 \times 10^{-10}$ |
| Cynomolgus monkey EGFR | $9.37 \times 10^5$ | $1.963 \times 10^{-4}$ | $2.095 \times 10^{-10}$ |
| hu8C4 × Vectibix scFv | | | |
| Human EGFR | $7.776 \times 10^4$ | $1.257 \times 10^{-4}$ | $1.617 \times 10^{-9}$ |
| Cynomolgus monkey EGFR | $1.424 \times 10^5$ | $1.274 \times 10^{-4}$ | $8.942 \times 10^{-10}$ |

The data were used to prove that the hu8C4, hu8C4×Vectibix scFv bispecific antibodies of the present invention bind to c-Met ECD of human and cynomolgus monkey with an excellent affinity.

Example 9. Measurement of c-Met Antibody Binding Capacity to c-Met ECD, EGFR ECD Between Various Animal Species (ELISA)

Binding of c-Met antibody and bispecific antibody to c-Met ECD and EGFR ECD between mouse, cynomolgus monkey and human was measured by using ELISA.

Particularly, mouse c-Met (SiNo. Biological Inc, 50622-M08H), cynomolgus monkey c-Met (SiNo. Biological Inc, 90304-CO8H), human c-Met (R&D Systems, 358-MT), mouse EGFR (SiNo. Biological Inc, 51091-M08H), cynomolgus monkey EGFR (SiNo. Biological, 90285-008B) and human EGFR (Abcam, 155639) antigens were all divided into a 96-well plate at a concentration of 2 μg/ml, after which the resulting plate was reacted at 4° C. overnight. After being blocked at room temperature for 1 hour, hu8C4×Vectibix scFv bispecific antibody was sequentially diluted at a ratio of 1/5 from 100 nM to measure its binding capacity in 7 concentration sections (i.e., 100 nM, 20 nM, 4 nM, 800 pM, 160 pM, 32 pM and 6.4 pM).

After binding the hu8C4×Vectibix scFv bispecific antibody at room temperature for 1 hour, anti-human IgG, F(ab')$_2$ fragment specific-HRP conjugated antibody (Jackson Immunoresearch, 109-035-097) was diluted at a ratio of 1:2500, after which the resulting antibody was reacted at room temperature for 1 hour. Color development was made by using TMB (Sigma, T4444) solution, wherein its value was measured at an optical density of 450 nm and its ELISA results are shown in FIG. 9.

In result, it was identified that hu8C4 monospecific antibody and hu8C4×Vectibix scFv bispecific antibody did not bind to a mouse c-Met and a mouse EGFR, but bind to monkey and human c-Mets and EGFRs. Also, it was identified that a human IgG antibody, used as a negative control group, did not bind at all. The results above suggest that the c-Met antibody of the present invention is specific only to human and monkey c-Mets and EGFRs.

Example 10. Cross-Reactivity of c-Met Antibody to Various Receptors on the Surface of Cells Specificity of hu8C4 antibody specifically binding to c-Met according to the present invention as well as its cross-reactivity to other receptor tyrosine kinase antigens were analyzed by an indirect ELISA method, and 5 antigens of FGF R3, VEGFR R2, IGF IR, PDGF R and RON were selected out of key receptor tyrosine kinases to perform an analysis.

In this Example, human c-Met Fc chimera (R&D systems, 358-MT_CF), human FGF R3 (IIIc) Fc chimera (R&D systems, 766-FR), human IGF-I R (R&D systems, 391-GR-050), human PDGF Rβ Fc chimera (R&D systems, 385-PR_CF), human VEGF R2 Fc chimera (R&D systems, 357-KD_CF) and human MSP R/Ron (R&D systems, 1947-MS-050) were used as an antigen.

Each antigen was diluted in 0.05 M carbonate-bicarbonate (Sigma, C3041) buffer at a concentration of 1 μg/ml, after which the resulting antigen was added into each well of a 96-well plate (Corning, #2592), such that the resulting plate was coated at 4° C. overnight. The plate was washed once with TBS-T, after which TBS-T containing 4%—skim milk was added by 200 μl into each well of the resulting plate in order to inhibit a non-specific binding, such that the resulting plate was reacted at 37° C. for 1 hour. Then, the plate was washed once with TBS-T buffer, after which a primary antibody was sequentially diluted in TBS-T buffer containing 2%—skim milk from a highest concentration of 30 nM to 0.002 nM, such that the resulting antibody was added by 100 μk into each well, thus being reacted at 37° C. for 2 hours. After being washed three times with TBS-T buffer, an anti-human kappa light chains-peroxidase (Sigma, A7164) was diluted at a ratio of 1:5000 as a secondary antibody, after which the resulting antibody was added by 100 μl into each well, thus being reacted at 37° C. for 1 hour. Then, after being washed three times with TBS-T buffer, TMB solution (Sigma, T4444) was added by 100 μl into each well to carry out an color developing reaction, after which 2 N ammonium sulfate solution was added by 50 μl into each well to stop the reaction. An optical density was measured based on a value at a wavelength of 450 nm by using a microplate reader and a reference wavelength of 570 nm was used. A degree of binding of an anti-c-Met antibody to each antigen was proportionate to an optical density signal value, wherein results thereof are shown in Table 24.

TABLE 24

Binding specificity of anti-c-Met antibody hu8C4 to various antigens

| Ab. conc. | hu8C4 binding ($A_{450\ nm}$-$A_{570\ nm}$) | | | | | | | | | | |
|---|---|---|---|---|---|---|---|---|---|---|---|
| (nM) | c-Met | | IGF-IR | | RON | | PDGFR | | VEGFR2 | | FGFR3 | |
| 30.000 | 2.55 | 2.51 | 0.00 | 0.00 | 0.00 | 0.00 | 0.01 | 0.01 | 0.00 | 0.01 | 0.01 | 0.02 |
| 6.000 | 1.96 | 2.03 | 0.00 | 0.00 | 0.00 | 0.00 | −0.01 | −0.01 | −0.01 | −0.01 | 0.00 | 0.01 |
| 1.200 | 1.81 | 1.74 | 0.00 | 0.00 | 0.00 | 0.00 | −0.01 | −0.01 | −0.01 | −0.01 | 0.00 | 0.01 |
| 0.240 | 1.48 | 1.54 | 0.00 | 0.00 | 0.00 | 0.00 | −0.01 | −0.01 | −0.02 | −0.02 | −0.01 | 0.00 |
| 0.048 | 0.76 | 0.76 | 0.00 | 0.00 | 0.00 | 0.00 | −0.01 | −0.01 | −0.02 | −0.01 | 0.00 | 0.00 |
| 0.010 | 0.21 | 0.20 | 0.00 | 0.00 | 0.00 | 0.00 | −0.01 | −0.01 | −0.01 | −0.01 | 0.00 | 0.00 |
| 0.002 | 0.05 | 0.05 | 0.00 | 0.00 | 0.00 | 0.00 | −0.01 | −0.01 | −0.01 | −0.01 | 0.00 | 0.00 |
| Blank | 0.00 | 0.00 | 0.00 | 0.00 | 0.00 | 0.00 | 0.00 | 0.00 | 0.00 | 0.00 | 0.00 | 0.00 |

As seen in Table 24, the hu8C4 antibody of the present invention preferentially binds to c-Met, and it was identified that it did hardly bind to other antigens of FGF R3, VEGFR R2, IGF IR, PDGF R and RON.

Example 11. In Vitro Internalization Activity of c-Met Antibody and c-Met Level Inhibitory Activity of Bispecific Antibody It was identified that the c-Met antibody of the present invention had an in vitro internalization activity in tumor cells as well as an effect on reducing a receptor level by a bispecific antibody capable of simultaneously binding to c-Met and EGFR.

First of all, an antibody internalization occurs by a physiological activity of a normal receptor, wherein, when binding to a specific ligand, the receptor normally expressed outside cells becomes activated through a homo- or heterodimerization and causes a receptor-mediated endocytosis. An antibody specific to a receptor of a cell has a capacity to induce such phenomenon and is internalized into the cell by causing the endocytosis, thus inducing a decomposition of the receptor, reducing a degree of expression thereof, and possibly inhibiting a signal transduction by a certain receptor. An amount of antibodies bound outside cells may be detected by using a fluorescence-activated cell sorting (FACS) device, thus finding an amount of antibodies internalized inside the cells. In case of binding antibodies by using an antibody with FITC binding to an anti-human kappa LC as a secondary antibody for a light chain of an antibody to be measured, it is possible to quantitatively measure an amount of antibodies, which are not internalized, but remain binding to a target receptor outside cells, thus identifying an amount of internalized antibodies accordingly. It is possible to measure a background signal by a non-specific binding of an antibody used in a test by using a human IgG antibody, non-specific to an antigen, thus measuring a fluorescent signal by an actual specific binding.

In this Example, a MKN45 cell line (# JCRB0254), which was a stomach cancer cell line, was used to identify an in vitro internalization activity of c-Met antibody inside tumor cells. MKN45 expresses a c-Met receptor at a high level by amplification of MET gene, such that a phosphorylation of the c-Met receptor is induced in an HGF-nondependent way. A test was performed as follows to see if a c-Met receptor is internalized into a cell by an anti-c-Met antibody hu8C4, thus reducing a level of expression.

First of all, MKN45 stomach cancer cell lines were divided by $5.0 \times 10^5$ into each well of a 6-well plate containing an RPMI-1640 medium (2 ml) containing 10% (v/v) FBS, after which the plate was cultured under 37° C., RH 95% and 5% $CO_2$ conditions for 24 hours. An anti-c-Met antibody to be analyzed as well as an anti-IgG antibody (control group) were diluted to reach a final concentration of 100 nM, after which the resulting antibodies were reacted overnight. As a plate to be used as a non-internalized control group was treated as an anti-c-Met antibody and a human IgG antibody (control group), after which the resulting plate was reacted at 4° C. for 1 hour. Then, cells of each well were collected with 1 ml of an enzyme-free cell dissociation buffer (Gibco, #13151), after which the collected cells were washed twice with a cold PBS. As a secondary antibody, anti-human kappa LC-FITC (LSBio # LS-C60539) was diluted at a ratio of 1:2000, after which the resulting antibody was added thereinto, thus being reacted at 4° C. for 1 hour. Then, the cells were washed twice with PBS, after which the resulting cells were fixed with 100 μl of BD Cytofix (BD, #554655) and washed once with PBS, such that an FITC geo-mean (MFI) value, a degree of fluorescent staining, was measured by using a BD FACS Canto II parenchymatous cell analyzer. An amount of antibodies bound outside cells was obtained by a following formula, wherein results thereof are shown in Table 25.

Surface bound $Ab(\%) = [(MFI_{[37°\ C.\ exp.]} - MFI_{[IgG\ control]})/(MFI_{[4°\ C.\ control]} - MFI_{[IgG\ control]})] \times 100$

TABLE 25

Measurement of internalization of hu8C4 and OA-5D5 control antibodies to MKN45 stomach cancer cell line

| Antibody | OA-5D5 | hu8C4 |
|---|---|---|
| FITC MFI [IgG control] | 127 | 127 |
| FITC MFI [4° C. control] | 1763 | 1444 |
| FITC MFI [37° C. exp.] | 1724 | 858 |
| Surface bound Ab(%) | 98 | 56 |

As seen in Table 25 above, it can be shown that OA-5D5, an anti-c-Met antibody used as a control group, was hardly internalized into cells, while the hu8C4 antibody of the present invention was internalized about 40% or more into cells in MKN45 stomach cancer cell line. That is, it is shown that the hu8C4 antibody remarkably reduces a level of expression of a c-Met receptor.

Then, a test for measuring a receptor level on NCI-H820 lung cancer cell line was performed in order to identify an effect of reducing a receptor level by a bispecific antibody capable of simultaneously binding to c-Met receptor and EGFR receptor. The NCI-H820 cell line is a cell line suitable for measuring an effect of reducing a receptor level by an anti-c-Met×EGFR bispecific antibody, because a c-Met receptor was expressed in a level of about 83,000 SABC (specific antibody-binding capacity) and an EGFR receptor is expressed in a level of about 74,000 SABC.

First of all, NCI-H820 cell lines were divided by $1.0 \times 10^5$ into each well of a 6-well plate with an RPMI-1640 medium (2 ml) containing 10% (v/v) FBS, after which the resulting plate was cultured overnight under 37° C., RH 95% and 5% $CO_2$ conditions for 24 hours. Then, it was replaced with a serum-free medium, after which the resulting plate was cultured overnight under 37° C., RH 95% and 5% $CO_2$ conditions for 24 hours. Then, an anti-c-Met antibody, an anti-c-Met x EGFR bispecific antibody, an anti-EGFR antibody and a human IgG antibody as a control group, which were to be analyzed, were diluted and treated in a medium containing 2%—FBS to reach a final concentration of 10 nM, after which the resulting antibodies were cultured for 5 days. After that, cells of each well were collected with 1 ml of an enzyme-free cell dissociation buffer, after which the collected cells were washed twice with a cold PBS. Subsequently, goat F(ab')$_2$ anti-mouse IgG-CSF (R&D Systems Cat. # F0103B) was added by 10 µl into each well as a secondary antibody, thus being reacted at 4° C. for 1 hour. Then, the cells were washed twice with PBS, after which the resulting cells were fixed with 100 µl of BD Cytofix (BD, #554655) and washed once with PBS, such that an FITC geo-mean (MFI) value, a degree of fluorescent staining, was measured by using a BD FACS Canto II parenchymatous cell analyzer.

Figure 10:
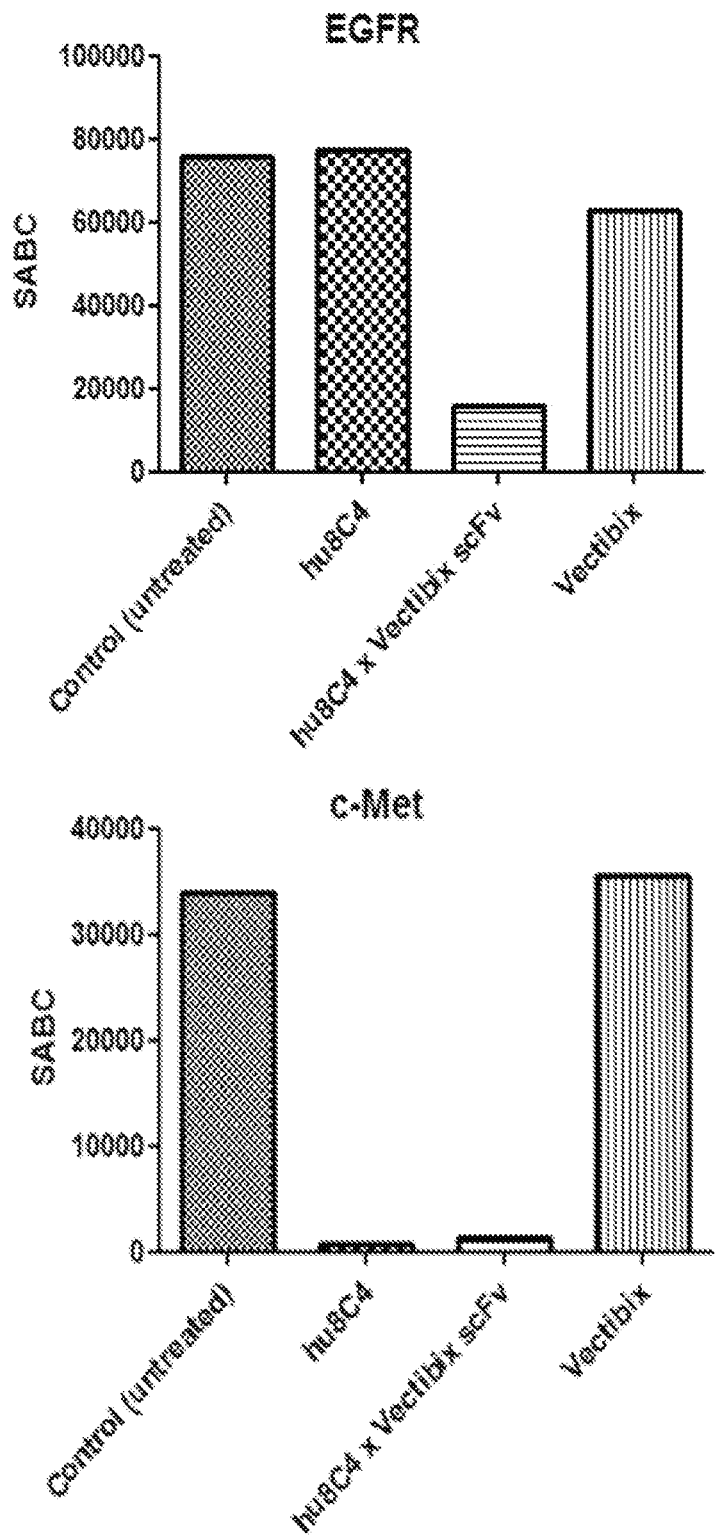
FIG. 10 shows results of measuring an effect of decreasing a receptor level by the bispecific antibody of the present invention in an NCI-H820 (NSCLC) cell line.

In result, when treating an anti-c-Met antibody hu8C4, an EGFR receptor was hardly decreased, but a c-Met receptor was remarkably decreased to a level of 2% (FIG. 10). Also, an anti-EGFR antibody Vectibix reduced the EGFR receptor to a level of about 83%, but a c-Met receptor was hardly decreased. By contrast, in case of treating the hu8C4×Vectibix bispecific antibody of the present invention simultaneously binding to c-Met and EGFR receptors, it was identified that the EGFR receptor was decreased to a level of about 21% and the c-Met receptor was decreased to a level of about 4%, respectively.

Thus, it was identified that the hu8C4×Vectibix bispecific antibody of the present invention remarkably reduced a level of expression of c-Met and EGFR receptors simultaneously.

Example 12. Identification of c-Met and EGFR In Vitro Signal Inhibitory Activity of Bispecific Antibody Then, an experiment using an NCI-H820 cell line was performed to identify an effect of the bispecific antibody of the present invention on the activity of antigen and signal transduction materials.

First of all, NCI-H820 cell lines were divided into a 6-well plate at a concentration of $5 \times 10^5$ cells per well, after which the resulting plate was cultured overnight under 37° C., 5% $CO_2$ conditions, such that it was replaced with a serum-free medium and cultured overnight again. An antibody was diluted and treated in a serum-free medium at a concentration of 100 nM, after which the resulting antibody was reacted for 24 hours, such that HGF (Gibco, PHG0254) and EGF (R&D Systems, 236-EG-200) were treated at a concentration of 50 ng/ml and 10 ng/ml respectively 15 minutes before collecting cells. Then, the cells were dissolved in a dissolution buffer to carry out a collection of cells, after which a protein concentration was quantified by using a Lowry assay method. 20 µg of protein was loaded onto each well and run in SDS-PAGE, after which blotting was performed in a nitrocellulose membrane. After blocking the membrane, all the primary antibodies were diluted and reacted at a ratio of 1:1,000, after which HRP-binding anti-rabbit antibody was diluted at a ratio of 1:5,000 and reacted as secondary cells. Then, the antibodies absorbed onto the membrane were reacted with enhanced chemiluminescence (ECL), after which the resulting antibodies were measured by using an LC-3000 device.

In result, as seen in FIG. 11, when treating hu8C4×Vectibix scFv bispecific antibody, the EGFR phosphorylation, Erk phosphorylation and Akt phosphorylation were remarkably decreased more than treating hu8C4 or Vectibix antibody alone.

Thus, the hu8C4×Vectibix scFv bispecific antibody of the present invention may reduce an activity of receptor such as EGFR, Erk, Akt, etc., and downstream signal transduction substances in NCI-H820 cell line. In result, it is shown that the antibody of the present invention shows an efficacy through a signal transduction inhibition.

Example 13. Identification of Tumor Cell Proliferation Inhibitory Activity in U-87 MG Xenograft Mouse Model An experiment was performed representatively by using hu8C4 IgG2×Vectibix scFv in order to identify a tumor cell proliferation inhibitory activity by the bispecific antibody of the present invention in an HGF-dependent U-87 MG cell xenograft model.

First of all, human glioblastoma U-87 MG cell lines were cultured under 37° C., 5% $CO_2$ conditions by using an EMEM (ATCC® 30-2003™) medium containing L-glutamine (300 mg/l), 25 mM HEPES, 25 mM $NaHCO_3$, 10% heat inactivated FBS and the like. Then, U-87 MG cells were subcutaneously inoculated by 200 µl into a flank of a 6 to 8 week-old male athymic nude mouse (Harlan) at a concentration of $1 \times 10^7$ per mouse. After identifying that a tumor volume formed in 25 days after inoculation reached 60-130 mm$^3$, a grouping was performed, after which a test material was intraperitoneally administered once a week for 4 weeks (total 5 times: 0, 7, 14, 21 and 28 days). The test material was administered 5 mg/kg, and a tumor volume and a mouse weight were measured twice a week. For data, a comparison between an excipient control group and a test material-administered group was generally verified by using Student t-test, and a statistical method used was Origin Pro 8.5 program. "Maximum inhibition %" indicates an inhibition % of tumor growth compared to a solvent-treated control group.

In result, a group administered with 3.5 mg/kg and 6.8 mg/kg of hu8C4 IgG2× Vectibix scFv had a maximum inhibition 96% for a tumor volume compared to a solvent control group, and a group administered with 1.5 mg/kg thereof had a maximum inhibition 80%, thus reducing a tumor volume to a significant level from a 7th day after administration until the final day of the test (p<0.01) (FIG. 12). Also, when compared to BsAB-01 as a positive control group, the bispecific antibody of the present invention reduced a tumor growth to a significant level (p<0.01).

Thus, it was identified from results above that the bispecific antibody of the present invention remarkably reduced a tumor growth, thus having an excellent antitumor efficacy.

Example 14. Identification of Tumor Cell Proliferation Inhibitory Activity in NCI-H820 Xenograft Mouse Model NCI-H820 cell line, which is a cell line with threonine (T) of EGFR amino acid no. 790 mutated into methionine (M) and with a MET gene amplified, is known as a resistant cell line of AZD9291 (osimertinib, tagrisso), which is a third generation EGFR TKI (Darren A. E. Cross, et al., Cancer Discov. 4(9): 1046-1061 (2014)). An evaluation was made in an NCI-H820 xenograft mouse model by representatively using hu8C4×Vectibix scFv out of the bispecific antibodies of the present invention, in order to see a tumor cell proliferation inhibitory activity of the bispecific antibody in NCI-H820 cell line having resistance to such EGFR TKI.

Particularly, a mouse used in this Example was a 6-week-old male mouse (Jackson Laboratory, STOCK Hgftm1.1 (HGF) Aveo Prkdcscid/J), wherein a mouse HGF gene was removed therefrom and transformed to express a human HGF gene. The NCI-H820 (ATCC, # HTB-181) cell line was inserted into a flask for cell culture along with an RPMI1640 medium containing 10% FBS, after which the resulting flask was cultured under 37° C., 5% $CO_2$ conditions. Then, the resulting cells were washed with PBS and 2.5% trypsin-EDTA (Gibco, 15090) was diluted 10 times, after which it was added thereinto to separate the cells. After that, a centrifugation (1,000 rpm, 5 min.) was performed to get rid of supernatant and obtain a cell suspension in a new medium. Subsequently, a cell viability was identified by a microscope, after which the resulting cells were diluted in a serum-free medium at a concentration of $5.0 \times 10^7$ cells/ml, thus preparing cell lines. The cell lines prepared were subcutaneously administered into a mouse by an amount of 0.1 ml/head. After administration, when a tumor size in a region with cell lines transplanted thereinto reached about 100-150 $mm^3$, cell lines were distributed so that a tumor size of each group can be evenly dispersed according to a ranked tumor size. Then, oncogenesis was identified twice a week from a 7th day after starting cell administration until 28th day after a day of grouping (day of starting an administration of test material) and after closing an administration of test material, after which a tumor's major axis and minor axis were measured by a calipers, thus calculating a tumor size ($ab^2/2$ (a: a length of major axis, b: a length of minor axis)). Statistical analysis was performed by Prism 5.03 (GraphPad Software Inc., San Diego, Calif., USA). If a p value is less than 0.05, it was judged as statistically significant.

In result, in all the groups administered with hu8C4× Vectibix scFv from a 4th day after starting an administration of test material until 28th day thereof, it was shown that a tumor proliferation inhibitory activity was significantly higher than a solvent control group ($p<0.001$), and it was also identified that a tumor inhibition ratio amounted to maximum 100% (FIG. 13). On the other hand, AZD9291 (Selleckchem), used as a positive control group, did not show a significant difference from the solvent control group.

Example 15. Identification of In Vitro Tumor Cell Proliferation Inhibitory Activity by a Combined Administration of 5G3 c-Met Antibody and HER2 Antibody An in vitro test on cell proliferation inhibitory activity was performed by NCI-H2170 cell line, in order to evaluate a tumor cell proliferation inhibitory activity according to a combination of the anti-c-Met antibody 5G3 of the present invention and anti-HER2 antibody. NCI-H2170 cell line (ATCC # CRL-5928) is a non-small cell lung cancer (NSCLC) tumor cell line, wherein, as a result of measuring its receptor level, EGFR was expressed in the level of about 2,700 specific antibody-binding capacity (SABC), while c-Met was expressed in the level of about 11,000 SABC.

Particularly, NCI-H2170 cells were diluted in an RPMI-1640 culture medium containing 10% (v/v) FBS, after which the resulting cells were added by 100 µl into a plate at a concentration of $3.0 \times 10^3$ cells per well, such that the resulting plate was cultured under 37° C., 95% RH and 5% (v/v) $CO_2$ conditions for 18-24 hours. Then, the cell culture medium of each well was removed therefrom, after which an RPMI1640 medium containing 2% (v/v) FBS was added by 100 µl into each well. After that, antibodies prepared at 2× of a final concentration (100 nM) were continuously diluted at a ratio of 1/10, such that the resulting antibodies were added by 100 µl into each well at six concentrations (i.e., 200 nM, 20 nM, 2 nM, 200 pM, 20 pM and 2 pM) for each antibody. The plate was cultured for 5 days under 37° C., 95% RH and 5% (v/v) $CO_2$ conditions, after which 20 µl of WST-8 solution (CCK-8, Dojindo) was added into each well on the final day to carry out color development for 1-2 hours, such that an optical density was measured at a wavelength of 450 nm by a microplate reader.

Figure 14:
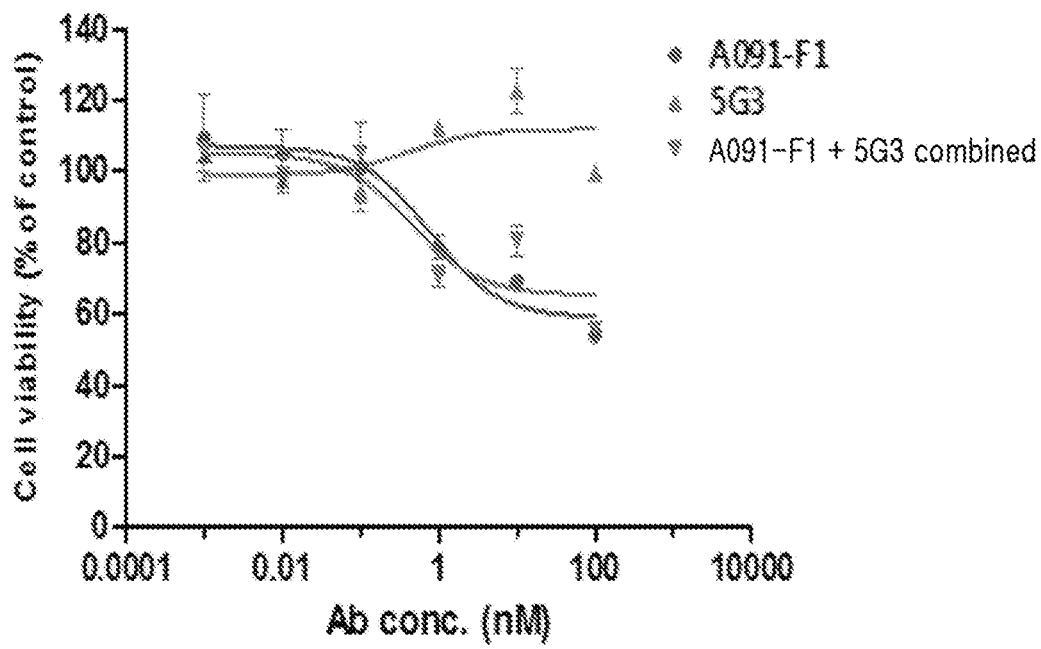
FIG. 14 shows results of analyzing a tumor cell proliferation inhibitory activity by treating the anti-c-Met antibody of the present invention and the anti-HER2 antibody by a combined therapy in an NCI-H2170 (NSCLC) cell line.
Figure 14:
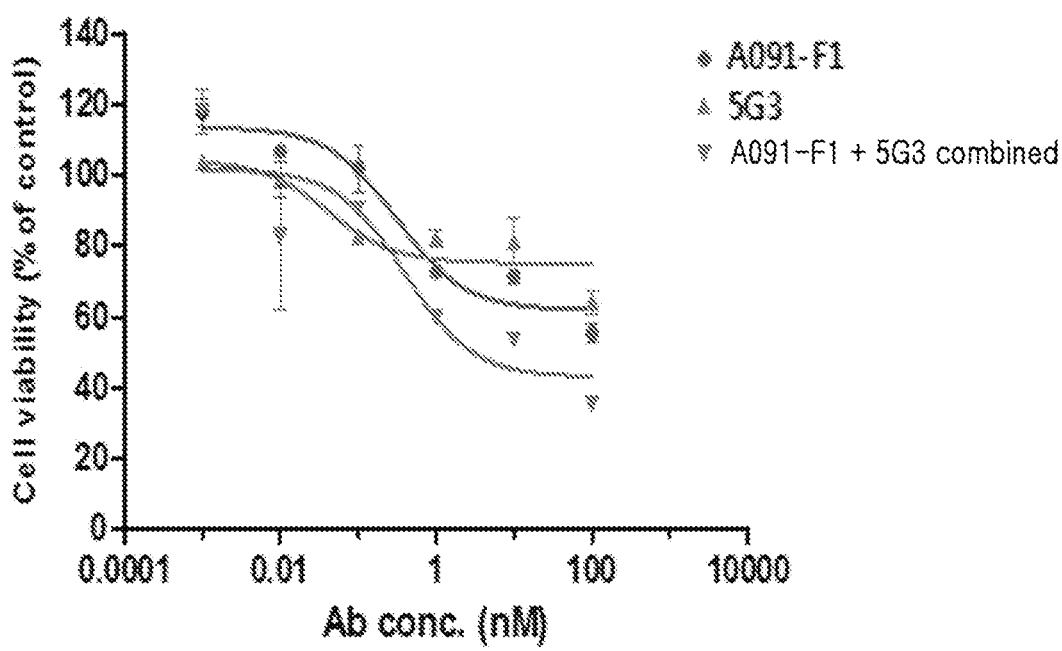

Results of cell proliferation inhibitory activity are shown in Table 26 and FIG. 14.

TABLE 26

In vitro tumor cell proliferation inhibitory activity by a combined therapy of anti-c-Met antibody and anti-HER2 antibody

| | Cell proliferation inhibition assay, $IC_{50}$ (nM) NCI-H2170 (NSCLC) | |
|---|---|---|
| Antibodies | No HGF | HGF 50 ng/ml |
| A091-E1 | >100 | >100 |
| 5G3 | >100 | >100 |
| A091-F1 + 5G3 combined | >100 | 11.22 |

As seen in Table 26, it was identified that a combined treatment of 5G3 and A091 antibody (Korea Patent Registration No. 10-1515535) as an anti-HER2 antibody had a more excellent tumor cell proliferation inhibitory capacity than a single treatment of each antibody in NCI-H2170 tumor cell line.

Example 16. Identification of In Vivo Tumor Cell Proliferation Inhibitory Activity by a Combined Administration of 5G3 c-Met Antibody and HER2 Antibody in an NCI-H2170 Xenograft Mouse Model as a Human Lung Cancer Cell Line An anticancer activity experiment was performed on an NCI-H2170 xenograft mouse model as a lung cancer cell line, in order to see a combined efficacy of HER2 antibody and c-Met antibody.

Figure 15:
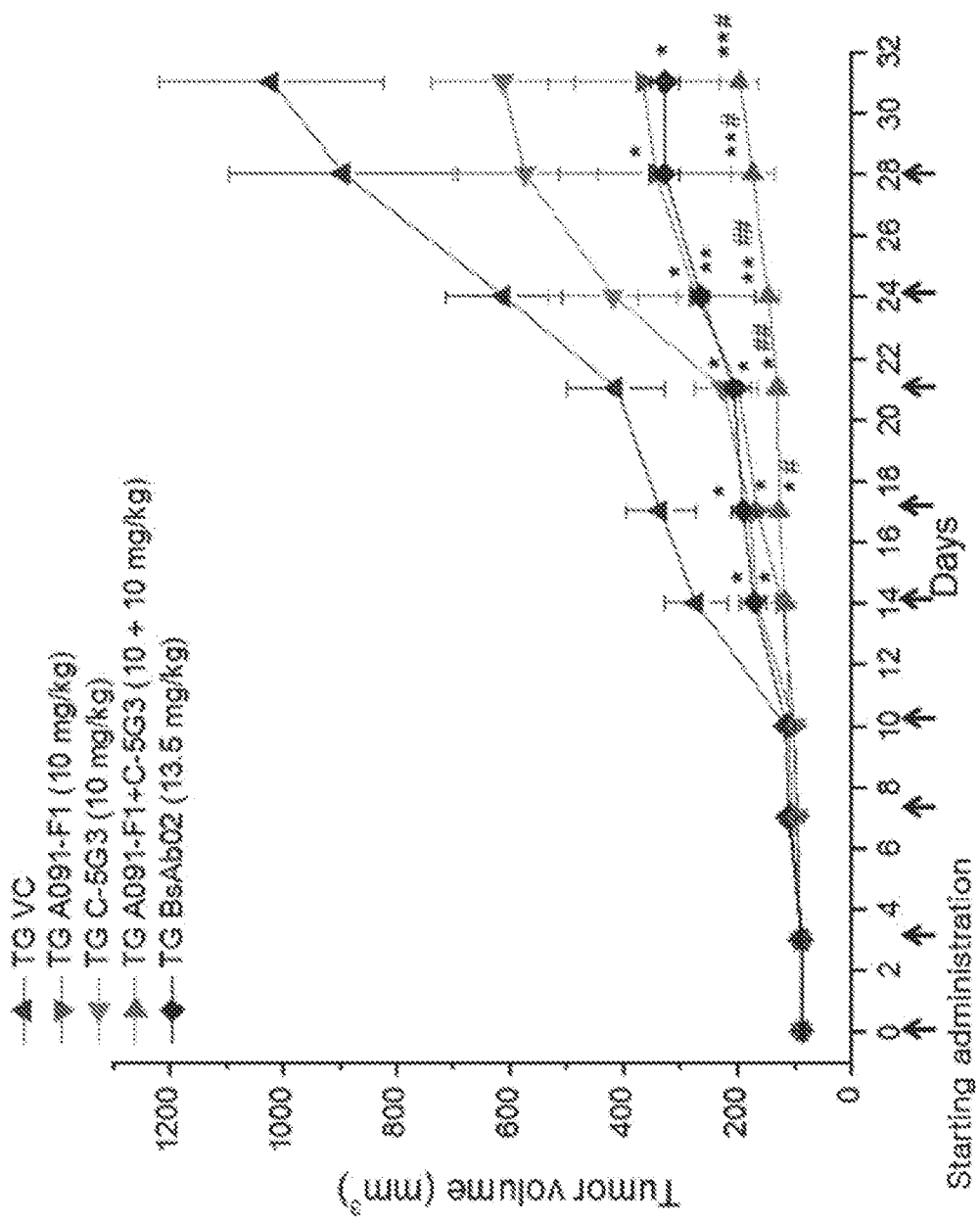
FIG. 15 shows results of measuring an anticancer effect of a combined therapy with the anti-c-Met antibody of the present invention and the anti-HER2 antibody in an NCI-H2170 (NSCLC) cell xenograft model.

Particularly, in this Example a tumor size of a mouse was measured by the same method as shown in Example 14 by using the same mouse as shown in Example 13 above. Results of evaluating an antitumor efficacy by a combination of A091 and 5G3 in an NCI-H2170 xenograft mouse model as a lung tumor cell are shown in FIG. 15.

In result, in case of carrying out a single administration of A091 alone or a combined administration of A091 and 5G3, a tumor volume was decreased to a significant level compared to a solvent control group from a 14th day after administration (p<0.05). Also, a group administered with a combination of A091 and 5G3 showed a significant decrease in a tumor volume compared to a group administered with A091 alone or a group administered with BsAB02 (US2010/0254988 A1) as a control bispecific antibody (p<0.01).

Example 17. Identification of Tumor Cell Proliferation Inhibitory Activity in NCI-H596 Xenograft Mouse Model As NCI-H596 cell line was a lung cancer cell line with a mutation in exon14 of c-Met, an evaluation was made on an NCI-H596 xenograft mouse model, in order to identify an anticancer effect of hu8C4×Vectibix scFv.

In this Example, a tumor size of a mouse was measured by using the same mouse and the same method as shown in Example 14 above.

Figure 16:
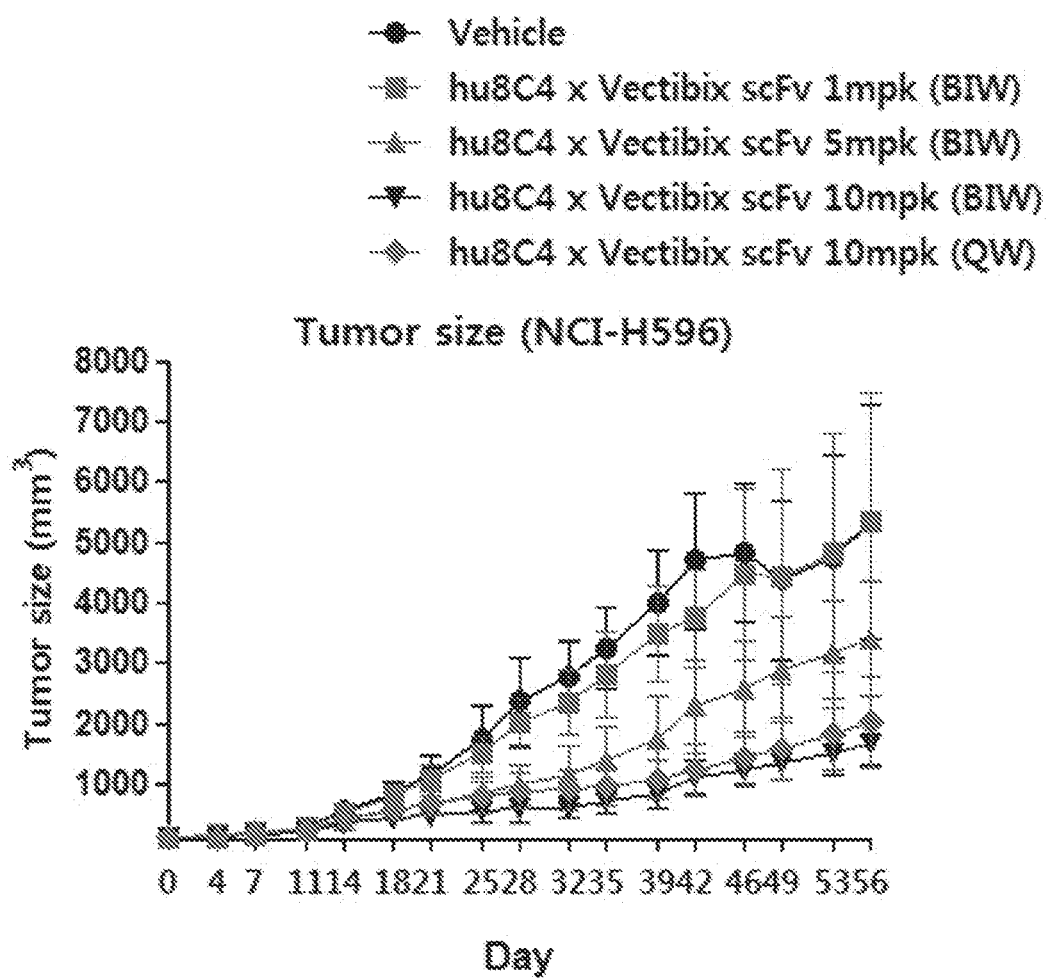
FIG. 16 shows results of measuring an anticancer effect of the bispecific antibody of the present invention in an NCI-H596 (NSCLC) cell xenograft model.

Results of evaluating an anticancer efficacy after administering hu8C4×Vectibix scFv once or twice a week for total 4 weeks in an NCI-H596 xenograft model as a lung tumor cell are shown in FIG. 16.

As a result of measuring a tumor size, a level of tumor size in a group administered with hu8C4×Vectibix scFv 10 mg/kg twice a week showed a statistically significant difference compared to a control group from an 11th day after starting an administration of test material until the end of an experiment, and levels of tumor sizes in a group administered with hu8C4×Vectibix scFv 5 mg/kg twice a week and a group administered with hu8C4×Vectibix scFv 10 mg/kg once a week were also significantly lower compared to a control group from an 18th day after starting an administration of test material. Also, a level of tumor size in a group administered with test material had a tendency of change in a dose-correlated way according to a test material dose, and a tumor size of a test group was lower compared to a control group even after a final day of administering a test material (Day 28).

Example 18. Identification of Tumor Cell Proliferation Inhibitory Activity in EBC-1 Xenograft Mouse Model As EBC-1 was a lung cancer cell line with an amplification of c-Met gene, an evaluation was made on an EBC-1 xenograft mouse model, in order to identify an anticancer effect of hu8C4×Vectibix scFv.

A mouse used in this Example was a six-week-old female athymic nude mouse (Harlan). EBC-1 (JCRB, # JCRB0820) cell lines were inserted into a flask for cell culture together with an EMEM medium containing 10% FBS, after which the resulting cell lines were cultured under 37° C., 5% $CO_2$ conditions. Cell lines were prepared in such a way that the resulting cell lines were diluted in a serum-free medium at a concentration of $5.0 \times 10^7$ cells/ml, after which the cell lines were subcutaneously administered into a mouse by an amount of 0.1 ml/head. When a tumor size in a region with cell lines transplanted thereinto reached about 100-150 $mm^3$, hu8C4× Vectibix scFv was administered once or twice a week for total 4 weeks, after which a tumor size of the mouse was measured by the same method as shown in Example 14.

Figure 17:
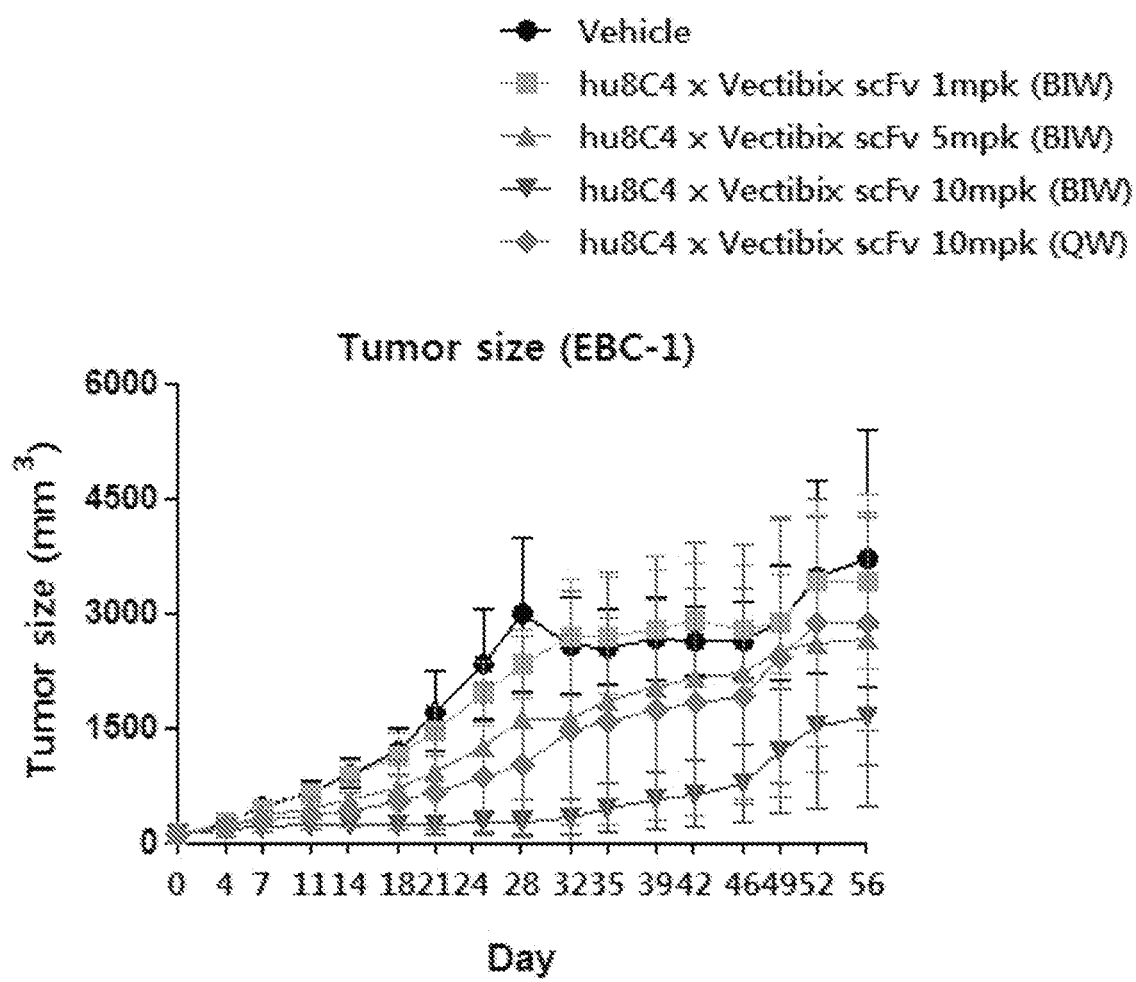
FIG. 17 shows results of measuring an anticancer effect of the bispecific antibody of the present invention in an EBC-1 (NSCLC) cell xenograft model.

Results of evaluating an anticancer efficacy by hu8C4×Vectibix scFv in an EBC-1 xenograft model as a lung cancer cell are shown in FIG. 17.

As a result of measuring a tumor size, a level of tumor size in a group administered with hu8C4×Vectibix scFv 10 mg/kg twice a week showed a statistically significant difference compared to a control group from a 7th day after starting an administration of test material until a 56th day after starting an administration of test material. A group administered with hu8C4×Vectibix scFv 5 mg/kg twice a week and a group administered with the same once a week showed a significant low level compared to a control group from an 18th day after starting an administration of test material. Also, a level of tumor size in a group administered with test material had a tendency of change in a dose-correlated way according to a test material dose, and a level of tumor size in a group administered with hu8C4×Vectibix scFv 10 mg/kg twice a week during an observation period after a final day (Day 28) of administering a test material was significantly low compared to a control group until a 56th day after starting an administration of test material. In particular, it was found that one individual in a group administered with hu8C4×Vectibix scFv 10 mg/kg twice a week had a complete response on an 18th day after starting an administration of test material.

Example 19. Effect of Reducing c-Met and EGFR on the Surface of Cancer Cells by Bispecific Antibody An effect of reducing c-Met and EGFR on the surface of in vitro tumor cells by the bispecific antibody (hu8C4×Vectibix scFv) of the present invention was identified and compared with an effect of the c-Met antibody (hu8C4) of the present invention, vectibix, c-Met/EGFR combination, and other antibodies.

A receptor generally located on a cell membrane was internalized into a cell when binding to an antibody, thus an amount thereof located on the cell membrane was decreased. A decrease in the receptor on such cell membrane causes an inhibition of receptor activation and a decrease in a downstream signal thereof by a ligand binding.

In this Example, a lung adenocarcinoma cell line HCC827 was used to observe a decrease in c-Met and EGFR on a cell membrane. HCC827 has an EGFR E746-A750 deletion mutation and overexpresses c-Met. HCC827 was treated with the bispecific antibody (hu8C4×Vectibix scFv) of the present invention and other antibodies, after which immunofluorescence staining was performed by an antibody specific to c-Met and EGFR, such that the resulting cell line was analyzed with a fluorescence activated cell sorter, thus measuring an amount of c-Met and EGFR on the surface of cells. A detailed method is as follows.

Figure 18:
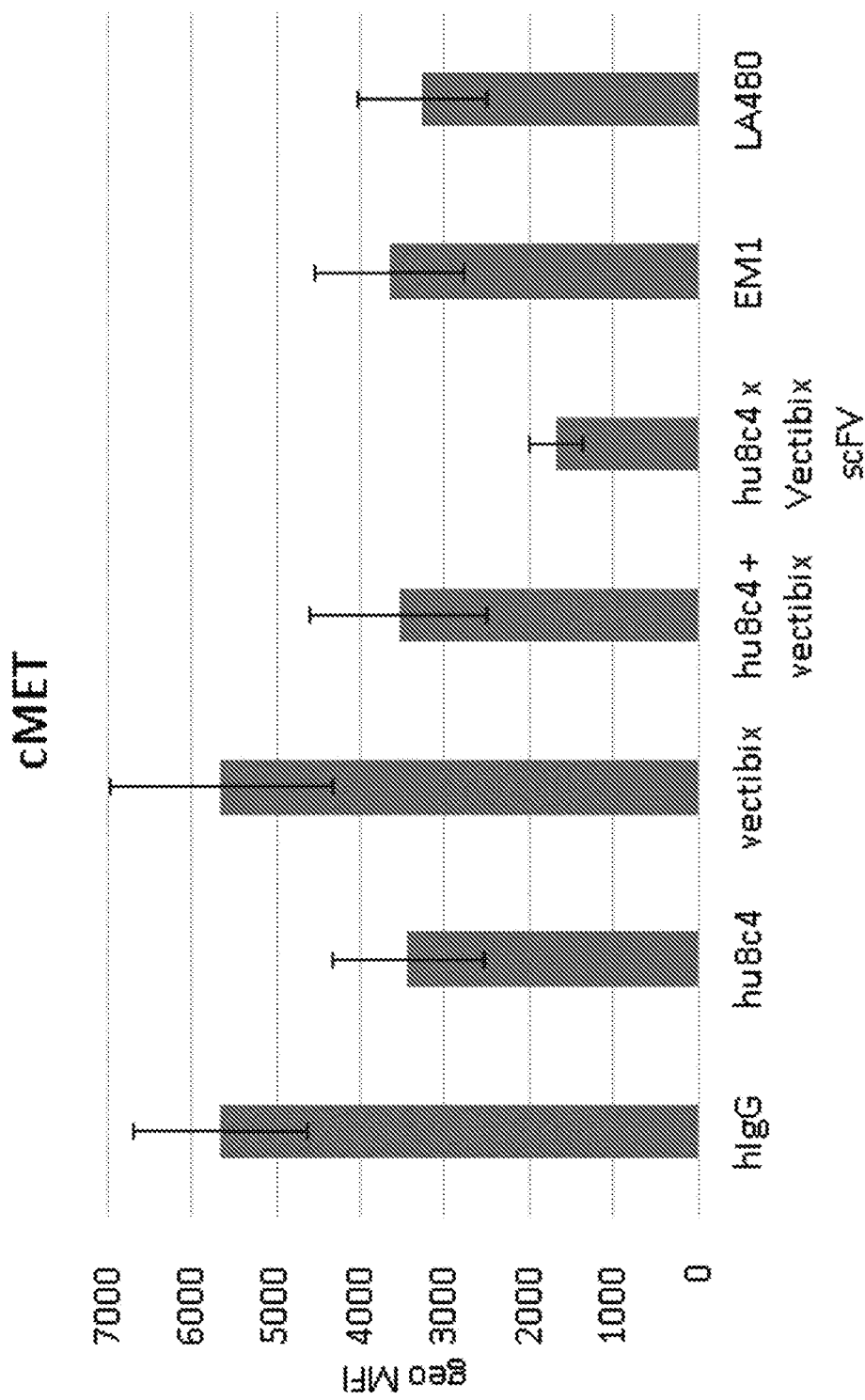
FIG. 18 shows results of indicating an amount of c-Met on the surface of cells, measured after treating an HCC827 cell line with a bispecific antibody (hu8C4× Vectibix scFv), etc.
Figure 19:
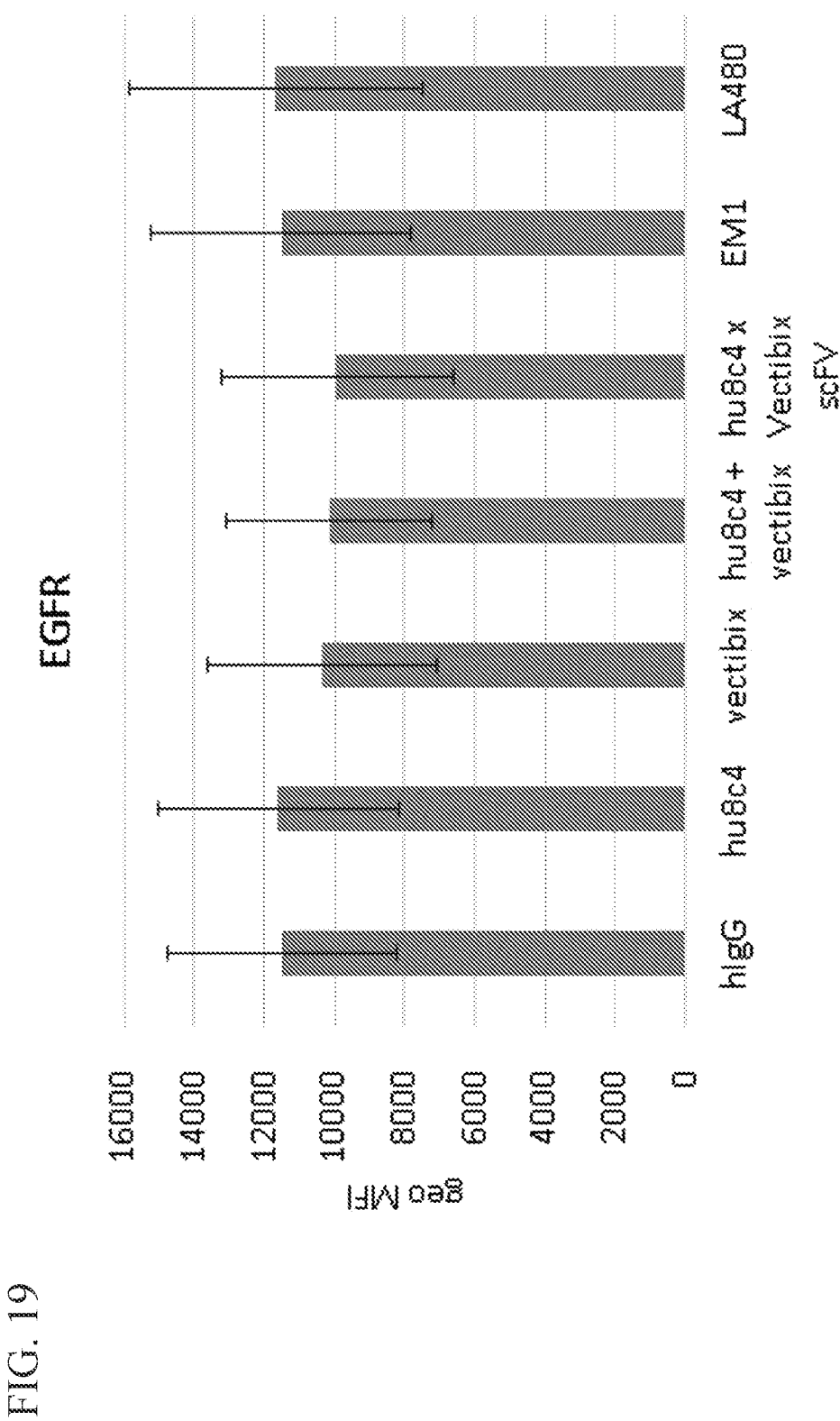
FIG. 19 shows results of indicating an amount of EGFR on the surface of cells, measured after treating an HCC827 cell line with a bispecific antibody (hu8C4× Vectibix scFv), etc.

First of all, HCC827 cells (ATCC® CRL-2868™) were divided by $3.0 \times 10^5$ into each well of a 6-well plate containing an RPMI-1640 medium (2 ml) containing 10% (v/v) FBS, after which the plate was cultured under 37° C., RH 95% and 5% $CO_2$ conditions for 24 hours. The bispecific antibody (hu8C4×Vectibix scFv) of the present invention, the c-Met antibody (hu8C4) of the present invention, vectibix, a mixture of the c-Met antibody (hu8C4) of the present invention and vectibix, C-EM1 and LA480 were diluted to reach a final concentration of 100 nM, after which the resulting antibodies were treated and reacted for 18 hours. As a plate to be used as a non-decreasing control group with c-Met and EGFR, a human IgG antibody was treated and reacted for 18 hours. Then, cells of each well were collected by 500 μl of an enzyme-free cell dissociation buffer (Gibco, #13151), after which cells were separated from the enzyme-free cell dissociation buffer by a centrifugal separator, such that the enzyme-free cell dissociation buffer was removed therefrom. For immunofluorescence staining, a goat-derived c-Met antibody (R&D systems, AF276), a goat-derived EGFR antibody (R&D systems, AF231) or a non-specific goat-derived antibody for measuring an amount of staining were mixed by 2 µg respectively with 200 µl of a cold PBS containing 2% (v/v) FBS, after which the resulting antibodies were treated into each well, such that the resulting plate was reacted at 4° C. for 1 hour. Then, the resulting plate was washed twice with a cold PBS containing 2% (v/v) FBS. ALEXA488 was bound as a secondary antibody, after which 1 µl of a donkey-derived antibody (Thermo Fisher, A-11055) binding to a goat antibody was diluted with 200 µl of a cold PBS containing 2% (v/v) FBS, such that the resulting antibody was used. After being reacted with the secondary antibody at 4° C. for 1 hour, the resulting cells were washed twice with a cold PBS containing 2% (v/v) FBS, after which the resulting cells were fixed by using 200 µl of BD Cytofix (BD, #554655). After being washed once with PBS, an ALEXA488 Geomean (MFI) value, a degree of fluorescent staining, was measured by using a BD FACS Canto II fluorescence activated cell sorter. An amount of c-Met and EGFR located on a cell membrane was indicated as geo mean fluorescence intensity (MFI) by a following formula. With regard to values obtained after repeatedly performing a test three times, an average and standard deviation thereof are shown in Table 27 and FIGS. 18 and 19.

$$\text{c-Met or EGFR surface amount} = \text{geo } MFI_{[experimental\ group]} - \text{geo } MFI_{[non\text{-}specific\ goat\text{-}derived\ antibody]}$$

TABLE 27

Amount of c-Met and EGFR on the surface of cells measured after treating HCC827 cell line with bispecific antibody (hu8C4 × Vectibix scFv), etc.

|  | c-Met | | EGFR | |
| --- | --- | --- | --- | --- |
| Treated antibody | Means (geo MFI) | S.D. | Means (geo MFI) | S.D. |
| human IgG | 5653 | 1032 | 11494 | 3276 |
| hu8C4 | 3436 | 892 | 11593 | 3448 |
| Vectibix | 5653 | 1309 | 10326 | 3256 |
| hu8C4 + Vectibix combined | 3551 | 1047 | 10111 | 2932 |
| hu8C4 × Vectibix scFv | 1689 | 321 | 9930 | 3305 |
| C-EM1 | 3665 | 878 | 11503 | 3715 |
| C-LA480 | 3267 | 764 | 11655 | 4156 |

As seen in Table 27 above, all the antibodies binding to c-Met decreased c-Met on the surface of cells by 40~70%, while antibodies binding to EGFR showed an insignificant effect of decreasing by 10-15%. Further considering an effect of reducing c-Met, hu8C4, combination of hu8C4+Vectibix, C-EM1 and C-LA480 decreased c-Met on the surface of cells by about 40% or so, while hu8C4×Vectibix scFv decreased c-Met on the surface of cells by 70%, thus showing a more excellent effect of reducing c-Met on the surface of cells than other antibodies and a combination of antibodies.

Results above show that the bispecific antibody (hu8C4× Vectibix scFv) of the present invention remarkably decreases an amount of c-Met on the surface of cells.

Example 20. Epitope Mapping

To figure out an epitope of the bispecific antibody (hu8C4×Vectibix scFv) of the present invention on a human c-Met antigen, its analysis was commissioned to the molecule model design support team of the Osong Medical Innovation Foundation (KBIO, Korea). The analysis was performed by hydrogen-deuterium exchange mass spectrometry (HDX-MS).

c-Met sema domain consists of two α/β chains, thus identifying each coverage for the two chains. Due to a presence of a number of disulfide bonds in a sample, a peptide coverage was optimized by adjusting a quench holding time, a TCEP concentration, a pepsin concentration, etc. Finally, an experiment was performed under quench buffer conditions with 100 mM K. Phosphate, 125 mM TCEP, 0.5 M Guanidine-HCl and pH 2.66.

Antigens and antibodies were prepared at a concentration of 3.3 mg/ml and 65 mg/ml respectively, and 37 pmol of cMET antigens and 36 pmol of antibodies were bound 3 hours before the experiment. A deuterium labeling buffer was reacted for 0, 0.33, 10, 60 and 240 minutes. Labeling was stopped with a quench buffer in accordance with each labeling time and vortexing was performed, after which they were immediately frozen in liquid nitrogen, thus being stored at −80° C. before the analysis. The resulting antigens and antibodies were loaded onto a pepsin column and analyzed with a mass spectrometer (MS).

Figure 20:
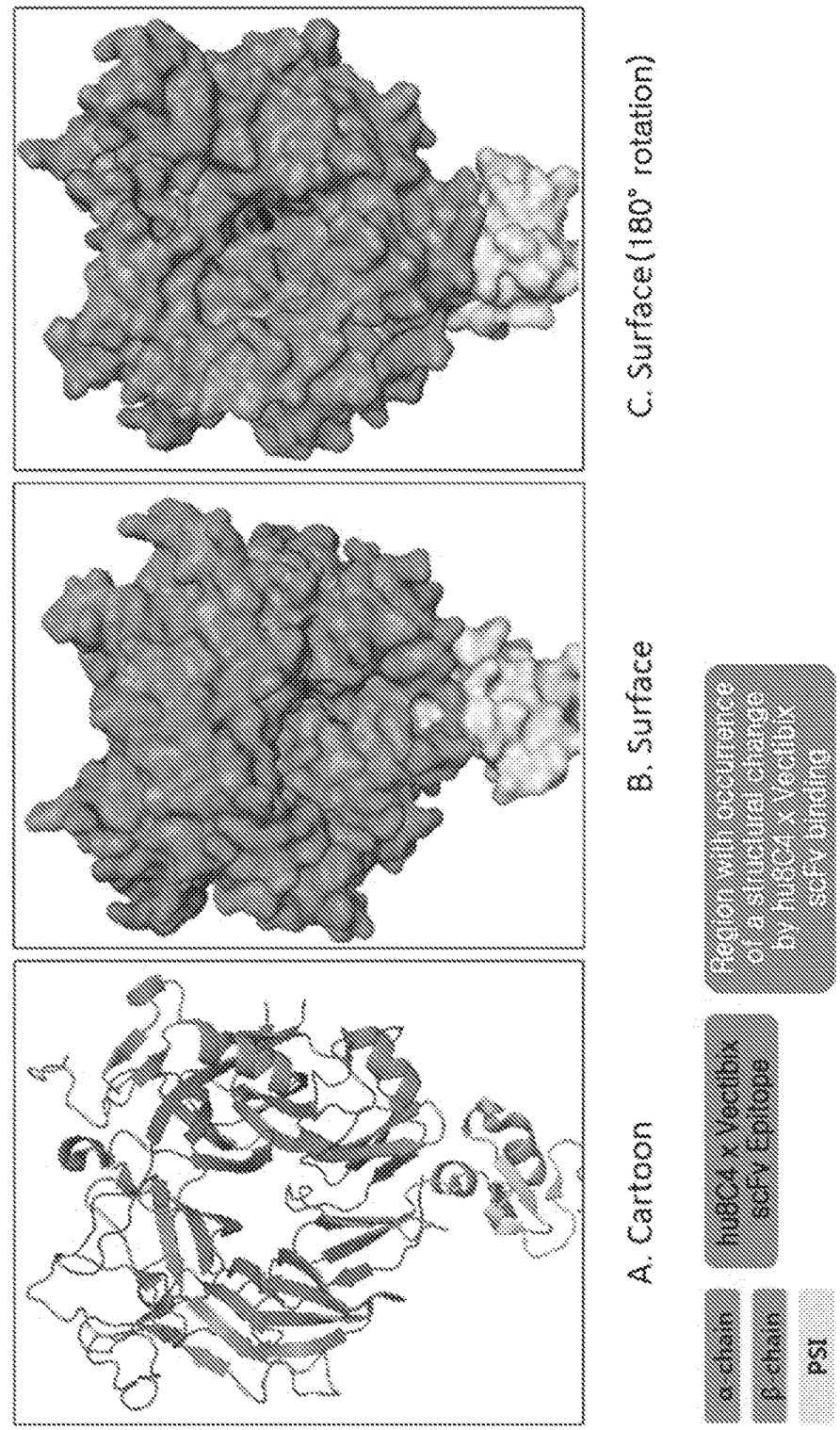
FIG. 20A-C shows results of indicating an epitope of a bispecific antibody, analyzed by a hydrogen-deuterium exchange mass spectrometry (HDX-MS), in a tertiary structure.

As a result of the analysis, it was identified that the bispecific antibody (hu8C4×Vectibix scFv) of the present invention binds to a 3-dimensional form of epitopes in 4 regions of Y321-L329 (SEQ. No. 331), I333-I341 (SEQ. No. 332), P366-D372 (SEQ. No. 333), and Q464-S474 (SEQ. No. 334) of a human c-Met sema domain β chain (Table 28). A labeling was performed on a tertiary structure of a human c-Met antigen (PDB No. 4K3J) by using a PyMOL program, wherein results thereof are shown in FIG. 20.

TABLE 28

| Amino acid sequence of epitope region | | |
| --- | --- | --- |
| Epitope region | Amino acids sequence | SEQ ID NO |
| Y321-L329 | YVSKPGAQL | 331 |
| I333-I341 | IGASLNDDI | 332 |
| P366-D372 | PIKYVND | 333 |
| Q464-S474 | QVVVSRSGPST | 334 |

From the results above, it can be seen that the mouse antibody, humanized antibody, affinity-optimized antibody or antigen binding fragments thereof of the present invention, specifically binding to c-Met, selectively act on c-Met, wherein they show an excellent cancer cell proliferation inhibitory activity as well as a remarkably excellent anti-cancer activity even by a little amount thereof, thus effectively preventing or treating cancer.

While specific portions of the present invention have been described in detail above, it is apparent to those skilled in the art that such detailed descriptions are set forth to illustrate exemplary embodiments only, but are not construed to limit the scope of the present invention. Thus, it should be understood that the substantial scope of the present invention is defined by the accompanying claims and equivalents thereto.

The invention claimed is:

1. An antibody or an antigen binding fragment thereof that specifically binds to a hepatocyte growth factor receptor (c-Met), wherein the antibody is:
   (a) an antibody comprising a light chain variable region comprising a light chain CDR1 represented by SEQ ID NO: 1; a light chain CDR2 represented by SEQ ID NO: 2; a light chain CDR3 represented by SEQ ID NO: 3, and a heavy chain variable region comprising a heavy chain CDR1 represented by SEQ ID NO: 7; a heavy chain CDR2 represented by SEQ ID NO: 8; and a heavy chain CDR3 represented by SEQ ID NO: 9; or
   (b) an affinity-optimized antibodies thereof, wherein the affinity-optimized antibody comprises:
   (i) a light chain variable region represented by SEQ ID NO: 21 and a heavy chain variable region represented by SEQ ID NO: 302;
   (ii) a light chain variable region represented by SEQ ID NO: 21 and a heavy chain variable region represented by SEQ ID NO: 305;
   (iii) a light chain variable region represented by SEQ ID NO: 310 and a heavy chain variable region represented by SEQ ID NO: 23;
   (iv) a light chain variable region represented by SEQ ID NO: 308 and a heavy chain variable region represented by SEQ ID NO: 305;
   (v) a light chain variable region represented by SEQ ID NO: 306 and a heavy chain variable region represented by SEQ ID NO: 303;
   (vi) a light chain variable region represented by SEQ ID NO: 307 and a heavy chain variable region represented by SEQ ID NO: 304;
   (vii) a light chain variable region represented by SEQ ID NO: 308 and a heavy chain variable region represented by SEQ ID NO: 304;
   (viii) a light chain variable region represented by SEQ ID NO: 309 and a heavy chain variable region represented by SEQ ID NO: 304;
   (ix) a light chain variable region represented by SEQ ID NO: 311 and a heavy chain variable region represented by SEQ ID NO: 304; or
   (x) a light chain variable region represented by SEQ ID NO: 306 and a heavy chain variable region represented by SEQ ID NO: 302.

2. The antibody or the antigen binding fragment thereof according to claim 1, wherein the antibody comprises: a light chain variable region represented by SEQ ID NO: 13 and a heavy chain variable region represented by SEQ ID NO: 15.

3. The antibody or the antigen binding fragment thereof according to claim 1, wherein the antibody comprises:
   (a) a light chain variable region represented by SEQ ID NO: 21 and a heavy chain variable region represented by SEQ ID NO: 23;
   (b) a light chain variable region represented by SEQ ID NO: 22 and a heavy chain variable region represented by SEQ ID NO: 24.

4. The antibody or the antigen binding fragment thereof according to claim 1, wherein the antibody comprises a hinge region represented by any one of SEQ ID NO: 37 to SEQ ID NO: 44.

5. The antibody or the antigen binding fragment thereof according to claim 1, wherein heavy chain C-terminus of the antibody that specifically binds to c-Met is linked to an antibody or an antigen binding fragment thereof binding to EGFR.

6. The antibody or the antigen binding fragment thereof according to claim 5, wherein the antigen binding fragment binding to the EGFR is Fab, Fab', F(ab')$_2$ or Fv.

7. The antibody or the antigen binding fragment thereof according to claim 6, wherein the Fv is scFv fragment comprising an amino acid sequence represented by SEQ ID NO: 313, SEQ ID NO: 314 or SEQ ID NO: 315.

8. The antibody or the antigen binding fragment thereof according to claim 5, wherein heavy chain C-terminus of the antibody that specifically binds to c-Met and the antibody or the antigen binding fragment thereof binding to EGFR, are linked by a connector represented by SEQ ID NO: 312, and wherein the antibody or the antigen binding fragment thereof specifically binds to a hepatocyte growth factor receptor (c-Met) and specifically binds to an epidermal growth factor receptor (EGFR).

9. The antibody or the antigen binding fragment thereof according to claim 1, wherein the antigen binding fragment is Fab, Fab', F(ab')$_2$ or Fv.

10. A composition, comprising an antibody or an antigen binding fragment thereof that specifically binds to a hepatocyte growth factor receptor (c-Met) and a pharmaceutically acceptable carrier, wherein the antibody is:
   (a) an antibody comprising a light chain variable region comprising a light chain CDR1 represented by SEQ ID NO: 1; a light chain CDR2 represented by SEQ ID NO: 2; a light chain CDR3 represented by SEQ ID NO: 3, and a heavy chain variable region comprising a heavy chain CDR1 represented by SEQ ID NO: 7; a heavy chain CDR2 represented by SEQ ID NO: 8; and a heavy chain CDR3 represented by SEQ ID NO: 9; or
   (b) an affinity-optimized antibodies thereof, wherein the affinity-optimized antibody comprises:
   (i) a light chain variable region represented by SEQ ID NO: 21 and a heavy chain variable region represented by SEQ ID NO: 302;
   (ii) a light chain variable region represented by SEQ ID NO: 21 and a heavy chain variable region represented by SEQ ID NO: 305;
   (iii) a light chain variable region represented by SEQ ID NO: 310 and a heavy chain variable region represented by SEQ ID NO: 23;

(iv) a light chain variable region represented by SEQ ID NO: 308 and a heavy chain variable region represented by SEQ ID NO: 305;
(v) a light chain variable region represented by SEQ ID NO: 306 and a heavy chain variable region represented by SEQ ID NO: 303;
(vi) a light chain variable region represented by SEQ ID NO: 307 and a heavy chain variable region represented by SEQ ID NO: 304;
(vii) a light chain variable region represented by SEQ ID NO: 308 and a heavy chain variable region represented by SEQ ID NO: 304;
(viii) a light chain variable region represented by SEQ ID NO: 309 and a heavy chain variable region represented by SEQ ID NO: 304;
(ix) a light chain variable region represented by SEQ ID NO: 311 and a heavy chain variable region represented by SEQ ID NO: 304; or
(x) a light chain variable region represented by SEQ ID NO: 306 and a heavy chain variable region represented by SEQ ID NO: 302.

11. The composition according to claim 10, wherein heavy chain C-terminus of the antibody that specifically binds to c-Met is linked to an antibody or an antigen binding fragment thereof binding to EGFR.

* * * * *

SEQUENCE LISTING

<160> NUMBER OF SEQ ID NOS: 335

<210> SEQ ID NO 1
<211> LENGTH: 11
<212> TYPE: PRT
<213> ORGANISM: Artificial Sequence
<220> FEATURE:
<223> OTHER INFORMATION: hybridoma 8C4 light chain CDR 1

<400> SEQUENCE: 1

Gly Ala Ser Glu Asn Ile Tyr Gly Ala Leu Asn
1               5                   10

<210> SEQ ID NO 2
<211> LENGTH: 7
<212> TYPE: PRT
<213> ORGANISM: Artificial Sequence
<220> FEATURE:
<223> OTHER INFORMATION: hybridoma 8C4 light chain CDR 2

<400> SEQUENCE: 2

Gly Ala Thr Asn Leu Ala Asp
1               5

<210> SEQ ID NO 3
<211> LENGTH: 9
<212> TYPE: PRT
<213> ORGANISM: Artificial Sequence
<220> FEATURE:
<223> OTHER INFORMATION: hybridoma 8C4 light chain CDR 3

<400> SEQUENCE: 3

Gln Asn Val Leu Ser Ser Pro Tyr Thr
1               5

<210> SEQ ID NO 4
<211> LENGTH: 10
<212> TYPE: PRT
<213> ORGANISM: Artificial Sequence
<220> FEATURE:
<223> OTHER INFORMATION: hybridoma 5G3 light chain CDR 1

<400> SEQUENCE: 4

Ser Ala Thr Ser Ser Val Arg Tyr Met Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: hybridoma 5G3 light chain CDR 2

<400> SEQUENCE: 5

Asp Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: hybridoma 5G3 light chain CDR 3

<400> SEQUENCE: 6

Gln Gln Trp Ser Ser Tyr Pro Arg Thr
1               5

```
<210> SEQ ID NO 7
<211> LENGTH: 5
<212> TYPE: PRT
<213> ORGANISM: Artificial Sequence
<220> FEATURE:
<223> OTHER INFORMATION: hybridoma 8C4 heavy chain CDR 1

<400> SEQUENCE: 7

Asp Tyr Tyr Ile Asn
1               5

<210> SEQ ID NO 8
<211> LENGTH: 17
<212> TYPE: PRT
<213> ORGANISM: Artificial Sequence
<220> FEATURE:
<223> OTHER INFORMATION: hybridoma 8C4 heavy chain CDR 2

<400> SEQUENCE: 8

Glu Ile Phe Pro Gly Ser Gly Asn Thr His Phe Ser Ala Arg Phe Lys
1               5                   10                  15

Gly

<210> SEQ ID NO 9
<211> LENGTH: 7
<212> TYPE: PRT
<213> ORGANISM: Artificial Sequence
<220> FEATURE:
<223> OTHER INFORMATION: hybridoma 8C4 heavy chain CDR 3

<400> SEQUENCE: 9

Gly Asp Tyr Gly Phe Leu Tyr
1               5

<210> SEQ ID NO 10
<211> LENGTH: 5
<212> TYPE: PRT
<213> ORGANISM: Artificial Sequence
<220> FEATURE:
<223> OTHER INFORMATION: hybridoma 5G3 heavy chain CDR 1

<400> SEQUENCE: 10

Asp Tyr Thr Leu His
1               5

<210> SEQ ID NO 11
<211> LENGTH: 17
<212> TYPE: PRT
<213> ORGANISM: Artificial Sequence
<220> FEATURE:
<223> OTHER INFORMATION: hybridoma 5G3 heavy chain CDR 2

<400> SEQUENCE: 11

Tyr Ile Asn Pro Tyr Ser Gly Tyr Thr Asn Tyr Asn Gln Lys Phe Lys
1               5                   10                  15

Asp

<210> SEQ ID NO 12
<211> LENGTH: 5
<212> TYPE: PRT
<213> ORGANISM: Artificial Sequence
<220> FEATURE:
<223> OTHER INFORMATION: hybridoma 5G3 heavy chain CDR 3

<400> SEQUENCE: 12
```

Gly His Met Asp Tyr
1               5

<210> SEQ ID NO 13
<211> LENGTH: 107
<212> TYPE: PRT
<213> ORGANISM: Artificial Sequence
<220> FEATURE:
<223> OTHER INFORMATION: hybridoma 8C4 light chain variable region

<400> SEQUENCE: 13

Asp Ile Leu Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Phe Ser Leu Lys Ile Thr Ser Leu His Pro
65                  70                  75                  80

Asp Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 14
<211> LENGTH: 106
<212> TYPE: PRT
<213> ORGANISM: Artificial Sequence
<220> FEATURE:
<223> OTHER INFORMATION: hybridoma 5G3 light chain variable region

<400> SEQUENCE: 14

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Arg Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Gly Arg Phe Ser Gly Ser
    50                  55                  60

Gly Ser Gly Thr Ser Asn Ser Leu Thr Ile Ser Arg Leu Glu Ala Glu
65                  70                  75                  80

Asp Ala Ala Thr Tyr Tyr Cys Gln Gln Trp Ser Ser Tyr Pro Arg Thr
                85                  90                  95

Phe Gly Gly Gly Thr Lys Leu Glu Ile Lys
            100                 105

<210> SEQ ID NO 15
<211> LENGTH: 116
<212> TYPE: PRT
<213> ORGANISM: Artificial Sequence
<220> FEATURE:
<223> OTHER INFORMATION: hybridoma 8C4 heavy chain variable region

<400> SEQUENCE: 15

Glu Val Gln Leu Gln Gln Ser Gly Ala Glu Leu Ala Arg Pro Gly Ala
1               5                   10                  15

```
Ser Val Lys Leu Ser Cys Lys Ala Ser Gly Tyr Thr Phe Ser Asp Tyr
            20                  25                  30

Tyr Ile Asn Trp Val Lys Gln Gly Thr Gly Gln Gly Leu Glu Trp Ile
        35                  40                  45

Gly Glu Ile Phe Pro Gly Ser Gly Asn Thr His Phe Ser Ala Arg Phe
50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Thr Asp Ser Ala Val Tyr Phe Cys
                85                  90                  95

Ala Gly Gly Asp Tyr Gly Phe Leu Tyr Trp Gly Arg Gly Thr Leu Val
            100                 105                 110

Thr Val Ser Ala
        115

<210> SEQ ID NO 16
<211> LENGTH: 114
<212> TYPE: PRT
<213> ORGANISM: Artificial Sequence
<220> FEATURE:
<223> OTHER INFORMATION: hybridoma 5G3 heavy chain variable region

<400> SEQUENCE: 16

Gln Gly Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Asp Tyr
            20                  25                  30

Thr Leu His Trp Val Lys Gln Arg Pro Gly Gln Gly Leu Glu Trp Ile
        35                  40                  45

Gly Tyr Ile Asn Pro Tyr Ser Gly Tyr Thr Asn Tyr Asn Gln Lys Phe
50                  55                  60

Lys Asp Lys Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Phe Tyr Cys
                85                  90                  95

Ala Arg Gly His Met Asp Tyr Trp Gly Gln Gly Thr Ser Val Thr Val
            100                 105                 110

Ser Ser

<210> SEQ ID NO 17
<211> LENGTH: 321
<212> TYPE: DNA
<213> ORGANISM: Artificial Sequence
<220> FEATURE:
<223> OTHER INFORMATION: hybridoma 8C4 light chain variable region

<400> SEQUENCE: 17
gatattctga tgacccagtc tccagcttca ctgtctgcat ctgtgggaga aactgtcacc      60
atcacatgtg agcaagtga gaatatttac ggtgctttaa attggtatca gcgaaaacag     120
ggaaaatctc ctcagctcct gatctatggt gcaaccaact ggcagatgg catgtcatcg     180 aggttcagtg gcagtgggtc tggtagacag ttttctctca agatcactag cctgcatcct     240
gacgatgttg caacgtatta ctgtcaaaat gtgctaagta gtccgtacac gttcggaggg     300
gggaccaagc tggaaatcaa a                                               321

<210> SEQ ID NO 18
<211> LENGTH: 318
```

<212> TYPE: DNA
<213> ORGANISM: Artificial Sequence
<220> FEATURE:
<223> OTHER INFORMATION: hybridoma 5G3 light chain variable region

<400> SEQUENCE: 18

```
caaattgttc tcacccagtc tccagcaatc atgtctgcat ctccagggga gaaggtcacc    60
atgacctgca gtgccacctc aagtgtacgt tacatgtact ggtaccagca gaagccagga   120
tcctccccca gactcctgat ttatgacaca tccaacctgg cttctggagt ccctggtcgc   180
ttcagcggca gtgggtctgg gacctctaac tctctcacaa tcagccgatt ggaggctgaa   240
gatgctgcca cttattactg ccagcagtgg agtagttacc cacggacgtt cggtggaggc   300
accaagctgg aaatcaaa                                                 318
```

<210> SEQ ID NO 19
<211> LENGTH: 348
<212> TYPE: DNA
<213> ORGANISM: Artificial Sequence
<220> FEATURE:
<223> OTHER INFORMATION: hybridoma 8C4 heavy chain variable region

<400> SEQUENCE: 19

```
gaggttcagc tgcagcagtc tggagctgag ctggcgaggc ccggggcttc agtgaagctg    60
tcctgcaagg cttctggcta caccttcagt gactactata aaactgggt gaagcagggg    120
actggacagg ccttgagtg gattggagag attttcctg gaagtggaaa tactcacttc    180
agtgcgaggt tcaagggcaa ggccacactg actgcagaca atcctccag cacagcctac    240
atgcagctca gcagcctgac atctacggac tctgcagtct atttctgtgc cggggggtgac    300
tacgggtttc tttactgggg ccagggact ctggtcactg tctctgca                348
```

<210> SEQ ID NO 20
<211> LENGTH: 342
<212> TYPE: DNA
<213> ORGANISM: Artificial Sequence
<220> FEATURE:
<223> OTHER INFORMATION: hybridoma 5G3 heavy chain variable region

<400> SEQUENCE: 20

```
cagggccagc tgcagcagtc tggggctgaa ctggcaagac ctggggcctc agtgaagatg    60
tcctgcaagg cttctggcta cacctttact gactacacgc tgcactgggt aaaacagagg   120
cctggacagg gtctggaatg gattggatac attaatcctt acagtggtta ctaattac    180
aatcagaaat tcaaggacaa ggccacattg actgcagaca atcctccag cacagcctac    240
atgcaactga gcggcctgac atctgaagac tctgcagtct tttattgtgc aagaggacat   300
atggactact ggggtcaagg aacctcagtc accgtctcct ca                      342
```

<210> SEQ ID NO 21
<211> LENGTH: 107
<212> TYPE: PRT
<213> ORGANISM: Artificial Sequence
<220> FEATURE:
<223> OTHER INFORMATION: hu8C4-1 light chain variable region

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Gly Ala Ser Glu Asn Ile Tyr Gly Ala
             20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
 50                  55                  60

Ser Gly Ser Gly Arg Asp Phe Thr Phe Thr Ile Ser Ser Leu Gln Pro
 65                  70                  75                  80

Glu Asp Ile Ala Thr Tyr Tyr Cys Gln Asn Val Leu Ser Ser Pro Tyr
                 85                  90                  95

Thr Phe Gly Gln Gly Thr Lys Val Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: hu8C4-2 light chain variable region

<400> SEQUENCE: 22

Asp Ile Gln Met Thr Gln Ser Pro Ser Ser Leu Ser Ala Ser Val Gly
 1               5                  10                  15

Asp Arg Val Thr Ile Thr Cys Gly Ala Ser Glu Asn Ile Tyr Gly Ala
                 20                  25                  30

Leu Asn Trp Tyr Gln Gln Lys Pro Gly Lys Val Pro Lys Leu Leu Ile
            35                  40                  45

Tyr Gly Ala Thr Asn Leu Ala Asp Gly Val Pro Ser Arg Phe Ser Gly
 50                  55                  60

Ser Gly Ser Gly Arg Asp Phe Thr Leu Thr Ile Ser Ser Leu Gln Pro
 65                  70                  75                  80

Glu Asp Val Ala Thr Tyr Tyr Cys Gln Asn Val Leu Ser Ser Pro Tyr
                 85                  90                  95

Thr Phe Gly Gln Gly Thr Lys Val Glu Ile Lys
            100                 105

<210> SEQ ID NO 23
<211> LENGTH: 116
<212> TYPE: PRT
<213> ORGANISM: Artificial Sequence
<220> FEATURE:
<223> OTHER INFORMATION: hu8C4-1 heavy chain variable region

<400> SEQUENCE: 23

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Ser Asp Tyr
                 20                  25                  30

Tyr Ile Asn Trp Val Arg Gln Ala Pro Gly Lys Gly Leu Glu Trp Ile
            35                  40                  45

Gly Glu Ile Phe Pro Gly Ser Gly Asn Thr His Phe Ser Ala Arg Phe
 50                  55                  60

Lys Gly Arg Ala Thr Leu Ser Ala Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Gly Gly Asp Tyr Gly Phe Leu Tyr Trp Gly Gln Gly Thr Leu Val
            100                 105                 110

Thr Val Ser Ser
            115

<210> SEQ ID NO 24
<211> LENGTH: 116
<212> TYPE: PRT
<213> ORGANISM: Artificial Sequence
<220> FEATURE:
<223> OTHER INFORMATION: hu8C4-2 heavy chain variable region

<400> SEQUENCE: 24

Gln Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Ile Arg Gln Ala Pro Gly Lys Gly Leu Glu Trp Ile
        35                  40                  45

Gly Glu Ile Phe Pro Gly Ser Gly Asn Thr His Phe Ser Ala Arg Phe
    50                  55                  60

Lys Gly Arg Ala Thr Ile Ser Ala Asp Lys Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Gly Gly Asp Tyr Gly Phe Leu Tyr Trp Gly Gln Gly Thr Leu Val
            100                 105                 110

Thr Val Ser Ser
        115

<210> SEQ ID NO 25
<211> LENGTH: 321
<212> TYPE: DNA
<213> ORGANISM: Artificial Sequence
<220> FEATURE:
<223> OTHER INFORMATION: hu8C4-1 light chain variable region

<400> SEQUENCE: 25
gatatccaga tgacccagtc tcccagcagt ctttccgctt ctgtgggtga tagggtgacg     60
ataacttgcg gagcaagtga gaatatttac ggtgctttaa attggtacca gcagaagcct    120
gggaaagctc caaagctgct gatctatggt gcaaccaact ggcagatgg cgtccctagc    180 aggttcagcg gcagtggaag cggcagagac ttcactttca caatctcctc cctgcaaccc    240
gaggacattg caacctacta ttgtcaaaat gtgctaagta gtccgtacac gtttggccag    300
ggaaccaagg ttgaaattaa a                                              321

<210> SEQ ID NO 26
<211> LENGTH: 321
<212> TYPE: DNA
<213> ORGANISM: Artificial Sequence
<220> FEATURE:
<223> OTHER INFORMATION: hu8C4-2 light chain variable region

<400> SEQUENCE: 26
gacatccaga tgacccagtc tccatcctcc ctgtctgcat ctgtaggaga cagagtcacc     60
atcacttgcg gagcaagtga gaatatttac ggtgctttaa attggtatca gcagaaacca    120
gggaaagttc ctaagctcct gatctatggt gcaaccaact ggcagatgg ggtcccatct    180 cggttcagtg gcagtggatc tgggcgagat ttcactctca ccatcagcag cctgcagcct    240
gaagatgttg caacttatta ctgtcaaaat gtgctaagta gtccgtacac gtttggccag    300
ggaaccaagg ttgaaattaa a                                              321

<210> SEQ ID NO 27
<211> LENGTH: 348
<212> TYPE: DNA
<213> ORGANISM: Artificial Sequence
<220> FEATURE:
<223> OTHER INFORMATION: hu8C4-1 heavy chain variable region

<400> SEQUENCE: 27

```
gaggttcagt tagtggaatc cggaggagga ctggtgcagc ctggtggaag tttgaggctg      60
tcatgcgcag ccagtggcta caccttcagt gactactata taaactgggt aagacaggct     120
cccggaaaag gctggagtg gattggagag attttcctg aagtggaaa tactcacttc        180
agtgcgaggt tcaagggccg agccaccctc tcagcagaca aaagcaagaa taccgcctat     240
ctgcagatga atagccttcg cgcagaagat actgccgtgt attactgtgc cggggggtgac    300
tacgggtttc tttactgggg acagggcacc ttggtgacag tctcttct                  348
```

<210> SEQ ID NO 28
<211> LENGTH: 348
<212> TYPE: DNA
<213> ORGANISM: Artificial Sequence
<220> FEATURE:
<223> OTHER INFORMATION: hu8C4-2 heavy chain variable region

<400> SEQUENCE: 28

```
caggttcagt tagtggaatc cggaggagga ctggtgaagc ctggtggaag tttgaggctg      60
tcatgcgcag ccagtggcta caccttcagt gactactata taaactggat cagacaggct     120
cccggaaaag gctggagtg gattggagag attttcctg aagtggaaa tactcacttc        180
agtgcgaggt tcaagggccg agccaccatc tcagcagaca aagcgaagaa tagcgcctat     240
ctgcagatga atagccttcg cgcagaagat actgccgtgt attactgtgc cggggggtgac    300
tacgggtttc tttactgggg acagggcacc ttggtgacag tctcttct                  348
```

<210> SEQ ID NO 29
<211> LENGTH: 106
<212> TYPE: PRT
<213> ORGANISM: Artificial Sequence
<220> FEATURE:
<223> OTHER INFORMATION: hu5G3-1 light chain variable region

<400> SEQUENCE: 29

```
Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Arg Tyr Met
            20                  25                  30

Tyr Trp Tyr Gln Gln Lys Pro Gly Gln Ser Pro Arg Leu Leu Ile Tyr
        35                  40                  45

Asp Thr Ser Asn Leu Ala Ser Gly Ile Pro Ala Arg Phe Ser Gly Ser
    50                  55                  60

Gly Ser Gly Thr Asp Asn Thr Leu Thr Ile Ser Arg Leu Glu Pro Glu
65                  70                  75                  80

Asp Phe Ala Val Tyr Tyr Cys Gln Gln Trp Ser Ser Tyr Pro Arg Thr
                85                  90                  95

Phe Gly Gly Gly Thr Lys Val Glu Ile Lys
            100                 105
```

<210> SEQ ID NO 30
<211> LENGTH: 106
<212> TYPE: PRT

<213> ORGANISM: Artificial Sequence
<220> FEATURE:
<223> OTHER INFORMATION: hu5G3-2 light chain variable region

<400> SEQUENCE: 30

Asp Ile Gln Met Thr Gln Ser Pro Ser Leu Ser Ala Ser Val Gly
1               5                   10                  15

Asp Arg Val Thr Ile Thr Cys Ser Ala Thr Ser Ser Val Arg Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Tyr Pro Arg Thr
                85                  90                  95

Phe Gly Gln Gly Thr Lys Val Glu Ile Lys
            100                 105

<210> SEQ ID NO 31
<211> LENGTH: 114
<212> TYPE: PRT
<213> ORGANISM: Artificial Sequence
<220> FEATURE:
<223> OTHER INFORMATION: hu5G3-1 heavy chain variable region

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Thr Leu His Trp Val Arg Gln Ala Pro Gly Gln Gly Leu Glu Trp Ile
        35                  40                  45

Gly Tyr Ile Asn Pro Tyr Ser Gly Tyr Thr Asn Tyr Asn Gln Lys Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Met Asp Tyr Trp Gly Gln Gly Thr Leu Val Thr Val
            100                 105                 110

Ser Ser

<210> SEQ ID NO 32
<211> LENGTH: 114
<212> TYPE: PRT
<213> ORGANISM: Artificial Sequence
<220> FEATURE:
<223> OTHER INFORMATION: hu5G3-2 heavy chain variable region

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Thr Leu His Trp Val Arg Gln Ala Pro Gly Lys Gly Leu Glu Trp Val
        35                  40                  45

```
Gly Tyr Ile Asn Pro Tyr Ser Gly Tyr Thr Asn Tyr Asn Gln Lys Phe
            50                  55                  60

Lys Asp Arg Ala Thr Leu Ser Ala Asp Lys Ser Lys Asn Thr Ala Tyr
 65                  70                  75                  80

Leu Gln Met Asn Ser Leu Arg Ala Glu Asp Thr Ala Val Phe Tyr Cys
                 85                  90                  95

Ala Arg Gly His Met Asp Tyr Trp Gly Gln Gly Thr Leu Val Thr Val
            100                 105                 110

Ser Ser
```

<210> SEQ ID NO 33
<211> LENGTH: 318
<212> TYPE: DNA
<213> ORGANISM: Artificial Sequence
<220> FEATURE:
<223> OTHER INFORMATION: hu5G3-1 light chain variable region

<400> SEQUENCE: 33

```
gaaattgtgt tgacacagtc tccagccacc ctgtctttgt ctccagggga aagagccacc    60
ctctcctgca gtgccacctc aagtgtacgt tacatgtact ggtaccagca gaaacctggc   120
cagtctccca ggctcctcat ctatgacaca tccaacctgg cttctggcat cccagcaagg   180
ttcagtggca gtgggtctgg gacagacaac actctcacca tcagcagact ggagcctgaa   240
gattttgcag tttattactg tcagcagtgg agtagttacc cacggacgtt cggcggaggg   300
accaaggtgg agatcaaa                                                 318
```

<210> SEQ ID NO 34
<211> LENGTH: 318
<212> TYPE: DNA
<213> ORGANISM: Artificial Sequence
<220> FEATURE:
<223> OTHER INFORMATION: hu5G3-2 light chain variable region

<400> SEQUENCE: 34

```
gacatccaga tgactcagag tccctcttct ctgtctgcct cagtgggaga tcgggtcaca    60
atcacatgtt cagcaacaag ctcagtgcga tacatgtatt ggtaccagca gaagccaggc   120
aaagccccaa agctgctgat ctatgacaca tctaatctgg ccagcggcgt cccatctcgc   180
ttctcaggct ccggaagcgg tactgatttt accctgacta tttcttcctt gcagcctgag   240
gacttcgcaa cctattattg ccagcagtgg tctagctacc ctcgcacatt cggccaggga   300
accaaggtcg aaattaaa                                                 318
```

<210> SEQ ID NO 35
<211> LENGTH: 342
<212> TYPE: DNA
<213> ORGANISM: Artificial Sequence
<220> FEATURE:
<223> OTHER INFORMATION: hu5G3-1 heavy chain variable region

<400> SEQUENCE: 35

```
caggtgcagc tggtgcagtc tggggctgag gtgaagaagc ctggggcctc agtgaaggtt    60
tcctgcaagg catctggata caccttcacc gactacgc tgcactgggt gcgacaggcc    120
cctggacaag gcttgagtg gataggatac attaatcctt acagtggtta tactaattac   180
aatcagaaat tcaaggacag agtcaccttg accgcagaca atccacgag cacagcctac   240
atggagctga gcagcctgag atctgaggac acggccgtgt attactgtgc tagaggacat   300
atggactact ggggccaagg aaccctggtc accgtctcct ca                      342
```

<210> SEQ ID NO 36
<211> LENGTH: 342
<212> TYPE: DNA
<213> ORGANISM: Artificial Sequence
<220> FEATURE:
<223> OTHER INFORMATION: hu5G3-2 heavy chain variable region

<400> SEQUENCE: 36

```
gaagtccaac ttgtggagtc aggaggcggg ctcgtgcagc caggcggatc attgcgactt      60
tcttgtgctg cctcaggta caccttcact gattatacct tgcattgggt tcgccaagca     120
cccggtaagg gtctcgaatg ggtaggatac attaatccat acagcggcta caccaactac    180
aaccagaaat tcaaagacag ggctacccct agtgccgaca gtctaagaa caccgcctac     240 cttcagatga actcccttag agccgaggat actgctgtgt tttattgcgc taggggtcat    300
atggactact ggggacaggg gaccttggtg actgtgtctt cc                       342
```

<210> SEQ ID NO 37
<211> LENGTH: 15
<212> TYPE: PRT
<213> ORGANISM: Artificial Sequence
<220> FEATURE:
<223> OTHER INFORMATION: Hinge of IgG1 CH constant region

<400> SEQUENCE: 37

Glu Pro Lys Ser Cys Asp Lys Thr His Thr Cys Pro Pro Cys Pro
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Variant of IgG1 CH Hinge

<400> SEQUENCE: 38

Glu Pro Lys Ser Cys Asp Lys Thr His Thr Cys Pro Pro Cys Pro
1               5                   10                  15

<210> SEQ ID NO 39
<211> LENGTH: 10
<212> TYPE: PRT
<213> ORGANISM: Artificial Sequence
<220> FEATURE:
<223> OTHER INFORMATION: Variant of IgG1 CH Hinge

<400> SEQUENCE: 39

Glu Cys Cys Val Glu Cys Pro Pro Cys Pro
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Variant of IgG1 CH Hinge

<400> SEQUENCE: 40

Glu Arg Lys Cys Cys Cys Pro Pro Cys Pro
1               5                   10

<210> SEQ ID NO 41
<211> LENGTH: 8
<212> TYPE: PRT

<213> ORGANISM: Artificial Sequence
<220> FEATURE:
<223> OTHER INFORMATION: Variant of IgG1 CH Hinge

<400> SEQUENCE: 41

Glu Cys Cys Cys Pro Pro Cys Pro
1               5

<210> SEQ ID NO 42
<211> LENGTH: 11
<212> TYPE: PRT
<213> ORGANISM: Artificial Sequence
<220> FEATURE:
<223> OTHER INFORMATION: Variant of IgG1 CH Hinge

<400> SEQUENCE: 42

Glu Lys Cys Cys Val Glu Cys Pro Pro Cys Pro
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Variant of IgG1 CH Hinge

<400> SEQUENCE: 43

Glu Arg Lys Cys Cys Val Cys Pro Pro Cys Pro
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Variant of IgG1 CH Hinge

<400> SEQUENCE: 44

Glu Lys Cys Cys Val Cys Pro Pro Cys Pro
1               5                   10

<210> SEQ ID NO 45
<211> LENGTH: 45
<212> TYPE: DNA
<213> ORGANISM: Artificial Sequence
<220> FEATURE:
<223> OTHER INFORMATION: Hinge of IgG1 CH constant region

<400> SEQUENCE: 45
gagcccaaat cttgtgacaa aactcacaca tgcccaccgt gccca                45

<210> SEQ ID NO 46
<211> LENGTH: 36
<212> TYPE: DNA
<213> ORGANISM: Artificial Sequence
<220> FEATURE:
<223> OTHER INFORMATION: Variant of IgG1 CH Hinge

<400> SEQUENCE: 46
gagcgaaaat gttgtgtcga gtgcccaccg tgccca                          36

<210> SEQ ID NO 47
<211> LENGTH: 30
<212> TYPE: DNA
<213> ORGANISM: Artificial Sequence
<220> FEATURE:
<223> OTHER INFORMATION: Variant of IgG1 CH Hinge

```
<400> SEQUENCE: 47
gagtgttgtg tcgagtgccc accgtgccca                                        30

<210> SEQ ID NO 48
<211> LENGTH: 30
<212> TYPE: DNA
<213> ORGANISM: Artificial Sequence
<220> FEATURE:
<223> OTHER INFORMATION: Variant of IgG1 CH Hinge

<400> SEQUENCE: 48
gagcgaaaat gttgttgccc accgtgccca                                        30

<210> SEQ ID NO 49
<211> LENGTH: 24
<212> TYPE: DNA
<213> ORGANISM: Artificial Sequence
<220> FEATURE:
<223> OTHER INFORMATION: Variant of IgG1 CH Hinge

<400> SEQUENCE: 49
gagtgttgtt gcccaccgtg ccca                                              24

<210> SEQ ID NO 50
<211> LENGTH: 33
<212> TYPE: DNA
<213> ORGANISM: Artificial Sequence
<220> FEATURE:
<223> OTHER INFORMATION: Variant of IgG1 CH Hinge

<400> SEQUENCE: 50
gagaaatgtt gtgtcgagtg cccaccgtgc cca                                    33

<210> SEQ ID NO 51
<211> LENGTH: 33
<212> TYPE: DNA
<213> ORGANISM: Artificial Sequence
<220> FEATURE:
<223> OTHER INFORMATION: Variant of IgG1 CH Hinge

<400> SEQUENCE: 51
gagcgaaaat gttgtgtctg cccaccgtgc cca                                    33

<210> SEQ ID NO 52
<211> LENGTH: 30
<212> TYPE: DNA
<213> ORGANISM: Artificial Sequence
<220> FEATURE:
<223> OTHER INFORMATION: Variant of IgG1 CH Hinge

<400> SEQUENCE: 52
gagaaatgtt gtgtctgccc accgtgccca                                        30

<210> SEQ ID NO 53
<211> LENGTH: 15
<212> TYPE: PRT
<213> ORGANISM: Artificial Sequence
<220> FEATURE:
<223> OTHER INFORMATION: linker

<400> SEQUENCE: 53

Gly Gly Gly Gly Ser Gly Gly Gly Gly Ser Gly Gly Gly Gly Ser
1               5                   10                  15
```

```
<210> SEQ ID NO 54
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 54

Glu Ile Asp Pro Gly Ser Gly Asn Thr His Phe Ser Ala Arg Phe Lys
1               5                   10                  15
Gly

<210> SEQ ID NO 55
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 55

Glu Ile Glu Pro Gly Ser Gly Asn Thr His Phe Ser Ala Arg Phe Lys
1               5                   10                  15
Gly

<210> SEQ ID NO 56
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 56

Glu Ile Trp Pro Gly Ser Gly Asn Thr His Phe Ser Ala Arg Phe Lys
1               5                   10                  15
Gly

<210> SEQ ID NO 57
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 57

Glu Ile Tyr Pro Gly Ser Gly Asn Thr His Phe Ser Ala Arg Phe Lys
1               5                   10                  15
Gly

<210> SEQ ID NO 58
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 58

Glu Ile Phe Pro Gly Trp Gly Asn Thr His Phe Ser Ala Arg Phe Lys
1               5                   10                  15
Gly

<210> SEQ ID NO 59
<211> LENGTH: 17
<212> TYPE: PRT
<213> ORGANISM: Artificial Sequence
```

<220> FEATURE:
<223> OTHER INFORMATION: hu8C4 CH CDR2

<400> SEQUENCE: 59

Glu Ile Phe Pro Gly Tyr Gly Asn Thr His Phe Ser Ala Arg Phe Lys
1               5                   10                  15
Gly

<210> SEQ ID NO 60
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 60

Glu Ile Phe Pro Gly Ser Gly Tyr Thr His Phe Ser Ala Arg Phe Lys
1               5                   10                  15
Gly

<210> SEQ ID NO 61
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 61

Glu Ile Phe Pro Gly Ser Gly Asn Thr Trp Phe Ser Ala Arg Phe Lys
1               5                   10                  15
Gly

<210> SEQ ID NO 62
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 62

Glu Ile Phe Pro Gly Ser Gly Asn Thr Tyr Phe Ser Ala Arg Phe Lys
1               5                   10                  15
Gly

<210> SEQ ID NO 63
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 63

Glu Ile Phe Pro Gly Trp Gly Asn Thr Tyr Phe Ser Ala Arg Phe Lys
1               5                   10                  15
Gly

<210> SEQ ID NO 64
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 64

```
Gln Asp Tyr Gly Phe Leu Tyr
1               5

<210> SEQ ID NO 65
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 65

Glu Asp Tyr Gly Phe Leu Tyr
1               5

<210> SEQ ID NO 66
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 66

His Asp Tyr Gly Phe Leu Tyr
1               5

<210> SEQ ID NO 67
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 67

Asn Asp Tyr Gly Phe Leu Tyr
1               5

<210> SEQ ID NO 68
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 68

Val Glu Leu Gly Phe Leu Tyr
1               5

<210> SEQ ID NO 69
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 69

Phe Glu Thr Gly Tyr Tyr Leu
1               5

<210> SEQ ID NO 70
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 70
```

Gly Glu Tyr Gly Tyr Gln Asn
1               5

<210> SEQ ID NO 71
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 71

Trp Glu Tyr Gly Leu Ser Met
1               5

<210> SEQ ID NO 72
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 72

Glu Ile Phe Pro His Phe Thr Ser Asp His Phe Ser Ala Arg Phe Lys
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 73

Glu Ile Phe Pro Gly Ser Gly Asn Thr His Phe Ser Ala Trp Met Gly
1               5                   10                  15

Thr

<210> SEQ ID NO 74
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 74

Glu Ile Phe Pro Gly Ser Gly Asn Glu Ser Val Ser Phe Arg Phe Lys
1               5                   10                  15

Gly

<210> SEQ ID NO 75
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 75

Glu Ile Phe Pro Gly Ser Gly Asn Ser Ala Val Ile Ser Arg Phe Lys
1               5                   10                  15

Gly

<210> SEQ ID NO 76
<211> LENGTH: 17

<212> TYPE: PRT
<213> ORGANISM: Artificial Sequence
<220> FEATURE:
<223> OTHER INFORMATION: hu8C4 CH CDR2

<400> SEQUENCE: 76

Glu Ile Phe Pro Gly Ser Gly Asn His Thr Val Val Arg Arg Phe Lys
1               5                   10                  15
Gly

<210> SEQ ID NO 77
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 77

Glu Ile Phe Pro Gly Ser Gly Asn Leu Ser Met His Gly Arg Phe Lys
1               5                   10                  15
Gly

<210> SEQ ID NO 78
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 78

Glu Ile Phe Pro Gly Ser Gly Asn His Thr Pro Val Phe Arg Phe Lys
1               5                   10                  15
Gly

<210> SEQ ID NO 79
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 79

Glu Ile Phe Pro Gly Ser Gly Asn Pro Phe Leu Thr Ile Arg Phe Lys
1               5                   10                  15
Gly

<210> SEQ ID NO 80
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 80

Glu Ile Phe Pro Gly Ser Gly Asn Ser His Val Val Ser Arg Phe Lys
1               5                   10                  15
Gly

<210> SEQ ID NO 81
<211> LENGTH: 17
<212> TYPE: PRT
<213> ORGANISM: Artificial Sequence
<220> FEATURE:
<223> OTHER INFORMATION: hu8C4 CH CDR2

```
<400> SEQUENCE: 81

Glu Ile Phe Pro Gly Ser Gly Asn Leu Ser Gly Ile Arg Ser Phe Lys
1               5                   10                  15

Gly

<210> SEQ ID NO 82
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 82

Glu Ile Phe Pro Gly Ser Gly Asn Phe Phe His Gly Lys Arg Phe Lys
1               5                   10                  15

Gly

<210> SEQ ID NO 83
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 83

Glu Ile Phe Pro Gly Ser Gly Asn Pro Arg Leu Gly Ala Arg Phe Lys
1               5                   10                  15

Gly

<210> SEQ ID NO 84
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 84

Glu Ile Phe Pro Gly Ser Gly Asn Val Ser Gln Val Glu Arg Phe Lys
1               5                   10                  15

Gly

<210> SEQ ID NO 85
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 85

Glu Ile Phe Pro Gly Ser Gly Asn Phe His Gly Ala Ser Arg Phe Lys
1               5                   10                  15

Gly

<210> SEQ ID NO 86
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 86

Glu Ile Phe Pro Gly Ser Gly Asn Val Val Gly Gly Tyr Arg Phe Lys
```

<210> SEQ ID NO 87
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 87

Glu Ile Phe Pro Gly Ser Gly Asn Pro Met Tyr Asp Glu Arg Phe Lys
1               5                   10                  15
Gly

<210> SEQ ID NO 88
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 88

Glu Ile Phe Pro Gly Ser Gly Asn Ala Asp Leu Thr Ile Arg Phe Lys
1               5                   10                  15
Gly

<210> SEQ ID NO 89
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 89

Glu Ile Phe Pro Gly Ser Gly Asn Ser Thr Asn Leu Tyr Arg Phe Lys
1               5                   10                  15
Gly

<210> SEQ ID NO 90
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 90

Glu Ile Phe Pro Gly Ser Gly Asn Leu Asp Ile Pro Pro Arg Phe Lys
1               5                   10                  15
Gly

<210> SEQ ID NO 91
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 91

Glu Ile Phe Pro Gly Ser Gly Asn Thr His Phe Ser Ser Ala Pro Leu
1               5                   10                  15
Pro

```
<210> SEQ ID NO 92
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 92

Glu Ile Phe Pro Gly Ser Gly Asn Thr His Phe Ser Ser Glu Phe Val
1               5                   10                  15

Ser

<210> SEQ ID NO 93
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 93

Glu Ile Phe Pro Gly Ser Gly Asn Thr His Phe Ser Met Ser Glu Ser
1               5                   10                  15

Phe

<210> SEQ ID NO 94
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 94

Glu Ile Phe Pro Gly Ser Gly Asn Thr His Phe Ser Asp Gly Ser Arg
1               5                   10                  15

Asn

<210> SEQ ID NO 95
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 95

Glu Ile Phe Pro Gly Ser Gly Asn Thr His Phe Ser Ser Ser Val Ser
1               5                   10                  15

Arg

<210> SEQ ID NO 96
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 96

Glu Ile Phe Pro Gly Ser Gly Asn Thr His Phe Ser Arg Ser Val Ser
1               5                   10                  15

Gly

<210> SEQ ID NO 97
<211> LENGTH: 17
<212> TYPE: PRT
```

```
<213> ORGANISM: Artificial Sequence
<220> FEATURE:
<223> OTHER INFORMATION: hu8C4 CH CDR2

<400> SEQUENCE: 97

Glu Ile Phe Pro Gly Ser Gly Asn Thr His Phe Ser Gly Leu Ser Glu
1               5                   10                  15

Val

<210> SEQ ID NO 98
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 98

Glu Ile Phe Pro Gly Ser Gly Asn Thr His Phe Ser His Tyr Trp Ala
1               5                   10                  15

Ser

<210> SEQ ID NO 99
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 99

Glu Ile Phe Pro Gly Ser Gly Asn Thr His Phe Ser Thr Gly Leu Thr
1               5                   10                  15

Gln

<210> SEQ ID NO 100
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 100

Glu Ile Phe Pro Gly Ser Gly Asn Thr His Phe Ser Arg His Arg Leu
1               5                   10                  15

His

<210> SEQ ID NO 101
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 101

Glu Ile Phe Pro Gly Ser Gly Asn Thr His Phe Ser Val Pro Arg Ser
1               5                   10                  15

Met

<210> SEQ ID NO 102
<211> LENGTH: 17
<212> TYPE: PRT
<213> ORGANISM: Artificial Sequence
<220> FEATURE:
<223> OTHER INFORMATION: hu8C4 CH CDR2
```

```
<400> SEQUENCE: 102

Glu Ile Phe Pro Gly Ser Gly Asn Thr His Phe Ser Leu Gln Asp Tyr
1               5                   10                  15

Leu

<210> SEQ ID NO 103
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 103

Glu Ile Phe Pro Gly Ser Gly Asn Thr His Phe Ser Asp Gly Val Ser
1               5                   10                  15

Ser

<210> SEQ ID NO 104
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 104

Glu Ile Phe Pro Gly Ser Gly Asn Thr His Phe Ser Met Gln Gly Ser
1               5                   10                  15

Glu

<210> SEQ ID NO 105
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 105

Glu Ile Phe Pro Gly Ser Gly Asn Thr His Phe Ser Gly Asn Val His
1               5                   10                  15

Trp

<210> SEQ ID NO 106
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 106

Glu Ile Phe Pro Gly Ser Gly Asn Thr His Phe Ser Arg Ser Pro Thr
1               5                   10                  15

Pro

<210> SEQ ID NO 107
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 107

Glu Ile Phe Pro Gly Ser Gly Asn Thr His Phe Ser Leu Arg Met Phe
1               5                   10                  15
```

Pro

<210> SEQ ID NO 108
<211> LENGTH: 5
<212> TYPE: PRT
<213> ORGANISM: Artificial Sequence
<220> FEATURE:
<223> OTHER INFORMATION: hu8C4 CH CDR1

<400> SEQUENCE: 108

Asp Tyr Tyr Ala Asn
1               5

<210> SEQ ID NO 109
<211> LENGTH: 5
<212> TYPE: PRT
<213> ORGANISM: Artificial Sequence
<220> FEATURE:
<223> OTHER INFORMATION: hu8C4 CH CDR1

<400> SEQUENCE: 109

Gly Tyr Tyr Ile Asn
1               5

<210> SEQ ID NO 110
<211> LENGTH: 5
<212> TYPE: PRT
<213> ORGANISM: Artificial Sequence
<220> FEATURE:
<223> OTHER INFORMATION: hu8C4 CH CDR1

<400> SEQUENCE: 110

Gln Tyr Tyr Ile Asn
1               5

<210> SEQ ID NO 111
<211> LENGTH: 5
<212> TYPE: PRT
<213> ORGANISM: Artificial Sequence
<220> FEATURE:
<223> OTHER INFORMATION: hu8C4 CH CDR1

<400> SEQUENCE: 111

Asp Gln Tyr Ile Asn
1               5

<210> SEQ ID NO 112
<211> LENGTH: 5
<212> TYPE: PRT
<213> ORGANISM: Artificial Sequence
<220> FEATURE:
<223> OTHER INFORMATION: hu8C4 CH CDR1

<400> SEQUENCE: 112

Asp Tyr Tyr Gln Asn
1               5

<210> SEQ ID NO 113
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 113

Gly Asp Val Gly Phe Leu Tyr

```
1               5
```

<210> SEQ ID NO 114
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 114

```
Gly Asp Tyr Gly Phe Gln Tyr
1               5
```

<210> SEQ ID NO 115
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 115

```
Gly Asp Tyr Gly Phe Leu Gln
1               5
```

<210> SEQ ID NO 116
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 116

```
Gly Asp Gln Trp Leu Leu Cys
1               5
```

<210> SEQ ID NO 117
<211> LENGTH: 7
<212> TYPE: PRT
<213> ORGANISM: Artificial Sequence
<220> FEATURE:
<223> OTHER INFORMATION: hu8C4 CH CDR3

<400> SEQUENCE: 117

```
Trp Asp Tyr Gly Phe Leu Tyr
1               5
```

<210> SEQ ID NO 118
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 118

```
Glu Ile Phe Pro Asp Ser Ala Pro Ser His Phe Ser Ala Arg Phe Lys
1               5                   10                  15

Gly
```

<210> SEQ ID NO 119
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 119

```
Glu Ile Phe Pro Tyr Phe Leu Pro Pro His Phe Ser Ala Arg Phe Lys
1               5                   10                  15

Gly
```

<210> SEQ ID NO 120
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 120

```
Glu Ile Phe Pro Gly Pro Phe Thr Pro His Phe Ser Ala Arg Phe Lys
1               5                   10                  15

Gly
```

<210> SEQ ID NO 121
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 121

```
Glu Ile Phe Pro Gly Ser Asn Phe Gly His Phe Ser Ala Arg Phe Lys
1               5                   10                  15

Gly
```

<210> SEQ ID NO 122
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 122

```
Glu Ile Phe Pro Gly Trp Gly Asn Thr His Phe Ser Arg Ser Pro Thr
1               5                   10                  15

Pro
```

<210> SEQ ID NO 123
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 123

```
Glu Ile Phe Pro Gly Trp Gly Asn Ser His Val Val Ser Arg Phe Lys
1               5                   10                  15

Gly
```

<210> SEQ ID NO 124
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 124

```
Glu Ile Phe Pro Gly Tyr Gly Asn Thr Tyr Phe Ser Ala Arg Phe Lys
1               5                   10                  15

Gly
```

```
<210> SEQ ID NO 125
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 125

Glu Ile Phe Pro Gly Tyr Gly Asn Thr His Phe Ser Arg Ser Pro Thr
1               5                   10                  15

Pro

<210> SEQ ID NO 126
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 126

Glu Ile Phe Pro Gly Tyr Gly Asn Ser His Val Val Ser Arg Phe Lys
1               5                   10                  15

Gly

<210> SEQ ID NO 127
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 127

Glu Ile Phe Pro Gly Ser Gly Asn Thr Tyr Phe Ser Arg Ser Pro Thr
1               5                   10                  15

Pro

<210> SEQ ID NO 128
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 128

Glu Ile Phe Pro Gly Ser Gly Asn Ser His Val Val Arg Ser Pro Thr
1               5                   10                  15

Pro

<210> SEQ ID NO 129
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 129

Glu Ile Phe Pro Gly Ser Gly Asn Ser His Val Val Ser Ser Pro Thr
1               5                   10                  15

Pro

<210> SEQ ID NO 130
<211> LENGTH: 17
```

```
<212> TYPE: PRT
<213> ORGANISM: Artificial Sequence
<220> FEATURE:
<223> OTHER INFORMATION: hu8C4 CH CDR2

<400> SEQUENCE: 130

Glu Ile Phe Pro Asp Ser Ala Pro Ser Tyr Phe Ser Ala Arg Phe Lys
1               5                   10                  15

Gly

<210> SEQ ID NO 131
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 131

Glu Ile Phe Pro Gly Pro Phe Thr Pro Tyr Phe Ser Ala Arg Phe Lys
1               5                   10                  15

Gly

<210> SEQ ID NO 132
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 132

Glu Ile Phe Pro Gly Ser Asn Phe Gly Tyr Phe Ser Arg Ser Pro Thr
1               5                   10                  15

Pro

<210> SEQ ID NO 133
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 133

Glu Ile Phe Pro Asp Ser Ala Pro Ser His Val Val Ser Arg Phe Lys
1               5                   10                  15

Gly

<210> SEQ ID NO 134
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 134

Glu Ile Phe Pro Gly Pro Phe Thr Ser His Val Val Ser Arg Phe Lys
1               5                   10                  15

Gly

<210> SEQ ID NO 135
<211> LENGTH: 17
<212> TYPE: PRT
<213> ORGANISM: Artificial Sequence
<220> FEATURE:
<223> OTHER INFORMATION: hu8C4 CH CDR2
```

```
<400> SEQUENCE: 135

Glu Ile Phe Pro Gly Ser Asn Phe Ser His Val Val Ser Arg Phe Lys
1               5                   10                  15

Gly

<210> SEQ ID NO 136
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 136

Glu Ile Phe Pro Asp Ser Ala Pro Ser His Phe Ser Arg Ser Pro Thr
1               5                   10                  15

Pro

<210> SEQ ID NO 137
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 137

Glu Ile Phe Pro Gly Pro Phe Thr Pro His Phe Ser Arg Ser Pro Thr
1               5                   10                  15

Pro

<210> SEQ ID NO 138
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 138

Glu Ile Phe Pro Gly Ser Asn Phe Gly His Phe Ser Arg Ser Pro Thr
1               5                   10                  15

Pro

<210> SEQ ID NO 139
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 139

Glu Ile Phe Pro Asp Ser Ala Pro Ser His Val Val Ser Ser Pro Thr
1               5                   10                  15

Pro

<210> SEQ ID NO 140
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 140

Glu Ile Phe Pro Gly Pro Phe Thr Ser His Val Val Ser Ser Pro Thr
```

Pro

<210> SEQ ID NO 141
<211> LENGTH: 17
<212> TYPE: PRT
<213> ORGANISM: Artificial Sequence
<220> FEATURE:
<223> OTHER INFORMATION: hu8C4 CH CDR2

<400> SEQUENCE: 141

Glu Ile Phe Pro Gly Ser Asn Phe Ser His Val Val Ser Ser Pro Thr
1               5                   10                  15
Pro

<210> SEQ ID NO 142
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 142

Gln Asn Val Trp Ser Ser Pro Tyr Thr
1               5

<210> SEQ ID NO 143
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 143

Gln Asn Val Leu Asn Ser Pro Tyr Thr
1               5

<210> SEQ ID NO 144
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 144

Gln Asn Val Leu Glu Ser Pro Tyr Thr
1               5

<210> SEQ ID NO 145
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 145

Gln Asn Val Leu Lys Ser Pro Tyr Thr
1               5

<210> SEQ ID NO 146
<211> LENGTH: 9
<212> TYPE: PRT
<213> ORGANISM: Artificial Sequence
<220> FEATURE:
<223> OTHER INFORMATION: hu8C4 CL CDR3

```
<400> SEQUENCE: 146

Gln Asn Val Leu Tyr Ser Pro Tyr Thr
1               5

<210> SEQ ID NO 147
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 147

Gln Asn Val Leu Ser Arg Pro Tyr Thr
1               5

<210> SEQ ID NO 148
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 148

Gln Asn Val Leu Ser Ser Pro Glu Thr
1               5

<210> SEQ ID NO 149
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 149

Gln Asn Val Leu Ser Glu Pro Tyr Thr
1               5

<210> SEQ ID NO 150
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 150

Gln Asn Val Leu Glu Ser Pro Glu Thr
1               5

<210> SEQ ID NO 151
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 151

Gln Asn Val Leu Ser Val Pro Glu Thr
1               5

<210> SEQ ID NO 152
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 152
```

Gln Asn Val Leu Ser Leu Pro Glu Thr
1               5

<210> SEQ ID NO 153
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 153

Gln Asn Val Leu Ser Ile Pro Glu Thr
1               5

<210> SEQ ID NO 154
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 154

Gln Asn Val Leu Ser Met Pro Glu Thr
1               5

<210> SEQ ID NO 155
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 155

Gln Asn Ile Leu Ser Ser Pro Glu Thr
1               5

<210> SEQ ID NO 156
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 156

Gln Asn Leu Ile Ser Ser Pro Glu Thr
1               5

<210> SEQ ID NO 157
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 157

Gln Asn Met Ile Ser Ser Pro Glu Thr
1               5

<210> SEQ ID NO 158
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 158

```
Gln Asn Ile Ile Ser Leu Pro Glu Thr
1               5
```

<210> SEQ ID NO 159
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 159

```
Gln Asn Ile Ile Ser Ile Pro Glu Thr
1               5
```

<210> SEQ ID NO 160
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 160

```
Gln Asn Ser Leu Ser Ser Pro Glu Thr
1               5
```

<210> SEQ ID NO 161
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 161

```
Gln Asn Thr Leu Ser Ser Pro Glu Thr
1               5
```

<210> SEQ ID NO 162
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 162

```
Gln Asn Val Ser Ser Ser Pro Glu Thr
1               5
```

<210> SEQ ID NO 163
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 163

```
Gln Asn Val Ile Ser Ser Pro Glu Thr
1               5
```

<210> SEQ ID NO 164
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 164

```
Gln Asn Val Phe Ser Ser Pro Glu Thr
```

```
1               5

<210> SEQ ID NO 165
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 165

Gln Asn Val Tyr Ser Ser Pro Glu Thr
1               5

<210> SEQ ID NO 166
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 166

Gln Asn Val Arg Ser Ser Pro Glu Thr
1               5

<210> SEQ ID NO 167
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 167

Gln Asn Leu Val Ser Ser Pro Glu Thr
1               5

<210> SEQ ID NO 168
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 168

Gln Asn Leu Met Ser Ser Pro Glu Thr
1               5

<210> SEQ ID NO 169
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 169

Gln Asn Ile Met Ser Ser Pro Glu Thr
1               5

<210> SEQ ID NO 170
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 170

Gln Asn Val His Ser Ser Pro Glu Thr
1               5
```

```
<210> SEQ ID NO 171
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 171

Gln Asn Val Met Ser Ser Pro Glu Thr
1               5

<210> SEQ ID NO 172
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 172

Gln Asn Leu Leu Ser Ser Pro Glu Thr
1               5

<210> SEQ ID NO 173
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 173

Gln Ser Val Leu Phe Ser Pro Phe Ser
1               5

<210> SEQ ID NO 174
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 174

Gln Gln Val Leu Phe Phe Pro Glu Thr
1               5

<210> SEQ ID NO 175
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 175

Gln Asn Leu Leu Ser Pro Ser Phe Tyr
1               5

<210> SEQ ID NO 176
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 176

Gln Ser Val Leu Phe Ser Pro Phe Thr
1               5
```

```
<210> SEQ ID NO 177
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 177

Gln Asn Ile Leu Ser Ser Pro Leu Phe
1               5

<210> SEQ ID NO 178
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 178

Gln Asn Thr Leu His Tyr Ser Leu Val
1               5

<210> SEQ ID NO 179
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 179

Gln Gln Val Leu Phe Phe Pro Leu Leu
1               5

<210> SEQ ID NO 180
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 180

Gln Gln Val Leu Asp Phe Val Phe Tyr
1               5

<210> SEQ ID NO 181
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 181

Gln Asn Val Val Ser Ser Pro Glu Thr
1               5

<210> SEQ ID NO 182
<211> LENGTH: 7
<212> TYPE: PRT
<213> ORGANISM: Artificial Sequence
<220> FEATURE:
<223> OTHER INFORMATION: hu8C4 CL CDR2

<400> SEQUENCE: 182

Asp Ala Thr Asn Leu Ala Asp
1               5
```

```
<210> SEQ ID NO 183
<211> LENGTH: 7
<212> TYPE: PRT
<213> ORGANISM: Artificial Sequence
<220> FEATURE:
<223> OTHER INFORMATION: hu8C4 CL CDR2

<400> SEQUENCE: 183

Phe Ala Thr Asn Leu Ala Asp
1               5

<210> SEQ ID NO 184
<211> LENGTH: 7
<212> TYPE: PRT
<213> ORGANISM: Artificial Sequence
<220> FEATURE:
<223> OTHER INFORMATION: hu8C4 CL CDR2

<400> SEQUENCE: 184

His Ala Thr Asn Leu Ala Asp
1               5

<210> SEQ ID NO 185
<211> LENGTH: 7
<212> TYPE: PRT
<213> ORGANISM: Artificial Sequence
<220> FEATURE:
<223> OTHER INFORMATION: hu8C4 CL CDR2

<400> SEQUENCE: 185

Lys Ala Thr Asn Leu Ala Asp
1               5

<210> SEQ ID NO 186
<211> LENGTH: 7
<212> TYPE: PRT
<213> ORGANISM: Artificial Sequence
<220> FEATURE:
<223> OTHER INFORMATION: hu8C4 CL CDR2

<400> SEQUENCE: 186

Pro Ala Thr Asn Leu Ala Asp
1               5

<210> SEQ ID NO 187
<211> LENGTH: 7
<212> TYPE: PRT
<213> ORGANISM: Artificial Sequence
<220> FEATURE:
<223> OTHER INFORMATION: hu8C4 CL CDR2

<400> SEQUENCE: 187

Gln Ala Thr Asn Leu Ala Asp
1               5

<210> SEQ ID NO 188
<211> LENGTH: 7
<212> TYPE: PRT
<213> ORGANISM: Artificial Sequence
<220> FEATURE:
<223> OTHER INFORMATION: hu8C4 CL CDR2

<400> SEQUENCE: 188

Ser Ala Thr Asn Leu Ala Asp
1               5

<210> SEQ ID NO 189
```

```
<211> LENGTH: 7
<212> TYPE: PRT
<213> ORGANISM: Artificial Sequence
<220> FEATURE:
<223> OTHER INFORMATION: hu8C4 CL CDR2

<400> SEQUENCE: 189

Val Ala Thr Asn Leu Ala Asp
1               5

<210> SEQ ID NO 190
<211> LENGTH: 7
<212> TYPE: PRT
<213> ORGANISM: Artificial Sequence
<220> FEATURE:
<223> OTHER INFORMATION: hu8C4 CL CDR2

<400> SEQUENCE: 190

Tyr Ala Thr Asn Leu Ala Asp
1               5

<210> SEQ ID NO 191
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 191

Ile Thr Val Leu Ser Pro Pro Tyr Thr
1               5

<210> SEQ ID NO 192
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 192

Gln Asn Asn Leu Val Pro Pro Phe Asn
1               5

<210> SEQ ID NO 193
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 193

Gln His Val Leu Phe Leu Pro Tyr Val
1               5

<210> SEQ ID NO 194
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 194

Gln Ala Val Leu Thr Asn Ala Tyr Thr
1               5

<210> SEQ ID NO 195
<211> LENGTH: 9
```

```
<212> TYPE: PRT
<213> ORGANISM: Artificial Sequence
<220> FEATURE:
<223> OTHER INFORMATION: hu8C4 CL CDR3

<400> SEQUENCE: 195

Gln Asn Val Leu Arg Val Gly Tyr Leu
1               5

<210> SEQ ID NO 196
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 196

Gln Ser Val Leu Arg Val Gly Tyr Leu
1               5

<210> SEQ ID NO 197
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 197

Gln Asn Ile Ile Ser Ser Pro Tyr Thr
1               5

<210> SEQ ID NO 198
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 198

Gln Gln Val Leu Cys Glu Ser Phe Leu
1               5

<210> SEQ ID NO 199
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 199

Gln Asn Val Leu Ser Gln Ser Leu Leu
1               5

<210> SEQ ID NO 200
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 200

Gln Asn Val Leu Gln Pro Ser Tyr Leu
1               5

<210> SEQ ID NO 201
<211> LENGTH: 9
<212> TYPE: PRT
```

```
<213> ORGANISM: Artificial Sequence
<220> FEATURE:
<223> OTHER INFORMATION: hu8C4 CL CDR3

<400> SEQUENCE: 201

Gln Asn Leu Leu Phe Gln Pro Leu Ser
1               5

<210> SEQ ID NO 202
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 202

Gln Asn Val Leu Phe Gln Pro Leu Val
1               5

<210> SEQ ID NO 203
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 203

Gln Asn Gln Leu Asp Pro Ser Leu Phe
1               5

<210> SEQ ID NO 204
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 204

Met Asp Val Leu Glu Ser Pro Tyr Thr
1               5

<210> SEQ ID NO 205
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 205

Gln Ala Leu Leu Leu Ser Pro Tyr Thr
1               5

<210> SEQ ID NO 206
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 206

Gln Gln Leu Leu Glu Ser Pro Tyr Thr
1               5

<210> SEQ ID NO 207
<211> LENGTH: 9
<212> TYPE: PRT
<213> ORGANISM: Artificial Sequence
```

```
<220> FEATURE:
<223> OTHER INFORMATION: hu8C4 CL CDR3

<400> SEQUENCE: 207

Asn Leu Thr Leu Val Ser Pro Tyr Thr
1               5

<210> SEQ ID NO 208
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 208

Gly Asn Ile Leu Asp Ser Pro Tyr Thr
1               5

<210> SEQ ID NO 209
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 209

Glu Gln Val Leu Leu Ser Pro Tyr Thr
1               5

<210> SEQ ID NO 210
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 210

Asn Asn Leu Leu Asp Ser Pro Tyr Thr
1               5

<210> SEQ ID NO 211
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 211

Glu Glu Val Leu Ser Ser Pro Tyr Thr
1               5

<210> SEQ ID NO 212
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 212

Gln Asn Ile Leu Phe Val Asp Tyr Thr
1               5

<210> SEQ ID NO 213
<211> LENGTH: 9
<212> TYPE: PRT
<213> ORGANISM: Artificial Sequence
<220> FEATURE:
```

<223> OTHER INFORMATION: hu8C4 CL CDR3

<400> SEQUENCE: 213

Gln Asn Val Leu His Leu Asn Tyr Thr
1               5

<210> SEQ ID NO 214
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 214

Gln Asn Val Leu Gln Thr Pro Tyr Thr
1               5

<210> SEQ ID NO 215
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 215

Gln Asn Ile Leu His Pro Gly Tyr Thr
1               5

<210> SEQ ID NO 216
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 216

Gln Asn Val Leu Thr Arg Gly Tyr Thr
1               5

<210> SEQ ID NO 217
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 217

Glu Asn Ile Leu Tyr Ser Pro Tyr Thr
1               5

<210> SEQ ID NO 218
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 218

Gln Asn Val Leu Gly Gly Gly Gln Gly
1               5

<210> SEQ ID NO 219
<211> LENGTH: 9
<212> TYPE: PRT
<213> ORGANISM: Artificial Sequence
<220> FEATURE:
<223> OTHER INFORMATION: hu8C4 CL CDR3

```
<400> SEQUENCE: 219

Gln Asn Val Leu Glu His Pro Leu Ile
1               5

<210> SEQ ID NO 220
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 220

Gln Asn Val Leu Asp Asp Pro Phe Asp
1               5

<210> SEQ ID NO 221
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 221

Gln Asn Val Leu Asp Phe Pro Leu Leu
1               5

<210> SEQ ID NO 222
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 222

Gln Asn Val Leu Tyr Pro Ser Leu Val
1               5

<210> SEQ ID NO 223
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 223

Gln Asn Val Leu Phe Asp Gln Gln Ser
1               5

<210> SEQ ID NO 224
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 224

Gln Asn Val Leu Ser Asn Glu Glu Thr
1               5

<210> SEQ ID NO 225
<211> LENGTH: 9
<212> TYPE: PRT
<213> ORGANISM: Artificial Sequence
<220> FEATURE:
<223> OTHER INFORMATION: hu8C4 CL CDR3
```

```
<400> SEQUENCE: 225

Gln Asn Val Leu Lys His Pro Tyr Thr
1               5

<210> SEQ ID NO 226
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 226

Gln Asn Val Leu Ser Pro Gly Met Trp
1               5

<210> SEQ ID NO 227
<211> LENGTH: 7
<212> TYPE: PRT
<213> ORGANISM: Artificial Sequence
<220> FEATURE:
<223> OTHER INFORMATION: hu8C4 CL CDR2

<400> SEQUENCE: 227

Gly Ala Thr Gly Leu Ala Asp
1               5

<210> SEQ ID NO 228
<211> LENGTH: 7
<212> TYPE: PRT
<213> ORGANISM: Artificial Sequence
<220> FEATURE:
<223> OTHER INFORMATION: hu8C4 CL CDR2

<400> SEQUENCE: 228

Gly Ala Gln Asn Leu Ala Asp
1               5

<210> SEQ ID NO 229
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 229

Gly Ser Ser Arg Ser Ile Tyr Gly Ala Leu Asn
1               5                   10

<210> SEQ ID NO 230
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 230

Arg Ala Gly Arg Ser Ile Tyr Gly Ala Leu Asn
1               5                   10

<210> SEQ ID NO 231
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 231
```

Leu Gly Arg Arg Gly Ile Tyr Gly Ala Leu Asn
1               5                   10

<210> SEQ ID NO 232
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 232

Glu Val Gln Val Gly Ile Tyr Gly Ala Leu Asn
1               5                   10

<210> SEQ ID NO 233
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 233

Arg Pro Ser Glu Lys Ile Tyr Gly Ala Leu Asn
1               5                   10

<210> SEQ ID NO 234
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 234

Arg Ala Ser Ala Val Ile Tyr Gly Ala Leu Asn
1               5                   10

<210> SEQ ID NO 235
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 235

Lys Thr Gly Asp Leu Ile Tyr Gly Ala Leu Asn
1               5                   10

<210> SEQ ID NO 236
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 236

Ser Cys Arg Val Pro Ile Tyr Gly Ala Leu Asn
1               5                   10

<210> SEQ ID NO 237
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 237

Val Ala Ser Arg Gly Ile Tyr Gly Ala Leu Asn
1               5                   10

<210> SEQ ID NO 238
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 238

Arg Gly Arg Gln Asn Ile Tyr Gly Ala Leu Asn
1               5                   10

<210> SEQ ID NO 239
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 239

Ala Ala Pro Arg Gly Ile Tyr Gly Ala Leu Asn
1               5                   10

<210> SEQ ID NO 240
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 240

Ser Ala Pro Phe Lys Ile Tyr Gly Ala Leu Asn
1               5                   10

<210> SEQ ID NO 241
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 241

Leu Gly Met Asp Asp Ile Tyr Gly Ala Leu Asn
1               5                   10

<210> SEQ ID NO 242
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 242

Asn Val Arg Arg Gly Ile Tyr Gly Ala Leu Asn
1               5                   10

<210> SEQ ID NO 243
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 243

Asn Thr Ser Gly Arg Ile Tyr Gly Ala Leu Asn

<210> SEQ ID NO 244
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 244

Leu Val Ser Arg Pro Ile Tyr Gly Ala Leu Asn
1               5                   10

<210> SEQ ID NO 245
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 245

Trp Thr Asn Arg Pro Ile Tyr Gly Ala Leu Asn
1               5                   10

<210> SEQ ID NO 246
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 246

Arg Ile Pro Ser Ala Ile Tyr Gly Ala Leu Asn
1               5                   10

<210> SEQ ID NO 247
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 247

Gly Ala Thr Arg Gly Ile Tyr Gly Ala Leu Asn
1               5                   10

<210> SEQ ID NO 248
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 248

Glu Gly Gly Ser Pro Ile Tyr Gly Ala Leu Asn
1               5                   10

<210> SEQ ID NO 249
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 249

Gly Ala Ser Arg Gly Met Phe Arg Ala Leu Asn
1               5                   10

```
<210> SEQ ID NO 250
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 250

Gly Ala Ser Gly Leu Val Phe Ser Ala Leu Asn
1               5                   10

<210> SEQ ID NO 251
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 251

Gly Ala Ser Arg Gly Thr His Met Ala Leu Asn
1               5                   10

<210> SEQ ID NO 252
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 252

Gly Ala Ser Ser Arg Phe His Asn Ala Leu Asn
1               5                   10

<210> SEQ ID NO 253
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 253

Gly Ala Ser Arg Thr Ala Phe Thr Ala Leu Asn
1               5                   10

<210> SEQ ID NO 254
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 254

Gly Ala Ser Arg Ser Thr Phe Ser Ala Leu Asn
1               5                   10

<210> SEQ ID NO 255
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 255

Gly Ala Ser Gly Pro Met Phe Asp Ala Leu Asn
1               5                   10
```

```
<210> SEQ ID NO 256
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 256

Gly Ala Ser His Asp Leu Tyr Gly Ala Leu Asn
1               5                   10

<210> SEQ ID NO 257
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 257

Gly Ala Ser Gly Thr Leu Phe Gly Ala Leu Asn
1               5                   10

<210> SEQ ID NO 258
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 258

Gly Ala Ser Lys Ala Ala Phe Gly Ala Leu Asn
1               5                   10

<210> SEQ ID NO 259
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 259

Gly Ala Ser Glu Gly Ile Val Gly Ala Leu Asn
1               5                   10

<210> SEQ ID NO 260
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 260

Gly Ala Ser His Glu Ile His Val Ala Leu Asn
1               5                   10

<210> SEQ ID NO 261
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 261

Gly Ala Ser Arg Gly Val Phe Gly Ala Leu Asn
1               5                   10
```

```
<210> SEQ ID NO 262
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 262

Gly Ala Ser Gly Arg Val Arg Gly Ala Leu Asn
1               5                   10

<210> SEQ ID NO 263
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 263

Gly Ala Ser Thr Gly Ser Phe Ser Ala Leu Asn
1               5                   10

<210> SEQ ID NO 264
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 264

Gly Ala Ser Gly Asn Ser Phe Asp Ala Leu Asn
1               5                   10

<210> SEQ ID NO 265
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 265

Gly Ala Ser Glu Gln Ser Tyr Phe Ala Leu Asn
1               5                   10

<210> SEQ ID NO 266
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 266

Gly Ala Ser Phe Arg Gln Phe Ser Ala Leu Asn
1               5                   10

<210> SEQ ID NO 267
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 267

Gly Ala Ser Ala Pro Arg His Ser Ala Leu Asn
1               5                   10

<210> SEQ ID NO 268
```

```
<211> LENGTH: 11
<212> TYPE: PRT
<213> ORGANISM: Artificial Sequence
<220> FEATURE:
<223> OTHER INFORMATION: hu8C4 CL CDR1

<400> SEQUENCE: 268

Gly Ala Ser Met Pro Leu Phe His Ala Leu Asn
1               5                   10

<210> SEQ ID NO 269
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 269

Gln Asn Ile Leu Ser Ser Pro Tyr Thr
1               5

<210> SEQ ID NO 270
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 270

Gln Asn Val Leu Ser Met Pro Tyr Thr
1               5

<210> SEQ ID NO 271
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 271

Gln Asn Val Leu Ser Glu Pro Glu Thr
1               5

<210> SEQ ID NO 272
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 272

Gln Asn Val Leu Tyr Ser Pro Glu Thr
1               5

<210> SEQ ID NO 273
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 273

Gln Asn Val Leu Glu Glu Pro Tyr Thr
1               5

<210> SEQ ID NO 274
<211> LENGTH: 9
```

```
<212> TYPE: PRT
<213> ORGANISM: Artificial Sequence
<220> FEATURE:
<223> OTHER INFORMATION: hu8C4 CL CDR3

<400> SEQUENCE: 274

Gln Asn Val Leu Glu Leu Pro Glu Thr
1               5

<210> SEQ ID NO 275
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 275

Gln Asn Val Leu Glu Met Pro Glu Thr
1               5

<210> SEQ ID NO 276
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 276

Gln Asn Ile Leu Glu Ser Pro Glu Thr
1               5

<210> SEQ ID NO 277
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 277

Gln Asn Val Ile Glu Ser Pro Glu Thr
1               5

<210> SEQ ID NO 278
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 278

Gln Asn Val Met Glu Ser Pro Glu Thr
1               5

<210> SEQ ID NO 279
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 279

Gln Asn Leu Leu Glu Ser Pro Glu Thr
1               5

<210> SEQ ID NO 280
<211> LENGTH: 9
<212> TYPE: PRT
```

<213> ORGANISM: Artificial Sequence
<220> FEATURE:
<223> OTHER INFORMATION: hu8C4 CL CDR3

<400> SEQUENCE: 280

Gln Asn Val Leu Tyr Glu Pro Tyr Thr
1               5

<210> SEQ ID NO 281
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 281

Gln Asn Ile Leu Ser Glu Pro Glu Thr
1               5

<210> SEQ ID NO 282
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 282

Gln Asn Val Ile Ser Glu Pro Glu Thr
1               5

<210> SEQ ID NO 283
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 283

Gln Asn Val Met Ser Glu Pro Glu Thr
1               5

<210> SEQ ID NO 284
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 284

Gln Asn Leu Leu Ser Glu Pro Glu Thr
1               5

<210> SEQ ID NO 285
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 285

Gln Ser Val Leu Phe Glu Pro Phe Ser
1               5

<210> SEQ ID NO 286
<211> LENGTH: 9
<212> TYPE: PRT
<213> ORGANISM: Artificial Sequence

```
<220> FEATURE:
<223> OTHER INFORMATION: hu8C4 CL CDR3

<400> SEQUENCE: 286

Gln Ser Val Leu Phe Glu Pro Phe Thr
1               5

<210> SEQ ID NO 287
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 287

Gln Asn Ile Leu Tyr Ser Pro Glu Thr
1               5

<210> SEQ ID NO 288
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 288

Gln Asn Ile Leu Ser Leu Pro Glu Thr
1               5

<210> SEQ ID NO 289
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 289

Gln Asn Ile Leu Ser Met Pro Glu Thr
1               5

<210> SEQ ID NO 290
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 290

Gln Asn Val Leu Tyr Met Pro Glu Thr
1               5

<210> SEQ ID NO 291
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 291

Gln Asn Val Ile Ser Met Pro Glu Thr
1               5

<210> SEQ ID NO 292
<211> LENGTH: 9
<212> TYPE: PRT
<213> ORGANISM: Artificial Sequence
<220> FEATURE:
```

<223> OTHER INFORMATION: hu8C4 CL CDR3

<400> SEQUENCE: 292

Gln Asn Val Met Ser Met Pro Glu Thr
1               5

<210> SEQ ID NO 293
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 293

Gln Asn Leu Leu Ser Met Pro Glu Thr
1               5

<210> SEQ ID NO 294
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 294

Gln Asn Ile Ile Ser Ser Pro Glu Thr
1               5

<210> SEQ ID NO 295
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 295

Gln Asn Val Leu Tyr Leu Pro Glu Thr
1               5

<210> SEQ ID NO 296
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 296

Gln Asn Val Ile Tyr Ser Pro Glu Thr
1               5

<210> SEQ ID NO 297
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 297

Gln Asn Val Met Tyr Ser Pro Glu Thr
1               5

<210> SEQ ID NO 298
<211> LENGTH: 9
<212> TYPE: PRT
<213> ORGANISM: Artificial Sequence
<220> FEATURE:
<223> OTHER INFORMATION: hu8C4 CL CDR3

```
<400> SEQUENCE: 298

Gln Asn Leu Leu Tyr Ser Pro Glu Thr
1               5

<210> SEQ ID NO 299
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 299

Gln Asn Val Ile Ser Leu Pro Glu Thr
1               5

<210> SEQ ID NO 300
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 300

Gln Asn Val Met Ser Leu Pro Glu Thr
1               5

<210> SEQ ID NO 301
<211> LENGTH: 9
<212> TYPE: PRT
<213> ORGANISM: Artificial Sequence
<220> FEATURE:
<223> OTHER INFORMATION: hu8C4 CL CDR3

<400> SEQUENCE: 301

Gln Asn Leu Leu Ser Leu Pro Glu Thr
1               5

<210> SEQ ID NO 302
<211> LENGTH: 116
<212> TYPE: PRT
<213> ORGANISM: Artificial Sequence
<220> FEATURE:
<223> OTHER INFORMATION: AH71

<400> SEQUENCE: 302

Glu Val Gln Leu Val Glu Ser Gly Gly Gly Leu Val Gln Pro Gly Gly
1               5                  10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
        35                  40                  45

Gly Glu Ile Phe Pro Gly Trp Gly Asn Thr His Phe Ser Ala Arg Phe
    50                  55                  60

Lys Gly Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gln Asp Tyr Gly Phe Leu Tyr Trp Gly Gln Gly Thr Leu Val
            100                 105                 110

Thr Val Ser Ser
        115
```

```
<210> SEQ ID NO 303
<211> LENGTH: 116
<212> TYPE: PRT
<213> ORGANISM: Artificial Sequence
<220> FEATURE:
<223> OTHER INFORMATION: AH72

<400> SEQUENCE: 303

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
        35                  40                  45

Gly Glu Ile Phe Pro Gly Trp Gly Asn Thr His Phe Ser Arg Ser Pro
    50                  55                  60

Thr Pro Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gly Asp Tyr Gly Phe Leu Tyr Trp Gly Gln Gly Thr Leu Val
            100                 105                 110

Thr Val Ser Ser
            115

<210> SEQ ID NO 304
<211> LENGTH: 116
<212> TYPE: PRT
<213> ORGANISM: Artificial Sequence
<220> FEATURE:
<223> OTHER INFORMATION: AH73

<400> SEQUENCE: 304

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
        35                  40                  45

Gly Glu Ile Phe Pro Gly Trp Gly Asn Ser His Val Val Ser Arg Phe
    50                  55                  60

Lys Gly Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gly Asp Tyr Gly Phe Leu Tyr Trp Gly Gln Gly Thr Leu Val
            100                 105                 110

Thr Val Ser Ser
            115

<210> SEQ ID NO 305
<211> LENGTH: 116
<212> TYPE: PRT
<213> ORGANISM: Artificial Sequence
<220> FEATURE:
<223> OTHER INFORMATION: AH85

<400> SEQUENCE: 305

Glu Val Gln Leu Val Glu Ser Gly Gly Gly Leu Val Gln Pro Gly Gly
```

```
                1               5                   10                  15
            Ser Leu Arg Leu Ser Cys Ala Ala Ser Gly Tyr Thr Phe Ser Asp Tyr
                            20                  25                  30

Tyr Ile Asn Trp Val Arg Gln Ala Pro Gly Lys Gly Leu Glu Trp Ile
                        35                  40                  45

Gly Glu Ile Phe Pro Gly Trp Gly Asn Ser His Val Val Ser Arg Phe
                    50                  55                  60

Lys Gly Arg Ala Thr Leu Ser Asp Lys Ser Lys Asn Thr Ala Tyr
             65                 70                  75                  80

Leu Gln Met Asn Ser Leu Arg Ala Glu Asp Thr Ala Val Tyr Tyr Cys
                            85                  90                  95

Ala Gly Gln Asp Tyr Gly Phe Leu Tyr Trp Gly Gln Gly Thr Leu Val
                        100                 105                 110

Thr Val Ser Ser
                    115

<210> SEQ ID NO 306
<211> LENGTH: 107
<212> TYPE: PRT
<213> ORGANISM: Artificial Sequence
<220> FEATURE:
<223> OTHER INFORMATION: AL130

<400> SEQUENCE: 306

Asp Ile Gln Met Thr Gln Ser Pro Ser Ser Leu Ser Ala Ser Val Gly
             1               5                   10                  15

Asp Arg Val Thr Ile Thr Cys Gly Ala Ser Met Pro Leu Phe His Ala
                            20                  25                  30

Leu Asn Trp Tyr Gln Gln Lys Pro Gly Lys Ala Pro Lys Leu Leu Ile
                        35                  40                  45

Tyr Gly Ala Thr Asn Leu Ala Asp Gly Val Pro Ser Arg Phe Ser Gly
                    50                  55                  60

Ser Gly Ser Gly Arg Asp Phe Thr Phe Thr Ile Ser Ser Leu Gln Pro
             65                 70                  75                  80

Glu Asp Ile Ala Thr Tyr Tyr Cys Gln Asn Val Leu Ser Ser Pro Tyr
                            85                  90                  95

Thr Phe Gly Gln Gly Thr Lys Val Glu Ile Lys
                        100                 105

<210> SEQ ID NO 307
<211> LENGTH: 107
<212> TYPE: PRT
<213> ORGANISM: Artificial Sequence
<220> FEATURE:
<223> OTHER INFORMATION: AL135

<400> SEQUENCE: 307

Asp Ile Gln Met Thr Gln Ser Pro Ser Ser Leu Ser Ala Ser Val Gly
             1               5                   10                  15

Asp Arg Val Thr Ile Thr Cys Gly Ala Ser Glu Asn Ile Tyr Gly Ala
                            20                  25                  30

Leu Asn Trp Tyr Gln Gln Lys Pro Gly Lys Ala Pro Lys Leu Leu Ile
                        35                  40                  45

Tyr Gly Ala Thr Asn Leu Ala Asp Gly Val Pro Ser Arg Phe Ser Gly
                    50                  55                  60

Ser Gly Ser Gly Arg Asp Phe Thr Phe Thr Ile Ser Ser Leu Gln Pro
             65                 70                  75                  80
```

```
Glu Asp Ile Ala Thr Tyr Tyr Cys Gln Asn Val Leu Glu Glu Pro Tyr
                85                  90                  95

Thr Phe Gly Gln Gly Thr Lys Val Glu Ile Lys
            100                 105

<210> SEQ ID NO 308
<211> LENGTH: 107
<212> TYPE: PRT
<213> ORGANISM: Artificial Sequence
<220> FEATURE:
<223> OTHER INFORMATION: AL165

<400> SEQUENCE: 308

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Gly Leu Ala Asp Gly Val Pro Ser Arg Phe Ser Gly
    50                  55                  60

Ser Gly Ser Gly Arg Asp Phe Thr Phe Thr Ile Ser Ser Leu Gln Pro
65                  70                  75                  80

Glu Asp Ile Ala Thr Tyr Tyr Cys Gln Asn Val Leu Glu Ser Pro Tyr
                85                  90                  95

Thr Phe Gly Gln Gly Thr Lys Val Glu Ile Lys
            100                 105

<210> SEQ ID NO 309
<211> LENGTH: 107
<212> TYPE: PRT
<213> ORGANISM: Artificial Sequence
<220> FEATURE:
<223> OTHER INFORMATION: AL166

<400> SEQUENCE: 309

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Gly Leu Ala Asp Gly Val Pro Ser Arg Phe Ser Gly
    50                  55                  60

Ser Gly Ser Gly Arg Asp Phe Thr Phe Thr Ile Ser Ser Leu Gln Pro
65                  70                  75                  80

Glu Asp Ile Ala Thr Tyr Tyr Cys Gln Asn Val Leu Ser Glu Pro Tyr
                85                  90                  95

Thr Phe Gly Gln Gly Thr Lys Val Glu Ile Lys
            100                 105

<210> SEQ ID NO 310
<211> LENGTH: 107
<212> TYPE: PRT
<213> ORGANISM: Artificial Sequence
<220> FEATURE:
<223> OTHER INFORMATION: AL194

<400> SEQUENCE: 310

Asp Ile Gln Met Thr Gln Ser Pro Ser Ser Leu Ser Ala Ser Val Gly
```

```
                1               5                  10                 15
Asp Arg Val Thr Ile Thr Cys Gly Ala Ser Met Pro Leu Phe His Ala
                20                 25                 30

Leu Asn Trp Tyr Gln Gln Lys Pro Gly Lys Ala Pro Lys Leu Leu Ile
            35                 40                 45

Tyr Gly Ala Thr Asn Leu Ala Asp Gly Val Pro Ser Arg Phe Ser Gly
        50                 55                 60

Ser Gly Ser Gly Arg Asp Phe Thr Phe Thr Ile Ser Ser Leu Gln Pro
65                 70                 75                 80

Glu Asp Ile Ala Thr Tyr Tyr Cys Gln Asn Val Leu Ser Ile Pro Glu
                85                 90                 95

Thr Phe Gly Gln Gly Thr Lys Val Glu Ile Lys
            100                105

<210> SEQ ID NO 311
<211> LENGTH: 107
<212> TYPE: PRT
<213> ORGANISM: Artificial Sequence
<220> FEATURE:
<223> OTHER INFORMATION: AL195

<400> SEQUENCE: 311

Asp Ile Gln Met Thr Gln Ser Pro Ser Ser Leu Ser Ala Ser Val Gly
1               5                  10                 15

Asp Arg Val Thr Ile Thr Cys Gly Ala Ser Arg Ser Thr Phe Ser Ala
                20                 25                 30

Leu Asn Trp Tyr Gln Gln Lys Pro Gly Lys Ala Pro Lys Leu Leu Ile
            35                 40                 45

Tyr Gly Ala Thr Asn Leu Ala Asp Gly Val Pro Ser Arg Phe Ser Gly
        50                 55                 60

Ser Gly Ser Gly Arg Asp Phe Thr Phe Thr Ile Ser Ser Leu Gln Pro
65                 70                 75                 80

Glu Asp Ile Ala Thr Tyr Tyr Cys Gln Asn Val Leu Glu Glu Pro Tyr
                85                 90                 95

Thr Phe Gly Gln Gly Thr Lys Val Glu Ile Lys
            100                105

<210> SEQ ID NO 312
<211> LENGTH: 10
<212> TYPE: PRT
<213> ORGANISM: Artificial Sequence
<220> FEATURE:
<223> OTHER INFORMATION: Connecter

<400> SEQUENCE: 312

Gly Gly Gly Gly Ser Gly Gly Gly Gly Ser
1               5                  10

<210> SEQ ID NO 313
<211> LENGTH: 246
<212> TYPE: PRT
<213> ORGANISM: Artificial Sequence
<220> FEATURE:
<223> OTHER INFORMATION: Erbitux scFv HL

<400> SEQUENCE: 313

Gln Val Gln Leu Lys Gln Ser Gly Pro Gly Leu Val Gln Pro Ser Gln
1               5                  10                 15

Ser Leu Ser Ile Thr Cys Thr Val Ser Gly Phe Ser Leu Thr Asn Tyr
                20                 25                 30
```

```
Gly Val His Trp Val Arg Gln Ser Pro Gly Lys Cys Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Gly Gly Gly Ser Gly Gly Gly
            115                 120                 125

Ser Gly Gly Gly Gly Ser Gly Gly Gly Gly Ser Asp Ile Leu Leu Thr
    130                 135                 140

Gln Ser Pro Val Ile Leu Ser Val Ser Pro Gly Glu Arg Val Ser Phe
145                 150                 155                 160

Ser Cys Arg Ala Ser Gln Ser Ile Gly Thr Asn Ile His Trp Tyr Gln
                165                 170                 175

Gln Arg Thr Asn Gly Ser Pro Arg Leu Leu Ile Lys Tyr Ala Ser Glu
            180                 185                 190

Ser Ile Ser Gly Ile Pro Ser Arg Phe Ser Gly Ser Gly Ser Gly Thr
        195                 200                 205

Asp Phe Thr Leu Ser Ile Asn Ser Val Glu Ser Glu Asp Ile Ala Asp
    210                 215                 220

Tyr Tyr Cys Gln Gln Asn Asn Asn Trp Pro Thr Thr Phe Gly Cys Gly
225                 230                 235                 240

Thr Lys Leu Glu Leu Lys
            245

<210> SEQ ID NO 314
<211> LENGTH: 246
<212> TYPE: PRT
<213> ORGANISM: Artificial Sequence
<220> FEATURE:
<223> OTHER INFORMATION: Erbitux scFv LH

<400> SEQUENCE: 314

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Cys Gly Thr Lys Leu Glu Leu Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Lys Gln Ser Gly Pro Gly Leu Val Gln Pro Ser Gln Ser
    130                 135                 140
```

Leu Ser Ile Thr Cys Thr Val Ser Gly Phe Ser Leu Thr Asn Tyr Gly
145                 150                 155                 160

Val His Trp Val Arg Gln Ser Pro Gly Lys Cys Leu Glu Trp Leu Gly
                165                 170                 175

Val Ile Trp Ser Gly Gly Asn Thr Asp Tyr Asn Thr Pro Phe Thr Ser
            180                 185                 190

Arg Leu Ser Ile Asn Lys Asp Asn Ser Lys Ser Gln Val Phe Phe Lys
        195                 200                 205

Met Asn Ser Leu Gln Ser Asn Asp Thr Ala Ile Tyr Tyr Cys Ala Arg
    210                 215                 220

Ala Leu Thr Tyr Tyr Asp Tyr Glu Phe Ala Tyr Trp Gly Gln Gly Thr
225                 230                 235                 240

Leu Val Thr Val Ser Ala
                245

<210> SEQ ID NO 315
<211> LENGTH: 246
<212> TYPE: PRT
<213> ORGANISM: Artificial Sequence
<220> FEATURE:
<223> OTHER INFORMATION: Vectibix scFv

<400> SEQUENCE: 315

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Cys Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
                100                 105                 110

Thr Met Val Thr Val Ser Ser Gly Gly Gly Ser Gly Gly Gly Gly
            115                 120                 125

Ser Gly Gly Gly Gly Ser Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Gln Ala Ser Gln Asp Ile Ser Asn Tyr Leu Asn Trp Tyr Gln
                165                 170                 175

Gln Lys Pro Gly Lys Ala Pro Lys Leu Leu Ile Tyr Asp Ala Ser Asn
            180                 185                 190

Leu Glu Thr Gly Val Pro Ser Arg Phe Ser Gly Ser Gly Ser Gly Thr
        195                 200                 205

Asp Phe Thr Phe Thr Ile Ser Ser Leu Gln Pro Glu Asp Ile Ala Thr
    210                 215                 220

Tyr Phe Cys Gln His Phe Asp His Leu Pro Leu Ala Phe Gly Cys Gly
225                 230                 235                 240

Thr Lys Val Glu Ile Lys
                245

<210> SEQ ID NO 316
<211> LENGTH: 699
<212> TYPE: PRT
<213> ORGANISM: Artificial Sequence
<220> FEATURE:
<223> OTHER INFORMATION: hu8C4 x Erbitux scFv HL

<400> SEQUENCE: 316

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
        35                  40                  45

Gly Glu Ile Phe Pro Gly Ser Gly Asn Thr His Phe Ser Ala Arg Phe
    50                  55                  60

Lys Gly Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gly Asp Tyr Gly Phe Leu Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Arg Lys Cys Cys Val Glu Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365
```

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
        420                 425                 430

Thr Gln Lys Ser Leu Ser Leu Ser Pro Gly Lys Gly Gly Gly Gly Ser
            435                 440                 445

Gly Gly Gly Gly Ser Gln Val Gln Leu Lys Gln Ser Gly Pro Gly Leu
450                 455                 460

Val Gln Pro Ser Gln Ser Leu Ser Ile Thr Cys Thr Val Ser Gly Phe
465                 470                 475                 480

Ser Leu Thr Asn Tyr Gly Val His Trp Val Arg Gln Ser Pro Gly Lys
            485                 490                 495

Cys Leu Glu Trp Leu Gly Val Ile Trp Ser Gly Gly Asn Thr Asp Tyr
        500                 505                 510

Asn Thr Pro Phe Thr Ser Arg Leu Ser Ile Asn Lys Asp Asn Ser Lys
        515                 520                 525

Ser Gln Val Phe Phe Lys Met Asn Ser Leu Gln Ser Asn Asp Thr Ala
530                 535                 540

Ile Tyr Tyr Cys Ala Arg Ala Leu Thr Tyr Tyr Asp Tyr Glu Phe Ala
545                 550                 555                 560

Tyr Trp Gly Gln Gly Thr Leu Val Thr Val Ser Ala Gly Gly Gly Gly
            565                 570                 575

Ser Gly Gly Gly Gly Ser Gly Gly Gly Gly Ser Gly Gly Gly Gly Ser
        580                 585                 590

Asp Ile Leu Leu Thr Gln Ser Pro Val Ile Leu Ser Val Ser Pro Gly
        595                 600                 605

Glu Arg Val Ser Phe Ser Cys Arg Ala Ser Gln Ser Ile Gly Thr Asn
610                 615                 620

Ile His Trp Tyr Gln Gln Arg Thr Asn Gly Ser Pro Arg Leu Leu Ile
625                 630                 635                 640

Lys Tyr Ala Ser Glu Ser Ile Ser Gly Ile Pro Ser Arg Phe Ser Gly
            645                 650                 655

Ser Gly Ser Gly Thr Asp Phe Thr Leu Ser Ile Asn Ser Val Glu Ser
        660                 665                 670

Glu Asp Ile Ala Asp Tyr Tyr Cys Gln Gln Asn Asn Asn Trp Pro Thr
        675                 680                 685

Thr Phe Gly Cys Gly Thr Lys Leu Glu Leu Lys
        690                 695

<210> SEQ ID NO 317
<211> LENGTH: 699
<212> TYPE: PRT
<213> ORGANISM: Artificial Sequence
<220> FEATURE:
<223> OTHER INFORMATION: hu8C4 AH71 x Erbitux scFv HL

<400> SEQUENCE: 317

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

-continued

```
Tyr Ile Asn Trp Val Arg Gln Ala Pro Gly Lys Gly Leu Glu Trp Ile
         35                  40                  45

Gly Glu Ile Phe Pro Gly Trp Gly Asn Thr His Phe Ser Ala Arg Phe
 50                  55                  60

Lys Gly Arg Ala Thr Leu Ser Ala Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Gly Gln Asp Tyr Gly Phe Leu Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Arg Lys Cys Cys Val Glu Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys Gly Gly Gly Gly Ser
        435                 440                 445
```

Gly Gly Gly Gly Ser Gln Val Gln Leu Lys Gln Ser Gly Pro Gly Leu
                450                 455                 460

Val Gln Pro Ser Gln Ser Leu Ser Ile Thr Cys Thr Val Ser Gly Phe
465                 470                 475                 480

Ser Leu Thr Asn Tyr Gly Val His Trp Val Arg Gln Ser Pro Gly Lys
                485                 490                 495

Cys Leu Glu Trp Leu Gly Val Ile Trp Ser Gly Gly Asn Thr Asp Tyr
                500                 505                 510

Asn Thr Pro Phe Thr Ser Arg Leu Ser Ile Asn Lys Asp Asn Ser Lys
                515                 520                 525

Ser Gln Val Phe Phe Lys Met Asn Ser Leu Gln Ser Asn Asp Thr Ala
530                 535                 540

Ile Tyr Tyr Cys Ala Arg Ala Leu Thr Tyr Tyr Asp Tyr Glu Phe Ala
545                 550                 555                 560

Tyr Trp Gly Gln Gly Thr Leu Val Thr Val Ser Ala Gly Gly Gly Gly
                565                 570                 575

Ser Gly Gly Gly Gly Ser Gly Gly Gly Gly Ser Gly Gly Gly Gly Ser
                580                 585                 590

Asp Ile Leu Leu Thr Gln Ser Pro Val Ile Leu Ser Val Ser Pro Gly
                595                 600                 605

Glu Arg Val Ser Phe Ser Cys Arg Ala Ser Gln Ser Ile Gly Thr Asn
610                 615                 620

Ile His Trp Tyr Gln Gln Arg Thr Asn Gly Ser Pro Arg Leu Leu Ile
625                 630                 635                 640

Lys Tyr Ala Ser Glu Ser Ile Ser Gly Ile Pro Ser Arg Phe Ser Gly
                645                 650                 655

Ser Gly Ser Gly Thr Asp Phe Thr Leu Ser Ile Asn Ser Val Glu Ser
                660                 665                 670

Glu Asp Ile Ala Asp Tyr Tyr Cys Gln Gln Asn Asn Asn Trp Pro Thr
                675                 680                 685

Thr Phe Gly Cys Gly Thr Lys Leu Glu Leu Lys
                690                 695

<210> SEQ ID NO 318
<211> LENGTH: 699
<212> TYPE: PRT
<213> ORGANISM: Artificial Sequence
<220> FEATURE:
<223> OTHER INFORMATION: hu8C4 AH72 x Erbitux scFv HL

<400> SEQUENCE: 318

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
                20                  25                  30

Tyr Ile Asn Trp Val Arg Gln Ala Pro Gly Lys Gly Leu Glu Trp Ile
            35                  40                  45

Gly Glu Ile Phe Pro Gly Trp Gly Asn Thr His Phe Ser Arg Ser Pro
        50                  55                  60

Thr Pro Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gly Asp Tyr Gly Phe Leu Tyr Trp Gly Gln Gly Thr Leu Val
                100                 105                 110

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Arg Lys Cys Cys Val Glu Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys Gly Gly Gly Gly Ser
        435                 440                 445

Gly Gly Gly Gly Ser Gln Val Gln Leu Lys Gln Ser Gly Pro Gly Leu
450                 455                 460

Val Gln Pro Ser Gln Ser Leu Ser Ile Thr Cys Thr Val Ser Gly Phe
465                 470                 475                 480

Ser Leu Thr Asn Tyr Gly Val His Trp Val Arg Gln Ser Pro Gly Lys
                485                 490                 495

Cys Leu Glu Trp Leu Gly Val Ile Trp Ser Gly Gly Asn Thr Asp Tyr
            500                 505                 510

Asn Thr Pro Phe Thr Ser Arg Leu Ser Ile Asn Lys Asp Asn Ser Lys
        515                 520                 525

Ser Gln Val Phe Phe Lys Met Asn Ser Leu Gln Ser Asn Asp Thr Ala
```

```
                530             535             540
Ile Tyr Tyr Cys Ala Arg Ala Leu Thr Tyr Tyr Asp Tyr Glu Phe Ala
545                 550                 555                 560

Tyr Trp Gly Gln Gly Thr Leu Val Thr Val Ser Ala Gly Gly Gly Gly
                    565                 570                 575

Ser Gly Gly Gly Gly Ser Gly Gly Gly Ser Gly Gly Gly Gly Ser
                580                 585                 590

Asp Ile Leu Leu Thr Gln Ser Pro Val Ile Leu Ser Val Ser Pro Gly
            595                 600                 605

Glu Arg Val Ser Phe Ser Cys Arg Ala Ser Gln Ser Ile Gly Thr Asn
        610                 615                 620

Ile His Trp Tyr Gln Gln Arg Thr Asn Gly Ser Pro Arg Leu Leu Ile
625                 630                 635                 640

Lys Tyr Ala Ser Glu Ser Ile Ser Gly Ile Pro Ser Arg Phe Ser Gly
                    645                 650                 655

Ser Gly Ser Gly Thr Asp Phe Thr Leu Ser Ile Asn Ser Val Glu Ser
                660                 665                 670

Glu Asp Ile Ala Asp Tyr Tyr Cys Gln Gln Asn Asn Asn Trp Pro Thr
            675                 680                 685

Thr Phe Gly Cys Gly Thr Lys Leu Glu Leu Lys
        690                 695

<210> SEQ ID NO 319
<211> LENGTH: 699
<212> TYPE: PRT
<213> ORGANISM: Artificial Sequence
<220> FEATURE:
<223> OTHER INFORMATION: hu8C4 AH73 x Erbitux scFv HL

<400> SEQUENCE: 319

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
        35                  40                  45

Gly Glu Ile Phe Pro Gly Trp Gly Asn Ser His Val Val Ser Arg Phe
    50                  55                  60

Lys Gly Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gly Asp Tyr Gly Phe Leu Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

```
            195                 200                 205
Lys Val Asp Lys Lys Val Glu Arg Lys Cys Cys Val Glu Cys Pro Pro
    210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
        275                 280                 285
Glu Glu Gln Tyr Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
            340                 345                 350
Glu Leu Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys Gly Gly Gly Gly Ser
        435                 440                 445
Gly Gly Gly Gly Ser Gln Val Gln Leu Lys Gln Ser Gly Pro Gly Leu
    450                 455                 460
Val Gln Pro Ser Gln Ser Leu Ser Ile Thr Cys Thr Val Ser Gly Phe
465                 470                 475                 480
Ser Leu Thr Asn Tyr Gly Val His Trp Val Arg Gln Ser Pro Gly Lys
                485                 490                 495
Cys Leu Glu Trp Leu Gly Val Ile Trp Ser Gly Gly Asn Thr Asp Tyr
            500                 505                 510
Asn Thr Pro Phe Thr Ser Arg Leu Ser Ile Asn Lys Asp Asn Ser Lys
        515                 520                 525
Ser Gln Val Phe Phe Lys Met Asn Ser Leu Gln Ser Asn Asp Thr Ala
    530                 535                 540
Ile Tyr Tyr Cys Ala Arg Ala Leu Thr Tyr Tyr Asp Tyr Glu Phe Ala
545                 550                 555                 560
Tyr Trp Gly Gln Gly Thr Leu Val Thr Val Ser Ala Gly Gly Gly Gly
                565                 570                 575
Ser Gly Gly Gly Gly Ser Gly Gly Gly Gly Ser Gly Gly Gly Gly Ser
            580                 585                 590
Asp Ile Leu Leu Thr Gln Ser Pro Val Ile Leu Ser Val Ser Pro Gly
        595                 600                 605
Glu Arg Val Ser Phe Ser Cys Arg Ala Ser Gln Ser Ile Gly Thr Asn
    610                 615                 620
```

Ile His Trp Tyr Gln Gln Arg Thr Asn Gly Ser Pro Arg Leu Leu Ile
625                 630                 635                 640

Lys Tyr Ala Ser Glu Ser Ile Ser Gly Ile Pro Ser Arg Phe Ser Gly
            645                 650                 655

Ser Gly Ser Gly Thr Asp Phe Thr Leu Ser Ile Asn Ser Val Glu Ser
            660                 665                 670

Glu Asp Ile Ala Asp Tyr Tyr Cys Gln Gln Asn Asn Asn Trp Pro Thr
            675                 680                 685

Thr Phe Gly Cys Gly Thr Lys Leu Glu Leu Lys
            690                 695

<210> SEQ ID NO 320
<211> LENGTH: 699
<212> TYPE: PRT
<213> ORGANISM: Artificial Sequence
<220> FEATURE:
<223> OTHER INFORMATION: hu8C4 AH85 x Erbitux scFv HL

<400> SEQUENCE: 320

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
            35                  40                  45

Gly Glu Ile Phe Pro Gly Trp Gly Asn Ser His Val Val Ser Arg Phe
50                  55                  60

Lys Gly Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Gly Gln Asp Tyr Gly Phe Leu Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Arg Lys Cys Cys Val Glu Cys Pro Pro
            210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

```
Glu Glu Gln Tyr Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
                340                 345                 350
Glu Leu Thr Lys Asn Gln Val Ser Leu Thr Cys Leu Val Lys Gly Phe
                355                 360                 365
Tyr Pro Ser Asp Ile Ala Val Glu Trp Glu Ser Asn Gly Gln Pro Glu
370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
                420                 425                 430
Thr Gln Lys Ser Leu Ser Leu Ser Pro Gly Lys Gly Gly Gly Gly Ser
                435                 440                 445
Gly Gly Gly Gly Ser Gln Val Gln Leu Lys Gln Ser Gly Pro Gly Leu
450                 455                 460
Val Gln Pro Ser Gln Ser Leu Ser Ile Thr Cys Thr Val Ser Gly Phe
465                 470                 475                 480
Ser Leu Thr Asn Tyr Gly Val His Trp Val Arg Gln Ser Pro Gly Lys
                485                 490                 495
Cys Leu Glu Trp Leu Gly Val Ile Trp Ser Gly Gly Asn Thr Asp Tyr
                500                 505                 510
Asn Thr Pro Phe Thr Ser Arg Leu Ser Ile Asn Lys Asp Asn Ser Lys
                515                 520                 525
Ser Gln Val Phe Phe Lys Met Asn Ser Leu Gln Ser Asn Asp Thr Ala
                530                 535                 540
Ile Tyr Tyr Cys Ala Arg Ala Leu Thr Tyr Tyr Asp Tyr Glu Phe Ala
545                 550                 555                 560
Tyr Trp Gly Gln Gly Thr Leu Val Thr Val Ser Ala Gly Gly Gly Gly
                565                 570                 575
Ser Gly Gly Gly Gly Ser Gly Gly Gly Ser Gly Gly Gly Gly Ser
                580                 585                 590
Asp Ile Leu Leu Thr Gln Ser Pro Val Ile Leu Ser Val Ser Pro Gly
                595                 600                 605
Glu Arg Val Ser Phe Ser Cys Arg Ala Ser Gln Ser Ile Gly Thr Asn
                610                 615                 620
Ile His Trp Tyr Gln Gln Arg Thr Asn Gly Ser Pro Arg Leu Leu Ile
625                 630                 635                 640
Lys Tyr Ala Ser Glu Ser Ile Ser Gly Ile Pro Ser Arg Phe Ser Gly
                645                 650                 655
Ser Gly Ser Gly Thr Asp Phe Thr Leu Ser Ile Asn Ser Val Glu Ser
                660                 665                 670
Glu Asp Ile Ala Asp Tyr Tyr Cys Gln Gln Asn Asn Asn Trp Pro Thr
                675                 680                 685
Thr Phe Gly Cys Gly Thr Lys Leu Glu Leu Lys
                690                 695
```

```
<210> SEQ ID NO 321
<211> LENGTH: 699
<212> TYPE: PRT
<213> ORGANISM: Artificial Sequence
<220> FEATURE:
<223> OTHER INFORMATION: hu8C4 x Erbitux scFv LH

<400> SEQUENCE: 321
```

| Glu | Val | Gln | Leu | Val | Glu | Ser | Gly | Gly | Leu | Val | Gln | Pro | Gly | Gly |
|---|---|---|---|---|---|---|---|---|---|---|---|---|---|---|
| 1 | | | | 5 | | | | | 10 | | | | | 15 |

| Ser | Leu | Arg | Leu | Ser | Cys | Ala | Ala | Ser | Gly | Tyr | Thr | Phe | Ser | Asp | Tyr |
|---|---|---|---|---|---|---|---|---|---|---|---|---|---|---|---|
| | | | 20 | | | | | 25 | | | | | 30 | | |

| Tyr | Ile | Asn | Trp | Val | Arg | Gln | Ala | Pro | Gly | Lys | Gly | Leu | Glu | Trp | Ile |
|---|---|---|---|---|---|---|---|---|---|---|---|---|---|---|---|
| | | | 35 | | | | | 40 | | | | | 45 | | |

| Gly | Glu | Ile | Phe | Pro | Gly | Ser | Gly | Asn | Thr | His | Phe | Ser | Ala | Arg | Phe |
|---|---|---|---|---|---|---|---|---|---|---|---|---|---|---|---|
| | 50 | | | | | 55 | | | | | 60 | | | | |

| Lys | Gly | Arg | Ala | Thr | Leu | Ser | Ala | Asp | Lys | Ser | Lys | Asn | Thr | Ala | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Gly | Gly | Asp | Tyr | Gly | Phe | Leu | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

| Thr | Val | Ser | Ser | Ala | Ser | Thr | Lys | Gly | Pro | Ser | Val | Phe | Pro | Leu | Ala |
|---|---|---|---|---|---|---|---|---|---|---|---|---|---|---|---|
| | | 115 | | | | | 120 | | | | | 125 | | | |

| Pro | Ser | Ser | Lys | Ser | Thr | Ser | Gly | Gly | Thr | Ala | Ala | Leu | Gly | Cys | Leu |
|---|---|---|---|---|---|---|---|---|---|---|---|---|---|---|---|
| | 130 | | | | | 135 | | | | | 140 | | | | |

| Val | Lys | Asp | Tyr | Phe | Pro | Glu | Pro | Val | Thr | Val | Ser | Trp | Asn | Ser | Gly |
|---|---|---|---|---|---|---|---|---|---|---|---|---|---|---|---|
| 145 | | | | | 150 | | | | | 155 | | | | | 160 |

| Ala | Leu | Thr | Ser | Gly | Val | His | Thr | Phe | Pro | Ala | Val | Leu | Gln | Ser | Ser |
|---|---|---|---|---|---|---|---|---|---|---|---|---|---|---|---|
| | | | | 165 | | | | | 170 | | | | | 175 | |

| Gly | Leu | Tyr | Ser | Leu | Ser | Ser | Val | Val | Thr | Val | Pro | Ser | Ser | Ser | Leu |
|---|---|---|---|---|---|---|---|---|---|---|---|---|---|---|---|
| | | | 180 | | | | | 185 | | | | | 190 | | |

| Gly | Thr | Gln | Thr | Tyr | Ile | Cys | Asn | Val | Asn | His | Lys | Pro | Ser | Asn | Thr |
|---|---|---|---|---|---|---|---|---|---|---|---|---|---|---|---|
| | | 195 | | | | | 200 | | | | | 205 | | | |

| Lys | Val | Asp | Lys | Lys | Val | Glu | Arg | Lys | Cys | Cys | Val | Glu | Cys | Pro | Pro |
|---|---|---|---|---|---|---|---|---|---|---|---|---|---|---|---|
| | 210 | | | | | 215 | | | | | 220 | | | | |

| Cys | Pro | Ala | Pro | Glu | Leu | Leu | Gly | Gly | Pro | Ser | Val | Phe | Leu | Phe | Pro |
|---|---|---|---|---|---|---|---|---|---|---|---|---|---|---|---|
| 225 | | | | | 230 | | | | | 235 | | | | | 240 |

| Pro | Lys | Pro | Lys | Asp | Thr | Leu | Met | Ile | Ser | Arg | Thr | Pro | Glu | Val | Thr |
|---|---|---|---|---|---|---|---|---|---|---|---|---|---|---|---|
| | | | | 245 | | | | | 250 | | | | | 255 | |

| Cys | Val | Val | Val | Asp | Val | Ser | His | Glu | Asp | Pro | Glu | Val | Lys | Phe | Asn |
|---|---|---|---|---|---|---|---|---|---|---|---|---|---|---|---|
| | | | 260 | | | | | 265 | | | | | 270 | | |

| Trp | Tyr | Val | Asp | Gly | Val | Glu | Val | His | Asn | Ala | Lys | Thr | Lys | Pro | Arg |
|---|---|---|---|---|---|---|---|---|---|---|---|---|---|---|---|
| | | 275 | | | | | 280 | | | | | 285 | | | |

| Glu | Glu | Gln | Tyr | Asn | Ser | Thr | Tyr | Arg | Val | Val | Ser | Val | Leu | Thr | Val |
|---|---|---|---|---|---|---|---|---|---|---|---|---|---|---|---|
| | 290 | | | | | 295 | | | | | 300 | | | | |

| Leu | His | Gln | Asp | Trp | Leu | Asn | Gly | Lys | Glu | Tyr | Lys | Cys | Lys | Val | Ser |
|---|---|---|---|---|---|---|---|---|---|---|---|---|---|---|---|
| 305 | | | | | 310 | | | | | 315 | | | | | 320 |

| Asn | Lys | Ala | Leu | Pro | Ala | Pro | Ile | Glu | Lys | Thr | Ile | Ser | Lys | Ala | Lys |
|---|---|---|---|---|---|---|---|---|---|---|---|---|---|---|---|
| | | | | 325 | | | | | 330 | | | | | 335 | |

| Gly | Gln | Pro | Arg | Glu | Pro | Gln | Val | Tyr | Thr | Leu | Pro | Pro | Ser | Arg | Asp |
|---|---|---|---|---|---|---|---|---|---|---|---|---|---|---|---|
| | | | 340 | | | | | 345 | | | | | 350 | | |

| Glu | Leu | Thr | Lys | Asn | Gln | Val | Ser | Leu | Thr | Cys | Leu | Val | Lys | Gly | Phe |
|---|---|---|---|---|---|---|---|---|---|---|---|---|---|---|---|
| | | 355 | | | | | 360 | | | | | 365 | | | |

```
Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys Gly Gly Gly Gly Ser
        435                 440                 445

Gly Gly Gly Gly Ser Asp Ile Leu Leu Thr Gln Ser Pro Val Ile Leu
    450                 455                 460

Ser Val Ser Pro Gly Glu Arg Val Ser Phe Ser Cys Arg Ala Ser Gln
465                 470                 475                 480

Ser Ile Gly Thr Asn Ile His Trp Tyr Gln Gln Arg Thr Asn Gly Ser
                485                 490                 495

Pro Arg Leu Leu Ile Lys Tyr Ala Ser Glu Ser Ile Ser Gly Ile Pro
                500                 505                 510

Ser Arg Phe Ser Gly Ser Gly Ser Gly Thr Asp Phe Thr Leu Ser Ile
            515                 520                 525

Asn Ser Val Glu Ser Glu Asp Ile Ala Asp Tyr Tyr Cys Gln Gln Asn
530                 535                 540

Asn Asn Trp Pro Thr Thr Phe Gly Cys Gly Thr Lys Leu Glu Leu Lys
545                 550                 555                 560

Gly Gly Gly Gly Ser Gly Gly Gly Gly Ser Gly Gly Gly Gly Ser Gly
                565                 570                 575

Gly Gly Gly Ser Gln Val Gln Leu Lys Gln Ser Gly Pro Gly Leu Val
            580                 585                 590

Gln Pro Ser Gln Ser Leu Ser Ile Thr Cys Thr Val Ser Gly Phe Ser
        595                 600                 605

Leu Thr Asn Tyr Gly Val His Trp Val Arg Gln Ser Pro Gly Lys Cys
    610                 615                 620

Leu Glu Trp Leu Gly Val Ile Trp Ser Gly Gly Asn Thr Asp Tyr Asn
625                 630                 635                 640

Thr Pro Phe Thr Ser Arg Leu Ser Ile Asn Lys Asp Asn Ser Lys Ser
                645                 650                 655

Gln Val Phe Phe Lys Met Asn Ser Leu Gln Ser Asn Asp Thr Ala Ile
                660                 665                 670

Tyr Tyr Cys Ala Arg Ala Leu Thr Tyr Tyr Asp Tyr Glu Phe Ala Tyr
            675                 680                 685

Trp Gly Gln Gly Thr Leu Val Thr Val Ser Ala
    690                 695

<210> SEQ ID NO 322
<211> LENGTH: 699
<212> TYPE: PRT
<213> ORGANISM: Artificial Sequence
<220> FEATURE:
<223> OTHER INFORMATION: hu8C4 AH71 x Erbitux scFv LH

<400> SEQUENCE: 322

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30
```

-continued

Tyr Ile Asn Trp Val Arg Gln Ala Pro Gly Lys Gly Leu Glu Trp Ile
            35                  40                  45

Gly Glu Ile Phe Pro Gly Trp Gly Asn Thr His Phe Ser Ala Arg Phe
    50                  55                  60

Lys Gly Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gln Asp Tyr Gly Phe Leu Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Arg Lys Cys Cys Val Glu Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys Gly Gly Gly Gly Ser
        435                 440                 445

Gly Gly Gly Gly Ser Asp Ile Leu Leu Thr Gln Ser Pro Val Ile Leu

```
            450                 455                 460
Ser Val Ser Pro Gly Glu Arg Val Ser Phe Ser Cys Arg Ala Ser Gln
465                 470                 475                 480

Ser Ile Gly Thr Asn Ile His Trp Tyr Gln Gln Arg Thr Asn Gly Ser
                485                 490                 495

Pro Arg Leu Leu Ile Lys Tyr Ala Ser Glu Ser Ile Ser Gly Ile Pro
            500                 505                 510

Ser Arg Phe Ser Gly Ser Gly Ser Gly Thr Asp Phe Thr Leu Ser Ile
        515                 520                 525

Asn Ser Val Glu Ser Glu Asp Ile Ala Asp Tyr Tyr Cys Gln Gln Asn
    530                 535                 540

Asn Asn Trp Pro Thr Thr Phe Gly Cys Gly Thr Lys Leu Glu Leu Lys
545                 550                 555                 560

Gly Gly Gly Gly Ser Gly Gly Gly Ser Gly Gly Gly Gly Ser Gly
                565                 570                 575

Gly Gly Gly Ser Gln Val Gln Leu Lys Gln Ser Gly Pro Gly Leu Val
            580                 585                 590

Gln Pro Ser Gln Ser Leu Ser Ile Thr Cys Thr Val Ser Gly Phe Ser
        595                 600                 605

Leu Thr Asn Tyr Gly Val His Trp Val Arg Gln Ser Pro Gly Lys Cys
    610                 615                 620

Leu Glu Trp Leu Gly Val Ile Trp Ser Gly Gly Asn Thr Asp Tyr Asn
625                 630                 635                 640

Thr Pro Phe Thr Ser Arg Leu Ser Ile Asn Lys Asp Asn Ser Lys Ser
                645                 650                 655

Gln Val Phe Phe Lys Met Asn Ser Leu Gln Ser Asn Asp Thr Ala Ile
            660                 665                 670

Tyr Tyr Cys Ala Arg Ala Leu Thr Tyr Tyr Asp Tyr Glu Phe Ala Tyr
        675                 680                 685

Trp Gly Gln Gly Thr Leu Val Thr Val Ser Ala
    690                 695

<210> SEQ ID NO 323
<211> LENGTH: 699
<212> TYPE: PRT
<213> ORGANISM: Artificial Sequence
<220> FEATURE:
<223> OTHER INFORMATION: hu8C4 AH72 x Erbitux scFv LH

<400> SEQUENCE: 323

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
        35                  40                  45

Gly Glu Ile Phe Pro Gly Trp Gly Asn Thr His Phe Ser Arg Ser Pro
    50                  55                  60

Thr Pro Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gly Asp Tyr Gly Phe Leu Tyr Trp Gly Gln Gly Thr Leu Val
            100                 105                 110

Thr Val Ser Ser Ala Ser Thr Lys Gly Pro Ser Val Phe Pro Leu Ala
```

```
            115                 120                 125
Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Arg Lys Cys Cys Val Glu Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys Gly Gly Gly Gly Ser
        435                 440                 445

Gly Gly Gly Gly Ser Asp Ile Leu Leu Thr Gln Ser Pro Val Ile Leu
    450                 455                 460

Ser Val Ser Pro Gly Glu Arg Val Ser Phe Ser Cys Arg Ala Ser Gln
465                 470                 475                 480

Ser Ile Gly Thr Asn Ile His Trp Tyr Gln Gln Arg Thr Asn Gly Ser
                485                 490                 495

Pro Arg Leu Leu Ile Lys Tyr Ala Ser Glu Ser Ile Ser Gly Ile Pro
            500                 505                 510

Ser Arg Phe Ser Gly Ser Gly Ser Gly Thr Asp Phe Thr Leu Ser Ile
        515                 520                 525

Asn Ser Val Glu Ser Glu Asp Ile Ala Asp Tyr Tyr Cys Gln Gln Asn
    530                 535                 540
```

```
Asn Asn Trp Pro Thr Thr Phe Gly Cys Gly Thr Lys Leu Glu Leu Lys
545                 550                 555                 560

Gly Gly Gly Gly Ser Gly Gly Gly Ser Gly Gly Gly Ser Gly
                565                 570                 575

Gly Gly Gly Ser Gln Val Gln Leu Lys Gln Ser Gly Pro Gly Leu Val
            580                 585                 590

Gln Pro Ser Gln Ser Leu Ser Ile Thr Cys Thr Val Ser Gly Phe Ser
        595                 600                 605

Leu Thr Asn Tyr Gly Val His Trp Val Arg Gln Ser Pro Gly Lys Cys
    610                 615                 620

Leu Glu Trp Leu Gly Val Ile Trp Ser Gly Gly Asn Thr Asp Tyr Asn
625                 630                 635                 640

Thr Pro Phe Thr Ser Arg Leu Ser Ile Asn Lys Asp Asn Ser Lys Ser
                645                 650                 655

Gln Val Phe Phe Lys Met Asn Ser Leu Gln Ser Asn Asp Thr Ala Ile
            660                 665                 670

Tyr Tyr Cys Ala Arg Ala Leu Thr Tyr Tyr Asp Tyr Glu Phe Ala Tyr
        675                 680                 685

Trp Gly Gln Gly Thr Leu Val Thr Val Ser Ala
    690                 695
```

<210> SEQ ID NO 324
<211> LENGTH: 699
<212> TYPE: PRT
<213> ORGANISM: Artificial Sequence
<220> FEATURE:
<223> OTHER INFORMATION: hu8C4 AH73 x Erbitux scFv LH

<400> SEQUENCE: 324

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
        35                  40                  45

Gly Glu Ile Phe Pro Gly Trp Gly Asn Ser His Val Val Ser Arg Phe
    50                  55                  60

Lys Gly Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gly Asp Tyr Gly Phe Leu Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

-continued

```
Lys Val Asp Lys Lys Val Glu Arg Lys Cys Cys Val Glu Cys Pro Pro
            210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
        275                 280                 285
Glu Glu Gln Tyr Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
            340                 345                 350
Glu Leu Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys Gly Gly Gly Gly Ser
        435                 440                 445
Gly Gly Gly Gly Ser Asp Ile Leu Leu Thr Gln Ser Pro Val Ile Leu
    450                 455                 460
Ser Val Ser Pro Gly Glu Arg Val Ser Phe Ser Cys Arg Ala Ser Gln
465                 470                 475                 480
Ser Ile Gly Thr Asn Ile His Trp Tyr Gln Gln Arg Thr Asn Gly Ser
                485                 490                 495
Pro Arg Leu Leu Ile Lys Tyr Ala Ser Glu Ser Ile Ser Gly Ile Pro
            500                 505                 510
Ser Arg Phe Ser Gly Ser Gly Ser Gly Thr Asp Phe Thr Leu Ser Ile
        515                 520                 525
Asn Ser Val Glu Ser Glu Asp Ile Ala Asp Tyr Tyr Cys Gln Gln Asn
    530                 535                 540
Asn Asn Trp Pro Thr Thr Phe Gly Cys Gly Thr Lys Leu Glu Leu Lys
545                 550                 555                 560
Gly Gly Gly Gly Ser Gly Gly Gly Gly Ser Gly Gly Gly Gly Ser Gly
                565                 570                 575
Gly Gly Gly Ser Gln Val Gln Leu Lys Gln Ser Gly Pro Gly Leu Val
            580                 585                 590
Gln Pro Ser Gln Ser Leu Ser Ile Thr Cys Thr Val Ser Gly Phe Ser
        595                 600                 605
Leu Thr Asn Tyr Gly Val His Trp Val Arg Gln Ser Pro Gly Lys Cys
    610                 615                 620
```

Leu Glu Trp Leu Gly Val Ile Trp Ser Gly Gly Asn Thr Asp Tyr Asn
625                 630                 635                 640

Thr Pro Phe Thr Ser Arg Leu Ser Ile Asn Lys Asp Asn Ser Lys Ser
            645                 650                 655

Gln Val Phe Phe Lys Met Asn Ser Leu Gln Ser Asn Asp Thr Ala Ile
            660                 665                 670

Tyr Tyr Cys Ala Arg Ala Leu Thr Tyr Tyr Asp Tyr Glu Phe Ala Tyr
        675                 680                 685

Trp Gly Gln Gly Thr Leu Val Thr Val Ser Ala
    690                 695

<210> SEQ ID NO 325
<211> LENGTH: 699
<212> TYPE: PRT
<213> ORGANISM: Artificial Sequence
<220> FEATURE:
<223> OTHER INFORMATION: hu8C4 AH85 x Erbitux scFv LH

<400> SEQUENCE: 325

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
        35                  40                  45

Gly Glu Ile Phe Pro Gly Trp Gly Asn Ser His Val Val Ser Arg Phe
    50                  55                  60

Lys Gly Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gln Asp Tyr Gly Phe Leu Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Arg Lys Cys Cys Val Glu Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

```
Glu Glu Gln Tyr Asn Ser Thr Tyr Arg Val Val Ser Val Leu Thr Val
290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
                340                 345                 350
Glu Leu Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
                420                 425                 430
Thr Gln Lys Ser Leu Ser Leu Ser Pro Gly Lys Gly Gly Gly Gly Ser
            435                 440                 445
Gly Gly Gly Gly Ser Asp Ile Leu Leu Thr Gln Ser Pro Val Ile Leu
450                 455                 460
Ser Val Ser Pro Gly Glu Arg Val Ser Phe Ser Cys Arg Ala Ser Gln
465                 470                 475                 480
Ser Ile Gly Thr Asn Ile His Trp Tyr Gln Gln Arg Thr Asn Gly Ser
                485                 490                 495
Pro Arg Leu Leu Ile Lys Tyr Ala Ser Glu Ser Ile Ser Gly Ile Pro
                500                 505                 510
Ser Arg Phe Ser Gly Ser Gly Ser Gly Thr Asp Phe Thr Leu Ser Ile
            515                 520                 525
Asn Ser Val Glu Ser Glu Asp Ile Ala Asp Tyr Tyr Cys Gln Gln Asn
            530                 535                 540
Asn Asn Trp Pro Thr Thr Phe Gly Cys Gly Thr Lys Leu Glu Leu Lys
545                 550                 555                 560
Gly Gly Gly Gly Ser Gly Gly Gly Ser Gly Gly Gly Gly Ser Gly
                565                 570                 575
Gly Gly Gly Ser Gln Val Gln Leu Lys Gln Ser Gly Pro Gly Leu Val
            580                 585                 590
Gln Pro Ser Gln Ser Leu Ser Ile Thr Cys Thr Val Ser Gly Phe Ser
            595                 600                 605
Leu Thr Asn Tyr Gly Val His Trp Val Arg Gln Ser Pro Gly Lys Cys
610                 615                 620
Leu Glu Trp Leu Gly Val Ile Trp Ser Gly Gly Asn Thr Asp Tyr Asn
625                 630                 635                 640
Thr Pro Phe Thr Ser Arg Leu Ser Ile Asn Lys Asp Asn Ser Lys Ser
                645                 650                 655
Gln Val Phe Phe Lys Met Asn Ser Leu Gln Ser Asn Asp Thr Ala Ile
                660                 665                 670
Tyr Tyr Cys Ala Arg Ala Leu Thr Tyr Tyr Asp Tyr Glu Phe Ala Tyr
            675                 680                 685
Trp Gly Gln Gly Thr Leu Val Thr Val Ser Ala
690                 695
```

```
<210> SEQ ID NO 326
<211> LENGTH: 699
<212> TYPE: PRT
<213> ORGANISM: Artificial Sequence
<220> FEATURE:
<223> OTHER INFORMATION: hu8C4 x Vectibix scFv

<400> SEQUENCE: 326
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Gly | | | | | | | | | | | | | | |
| Ser | Leu | Arg | Leu | Ser | Cys | Ala | Ala | Ser | Gly | Tyr | Thr | Phe | Ser | Asp |
| | | | 20 | | | | | 25 | | | | | 30 | |
| Tyr | | | | | | | | | | | | | | |
| Tyr | Ile | Asn | Trp | Val | Arg | Gln | Ala | Pro | Gly | Lys | Gly | Leu | Glu | Trp |
| | | 35 | | | | | 40 | | | | | 45 | | |
| Ile | | | | | | | | | | | | | | |
| Gly | Glu | Ile | Phe | Pro | Gly | Ser | Gly | Asn | Thr | His | Phe | Ser | Ala | Arg |
| | 50 | | | | | 55 | | | | | 60 | | | |
| Phe | | | | | | | | | | | | | | |
| Lys | Gly | Arg | Ala | Thr | Leu | Ser | Ala | Asp | Lys | Ser | Lys | Asn | Thr | Ala |
| 65 | | | | | 70 | | | | | 75 | | | | | 80 |
| Tyr | | | | | | | | | | | | | | |
| Leu | Gln | Met | Asn | Ser | Leu | Arg | Ala | Glu | Asp | Thr | Ala | Val | Tyr | Tyr |
| | | | | 85 | | | | | 90 | | | | | 95 |
| Cys | | | | | | | | | | | | | | |
| Ala | Gly | Gly | Asp | Tyr | Gly | Phe | Leu | Tyr | Trp | Gly | Gln | Gly | Thr | Leu |
| | | | | 100 | | | | | 105 | | | | | 110 |
| Val | | | | | | | | | | | | | | |
| Thr | Val | Ser | Ser | Ala | Ser | Thr | Lys | Gly | Pro | Ser | Val | Phe | Pro | Leu |
| | | 115 | | | | | 120 | | | | | 125 | | |
| Ala | | | | | | | | | | | | | | |
| Pro | Ser | Ser | Lys | Ser | Thr | Ser | Gly | Gly | Thr | Ala | Ala | Leu | Gly | Cys |
| | 130 | | | | | 135 | | | | | 140 | | | |
| Leu | | | | | | | | | | | | | | |
| Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | | | | | | | | | | | | | | |
| Ala | Leu | Thr | Ser | Gly | Val | His | Thr | Phe | Pro | Ala | Val | Leu | Gln | Ser |
| | | | | 165 | | | | | 170 | | | | | 175 |
| Ser | | | | | | | | | | | | | | |
| Gly | Leu | Tyr | Ser | Leu | Ser | Ser | Val | Val | Thr | Val | Pro | Ser | Ser | Ser |
| | | | 180 | | | | | 185 | | | | | 190 | |
| Leu | | | | | | | | | | | | | | |
| Gly | Thr | Gln | Thr | Tyr | Ile | Cys | Asn | Val | Asn | His | Lys | Pro | Ser | Asn |
| | | 195 | | | | | 200 | | | | | 205 | | |
| Thr | | | | | | | | | | | | | | |
| Lys | Val | Asp | Lys | Lys | Val | Glu | Arg | Lys | Cys | Cys | Val | Glu | Cys | Pro |
| | 210 | | | | | 215 | | | | | 220 | | | |
| Pro | | | | | | | | | | | | | | |
| Cys | Pro | Ala | Pro | Glu | Leu | Leu | Gly | Gly | Pro | Ser | Val | Phe | Leu | Phe |
| 225 | | | | | 230 | | | | | 235 | | | | | 240 |
| Pro | | | | | | | | | | | | | | |
| Pro | Lys | Pro | Lys | Asp | Thr | Leu | Met | Ile | Ser | Arg | Thr | Pro | Glu | Val |
| | | | | 245 | | | | | 250 | | | | | 255 |
| Thr | | | | | | | | | | | | | | |
| Cys | Val | Val | Val | Asp | Val | Ser | His | Glu | Asp | Pro | Glu | Val | Lys | Phe |
| | | | 260 | | | | | 265 | | | | | 270 | |
| Asn | | | | | | | | | | | | | | |
| Trp | Tyr | Val | Asp | Gly | Val | Glu | Val | His | Asn | Ala | Lys | Thr | Lys | Pro |
| | | 275 | | | | | 280 | | | | | 285 | | |
| Arg | | | | | | | | | | | | | | |
| Glu | Glu | Gln | Tyr | Asn | Ser | Thr | Tyr | Arg | Val | Val | Ser | Val | Leu | Thr |
| | 290 | | | | | 295 | | | | | 300 | | | |
| Val | | | | | | | | | | | | | | |
| Leu | His | Gln | Asp | Trp | Leu | Asn | Gly | Lys | Glu | Tyr | Lys | Cys | Lys | Val |
| 305 | | | | | 310 | | | | | 315 | | | | | 320 |
| Ser | | | | | | | | | | | | | | |
| Asn | Lys | Ala | Leu | Pro | Ala | Pro | Ile | Glu | Lys | Thr | Ile | Ser | Lys | Ala |
| | | | | 325 | | | | | 330 | | | | | 335 |
| Lys | | | | | | | | | | | | | | |
| Gly | Gln | Pro | Arg | Glu | Pro | Gln | Val | Tyr | Thr | Leu | Pro | Pro | Ser | Arg |
| | | | 340 | | | | | 345 | | | | | 350 | |
| Asp | | | | | | | | | | | | | | |
| Glu | Leu | Thr | Lys | Asn | Gln | Val | Ser | Leu | Thr | Cys | Leu | Val | Lys | Gly |
| | | 355 | | | | | 360 | | | | | 365 | | |
| Phe | | | | | | | | | | | | | | |
| Tyr | Pro | Ser | Asp | Ile | Ala | Val | Glu | Trp | Glu | Ser | Asn | Gly | Gln | Pro |
| | | | | | | | | | | | | | | Glu |

```
                370             375             380
Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys Gly Gly Gly Gly Ser
        435                 440                 445

Gly Gly Gly Gly Ser Gln Val Gln Leu Gln Glu Ser Gly Pro Gly Leu
    450                 455                 460

Val Lys Pro Ser Glu Thr Leu Ser Leu Thr Cys Thr Val Ser Gly Gly
465                 470                 475                 480

Ser Val Ser Ser Gly Asp Tyr Tyr Trp Thr Trp Ile Arg Gln Ser Pro
                485                 490                 495

Gly Lys Cys Leu Glu Trp Ile Gly His Ile Tyr Tyr Ser Gly Asn Thr
            500                 505                 510

Asn Tyr Asn Pro Ser Leu Lys Ser Arg Leu Thr Ile Ser Ile Asp Thr
        515                 520                 525

Ser Lys Thr Gln Phe Ser Leu Lys Leu Ser Ser Val Thr Ala Ala Asp
    530                 535                 540

Thr Ala Ile Tyr Tyr Cys Val Arg Asp Arg Val Thr Gly Ala Phe Asp
545                 550                 555                 560

Ile Trp Gly Gln Gly Thr Met Val Thr Val Ser Ser Gly Gly Gly Gly
                565                 570                 575

Ser Gly Gly Gly Gly Ser Gly Gly Gly Gly Ser Gly Gly Gly Gly Ser
            580                 585                 590

Asp Ile Gln Met Thr Gln Ser Pro Ser Ser Leu Ser Ala Ser Val Gly
        595                 600                 605

Asp Arg Val Thr Ile Thr Cys Gln Ala Ser Gln Asp Ile Ser Asn Tyr
    610                 615                 620

Leu Asn Trp Tyr Gln Gln Lys Pro Gly Lys Ala Pro Lys Leu Leu Ile
625                 630                 635                 640

Tyr Asp Ala Ser Asn Leu Glu Thr Gly Val Pro Ser Arg Phe Ser Gly
                645                 650                 655

Ser Gly Ser Gly Thr Asp Phe Thr Phe Thr Ile Ser Ser Leu Gln Pro
            660                 665                 670

Glu Asp Ile Ala Thr Tyr Phe Cys Gln His Phe Asp His Leu Pro Leu
        675                 680                 685

Ala Phe Gly Cys Gly Thr Lys Val Glu Ile Lys
690                 695

<210> SEQ ID NO 327
<211> LENGTH: 699
<212> TYPE: PRT
<213> ORGANISM: Artificial Sequence
<220> FEATURE:
<223> OTHER INFORMATION: hu8C4 AH71 x Vectibix scFv

<400> SEQUENCE: 327

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
```

```
                35                  40                  45
Gly Glu Ile Phe Pro Gly Trp Gly Asn Thr His Phe Ser Ala Arg Phe
 50                  55                  60
Lys Gly Arg Ala Thr Leu Ser Ala Asp Lys Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Gly Gln Asp Tyr Gly Phe Leu Tyr Trp Gly Gln Gly Thr Leu Val
                100                 105                 110
Thr Val Ser Ser Ala Ser Thr Lys Gly Pro Ser Val Phe Pro Leu Ala
                115                 120                 125
Pro Ser Ser Lys Ser Thr Ser Gly Gly Thr Ala Ala Leu Gly Cys Leu
                130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
                195                 200                 205
Lys Val Asp Lys Lys Val Glu Arg Lys Cys Cys Val Glu Cys Pro Pro
210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
                260                 265                 270
Trp Tyr Val Asp Gly Val Glu Val His Asn Ala Lys Thr Lys Pro Arg
                275                 280                 285
Glu Glu Gln Tyr Asn Ser Thr Tyr Arg Val Val Ser Val Leu Thr Val
                290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
                340                 345                 350
Glu Leu Thr Lys Asn Gln Val Ser Leu Thr Cys Leu Val Lys Gly Phe
                355                 360                 365
Tyr Pro Ser Asp Ile Ala Val Glu Trp Glu Ser Asn Gly Gln Pro Glu
                370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
                420                 425                 430
Thr Gln Lys Ser Leu Ser Leu Ser Pro Gly Lys Gly Gly Gly Gly Ser
                435                 440                 445
Gly Gly Gly Gly Ser Gln Val Gln Leu Gln Glu Ser Gly Pro Gly Leu
                450                 455                 460
```

```
Val Lys Pro Ser Glu Thr Leu Ser Leu Thr Cys Thr Val Ser Gly Gly
465                 470                 475                 480

Ser Val Ser Ser Gly Asp Tyr Tyr Trp Thr Trp Ile Arg Gln Ser Pro
                485                 490                 495

Gly Lys Cys Leu Glu Trp Ile Gly His Ile Tyr Tyr Ser Gly Asn Thr
            500                 505                 510

Asn Tyr Asn Pro Ser Leu Lys Ser Arg Leu Thr Ile Ser Ile Asp Thr
            515                 520                 525

Ser Lys Thr Gln Phe Ser Leu Lys Leu Ser Ser Val Thr Ala Ala Asp
        530                 535                 540

Thr Ala Ile Tyr Tyr Cys Val Arg Asp Arg Val Thr Gly Ala Phe Asp
545                 550                 555                 560

Ile Trp Gly Gln Gly Thr Met Val Thr Val Ser Ser Gly Gly Gly Gly
                565                 570                 575

Ser Gly Gly Gly Gly Ser Gly Gly Gly Ser Gly Gly Gly Gly Ser
            580                 585                 590

Asp Ile Gln Met Thr Gln Ser Pro Ser Ser Leu Ser Ala Ser Val Gly
            595                 600                 605

Asp Arg Val Thr Ile Thr Cys Gln Ala Ser Gln Asp Ile Ser Asn Tyr
610                 615                 620

Leu Asn Trp Tyr Gln Gln Lys Pro Gly Lys Ala Pro Lys Leu Leu Ile
625                 630                 635                 640

Tyr Asp Ala Ser Asn Leu Glu Thr Gly Val Pro Ser Arg Phe Ser Gly
                645                 650                 655

Ser Gly Ser Gly Thr Asp Phe Thr Phe Thr Ile Ser Ser Leu Gln Pro
            660                 665                 670

Glu Asp Ile Ala Thr Tyr Phe Cys Gln His Phe Asp His Leu Pro Leu
            675                 680                 685

Ala Phe Gly Cys Gly Thr Lys Val Glu Ile Lys
        690                 695

<210> SEQ ID NO 328
<211> LENGTH: 699
<212> TYPE: PRT
<213> ORGANISM: Artificial Sequence
<220> FEATURE:
<223> OTHER INFORMATION: hu8C4 AH72 x Vectibix scFv

<400> SEQUENCE: 328

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
        35                  40                  45

Gly Glu Ile Phe Pro Gly Trp Gly Asn Thr His Phe Ser Arg Ser Pro
    50                  55                  60

Thr Pro Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gly Asp Tyr Gly Phe Leu Tyr Trp Gly Gln Gly Thr Leu Val
            100                 105                 110

Thr Val Ser Ser Ala Ser Thr Lys Gly Pro Ser Val Phe Pro Leu Ala
        115                 120                 125
```

```
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Arg Lys Cys Cys Val Glu Cys Pro Pro
210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
                260                 265                 270
Trp Tyr Val Asp Gly Val Glu Val His Asn Ala Lys Thr Lys Pro Arg
            275                 280                 285
Glu Glu Gln Tyr Asn Ser Thr Tyr Arg Val Val Ser Val Leu Thr Val
        290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
                340                 345                 350
Glu Leu Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
        370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
                420                 425                 430
Thr Gln Lys Ser Leu Ser Leu Ser Pro Gly Lys Gly Gly Gly Gly Ser
        435                 440                 445
Gly Gly Gly Gly Ser Gln Val Gln Leu Gln Glu Ser Gly Pro Gly Leu
    450                 455                 460
Val Lys Pro Ser Glu Thr Leu Ser Leu Thr Cys Thr Val Ser Gly Gly
465                 470                 475                 480
Ser Val Ser Ser Gly Asp Tyr Tyr Trp Thr Trp Ile Arg Gln Ser Pro
                485                 490                 495
Gly Lys Cys Leu Glu Trp Ile Gly His Ile Tyr Tyr Ser Gly Asn Thr
                500                 505                 510
Asn Tyr Asn Pro Ser Leu Lys Ser Arg Leu Thr Ile Ser Ile Asp Thr
            515                 520                 525
Ser Lys Thr Gln Phe Ser Leu Lys Leu Ser Ser Val Thr Ala Ala Asp
        530                 535                 540
```

```
Thr Ala Ile Tyr Tyr Cys Val Arg Asp Arg Val Thr Gly Ala Phe Asp
545                 550                 555                 560

Ile Trp Gly Gln Gly Thr Met Val Thr Val Ser Ser Gly Gly Gly Gly
            565                 570                 575

Ser Gly Gly Gly Gly Ser Gly Gly Gly Gly Ser Gly Gly Gly Gly Ser
            580                 585                 590

Asp Ile Gln Met Thr Gln Ser Pro Ser Ser Leu Ser Ala Ser Val Gly
            595                 600                 605

Asp Arg Val Thr Ile Thr Cys Gln Ala Ser Gln Asp Ile Ser Asn Tyr
            610                 615                 620

Leu Asn Trp Tyr Gln Gln Lys Pro Gly Lys Ala Pro Lys Leu Leu Ile
625                 630                 635                 640

Tyr Asp Ala Ser Asn Leu Glu Thr Gly Val Pro Ser Arg Phe Ser Gly
            645                 650                 655

Ser Gly Ser Gly Thr Asp Phe Thr Phe Thr Ile Ser Ser Leu Gln Pro
            660                 665                 670

Glu Asp Ile Ala Thr Tyr Phe Cys Gln His Phe Asp His Leu Pro Leu
            675                 680                 685

Ala Phe Gly Cys Gly Thr Lys Val Glu Ile Lys
            690                 695
```

<210> SEQ ID NO 329
<211> LENGTH: 699
<212> TYPE: PRT
<213> ORGANISM: Artificial Sequence
<220> FEATURE:
<223> OTHER INFORMATION: hu8C4 AH73 x Vectibix scFv

<400> SEQUENCE: 329

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
            35                  40                  45

Gly Glu Ile Phe Pro Gly Trp Gly Asn Ser His Val Val Ser Arg Phe
50                  55                  60

Lys Gly Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Gly Gly Asp Tyr Gly Phe Leu Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205
```

-continued

Lys Val Asp Lys Lys Val Glu Arg Lys Cys Cys Val Glu Cys Pro Pro
    210             215                 220

Cys Pro Ala Pro Glu Leu Leu Gly Gly Pro Ser Val Phe Leu Phe Pro
225             230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
        260                 265                 270

Trp Tyr Val Asp Gly Val Glu Val His Asn Ala Lys Thr Lys Pro Arg
    275                 280                 285

Glu Glu Gln Tyr Asn Ser Thr Tyr Arg Val Val Ser Val Leu Thr Val
290             295                 300

Leu His Gln Asp Trp Leu Asn Gly Lys Glu Tyr Lys Cys Lys Val Ser
305             310                 315                 320

Asn Lys Ala Leu Pro Ala Pro Ile Glu Lys Thr Ile Ser Lys Ala Lys
            325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
    355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385             390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys Gly Gly Gly Gly Ser
        435                 440                 445

Gly Gly Gly Gly Ser Gln Val Gln Leu Gln Glu Ser Gly Pro Gly Leu
    450                 455                 460

Val Lys Pro Ser Glu Thr Leu Ser Leu Thr Cys Thr Val Ser Gly Gly
465             470                 475                 480

Ser Val Ser Ser Gly Asp Tyr Tyr Trp Thr Trp Ile Arg Gln Ser Pro
            485                 490                 495

Gly Lys Cys Leu Glu Trp Ile Gly His Ile Tyr Tyr Ser Gly Asn Thr
            500                 505                 510

Asn Tyr Asn Pro Ser Leu Lys Ser Arg Leu Thr Ile Ser Ile Asp Thr
            515                 520                 525

Ser Lys Thr Gln Phe Ser Leu Lys Leu Ser Ser Val Thr Ala Ala Asp
    530                 535                 540

Thr Ala Ile Tyr Tyr Cys Val Arg Asp Arg Val Thr Gly Ala Phe Asp
545             550                 555                 560

Ile Trp Gly Gln Gly Thr Met Val Thr Val Ser Ser Gly Gly Gly Gly
            565                 570                 575

Ser Gly Gly Gly Gly Ser Gly Gly Gly Gly Ser Gly Gly Gly Gly Ser
            580                 585                 590

Asp Ile Gln Met Thr Gln Ser Pro Ser Ser Leu Ser Ala Ser Val Gly
            595                 600                 605

Asp Arg Val Thr Ile Thr Cys Gln Ala Ser Gln Asp Ile Ser Asn Tyr
            610                 615                 620

Leu Asn Trp Tyr Gln Gln Lys Pro Gly Lys Ala Pro Lys Leu Leu Ile

```
            625                 630                 635                 640

Tyr Asp Ala Ser Asn Leu Glu Thr Gly Val Pro Ser Arg Phe Ser Gly
                    645                 650                 655

Ser Gly Ser Gly Thr Asp Phe Thr Phe Thr Ile Ser Ser Leu Gln Pro
            660                 665                 670

Glu Asp Ile Ala Thr Tyr Phe Cys Gln His Phe Asp His Leu Pro Leu
            675                 680                 685

Ala Phe Gly Cys Gly Thr Lys Val Glu Ile Lys
            690                 695
```

<210> SEQ ID NO 330
<211> LENGTH: 699
<212> TYPE: PRT
<213> ORGANISM: Artificial Sequence
<220> FEATURE:
<223> OTHER INFORMATION: hu8C4 AH85 x Vectibix scFv

<400> SEQUENCE: 330

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Tyr
            20                  25                  30

Tyr Ile Asn Trp Val Arg Gln Ala Pro Gly Lys Gly Leu Glu Trp Ile
        35                  40                  45

Gly Glu Ile Phe Pro Gly Trp Gly Asn Ser His Val Val Ser Arg Phe
    50                  55                  60

Lys Gly Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Gln Asp Tyr Gly Phe Leu Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Arg Lys Cys Cys Val Glu Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
```

```
            290                 295                 300
Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
                340                 345                 350

Glu Leu Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys Gly Gly Gly Gly Ser
            435                 440                 445

Gly Gly Gly Gly Ser Gln Val Gln Leu Gln Glu Ser Gly Pro Gly Leu
450                 455                 460

Val Lys Pro Ser Glu Thr Leu Ser Leu Thr Cys Thr Val Ser Gly Gly
465                 470                 475                 480

Ser Val Ser Ser Gly Asp Tyr Tyr Trp Thr Trp Ile Arg Gln Ser Pro
                485                 490                 495

Gly Lys Cys Leu Glu Trp Ile Gly His Ile Tyr Tyr Ser Gly Asn Thr
                500                 505                 510

Asn Tyr Asn Pro Ser Leu Lys Ser Arg Leu Thr Ile Ser Ile Asp Thr
            515                 520                 525

Ser Lys Thr Gln Phe Ser Leu Lys Leu Ser Ser Val Thr Ala Ala Asp
            530                 535                 540

Thr Ala Ile Tyr Tyr Cys Val Arg Asp Arg Val Thr Gly Ala Phe Asp
545                 550                 555                 560

Ile Trp Gly Gln Gly Thr Met Val Thr Val Ser Ser Gly Gly Gly Gly
                565                 570                 575

Ser Gly Gly Gly Gly Ser Gly Gly Gly Gly Ser Gly Gly Gly Gly Ser
                580                 585                 590

Asp Ile Gln Met Thr Gln Ser Pro Ser Ser Leu Ser Ala Ser Val Gly
            595                 600                 605

Asp Arg Val Thr Ile Thr Cys Gln Ala Ser Gln Asp Ile Ser Asn Tyr
            610                 615                 620

Leu Asn Trp Tyr Gln Gln Lys Pro Gly Lys Ala Pro Lys Leu Leu Ile
625                 630                 635                 640

Tyr Asp Ala Ser Asn Leu Glu Thr Gly Val Pro Ser Arg Phe Ser Gly
                645                 650                 655

Ser Gly Ser Gly Thr Asp Phe Thr Phe Thr Ile Ser Ser Leu Gln Pro
                660                 665                 670

Glu Asp Ile Ala Thr Tyr Phe Cys Gln His Phe Asp His Leu Pro Leu
            675                 680                 685

Ala Phe Gly Cys Gly Thr Lys Val Glu Ile Lys
            690                 695

<210> SEQ ID NO 331
```

```
<211> LENGTH: 9
<212> TYPE: PRT
<213> ORGANISM: Artificial Sequence
<220> FEATURE:
<223> OTHER INFORMATION: Epitope region Y321~L329

<400> SEQUENCE: 331

Tyr Val Ser Lys Pro Gly Ala Gln Leu
1               5

<210> SEQ ID NO 332
<211> LENGTH: 9
<212> TYPE: PRT
<213> ORGANISM: Artificial Sequence
<220> FEATURE:
<223> OTHER INFORMATION: Epitope region I333~I341

<400> SEQUENCE: 332

Ile Gly Ala Ser Leu Asn Asp Asp Ile
1               5

<210> SEQ ID NO 333
<211> LENGTH: 7
<212> TYPE: PRT
<213> ORGANISM: Artificial Sequence
<220> FEATURE:
<223> OTHER INFORMATION: Epitope region P366~D372

<400> SEQUENCE: 333

Pro Ile Lys Tyr Val Asn Asp
1               5

<210> SEQ ID NO 334
<211> LENGTH: 11
<212> TYPE: PRT
<213> ORGANISM: Artificial Sequence
<220> FEATURE:
<223> OTHER INFORMATION: Epitope region Q464~S474

<400> SEQUENCE: 334

Gln Val Val Val Ser Arg Ser Gly Pro Ser Thr
1               5                   10

<210> SEQ ID NO 335
<211> LENGTH: 1390
<212> TYPE: PRT
<213> ORGANISM: Artificial Sequence
<220> FEATURE:
<223> OTHER INFORMATION: c-Met reference sequence

<400> SEQUENCE: 335

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
```

```
                100             105             110
Lys Asp Asn Ile Asn Met Ala Leu Val Val Asp Thr Tyr Tyr Asp Asp
            115                 120                 125
Gln Leu Ile Ser Cys Gly Ser Val Asn Arg Gly Thr Cys Gln Arg His
            130                 135             140
Val Phe Pro His Asn His Thr Ala Asp Ile Gln Ser Glu Val His Cys
145                 150                 155                 160
Ile Phe Ser Pro Gln Ile Glu Glu Pro Ser Gln Cys Pro Asp Cys Val
                165                 170                 175
Val Ser Ala Leu Gly Ala Lys Val Leu Ser Val Lys Asp Arg Phe
            180                 185                 190
Ile Asn Phe Phe Val Gly Asn Thr Ile Asn Ser Ser Tyr Phe Pro Asp
            195                 200                 205
His Pro Leu His Ser Ile Ser Val Arg Arg Leu Lys Glu Thr Lys Asp
            210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Val His Ala Phe Glu Ser Asn
                245                 250                 255
Asn Phe Ile Tyr Phe Leu Thr Val Gln Arg Glu Thr Leu Asp Ala Gln
                260                 265                 270
Thr Phe His Thr Arg Ile Ile Arg Phe Cys Ser Ile Asn Ser Gly Leu
            275                 280                 285
His Ser Tyr Met Glu Met Pro Leu Glu Cys Ile Leu Thr Glu Lys Arg
            290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
                340                 345                 350
Ser Ala Glu Pro Met Asp Arg Ser Ala Met Cys Ala Phe Pro Ile Lys
            355                 360                 365
Tyr Val Asn Asp Phe Phe Asn Lys Ile Val Asn Lys Asn Asn Val Arg
            370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
                420                 425                 430
Gln Phe Ser Glu Val Leu Leu Thr Ser Ile Ser Thr Phe Ile Lys Gly
            435                 440                 445
Asp Leu Thr Ile Ala Asn Leu Gly Thr Ser Glu Gly Arg Phe Met Gln
            450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
            500                 505                 510
Ile Pro Leu Asn Gly Leu Gly Cys Arg His Phe Gln Ser Cys Ser Gln
            515                 520                 525
```

```
Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
    755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
    835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
    915                 920                 925

Gln Asn Phe Thr Gly Leu Ile Ala Gly Val Val Ser Ile Ser Thr Ala
930                 935                 940
```

-continued

Leu Leu Leu Leu Leu Gly Phe Phe Leu Trp Leu Lys Arg Lys Gln
945                 950                 955                 960

Ile Lys Asp Leu Gly Ser Glu Leu Val Arg Tyr Asp Ala Arg Val His
            965                 970                 975

Thr Pro His Leu Asp Arg Leu Val Ser Ala Arg Ser Val Ser Pro Thr
        980                 985                 990

Thr Glu Met Val Ser Asn Glu Ser Val Asp Tyr Arg Ala Thr Phe Pro
    995                 1000                1005

Glu Asp Gln Phe Pro Asn Ser Ser Gln Asn Gly Ser Cys Arg Gln
    1010                1015                1020

Val Gln Tyr Pro Leu Thr Asp Met Ser Pro Ile Leu Thr Ser Gly
    1025                1030                1035

Asp Ser Asp Ile Ser Ser Pro Leu Leu Gln Asn Thr Val His Ile
    1040                1045                1050

Asp Leu Ser Ala Leu Asn Pro Glu Leu Val Gln Ala Val Gln His
    1055                1060                1065

Val Val Ile Gly Pro Ser Ser Leu Ile Val His Phe Asn Glu Val
    1070                1075                1080

Ile Gly Arg Gly His Phe Gly Cys Val Tyr His Gly Thr Leu Leu
    1085                1090                1095

Asp Asn Asp Gly Lys Lys Ile His Cys Ala Val Lys Ser Leu Asn
    1100                1105                1110

Arg Ile Thr Asp Ile Gly Glu Val Ser Gln Phe Leu Thr Glu Gly
    1115                1120                1125

Ile Ile Met Lys Asp Phe Ser His Pro Asn Val Leu Ser Leu Leu
    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn

-continued

```
              1340                1345                1350
Ala  Thr  Tyr  Val  Asn  Val  Lys  Cys  Val  Ala  Pro  Tyr  Pro  Ser  Leu
     1355                1360                1365

Leu  Ser  Ser  Glu  Asp  Asn  Ala  Asp  Asp  Glu  Val  Asp  Thr  Arg  Pro
     1370                1375                1380

Ala  Ser  Phe  Trp  Glu  Thr  Ser
     1385                1390
```

UNITED STATES PATENT AND TRADEMARK OFFICE
CERTIFICATE OF CORRECTION

PATENT NO. : 11,479,612 B2
APPLICATION NO. : 16/616345
DATED : October 25, 2022
INVENTOR(S) : Seung Kee Moon et al.

It is certified that error appears in the above-identified patent and that said Letters Patent is hereby corrected as shown below:

On the Title Page

Column 1, Line 2 (item (73) Assignee):
Delete "Corp." and insert -- Corp., (KR) --.

In the Specification

Column 1, Line 14:
Delete "PCI" and insert -- PCT --.

Signed and Sealed this
Twenty-first Day of March, 2023

Katherine Kelly Vidal
*Director of the United States Patent and Trademark Office*